(12) United States Patent
Baik et al.

(10) Patent No.: US 12,037,415 B2
(45) Date of Patent: Jul. 16, 2024

(54) PEPTIDE AND PHARMACEUTICAL COMPOSITION FOR TREATING AN EYE DISEASE COMPRISING THE SAME AS AN ACTIVE PHARMACEUTICAL INGREDIENT

(71) Applicant: YuYu Pharma, Inc., Seoul (KR)

(72) Inventors: Taegon Baik, Seoul (KR); Taek-Soo Kim, Gunpo-si (KR); Dae-Seong Lim, Seoul (KR); Deuk-young Goo, Seoul (KR)

(73) Assignee: Yuyu Pharma, Inc., Seoul (KR)

( * ) Notice: Subject to any disclaimer, the term of this patent is extended or adjusted under 35 U.S.C. 154(b) by 1038 days.

(21) Appl. No.: 16/614,123

(22) PCT Filed: May 17, 2018

(86) PCT No.: PCT/KR2018/005673
§ 371 (c)(1),
(2) Date: Jun. 9, 2020

(87) PCT Pub. No.: WO2018/225961
PCT Pub. Date: Dec. 13, 2018

(65) Prior Publication Data
US 2021/0024577 A1    Jan. 28, 2021

(30) Foreign Application Priority Data
May 17, 2017   (KR) .......................... 10-2017-0061250

(51) Int. Cl.
| C07K 7/06 | (2006.01) |
| A61K 38/00 | (2006.01) |
| C07K 7/02 | (2006.01) |

(52) U.S. Cl.
CPC ................ *C07K 7/02* (2013.01); *A61K 38/00* (2013.01)

(58) Field of Classification Search
CPC .................................. C07K 7/02; A61K 38/00
See application file for complete search history.

(56) References Cited

U.S. PATENT DOCUMENTS

| 6,037,135 | A | 3/2000 | Kubo et al. |
| 8,227,424 | B2 | 7/2012 | Sugihara et al. |
| 9,695,218 | B2 | 7/2017 | Yang et al. |
| 11,613,558 | B2 | 3/2023 | Baik et al. |
| 2014/0309400 | A1 | 10/2014 | Combette et al. |
| 2016/0215018 | A1 | 7/2016 | Yang et al. |
| 2019/0002528 | A1 | 1/2019 | Yang et al. |
| 2019/0111112 | A1 | 4/2019 | Yang |
| 2020/0270306 | A1 | 8/2020 | Baik et al. |
| 2021/0024577 | A1 | 1/2021 | Baik et al. |

FOREIGN PATENT DOCUMENTS

| EP | 3329929 | A1 | 6/2018 | |
| KR | 20100087188 | A | 8/2010 | |
| KR | 101438744 | B1 | 9/2014 | |
| KR | 20160079983 | A | 7/2016 | |
| KR | 101795653 | B1 | 11/2017 | |
| KR | 10-2018-0074928 | A | 7/2018 | |
| WO | WO-2007117444 | A2 * | 10/2007 | ........... C12N 15/111 |
| WO | WO-2009/039854 | A2 | 4/2009 | |
| WO | WO-2012/166610 | A1 | 12/2012 | |
| WO | WO-2015/088093 | A1 | 6/2015 | |
| WO | WO-2015/088096 | A1 | 6/2015 | |
| WO | WO-2016/104964 | A1 | 6/2016 | |
| WO | WO-2017/018613 | A1 | 2/2017 | |
| WO | WO-2017/101748 | A1 | 6/2017 | |
| WO | WO-2017/175963 | A1 | 10/2017 | |
| WO | WO-2018/225961 | A1 | 12/2018 | |
| WO | WO-2020/099925 | A2 | 5/2020 | |
| WO | WO-2021/191689 | A2 | 9/2021 | |

OTHER PUBLICATIONS

Hereditary Optic Neuropathies, Merck Manuals, accessed Mar. 27, 2017 at URL merckmanuals.com/professional/eye-disorders/optic-nerve-disorders/hereditary-optic-neuropathies, pp. 1-2 (Year: 2017).*
Hartong et al., "Retinitis pigmentosa," Lancet 368:1795-1809 (2006) (Year: 2006).*
Emerson et al., "Emerging therapies for the treatment of neovascular age-related macular degeneration and diabetic macular edema," Biodrugs 21:245-257 (2007) (Year: 2007).*
Nita et al, "Age-related macular degeneration and changes in the extracellular matrix," Med Sci Monit 20: 1003-1016 (2014) (Year: 2014).*
Diabetic retinopathy, Merck—accessed Jul. 3, 2021 at URL: merckmanuals.com/professional/eye-disorders/retinal-disorders/diabetic-retinopathy?query=ocular neovascular, 5 pages (Year: 2021).*
Keratoconus, Merck manuals, accessed Mar. 17, 2023 at URL merckmanuals.com/professional/eye-disorders/corneal-disorders/keratoconus, 2 pages (Year: 2023).*
Introduction to Corneal Disorders, Merck manuals, accessed Mar. 17, 2023 at URL merckmanuals.com/professional/eye-disorders/corneal-disorders/introduction-to-corneal-disorders?query=corneal disorders, 2 pages (Year: 2023).*
Lin et al., "dry eye disease: review of diagnostic approaches and treatments," Saudi Journal of ophthalmology 28:173-181 (2014) (Year: 2014).*

(Continued)

*Primary Examiner* — Julie Ha
*Assistant Examiner* — Kristina M Hellman
(74) *Attorney, Agent, or Firm* — Foley Hoag LLP; David P. Halsteaad; Laura A. Wzorek

(57) ABSTRACT

The present invention relates to peptides and pharmaceutical compositions thereof for treating eye diseases. Administering peptides of the present invention to the eye can increase the amount of tear secretion and repair corneal damage. Thus, these peptides and compositions can be advantageously used as therapeutic agents for treating eye diseases.

16 Claims, 133 Drawing Sheets
Specification includes a Sequence Listing.

(56) References Cited

OTHER PUBLICATIONS

NCBI reference sequence WP_147105221.1, accessed Mar. 19, 2023 at URL: ncbi.nlm.nih.gov/protein/WP_147105221.1?report=genbank&log$=protalign&blast_rank=1&RID=1EKRT8HK013, 1 page (Year: 2023).*

UniProtKB accession No. A0A6J5BXN2 was accessed Mar. 19, 2023 at URL rest.uniprot.org/uniprotkb/A0A6J5BXN2.txt, 1 page (Year: 2023).*

Extended European Search Report for EP Application No. EP 18812841 dated Mar. 3, 2021.

Kim et al., "Effects of chondrocyte-derived extracellular matrix in a dry eye mouse model," Mol Vision, 21: 1210-1223 (2015).

International Search Report and Written Opinion for International Application No. PCT/IB2019/001220 dated May 7, 2020.

Shankar et al., "Structural determinants of calcium signaling by RGD peptides in rat osteoclasts: integrin-dependent and-independent actions," Experimental Cell Research, 219: 364-371 (1995).

International Preliminary Report on Patentability for International Application No. PCT/IB2019/001220 dated May 18, 2021.

International Search Report and Written Opinion for International Application No. PCT/IB2021/000423 dated Nov. 17, 2021.

Lee et al., "Anti-inflammatory effect of hydroxyproline-GQDGLAGPK in desiccation stress-induced experimental dry eye mouse," Sci Rep, 7(7413): 1-12 (2017).

International Search Report and Written Opinion for International Application No. PCT/KR2018/005673 dated Oct. 24, 2018.

Partial Supplementary European Search Report for EP Application No. 19883897.1 dated May 16, 2023.

* cited by examiner

Fig. 1

| No. | Lot Number | Peptide Name | Sequence | M.W. | Purity (%) | Amount (mg) | Solubility (0.5mg/ml) |
|---|---|---|---|---|---|---|---|
| 1 | K161389 | YDE-001 | OGQEGLAGPK (O : Hydroxyproline) | 969.1 | >99.7% | 5.0mg 10.0mg | Water |
| 2 | K161390 | YDE-002 | OGQNGLAGPK (O : Hydroxyproline) | 954.0 | >99.7% | 5.0mg 10.0mg | Water |
| 3 | K161391 | YDE-003 | OGQQGLAGPK (O : Hydroxyproline) | 968.1 | >99.7% | 5.0mg 10.0mg | Water |
| 4 | K161392 | YDE-004 | OGQHGLAGPK (O : Hydroxyproline) | 977.1 | >99.7% | 5.0mg 10.0mg | Water |
| 5 | K161393 | YDE-005 | OGQKGLAGPK (O : Hydroxyproline) | 968.1 | >99.5% | 5.0mg 10.0mg | Water |
| 6 | K161394 | YDE-006 | OGQSGLAGPK (O : Hydroxyproline) | 927.0 | >98.9% | 5.0mg 10.0mg | Water |
| 7 | K161395 | YDE-007 | OGQTGLAGPK (O : Hydroxyproline) | 941.0 | >98.0% | 5.0mg 10.0mg | Water |
| 8 | K161396 | YDE-008 | OGQAGLAGPK (O : Hydroxyproline) | 911.0 | >98.8% | 5.0mg 10.0mg | Water |
| 9 | K161397 | YDE-009 | OGQVGLAGPK (O : Hydroxyproline) | 939.1 | >98.1% | 5.0mg 10.0mg | Water |
| 10 | K161398 | YDE-010 | OGQIGLAGPK (O : Hydroxyproline) | 953.1 | >99.0% | 5.0mg 10.0mg | Water |
| 11 | K161399 | YDE-011 | OGQLGLAGPK (O : Hydroxyproline) | 953.1 | >98.3% | 5.0mg 10.0mg | Water |
| 12 | K161400 | YDE-012 | OGQFGLAGPK (O : Hydroxyproline) | 987.1 | >98.9% | 5.0mg 10.0mg | Water |
| 13 | K161401 | YDE-013 | OGQYGLAGPK (O : Hydroxyproline) | 1003.1 | >98.7% | 5.0mg 10.0mg | Water |
| 14 | K161402 | YDE-014 | OGQWGLAGPK (O : Hydroxyproline) | 1026.2 | >98.5% | 5.0mg 10.0mg | Water |
| 15 | K161403 | YDE-015 | OGQDVLAGPK (O : Hydroxyproline) | 997.1 | >99.1% | 5.0mg 10.0mg | Water |
| 16 | K161404 | YDE-016 | OGQDILAGPK (O : Hydroxyproline) | 1011.1 | >99.4% | 5.0mg 10.0mg | Water |
| 17 | K161405 | YDE-017 | OGQDLLAGPK (O : Hydroxyproline) | 1011.1 | >98.0% | 5.0mg 10.0mg | Water |
| 18 | K161406 | YDE-018 | OGQDALAGPK (O : Hydroxyproline) | 969.1 | >99.6% | 5.0mg 10.0mg | Water |
| 19 | K161407 | YDE-019 | OGQDFLAGPK (O : Hydroxyproline) | 1045.2 | >99.6% | 5.0mg 10.0mg | Water |
| 20 | K161408 | YDE-020 | OGQDYLAGPK (O : Hydroxyproline) | 1061.2 | >99.2% | 5.0mg 10.0mg | Water |
| 21 | K161409 | YDE-021 | OGQDWLAGPK (O : Hydroxyproline) | 1084.2 | >98.1% | 5.0mg 10.0mg | Water |
| 22 | K161410 | YDE-022 | OGQDHLAGPK (O : Hydroxyproline) | 1035.1 | >98.3% | 5.0mg 10.0mg | Water |
| 23 | K161411 | YDE-023 | OGQDSLAGPK (O : Hydroxyproline) | 985.1 | >96.1% | 5.0mg 10.0mg | Water |
| 24 | K161412 | YDE-024 | OGQDTLAGPK (O : Hydroxyproline) | 999.1 | >98.9% | 5.0mg 10.0mg | Water |
| 25 | K161413 | YDE-025 | OGQD+Sar+LAGPK (Sar : me-Gly) (O : Hydroxyproline) | 969.1 | >95% | 5.0mg 10.0mg | Water |
| 26 | K161414 | YDE-026 | OGQS*GLAGPK (S* : homo-Ser) (O : Hydroxyproline) | 941.1 | >95% | 5.0mg 10.0mg | Water |
| 27 | K161415 | YDE-027 | OGQD'GLAGPK (D' : D(OMe)) (O : Hydroxyproline) | 969.1 | >95% | 5.0mg 10.0mg | Water |
| 28 | K161416 | YDE-028 | OGQN*GLAGPK (N* : N(NMe))(O : Hydroxyproline) | 968.1 | >95% | 5.0mg 10.0mg | Water |

Fig. 135

| Groups / Items | Body weights at ELGE surgery* | First test material topical eye drop [A] | 24 hrs after last treatment [B]* | Body weight gains [B-A] |
|---|---|---|---|---|
| Control | | | | |
| Sham | 213.63±21.04 | 305.50±33.53 | 340.50±38.46 | 35.00±11.19 |
| ELGE | 215.50±16.10 | 302.63±20.42 | 339.13±20.01 | 36.50±9.97 |
| Reference | | | | |
| DS | 220.50±8.70 | 304.50±13.11 | 340.63±10.20 | 36.13±5.38 |
| Test materials (0.3% solutions) | | | | |
| YY-102 | 211.88±12.89 | 302.00±20.70 | 337.75±25.95 | 35.75±6.84 |
| YDE-01 | 212.63±11.30 | 302.25±24.57 | 341.00±24.98 | 38.75±9.50 |
| YDE-02 | 210.38±10.89 | 302.00±15.96 | 338.00±22.39 | 36.00±12.29 |
| YDE-03 | 212.50±14.84 | 301.00±20.63 | 339.38±22.83 | 38.38±7.74 |
| YDE-04 | 217.50±16.25 | 302.50±19.66 | 338.50±21.44 | 36.00±10.97 |
| YDE-05 | 212.50±16.75 | 303.50±17.77 | 341.50±17.53 | 38.00±3.12 |
| YDE-06 | 212.38±19.00 | 306.38±25.21 | 345.13±21.06 | 38.75±6.14 |
| YDE-07 | 219.13±4.73 | 310.50±9.99 | 349.88±12.28 | 39.38±4.53 |
| YDE-08 | 213.38±13.99 | 307.00±13.73 | 345.63±17.87 | 38.63±7.01 |
| YDE-09 | 215.63±13.69 | 304.25±18.58 | 341.38±25.47 | 37.13±10.34 |
| YDE-10 | 216.00±12.99 | 305.25±13.82 | 343.63±16.36 | 38.38±6.44 |
| YDE-11 | 219.88±13.42 | 309.13±20.36 | 347.00±27.91 | 37.88±13.66 |
| YDE-12 | 222.13±9.98 | 311.00±15.57 | 349.88±21.70 | 38.88±9.08 |
| YDE-13 | 217.63±4.69 | 305.13±7.66 | 343.25±11.44 | 38.13±7.20 |
| YDE-14 | 216.75±15.53 | 301.25±20.11 | 339.75±26.99 | 38.50±9.94 |
| YDE-15 | 214.88±14.74 | 302.13±16.57 | 340.00±16.44 | 37.88±12.69 |
| YDE-16 | 213.50±18.31 | 299.50±16.42 | 337.38±20.50 | 37.88±7.57 |
| YDE-17 | 214.63±11.81 | 306.63±17.54 | 346.25±19.26 | 39.63±10.51 |
| YDE-18 | 213.88±13.24 | 307.88±13.27 | 347.38±23.02 | 39.50±14.68 |
| YDE-19 | 218.88±11.29 | 307.25±12.85 | 345.38±21.71 | 38.13±9.83 |
| YDE-20 | 217.88±9.61 | 300.75±16.79 | 339.25±15.68 | 38.50±5.71 |
| YDE-21 | 216.38±15.31 | 301.38±20.89 | 340.13±21.53 | 38.75±8.14 |
| YDE-22 | 219.38±10.85 | 304.13±14.56 | 343.50±21.37 | 39.38±9.30 |
| YDE-23 | 219.00±12.54 | 308.25±15.64 | 346.00±15.26 | 37.75±6.94 |
| YDE-24 | 212.13±18.41 | 298.38±25.85 | 334.00±31.75 | 35.63±10.29 |
| YDE-25 | 213.13±13.39 | 303.63±21.87 | 342.50±19.82 | 38.88±5.84 |
| YDE-26 | 213.63±14.71 | 305.75±23.07 | 343.25±29.09 | 37.50±9.38 |
| YDE-27 | 214.75±13.73 | 306.63±25.44 | 345.38±26.40 | 38.76±10.02 |
| YDE-28 | 212.75±13.36 | 297.63±21.12 | 336.38±22.02 | 38.75±7.63 |

Fig. 136

| Groups | Body weights at ELGE surgery* | First test material topical eye drop [A] | 24 hrs after last treatment [B]* | Body weight gains [B-A] |
|---|---|---|---|---|
| Control | | | | |
| Sham | 242.38±7.73 | 320.25±9.91 | 363.38±27.21 | 43.13±19.71 |
| ELGE | 243.88±3.83 | 329.25±18.90 | 367.50±19.89 | 38.25±11.40 |
| Reference | | | | |
| DS | 246.63±15.68 | 330.50±23.33 | 369.63±37.46 | 39.13±25.56 |
| YY-101 | 241.25±4.37 | 318.88±10.91 | 356.25±18.16 | 37.38±7.82 |
| YY-102 | 242.38±11.46 | 318.75±15.20 | 361.25±23.56 | 42.50±9.41 |
| Test materials (0.3% solutions) | | | | |
| YDE-029 | 242.25±16.63 | 327.38±18.75 | 373.75±28.50 | 46.38±12.49 |
| YDE-030 | 243.25±10.26 | 315.88±14.96 | 355.50±29.68 | 39.63±16.61 |
| YDE-031 | 241.00±15.82 | 316.75±27.58 | 359.00±39.87 | 42.25±14.96 |
| YDE-032 | 242.75±9.32 | 324.25±14.59 | 365.38±16.16 | 41.13±10.12 |
| YDE-033 | 243.50±11.96 | 327.50±17.57 | 377.13±26.59 | 49.63±16.27 |
| YDE-034 | 243.88±8.68 | 322.63±17.15 | 361.63±19.08 | 39.00±4.99 |
| YDE-035 | 240.88±11.29 | 321.00±22.17 | 358.50±29.18 | 37.50±20.36 |
| YDE-036 | 242.25±14.01 | 329.38±21.07 | 378.38±24.20 | 49.00±10.81 |
| YDE-037 | 244.50±10.94 | 324.88±17.36 | 369.13±21.43 | 44.25±8.83 |
| YDE-039 | 242.88±7.14 | 325.25±15.51 | 363.25±28.35 | 38.00±15.41 |
| YDE-040 | 241.13±13.39 | 319.25±14.10 | 357.00±27.93 | 37.75±19.37 |
| YDE-041 | 244.75±14.49 | 322.88±22.47 | 366.13±37.43 | 43.25±16.97 |
| YDE-042 | 239.13±8.29 | 323.38±8.28 | 372.38±19.46 | 49.00±13.54 |
| YDE-043 | 246.25±7.92 | 324.00±14.31 | 361.25±19.20 | 37.25±13.63 |

Fig. 137

Sprague-Dawley Rat – Left Eye

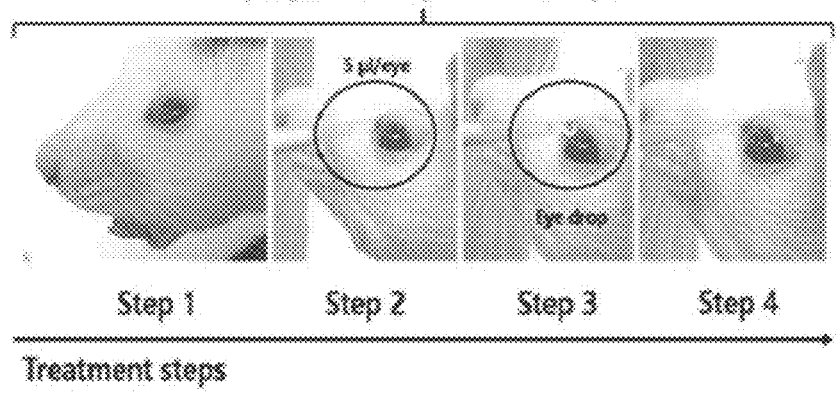

Step 1  Step 2  Step 3  Step 4

Treatment steps

Fig. 140

| Groups | Tear volumes (mm) after test material topical eye drop | | |
|---|---|---|---|
| Items | -1 day | 7 day | 14 day |
| Control | | | |
| Sham | 8.34±0.73 | 8.56±0.76 | 8.63±0.93 |
| ELGE | 3.54±0.78a | 2.65±0.85a | 3.27±1.06a |
| Reference | | | |
| DS | 3.53±0.66a | 4.10±1.07ad | 4.80±0.94ad |
| Test materials (0.3% solutions) | | | |
| YY-102 | 3.58±0.93a | 4.59±1.43ac | 5.77±1.99ac |
| YDE-01 | 3.55±0.93a | 4.88±1.62ac | 5.92±2.19ac |
| YDE-02 | 3.59±0.75a | 3.84±1.16a | 5.01±1.67ad |
| YDE-03 | 3.56±0.74a | 4.13±1.76ad | 4.88±1.57ad |
| YDE-04 | 3.57±0.55a | 3.42±1.06a | 5.19±1.84ad |
| YDE-05 | 3.56±0.86a | 3.85±0.93a | 5.08±1.91ad |
| YDE-06 | 3.56±0.65a | 3.44±1.69a | 5.35±1.68ad |
| YDE-07 | 3.53±0.68a | 3.91±1.28a | 5.45±1.26ad |
| YDE-08 | 3.54±0.82a | 4.57±1.25ac | 6.10±2.36ac |
| YDE-09 | 3.56±0.78a | 3.76±1.21a | 4.54±1.11a |
| YDE-10 | 3.52±0.61a | 3.42±1.31a | 4.35±1.36a |
| YDE-11 | 3.56±0.88a | 4.22±1.45ad | 6.16±2.16ac |
| YDE-12 | 3.55±0.71a | 3.68±0.99a | 5.67±1.86ac |
| YDE-13 | 3.55±0.49a | 5.27±1.50ac | 5.49±1.92ac |
| YDE-14 | 3.55±0.66a | 3.81±1.21a | 5.62±1.85ac |
| YDE-15 | 3.54±0.73a | 4.03±2.19ad | 6.65±2.13bc |
| YDE-16 | 3.56±0.93a | 4.59±1.13ac | 5.98±2.27ac |
| YDE-17 | 3.54±0.91a | 4.00±1.22ad | 4.89±1.50a |
| YDE-18 | 3.58±0.68a | 3.75±1.54a | 4.99±1.60ad |
| YDE-19 | 3.58±0.63a | 4.84±1.39ac | 4.52±1.07a |
| YDE-20 | 3.56±0.86a | 3.41±1.47a | 4.20±1.35a |
| YDE-21 | 3.55±0.72a | 4.08±1.33ad | 4.90±1.13a |
| YDE-22 | 3.50±0.75a | 3.19±0.67a | 4.10±0.95a |
| YDE-23 | 3.51±0.72a | 5.32±2.30ac | 5.78±2.23ac |
| YDE-24 | 3.53±0.63a | 3.85±1.30a | 5.72±1.36ac |
| YDE-25 | 3.56±0.75a | 3.21±0.72a | 4.72±2.19a |
| YDE-26 | 3.57±0.57a | 4.32±1.47ad | 6.01±1.83ac |
| YDE-27 | 3.57±0.64a | 2.82±0.86a | 3.95±1.52a |
| YDE-28 | 3.56±0.91a | 4.04±0.99ad | 4.73±1.18a |

| Items<br>Groups | Tear volumes (mm) after test material topical eye drop | | |
|---|---|---|---|
| | -1 day | 7 days | 14 days |
| Control | | | |
| Sham | 10.90±1.69 | 10.38±1.08 | 10.28±0.69 |
| ELGE | 4.81±1.09[a] | 4.37±0.83[b] | 4.70±0.65[b] |
| Reference | | | |
| DS | 4.74±1.30[a] | 5.72±1.28[bc] | 6.56±1.15[bd] |
| YY-101 | 4.86±1.08[a] | 5.36±0.68[bc] | 6.25±0.68[bd] |
| YY-102 | 4.94±0.71[a] | 5.77±1.01[bc] | 6.60±0.64[bd] |
| Test materials (0.3% solutions) | | | |
| YDE-029 | 4.72±1.05[a] | 5.33±1.43[b] | 6.03±1.71[b] |
| YDE-030 | 4.93±1.15[a] | 5.69±1.79[b] | 6.65±2.17[b] |
| YDE-031 | 4.70±0.69[a] | 5.63±1.97[b] | 5.91±0.85[bc] |
| YDE-032 | 4.94±1.04[a] | 5.58±0.80[bc] | 5.03±0.93[b] |
| YDE-033 | 4.77±1.32[a] | 4.99±1.20[b] | 4.54±1.16[b] |
| YDE-034 | 4.88±1.07[a] | 6.16±1.01[bd] | 6.43±1.86[b] |
| YDE-035 | 4.92±1.18[a] | 4.96±0.96[b] | 6.25±0.79[bd] |
| YDE-036 | 4.83±1.07[a] | 4.95±1.05[b] | 5.13±1.03[b] |
| YDE-037 | 4.68±0.83[a] | 4.98±0.66[b] | 5.80±0.96[bc] |
| YDE-039 | 4.81±1.27[a] | 6.04±1.01[bd] | 6.44±1.96[bc] |
| YDE-040 | 4.77±0.91[a] | 5.77±1.05[bc] | 8.63±1.53[cd] |
| YDE-041 | 4.87±1.19[a] | 5.01±1.26[b] | 6.25±2.15[b] |
| YDE-042 | 4.83±0.84[a] | 6.30±1.08[bd] | 7.97±1.48[cd] |
| YDE-043 | 4.86±0.81[a] | 5.90±1.06[bd] | 8.16±1.42[bd] |

Fig. 145

| Groups \ Items | Fluorescent stained cornea areas (%) |
|---|---|
| Control | |
| Sham | 2.62±1.71 |
| ELGE | 57.34±12.83[a] |
| Reference | |
| DS | 35.40±13.32[a] |
| Test materials (0.3% solutions) | |
| YY-102 | 27.48±14.37[ac] |
| YDE-01 | 25.49±11.62[ac] |
| YDE-02 | 38.26±11.25[ac] |
| YDE-03 | 40.45±6.46[ac] |
| YDE-04 | 35.05±11.74[ac] |
| YDE-05 | 37.98±11.53[ac] |
| YDE-06 | 33.23±13.26[ac] |
| YDE-07 | 32.79±10.77[ac] |
| YDE-08 | 20.32±11.87[ac] |
| YDE-09 | 41.50±7.86[ac] |
| YDE-10 | 49.29±12.06[a] |
| YDE-11 | 18.11±11.61[ac] |
| YDE-12 | 31.01±11.38[ac] |
| YDE-13 | 32.24±7.84[ac] |
| YDE-14 | 31.15±10.87[ac] |
| YDE-15 | 15.95±6.48[bc] |
| YDE-16 | 24.57±10.34[ac] |
| YDE-17 | 39.76±7.42[ac] |
| YDE-18 | 38.19±10.96[ac] |
| YDE-19 | 40.39±12.57[ac] |
| YDE-20 | 47.84±13.47[a] |
| YDE-21 | 37.00±10.49[ac] |
| YDE-22 | 47.82±10.01[a] |
| YDE-23 | 26.51±8.18[ac] |
| YDE-24 | 30.63±10.41[ac] |
| YDE-25 | 47.10±11.45[a] |
| YDE-26 | 22.63±11.23[ac] |
| YDE-27 | 50.24±11.94[a] |
| YDE-28 | 41.17±10.25[ac] |

Fig. 147

| Groups | Items Fluorescent stained cornea areas (%) |
|---|---|
| Control | |
| Sham | 1.53±0.65 |
| ELGE | 66.71±10.02[b] |
| Reference | |
| DS | 30.03±10.97[bd] |
| YY-101 | 33.80±11.11[bd] |
| YY-102 | 27.89±7.10[bd] |
| Test materials (0.3% solutions) | |
| YDE-029 | 63.45±11.57[b] |
| YDE-030 | 30.60±13.61[bd] |
| YDE-031 | 33.35±11.01[bd] |
| YDE-032 | 58.90±19.81[b] |
| YDE-033 | 60.55±21.22[b] |
| YDE-034 | 32.17±12.94[bd] |
| YDE-035 | 27.62±6.51[bd] |
| YDE-036 | 57.87±22.91[b] |
| YDE-037 | 36.30±9.75[bd] |
| YDE-039 | 29.94±11.40[bd] |
| YDE-040 | 18.33±9.41[bd] |
| YDE-041 | 46.38±26.65[b] |
| YDE-042 | 20.72±11.37[bd] |
| YDE-043 | 19.04±7.36[bd] |

Dose Response of hEGF(48hrs) Plate 3

Dose Response of hEGF(48hrs) Plate 4

Fig. 160
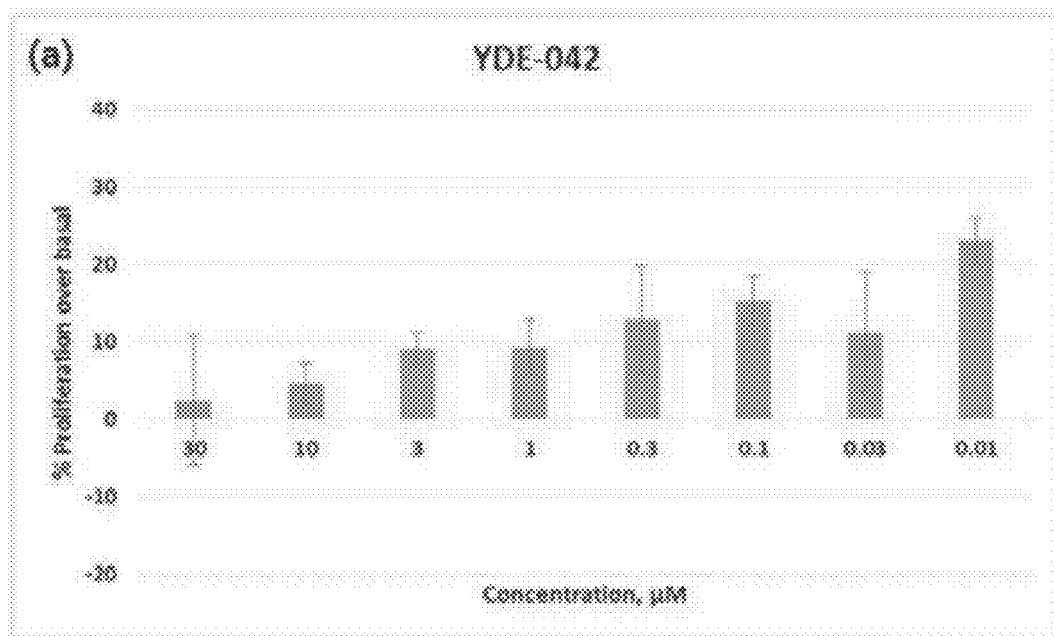
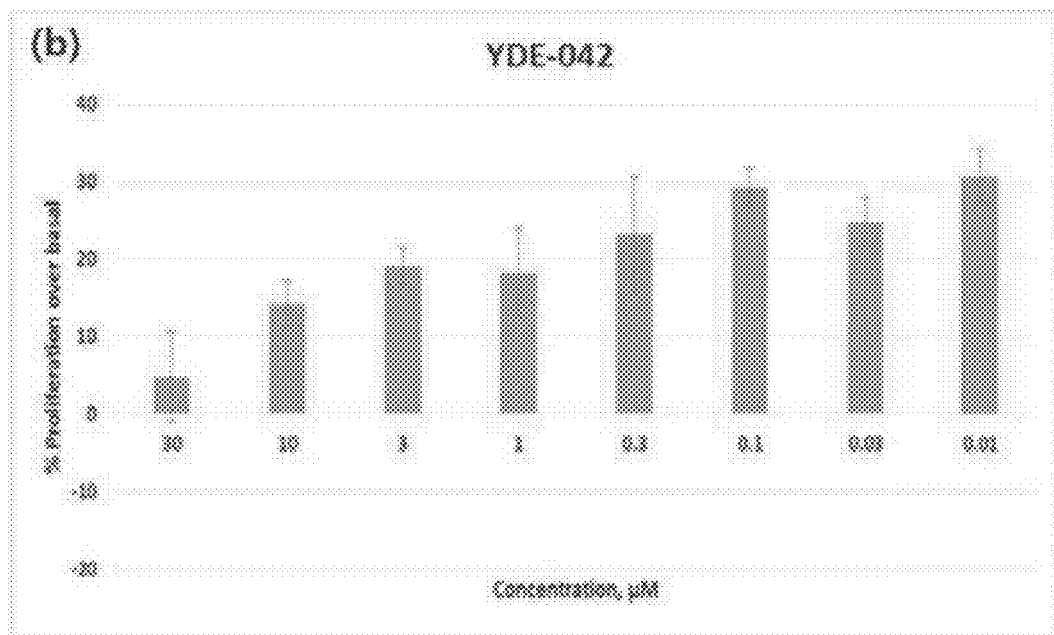

Fig. 161
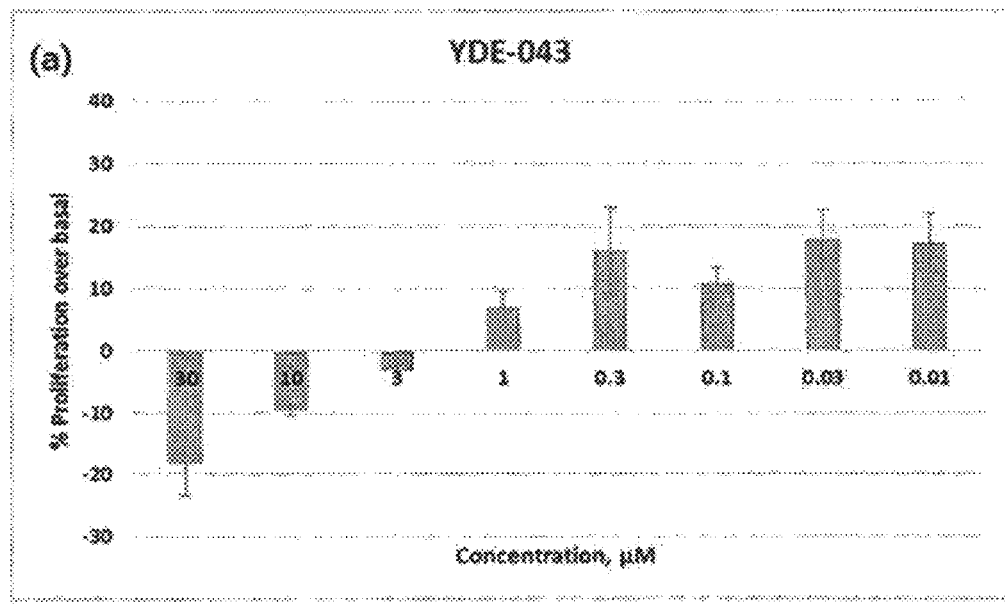
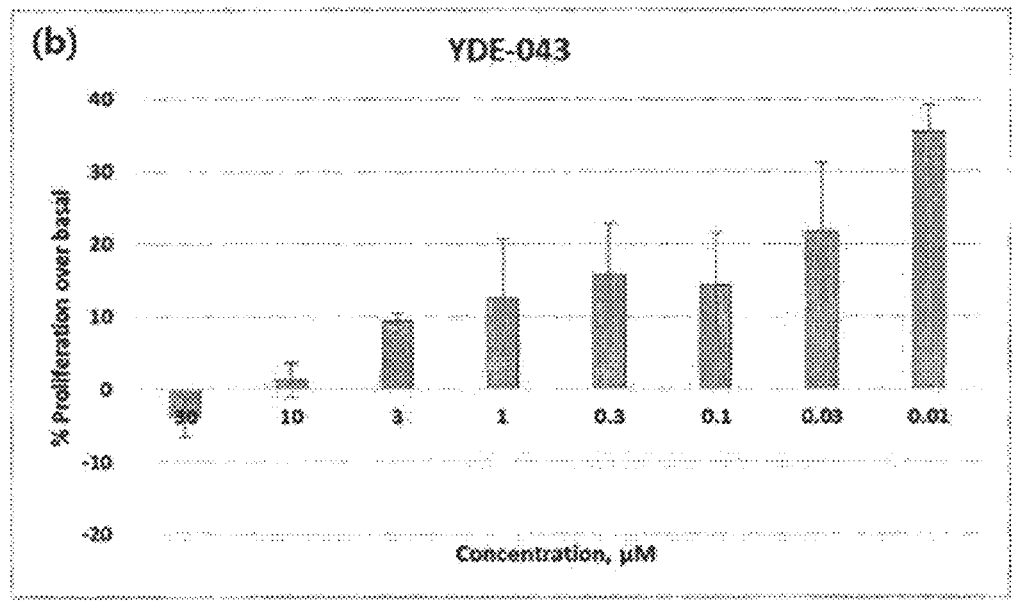

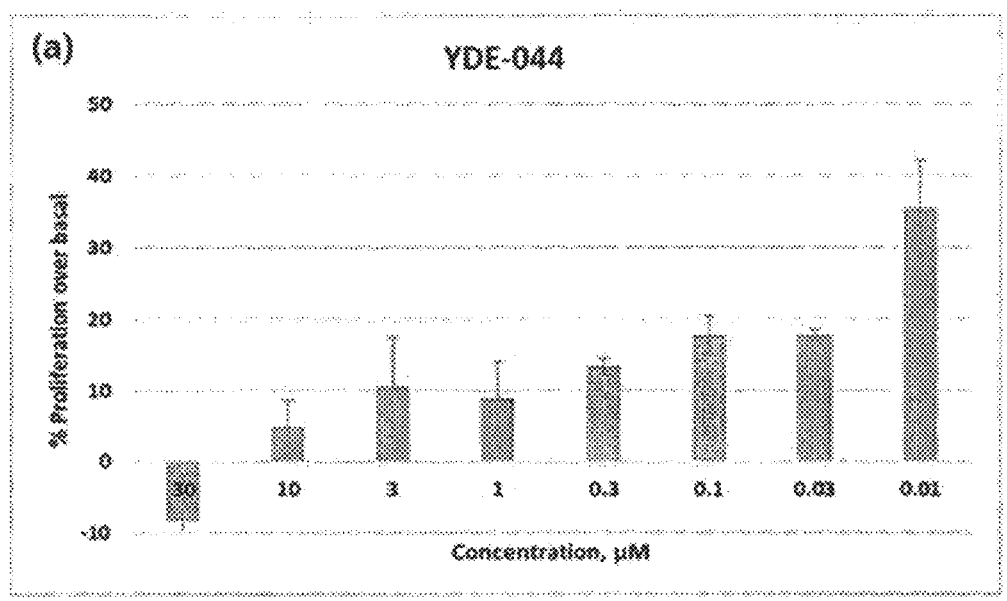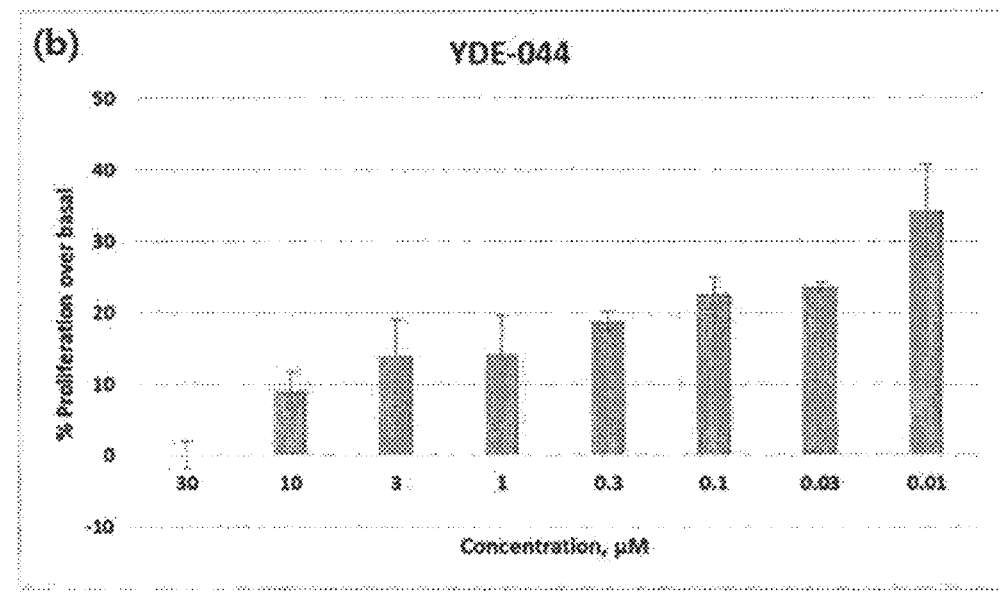
Fig. 162

Fig. 164
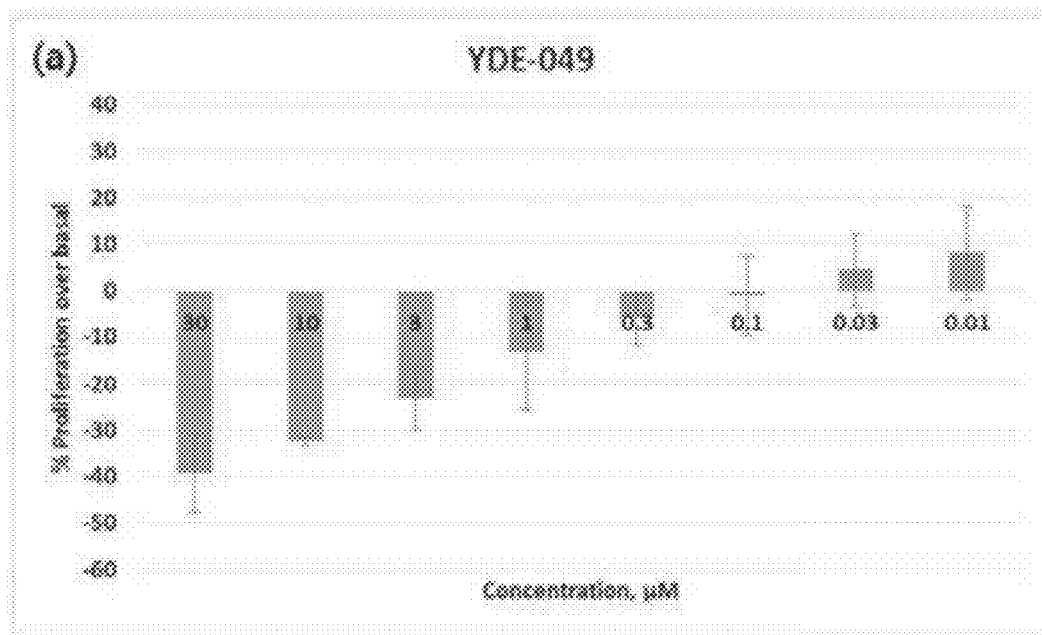
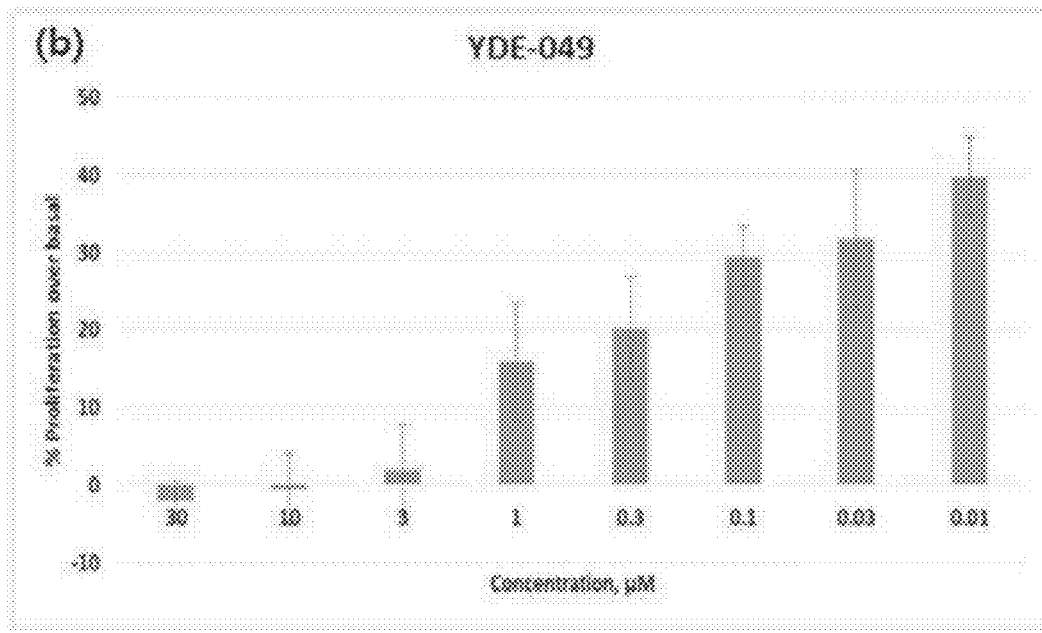

Fig. 165
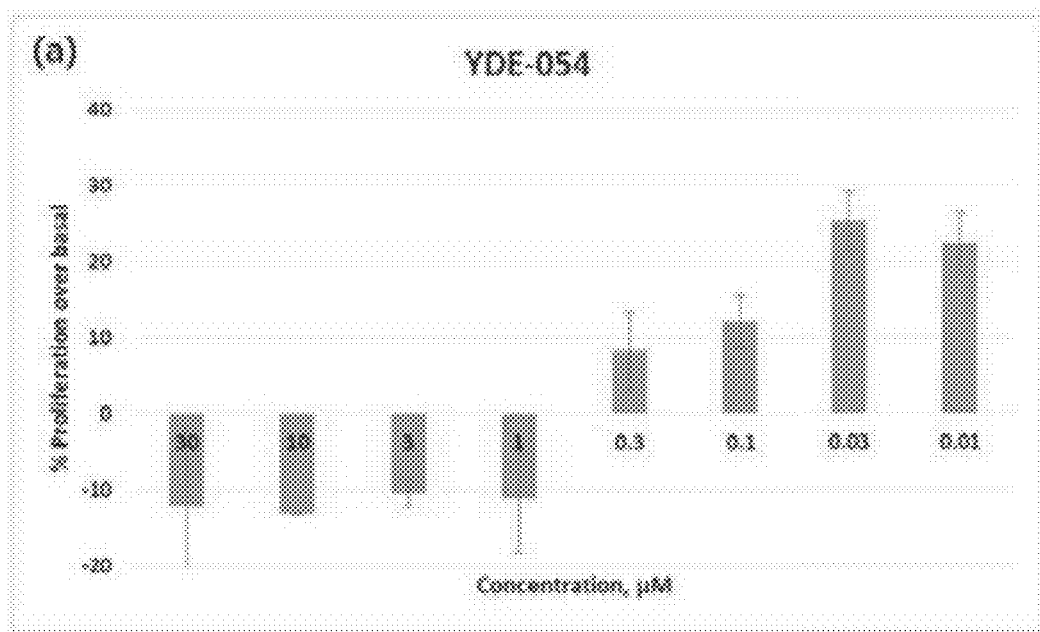
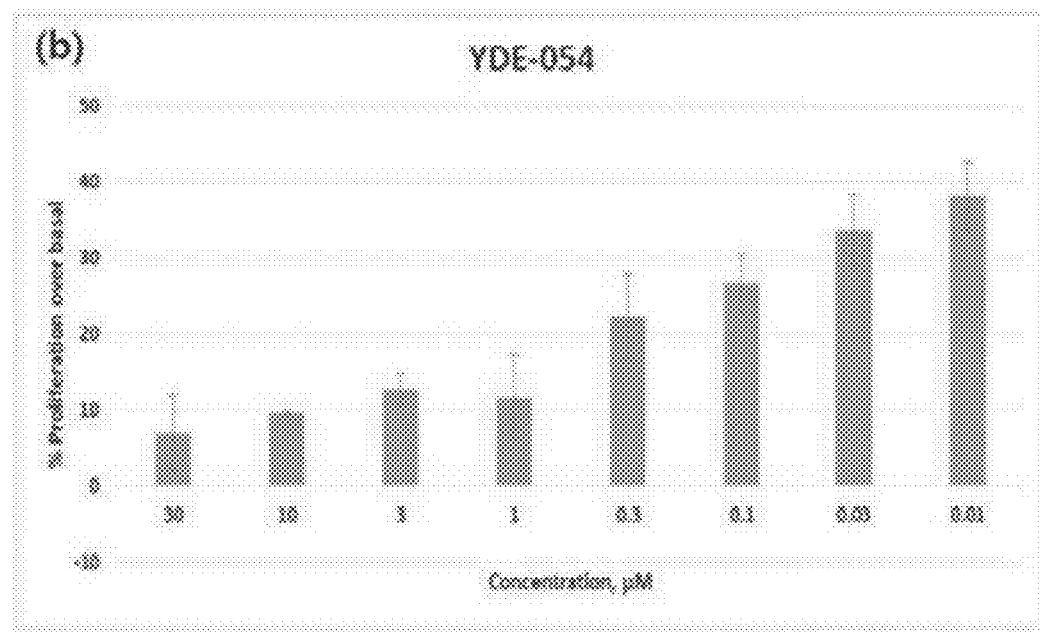

Fig. 167
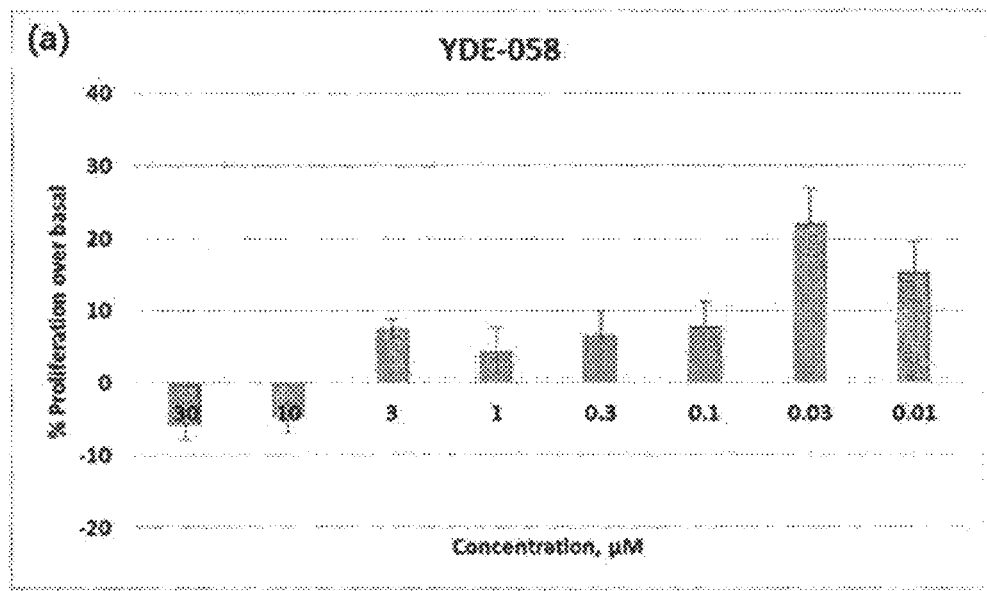
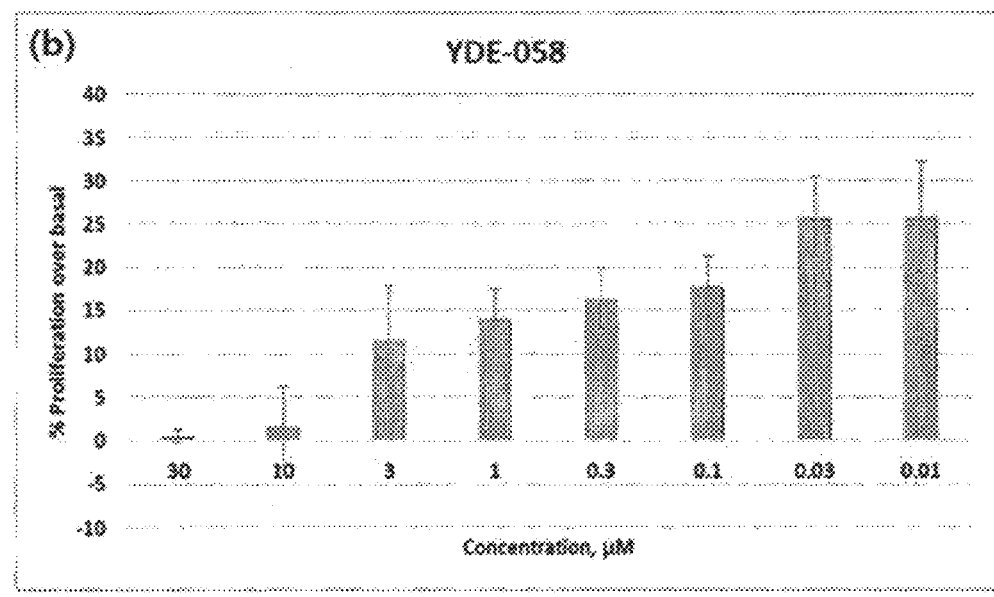

SEQUENCE LISTING

<160> NUMBER OF SEQ ID NOS: 126

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: Amino acid sequence for YDE-001
<220> FEATURE:
<221> NAME/KEY: MOD_RES

```
<222> LOCATION: (1)..(1)
<223> OTHER INFORMATION: 4Hyp

<400> SEQUENCE: 1

Pro Gly Gln Glu Gly Leu Ala Gly Pro Lys
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Amino acid sequence for YDE-002
<220> FEATURE:
<221> NAME/KEY: MOD_RES
<222> LOCATION: (1)..(1)
<223> OTHER INFORMATION: 4Hyp

<400> SEQUENCE: 2

Pro Gly Gln Asn Gly Leu Ala Gly Pro Lys
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Amino acid sequence for YDE-003
<220> FEATURE:
<221> NAME/KEY: MOD_RES
<222> LOCATION: (1)..(1)
<223> OTHER INFORMATION: 4Hyp

<400> SEQUENCE: 3

Pro Gly Gln Gln Gly Leu Ala Gly Pro Lys
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Amino acid sequence for YDE-004
<220> FEATURE:
<221> NAME/KEY: MOD_RES
<222> LOCATION: (1)..(1)
<223> OTHER INFORMATION: 4Hyp

<400> SEQUENCE: 4

Pro Gly Gln His Gly Leu Ala Gly Pro Lys
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Amino acid sequence for YDE-005
<220> FEATURE:
```

<221> NAME/KEY: MOD_RES
<222> LOCATION: (1)..(1)
<223> OTHER INFORMATION: 4Hyp

<400> SEQUENCE: 5

Pro Gly Gln Lys Gly Leu Ala Gly Pro Lys
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Amino acid sequence for YDE-006
<220> FEATURE:
<221> NAME/KEY: MOD_RES
<222> LOCATION: (1)..(1)
<223> OTHER INFORMATION: 4Hyp

<400> SEQUENCE: 6

Pro Gly Gln Ser Gly Leu Ala Gly Pro Lys
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Amino acid sequence for YDE-007
<220> FEATURE:
<221> NAME/KEY: MOD_RES
<222> LOCATION: (1)..(1)
<223> OTHER INFORMATION: 4Hyp

<400> SEQUENCE: 7

Pro Gly Gln Thr Gly Leu Ala Gly Pro Lys
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Amino acid sequence for YDE-008
<220> FEATURE:
<221> NAME/KEY: MOD_RES
<222> LOCATION: (1)..(1)
<223> OTHER INFORMATION: 4Hyp

<400> SEQUENCE: 8

Pro Gly Gln Ala Gly Leu Ala Gly Pro Lys
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Amino acid sequence for YDE-009

```
<220> FEATURE:
<221> NAME/KEY: MOD_RES
<222> LOCATION: (1)..(1)
<223> OTHER INFORMATION: 4Hyp

<400> SEQUENCE: 9

Pro Gly Gln Val Gly Leu Ala Gly Pro Lys
1               5                   10

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Amino acid sequence for YDE-010
<220> FEATURE:
<221> NAME/KEY: MOD_RES
<222> LOCATION: (1)..(1)
<223> OTHER INFORMATION: 4Hyp

<400> SEQUENCE: 10

Pro Gly Gln Ile Gly Leu Ala Gly Pro Lys
1               5                   10

<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Amino acid sequence for YDE-011
<220> FEATURE:
<221> NAME/KEY: MOD_RES
<222> LOCATION: (1)..(1)
<223> OTHER INFORMATION: 4Hyp

<400> SEQUENCE: 11

Pro Gly Gln Leu Gly Leu Ala Gly Pro Lys
1               5                   10

<210> SEQ ID NO 12
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Amino acid sequence for YDE-012
<220> FEATURE:
<221> NAME/KEY: MOD_RES
<222> LOCATION: (1)..(1)
<223> OTHER INFORMATION: 4Hyp

<400> SEQUENCE: 12

Pro Gly Gln Phe Gly Leu Ala Gly Pro Lys
1               5                   10

<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<223> OTHER INFORMATION: Amino acid sequence for YDE-013
<220> FEATURE:
<221> NAME/KEY: MOD_RES
<222> LOCATION: (1)..(1)
<223> OTHER INFORMATION: 4Hyp

<400> SEQUENCE: 13

Pro Gly Gln Tyr Gly Leu Ala Gly Pro Lys
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Amino acid sequence for YDE-014
<220> FEATURE:
<221> NAME/KEY: MOD_RES
<222> LOCATION: (1)..(1)
<223> OTHER INFORMATION: 4Hyp

<400> SEQUENCE: 14

Pro Gly Gln Trp Gly Leu Ala Gly Pro Lys
1               5                   10

<210> SEQ ID NO 15
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Amino acid sequence for YDE-026
<220> FEATURE:
<221> NAME/KEY: MOD_RES
<222> LOCATION: (1)..(1)
<223> OTHER INFORMATION: 4Hyp
<220> FEATURE:
<221> NAME/KEY: MOD_RES
<222> LOCATION: (4)..(4)
<223> OTHER INFORMATION: Homo-Ser

<400> SEQUENCE: 15

Pro Gly Gln Ser Gly Leu Ala Gly Pro Lys
1               5                   10

<210> SEQ ID NO 16
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Amino acid sequence for YDE-027
<220> FEATURE:
<221> NAME/KEY: MOD_RES
<222> LOCATION: (1)..(1)
<223> OTHER INFORMATION: 4Hyp
<220> FEATURE:
<221> NAME/KEY: MOD_RES
<222> LOCATION: (4)..(4)
<223> OTHER INFORMATION: Methylation, Asp(Me)

<400> SEQUENCE: 16

Pro Gly Gln Asp Gly Leu Ala Gly Pro Lys
1               5                   10
```

```
<210> SEQ ID NO 17
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Amino acid sequence for YDE-028
<220> FEATURE:
<221> NAME/KEY: MOD_RES
<222> LOCATION: (1)..(1)
<223> OTHER INFORMATION: 4Hyp
<220> FEATURE:
<221> NAME/KEY: MOD_RES
<222> LOCATION: (4)..(4)
<223> OTHER INFORMATION: Methylation, Asn(Me)

<400> SEQUENCE: 17

Pro Gly Gln Asn Gly Leu Ala Gly Pro Lys
1               5                   10

<210> SEQ ID NO 18
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Amino acid sequence for YDE-057
<220> FEATURE:
<221> NAME/KEY: MOD_RES
<222> LOCATION: (1)..(1)
<223> OTHER INFORMATION: D-4Hyp(2R, 4S)

<400> SEQUENCE: 18

Pro Gly Gln Leu Gly Leu Ala Gly Pro Lys
1               5                   10

<210> SEQ ID NO 19
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Amino acid sequence for YDE-058
<220> FEATURE:
<221> NAME/KEY: MOD_RES
<222> LOCATION: (1)..(1)
<223> OTHER INFORMATION: D-4Hyp(2R, 4S)
<220> FEATURE:
<221> NAME/KEY: MOD_RES
<222> LOCATION: (3)..(3)
<223> OTHER INFORMATION: D-Gln
<220> FEATURE:
<221> NAME/KEY: MOD_RES
<222> LOCATION: (4)..(4)
<223> OTHER INFORMATION: D-Leu
<220> FEATURE:
<221> NAME/KEY: MOD_RES
<222> LOCATION: (6)..(6)
<223> OTHER INFORMATION: D-Leu
<220> FEATURE:
<221> NAME/KEY: MOD_RES
<222> LOCATION: (7)..(7)
<223> OTHER INFORMATION: D-Ala
<220> FEATURE:
<221> NAME/KEY: MOD_RES
<222> LOCATION: (9)..(9)
<223> OTHER INFORMATION: D-Pro
<220> FEATURE:
```

```
<221> NAME/KEY: MOD_RES
<222> LOCATION: (10)..(10)
<223> OTHER INFORMATION: D-Lys

<400> SEQUENCE: 19

Pro Gly Gln Leu Gly Leu Ala Gly Pro Lys
1               5                   10

<210> SEQ ID NO 20
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Amino acid sequence for YDE-060
<220> FEATURE:
<221> NAME/KEY: MOD_RES
<222> LOCATION: (1)..(1)
<223> OTHER INFORMATION: D-4Hyp(2R, 4R)
<220> FEATURE:
<221> NAME/KEY: MOD_RES
<222> LOCATION: (3)..(3)
<223> OTHER INFORMATION: D-Gln
<220> FEATURE:
<221> NAME/KEY: MOD_RES
<222> LOCATION: (4)..(4)
<223> OTHER INFORMATION: D-Leu
<220> FEATURE:
<221> NAME/KEY: MOD_RES
<222> LOCATION: (6)..(6)
<223> OTHER INFORMATION: D-Leu
<220> FEATURE:
<221> NAME/KEY: MOD_RES
<222> LOCATION: (7)..(7)
<223> OTHER INFORMATION: D-Ala
<220> FEATURE:
<221> NAME/KEY: MOD_RES
<222> LOCATION: (9)..(9)
<223> OTHER INFORMATION: D-Pro
<220> FEATURE:
<221> NAME/KEY: MOD_RES
<222> LOCATION: (10)..(10)
<223> OTHER INFORMATION: D-Lys

<400> SEQUENCE: 20

Pro Gly Gln Leu Gly Leu Ala Gly Pro Lys
1               5                   10

<210> SEQ ID NO 21
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Amino acid sequence for YDE-015
<220> FEATURE:
<221> NAME/KEY: MOD_RES
<222> LOCATION: (1)..(1)
<223> OTHER INFORMATION: 4Hyp

<400> SEQUENCE: 21

Pro Gly Gln Asp Val Leu Ala Gly Pro Lys
1               5                   10

<210> SEQ ID NO 22
<211> LENGTH: 10
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<223> OTHER INFORMATION: Amino acid sequence for YDE-016
<220> FEATURE:
<221> NAME/KEY: MOD_RES
<222> LOCATION: (1)..(1)
<223> OTHER INFORMATION: 4Hyp

<400> SEQUENCE: 22

Pro Gly Gln Asp Ile Leu Ala Gly Pro Lys
1               5                   10

<210> SEQ ID NO 23
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Amino acid sequence for YDE-017
<220> FEATURE:
<221> NAME/KEY: MOD_RES
<222> LOCATION: (1)..(1)
<223> OTHER INFORMATION: 4Hyp

<400> SEQUENCE: 23

Pro Gly Gln Asp Leu Leu Ala Gly Pro Lys
1               5                   10

<210> SEQ ID NO 24
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Amino acid sequence for YDE-018
<220> FEATURE:
<221> NAME/KEY: MOD_RES
<222> LOCATION: (1)..(1)
<223> OTHER INFORMATION: 4Hyp

<400> SEQUENCE: 24

Pro Gly Gln Asp Ala Leu Ala Gly Pro Lys
1               5                   10

<210> SEQ ID NO 25
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Amino acid sequence for YDE-019
<220> FEATURE:
<221> NAME/KEY: MOD_RES
<222> LOCATION: (1)..(1)
<223> OTHER INFORMATION: 4Hyp

<400> SEQUENCE: 25

Pro Gly Gln Asp Phe Leu Ala Gly Pro Lys
1               5                   10

<210> SEQ ID NO 26
<211> LENGTH: 10
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<223> OTHER INFORMATION: Amino acid sequence for YDE-020
<220> FEATURE:
<221> NAME/KEY: MOD_RES
<222> LOCATION: (1)..(1)
<223> OTHER INFORMATION: 4Hyp

<400> SEQUENCE: 26

Pro Gly Gln Asp Tyr Leu Ala Gly Pro Lys
1               5                   10

<210> SEQ ID NO 27
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Amino acid sequence for YDE-021
<220> FEATURE:
<221> NAME/KEY: MOD_RES
<222> LOCATION: (1)..(1)
<223> OTHER INFORMATION: 4Hyp

<400> SEQUENCE: 27

Pro Gly Gln Asp Trp Leu Ala Gly Pro Lys
1               5                   10

<210> SEQ ID NO 28
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Amino acid sequence for YDE-022
<220> FEATURE:
<221> NAME/KEY: MOD_RES
<222> LOCATION: (1)..(1)
<223> OTHER INFORMATION: 4Hyp

<400> SEQUENCE: 28

Pro Gly Gln Asp His Leu Ala Gly Pro Lys
1               5                   10

<210> SEQ ID NO 29
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Amino acid sequence for YDE-023
<220> FEATURE:
<221> NAME/KEY: MOD_RES
<222> LOCATION: (1)..(1)
<223> OTHER INFORMATION: 4Hyp

<400> SEQUENCE: 29

Pro Gly Gln Asp Ser Leu Ala Gly Pro Lys
1               5                   10

<210> SEQ ID NO 30
<211> LENGTH: 10
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Amino acid sequence for YDE-024
<220> FEATURE:
<221> NAME/KEY: MOD_RES
<222> LOCATION: (1)..(1)
<223> OTHER INFORMATION: 4Hyp

<400> SEQUENCE: 30

Pro Gly Gln Asp Thr Leu Ala Gly Pro Lys
1               5                   10

<210> SEQ ID NO 31
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Amino acid sequence for YDE-025
<220> FEATURE:
<221> NAME/KEY: MOD_RES
<222> LOCATION: (1)..(1)
<223> OTHER INFORMATION: 4Hyp
<220> FEATURE:
<221> NAME/KEY: MOD_RES
<222> LOCATION: (5)..(5)
<223> OTHER INFORMATION: (N-Me)Gly

<400> SEQUENCE: 31

Pro Gly Gln Asp Gly Leu Ala Gly Pro Lys
1               5                   10

<210> SEQ ID NO 32
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Amino acid sequence for YDE-051
<220> FEATURE:
<221> NAME/KEY: MOD_RES
<222> LOCATION: (1)..(1)
<223> OTHER INFORMATION: 4Hyp

<400> SEQUENCE: 32

Pro Gly Gln Leu Ala Leu Ala Gly Pro Lys
1               5                   10

<210> SEQ ID NO 33
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Amino acid sequence for YDE-029
<220> FEATURE:
<221> NAME/KEY: MOD_RES
<222> LOCATION: (1)..(1)
<223> OTHER INFORMATION: 4Hyp

<400> SEQUENCE: 33

Pro Gly Gln Leu Gly Leu Ala Gly Pro Tyr
1               5                   10
```

```
<210> SEQ ID NO 34
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Amino acid sequence for YDE-030
<220> FEATURE:
<221> NAME/KEY: MOD_RES
<222> LOCATION: (1)..(1)
<223> OTHER INFORMATION: 4Hyp

<400> SEQUENCE: 34

Pro Gly Gln Leu Gly Leu Ala Gly Pro Leu
1               5                   10

<210> SEQ ID NO 35
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Amino acid sequence for YDE-031
<220> FEATURE:
<221> NAME/KEY: MOD_RES
<222> LOCATION: (1)..(1)
<223> OTHER INFORMATION: 4Hyp

<400> SEQUENCE: 35

Pro Gly Gln Leu Gly Leu Ala Gly Pro Glu
1               5                   10

<210> SEQ ID NO 36
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Amino acid sequence for YDE-032
<220> FEATURE:
<221> NAME/KEY: MOD_RES
<222> LOCATION: (1)..(1)
<223> OTHER INFORMATION: 4Hyp

<400> SEQUENCE: 36

Pro Gly Gln Leu Gly Leu Ala Gly Pro Gln
1               5                   10

<210> SEQ ID NO 37
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Amino acid sequence for YDE-033
<220> FEATURE:
<221> NAME/KEY: MOD_RES
<222> LOCATION: (1)..(1)
<223> OTHER INFORMATION: 4Hyp
<220> FEATURE:
<221> NAME/KEY: MOD_RES
<222> LOCATION: (10)..(10)
<223> OTHER INFORMATION: Nle(6-OH)
```

```
<400> SEQUENCE: 37

Pro Gly Gln Leu Gly Leu Ala Gly Pro Leu
1               5                   10

<210> SEQ ID NO 38
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Amino acid sequence for YDE-056
<220> FEATURE:
<221> NAME/KEY: MOD_RES
<222> LOCATION: (1)..(1)
<223> OTHER INFORMATION: 4Hyp

<400> SEQUENCE: 38

Pro Gly Gln Leu Gly Leu Ala Gly Pro Ala
1               5                   10

<210> SEQ ID NO 39
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Amino acid sequence for YDE-073
<220> FEATURE:
<221> NAME/KEY: MOD_RES
<222> LOCATION: (1)..(1)
<223> OTHER INFORMATION: D-4Hyp(2R, 4S)

<400> SEQUENCE: 39

Pro Gly Gln Leu Gly Leu Ala Gly Pro Ala
1               5                   10

<210> SEQ ID NO 40
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Amino acid sequence for YDE-035
<220> FEATURE:
<221> NAME/KEY: MOD_RES
<222> LOCATION: (1)..(1)
<223> OTHER INFORMATION: (4-oxo)Pro

<400> SEQUENCE: 40

Pro Gly Gln Leu Gly Leu Ala Gly Pro Lys
1               5                   10

<210> SEQ ID NO 41
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Amino acid sequence for YDE-036
<220> FEATURE:
<221> NAME/KEY: MOD_RES
<222> LOCATION: (1)..(1)
```

```
<223> OTHER INFORMATION: (5-oxo)Pro

<400> SEQUENCE: 41

Pro Gly Gln Leu Gly Leu Ala Gly Pro Lys
1               5                   10

<210> SEQ ID NO 42
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Amino acid sequence for YDE-037

<400> SEQUENCE: 42

Pro Gly Gln Leu Gly Leu Ala Gly Pro Lys
1               5                   10

<210> SEQ ID NO 43
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Amino acid sequence for YDE-038
<220> FEATURE:
<221> NAME/KEY: MOD_RES
<222> LOCATION: (1)..(1)
<223> OTHER INFORMATION: (4-hydroxyMe)Pro

<400> SEQUENCE: 43

Pro Gly Gln Leu Gly Leu Ala Gly Pro Lys
1               5                   10

<210> SEQ ID NO 44
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Amino acid sequence for YDE-039
<220> FEATURE:
<221> NAME/KEY: MOD_RES
<222> LOCATION: (1)..(1)
<223> OTHER INFORMATION: (4-Fluoro)Pro

<400> SEQUENCE: 44

Pro Gly Gln Leu Gly Leu Ala Gly Pro Lys
1               5                   10

<210> SEQ ID NO 45
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Amino acid sequence for YDE-040
<220> FEATURE:
<221> NAME/KEY: MOD_RES
<222> LOCATION: (1)..(1)
<223> OTHER INFORMATION: (4-Dimethyl)Pro

<400> SEQUENCE: 45
```

-continued

Pro Gly Gln Leu Gly Leu Ala Gly Pro Lys
1               5                   10

<210> SEQ ID NO 46
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Amino acid sequence for YDE-044
<220> FEATURE:
<221> NAME/KEY: MOD_RES
<222> LOCATION: (1)..(1)
<223> OTHER INFORMATION: (4-Me)Pro

<400> SEQUENCE: 46

Pro Gly Gln Leu Gly Leu Ala Gly Pro Lys
1               5                   10

<210> SEQ ID NO 47
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Amino acid sequence for YDE-045
<220> FEATURE:
<221> NAME/KEY: MOD_RES
<222> LOCATION: (1)..(1)
<223> OTHER INFORMATION: (5-Me)Pro

<400> SEQUENCE: 47

Pro Gly Gln Leu Gly Leu Ala Gly Pro Lys
1               5                   10

<210> SEQ ID NO 48
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Amino acid sequence for YDE-049
<220> FEATURE:
<221> NAME/KEY: MOD_RES
<222> LOCATION: (1)..(1)
<223> OTHER INFORMATION: 4Hyp

<400> SEQUENCE: 48

Pro Gly Ala Leu Gly Leu Ala Gly Pro Lys
1               5                   10

<210> SEQ ID NO 49
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Amino acid sequence for YDE-052
<220> FEATURE:
<221> NAME/KEY: MOD_RES
<222> LOCATION: (1)..(1)
<223> OTHER INFORMATION: 4Hyp

```
<400> SEQUENCE: 49

Pro Gly Gln Leu Gly Ala Ala Gly Pro Lys
1               5                   10

<210> SEQ ID NO 50
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Amino acid sequence for YDE-054
<220> FEATURE:
<221> NAME/KEY: MOD_RES
<222> LOCATION: (1)..(1)
<223> OTHER INFORMATION: 4Hyp

<400> SEQUENCE: 50

Pro Gly Gln Leu Gly Leu Ala Ala Pro Lys
1               5                   10

<210> SEQ ID NO 51
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Amino acid sequence for YDE-048
<220> FEATURE:
<221> NAME/KEY: MOD_RES
<222> LOCATION: (1)..(1)
<223> OTHER INFORMATION: 4Hyp

<400> SEQUENCE: 51

Pro Ala Gln Leu Gly Leu Ala Gly Pro Lys
1               5                   10

<210> SEQ ID NO 52
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Amino acid sequence for YDE-074
<220> FEATURE:
<221> NAME/KEY: MOD_RES
<222> LOCATION: (1)..(1)
<223> OTHER INFORMATION: D-4Hyp(2R, 4S)

<400> SEQUENCE: 52

Pro Ala Gln Leu Gly Leu Ala Gly Pro Ala
1               5                   10

<210> SEQ ID NO 53
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Amino acid sequence for YDE-072
<220> FEATURE:
<221> NAME/KEY: MOD_RES
<222> LOCATION: (1)..(1)
<223> OTHER INFORMATION: D-4Hyp(2R, 4S)
```

```
<400> SEQUENCE: 53

Pro Ala Gln Leu Gly Leu Ala Gly Pro Lys
1               5                   10

<210> SEQ ID NO 54
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Amino acid sequence for YDE-047

<400> SEQUENCE: 54

Ala Gly Gln Leu Gly Leu Ala Gly Pro Lys
1               5                   10

<210> SEQ ID NO 55
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Amino acid sequence for YDE-055
<220> FEATURE:
<221> NAME/KEY: MOD_RES
<222> LOCATION: (1)..(1)
<223> OTHER INFORMATION: 4Hyp

<400> SEQUENCE: 55

Pro Gly Gln Leu Gly Leu Ala Gly Ala Lys
1               5                   10

<210> SEQ ID NO 56
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Amino acid sequence for YDE-041
<220> FEATURE:
<221> NAME/KEY: MOD_RES
<222> LOCATION: (1)..(1)
<223> OTHER INFORMATION: 4Hyp

<400> SEQUENCE: 56

Pro Gly Gln Leu Gly Leu Ala
1               5

<210> SEQ ID NO 57
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Amino acid sequence for YDE-059
<220> FEATURE:
<221> NAME/KEY: MOD_RES
<222> LOCATION: (1)..(1)
<223> OTHER INFORMATION: 4Hyp

<400> SEQUENCE: 57
```

Pro Gly Gln Glu Gly Lys Gly
1               5

<210> SEQ ID NO 58
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Amino acid sequence for YDE-042
<220> FEATURE:
<221> NAME/KEY: MOD_RES
<222> LOCATION: (1)..(1)
<223> OTHER INFORMATION: 4Hyp

<400> SEQUENCE: 58

Pro Gly Gln Leu Gly Leu
1               5

<210> SEQ ID NO 59
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Amino acid sequence for YDE-064
<220> FEATURE:
<221> NAME/KEY: MOD_RES
<222> LOCATION: (1)..(1)
<223> OTHER INFORMATION: D-4Hyp(2R, 4S)
<220> FEATURE:
<221> NAME/KEY: MOD_RES
<222> LOCATION: (3)..(3)
<223> OTHER INFORMATION: D-Gln
<220> FEATURE:
<221> NAME/KEY: MOD_RES
<222> LOCATION: (4)..(4)
<223> OTHER INFORMATION: D-Leu
<220> FEATURE:
<221> NAME/KEY: MOD_RES
<222> LOCATION: (6)..(6)
<223> OTHER INFORMATION: D-Leu

<400> SEQUENCE: 59

Pro Gly Gln Leu Gly Leu
1               5

<210> SEQ ID NO 60
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Amino acid sequence for YDE-043
<221> NAME/KEY: MOD_RES
<222> LOCATION: (1)..(1)
<223> OTHER INFORMATION: 4Hyp

<400> SEQUENCE: 60

Pro Gly Gln Leu Gly
1               5

<210> SEQ ID NO 61
<211> LENGTH: 5
<212> TYPE: PRT

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Amino acid sequence for YDE-066
<220> FEATURE:
<221> NAME/KEY: MOD_RES
<222> LOCATION: (1)..(1)
<223> OTHER INFORMATION: 4Hyp
<220> FEATURE:
<221> NAME/KEY: MOD_RES
<222> LOCATION: (4)..(4)
<223> OTHER INFORMATION: D-Leu

<400> SEQUENCE: 61

Pro Gly Gln Leu Gly
1               5

<210> SEQ ID NO 62
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Amino acid sequence for YDE-075
<220> FEATURE:
<221> NAME/KEY: MOD_RES
<222> LOCATION: (1)..(1)
<223> OTHER INFORMATION: D-4Hyp(2R, 4S)

<400> SEQUENCE: 62

Pro Gly Gln Leu Gly
1               5

<210> SEQ ID NO 63
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Amino acid sequence for YDE-034
<220> FEATURE:
<221> NAME/KEY: MOD_RES
<222> LOCATION: (1)..(1)
<223> OTHER INFORMATION: 4Hyp(2S, 4S)

<400> SEQUENCE: 63

Pro Gly Gln Leu Gly Leu Ala Gly Pro Lys
1               5                   10

<210> SEQ ID NO 64

<400> SEQUENCE: 64

000

<210> SEQ ID NO 65

<400> SEQUENCE: 65

000

<210> SEQ ID NO 66

<400> SEQUENCE: 66
```

000

<210> SEQ ID NO 67

<400> SEQUENCE: 67

000

<210> SEQ ID NO 68

<400> SEQUENCE: 68

000

<210> SEQ ID NO 69

<400> SEQUENCE: 69

000

<210> SEQ ID NO 70

<400> SEQUENCE: 70

000

<210> SEQ ID NO 71

<400> SEQUENCE: 71

000

<210> SEQ ID NO 72

<400> SEQUENCE: 72

000

<210> SEQ ID NO 73

<400> SEQUENCE: 73

000

<210> SEQ ID NO 74

<400> SEQUENCE: 74

000

<210> SEQ ID NO 75

<400> SEQUENCE: 75

000

<210> SEQ ID NO 76

<400> SEQUENCE: 76

000

<210> SEQ ID NO 77

<400> SEQUENCE: 77

000

<210> SEQ ID NO 78

<400> SEQUENCE: 78

000

<210> SEQ ID NO 79

<400> SEQUENCE: 79

000

<210> SEQ ID NO 80

<400> SEQUENCE: 80

000

<210> SEQ ID NO 81

<400> SEQUENCE: 81

000

<210> SEQ ID NO 82

<400> SEQUENCE: 82

000

<210> SEQ ID NO 83

<400> SEQUENCE: 83

000

<210> SEQ ID NO 84

<400> SEQUENCE: 84

000

<210> SEQ ID NO 85

<400> SEQUENCE: 85

000

<210> SEQ ID NO 86

<400> SEQUENCE: 86

000

<210> SEQ ID NO 87

<400> SEQUENCE: 87

000

<210> SEQ ID NO 88

<400> SEQUENCE: 88

000

<210> SEQ ID NO 89

```
<400> SEQUENCE: 89

000

<210> SEQ ID NO 90

<400> SEQUENCE: 90

000

<210> SEQ ID NO 91

<400> SEQUENCE: 91

000

<210> SEQ ID NO 92

<400> SEQUENCE: 92

000

<210> SEQ ID NO 93

<400> SEQUENCE: 93

000

<210> SEQ ID NO 94

<400> SEQUENCE: 94

000

<210> SEQ ID NO 95

<400> SEQUENCE: 95

000

<210> SEQ ID NO 96

<400> SEQUENCE: 96

000

<210> SEQ ID NO 97

<400> SEQUENCE: 97

000

<210> SEQ ID NO 98

<400> SEQUENCE: 98

000

<210> SEQ ID NO 99

<400> SEQUENCE: 99

000

<210> SEQ ID NO 100
<211> LENGTH: 10
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4Hyp(2S, 4R)
<220> FEATURE:
<221> NAME/KEY: MOD_RES
<222> LOCATION: (4)..(4)
<223> OTHER INFORMATION: Aspartimide

<400> SEQUENCE: 100

Pro Gly Gln Asp Gly Leu Ala Gly Pro Lys
1               5                   10

<210> SEQ ID NO 101
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4Hyp
<220> FEATURE:
<221> NAME/KEY: MOD_RES
<222> LOCATION: (4)..(4)
<223> OTHER INFORMATION: Aspartimide

<400> SEQUENCE: 101

Pro Gly Gln Asp Gly Leu Ala Gly Pro Lys
1               5                   10

<210> SEQ ID NO 102
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4Hyp(2S, 4R)
<220> FEATURE:
<221> NAME/KEY: MOD_RES
<222> LOCATION: (5)..(5)
<223> OTHER INFORMATION: (N-Me)Gly

<400> SEQUENCE: 102

Pro Gly Gln Asp Gly Leu Ala Gly Pro Lys
1               5                   10

<210> SEQ ID NO 103

<400> SEQUENCE: 103

000

<210> SEQ ID NO 104
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104
```

```
Pro Gly Gln Asp Gly Leu Ala Gly Pro Lys
1               5                   10

<210> SEQ ID NO 105
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Amino acid sequence for YY-101
<220> FEATURE:
<221> NAME/KEY: MOD_RES
<222> LOCATION: (1)..(1)
<223> OTHER INFORMATION: 4Hyp(2S, 4R)

<400> SEQUENCE: 105

Pro Gly Gln Asp Gly Leu Ala Gly Pro Lys
1               5                   10

<210> SEQ ID NO 106
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Amino acid sequence for YY-102
<220> FEATURE:
<221> NAME/KEY: MOD_RES
<222> LOCATION: (1)..(1)
<223> OTHER INFORMATION: 4Hyp(2S, 4R)
<220> FEATURE:
<221> NAME/KEY: MOD_RES
<222> LOCATION: (4)..(4)
<223> OTHER INFORMATION: Aspartimide

<400> SEQUENCE: 106

Pro Gly Gln Asp Gly Leu Ala Gly Pro Lys
1               5                   10

<210> SEQ ID NO 107
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Amino acid sequence for YDE-050
<220> FEATURE:
<221> NAME/KEY: MOD_RES
<222> LOCATION: (1)..(1)
<223> OTHER INFORMATION: 4Hyp

<400> SEQUENCE: 107

Pro Gly Gln Ala Gly Leu Ala Gly Pro Lys
1               5                   10

<210> SEQ ID NO 108
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Amino acid sequence for YDE-053
<220> FEATURE:
```

```
<221> NAME/KEY: MOD_RES
<222> LOCATION: (1)..(1)
<223> OTHER INFORMATION: 4Hyp

<400> SEQUENCE: 108

Pro Gly Gln Leu Gly Leu Ala Gly Pro Lys
1               5                   10

<210> SEQ ID NO 109

<400> SEQUENCE: 109

000

<210> SEQ ID NO 110

<400> SEQUENCE: 110

000

<210> SEQ ID NO 111

<400> SEQUENCE: 111

000

<210> SEQ ID NO 112

<400> SEQUENCE: 112

000

<210> SEQ ID NO 113

<400> SEQUENCE: 113

000

<210> SEQ ID NO 114

<400> SEQUENCE: 114

000

<210> SEQ ID NO 115

<400> SEQUENCE: 115

000

<210> SEQ ID NO 116

<400> SEQUENCE: 116

000

<210> SEQ ID NO 117

<400> SEQUENCE: 117

000

<210> SEQ ID NO 118

<400> SEQUENCE: 118

000
```

<210> SEQ ID NO 119

<400> SEQUENCE: 119

000

<210> SEQ ID NO 120
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4Hyp
<220> FEATURE:
<221> NAME/KEY: MOD_RES
<222> LOCATION: (4)..(4)
<223> OTHER INFORMATION: Glu, Asn, Gln, His, Lys, Ser, Thr, Ala, Val,
      Ile, Leu, Phe, Tyr, Trp, homo-Ser, Asp(Me), or Asn(Me)

<400> SEQUENCE: 120

Pro Gly Gln Xaa Gly Leu Ala Gly Pro Lys
1               5                   10

<210> SEQ ID NO 121
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4Hyp
<220> FEATURE:
<221> NAME/KEY: MOD_RES
<222> LOCATION: (5)..(5)
<223> OTHER INFORMATION: Val, Ile, Leu, Ala, Phe, Tyr, Trp, Ser, Thr, or
      (N-Me)Gly

<400> SEQUENCE: 121

Pro Gly Gln Asp Xaa Leu Ala Gly Pro Lys
1               5                   10

<210> SEQ ID NO 122
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4Hyp
<220> FEATURE:
<221> NAME/KEY: MOD_RES
<222> LOCATION: (10)..(10)
<223> OTHER INFORMATION: Tyr, Leu, Glu, Gln, Ala, or Nle(6-OH)

<400> SEQUENCE: 122

Pro Gly Gln Leu Gly Leu Ala Gly Pro Xaa
1               5                   10

<210> SEQ ID NO 123
<211> LENGTH: 10
<212> TYPE: PRT

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (2S,4S)-4-hydroxypyrrolidine-2-carboxylic acid,
      (S)-4-oxopryrrolidine-2-carboxylic acid,
      (S)-5-oxopryrrolidine-2-carboxylic acid, L-proline,
      (2S,4R)-4-(hydroxymethyl)pyrrolidine-2-carboxylic acid,
<220> FEATURE:
<221> NAME/KEY: MOD_RES
<222> LOCATION: (1)..(1)
<223> OTHER INFORMATION: CONT. FROM ABOVE: (2S,4R)-4-fluoropyrrolidine-
      2-carboxylic acid, (2S,4R)-4-methylpyrrolidine-2-carboxylic acid,
      (2S,5R)-5-methylpyrrolidine-2-carboxylic acid
      or (S)-4,4-dimethylpyrrolidine-2-carboxylic acid

<400> SEQUENCE: 123

Xaa Gly Gln Leu Gly Leu Ala Gly Pro Lys
1               5                   10

<210> SEQ ID NO 124
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4Hyp

<400> SEQUENCE: 124

Pro Gly Gln Asp Gly Leu Ala Gly Pro Lys
1               5                   10

<210> SEQ ID NO 125
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4Hyp

<400> SEQUENCE: 125

Pro Gly Gln Glu Gly Lys Gly
1               5

<210> SEQ ID NO 126
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-4Hyp(2R, 4S)

<400> SEQUENCE: 126

Pro Gly Gln Leu Gly
1               5
```

PEPTIDE AND PHARMACEUTICAL COMPOSITION FOR TREATING AN EYE DISEASE COMPRISING THE SAME AS AN ACTIVE PHARMACEUTICAL INGREDIENT

CROSS-REFERENCE TO RELATED APPLICATIONS

This application is a U.S. National Stage Application of International Application No. PCT/KR18/05673, filed May 17, 2018 which claims the benefit of foreign priority to Republic of Korea Patent Application No. 10-2017-0061250, filed May 17, 2017. International Application No. PCT/KR18/05673 is hereby incorporated by reference in its entirety.

SEQUENCE LISTING

The instant application contains a Sequence Listing which has been submitted electronically in ASCII format and is hereby incorporated by reference in its entirety. Said ASCII copy, created on Jul. 19, 2023, is named YUH-00101_SL.txt and is 29,661 bytes in size.

TECHNICAL FIELD

The present invention relates to novel peptides and pharmaceutical compositions for treating eye diseases that comprises the same as an active pharmaceutical ingredient.

BACKGROUND ART

Dry eye syndrome or keratoconjunctivitis sicca may be defined, in a broad sense, as damage to the ocular surface due to tear secretion disorders (Joossen C et al., *Exp. Eye Res.*, 146:172-8, 2016). Dry eye syndrome is known to cause tear secretion disorders and damage and discomfort to the eyeball due to a combination of various factors. Although the onset of dry eye syndrome is closely related to age, the incidence thereof is increasing in younger age groups due to a long-term exposure to a dry environment as the use of contact lenses, computers, and smart devices (Stern M E et al., *Int. Rev. Immunol.*, 32: 19-41, 2013).

Specifically, dry eye syndrome reduces the mucus secretion of the corneal and conjunctival epithelia and that of the mucus-secreting goblet cells, resulting in a sharp decrease in the lubrication of the eyeball. In addition, dry eye syndrome causes damage to the corneal surface, thereby increasing the penetration of a fluorescein dye into the cornea. These symptoms of dry eye syndrome can be evaluated as changes in the tear secretion through the Schirmer test, which uses cobalt chloride paper. Further, the damage to the cornea that may accompany dry eye syndrome can be easily evaluated using a general fluorescent dye and a slit-lamp fluorophotometer.

In the meantime, most of the treatments for dry eye syndrome are confined to symptom therapies, the treatment efficiency of which is often very low. Currently, artificial tears are the first choice for the treatment of dry eye syndrome. Since artificial tears as a representative symptom therapy merely supplement the insufficient tears; moreover, they suffer from the disadvantage that they need to be administered to the eyes frequently (Kim C S et al., *Nutrients* 8. pii: E750, 2016). Sodium hyaluronate and eye drops derived from autologous serum have been developed and used in patients suffering from dry eye syndrome. In addition, such synthetic compounds as rebamipide (OPC-127959) and diquafosol sodium, which promote the secretion of tears and mucus, have been developed and used. Long-term use of these drugs, however, may give rise to various side effects such as ocular hyperemia and corneal calcification (Bernauer W et al., *Br J. Ophthalmol.*, 90:285-8, 2006). Therefore, there has been a demand for the development of a safe and effective therapeutic agent for treating dry eye syndrome.

DISCLOSURE OF THE INVENTION

Problem to be Solved by the Invention

Therefore, the present inventors have endeavored to develop safe and effective therapeutic agents for treating an eye disease and, as a result, completed the present invention by way of synthesizing new peptides, administering them to the eyes of rats with dry eye syndrome, and confirming the eye protection effect through the Schirmer test and the fluorescent dye deposition test.

Means for Solving the Problem

In order to achieve the object of the present invention, one aspect of the present invention provides a compound represented by Formula 1.

Further, another aspect of the present invention provides a peptide having an amino acid sequence represented by HyP-Gly-Gln-Xaa-Gly-Leu-Ala-Gly-Pro-Lys (SEQ ID NO 120). Here, Xaa may be one selected from the group consisting of Glu, Asn, Gln, His, Lys, Ser, Thr, Ala, Val, Ile, Leu, Phe, Tyr, Trp, homo-Ser, Asp(Me), and Asn(Me).

In addition, still another aspect of the present invention provides a peptide having an amino acid sequence represented by HyP-Gly-Gln-Asp-Xaa-Leu-Ala-Gly-Pro-Lys (SEQ ID NO 121). Here, Xaa may be one selected from the group consisting of Val, Ile, Leu, Ala, Phe, Tyr, Trp, Ser, Thr, and (N-Me)Gly.

Further, still another aspect of the present invention provides a peptide having an amino acid sequence represented by HyP-Gly-Gln-Leu-Gly-Leu-Ala-Gly-Pro-Xaa (SEQ ID NO 122). Here, Xaa may be one selected from the group consisting of Tyr, Leu, Glu, Gln, Ala, and Nle(6-OH).

In addition, still another aspect of the present invention provides a peptide having an amino acid sequence represented by PD-Gly-Gln-Leu-Gly-Leu-Ala-Gly-Pro-Lys (SEQ ID NO 123). Here, PD may be any one selected from the group consisting of the following formulae.

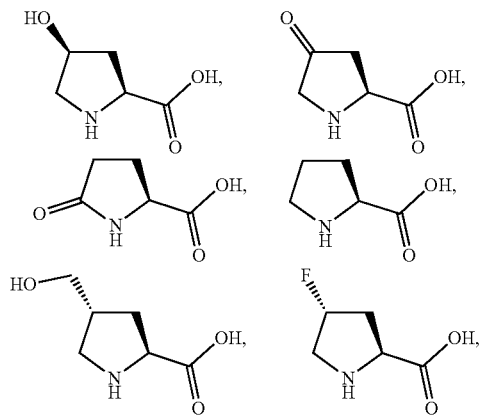

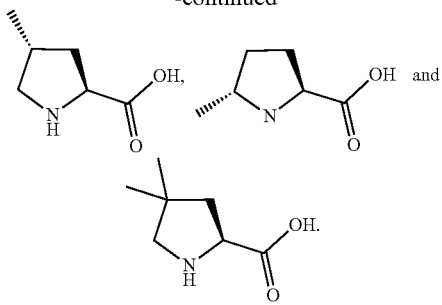

Further, still another aspect of the present invention provides a peptide having any one amino acid sequence selected from the group consisting of Ala-Gly-Gln-Leu-Gly-Leu-Ala-Gly-Pro-Lys (SEQ ID NO: 54), Hyp-Gly-Gln-Leu-Gly-Leu-Ala-Gly-Ala-Lys (SEQ ID NO: 55), HyP-Gly-Gln-Leu-Gly-Leu-Ala (SEQ ID NO: 56), HyP-Gly-Gln-Glu-Gly-Leu-Gly (SEQ ID NO: 57), HyP-Gly-Gln-Leu-Gly-Leu (SEQ ID NO: 58), D-HyP(2R, 4S)-Gly-D-Gln-D-Leu-Gly-D-Leu (SEQ ID NO: 59), HyP-Gly-Gln-Leu-Gly (SEQ ID NO: 60), HyP-Gly-Gln-D-Leu-Gly (SEQ ID NO: 61), and D-HyP(2R, 4S)-Gly-Gln-Leu-Gly (SEQ ID NO: 62).

In addition, still another aspect of the present invention provides a compound represented by Formula 8:

[Formula 8]

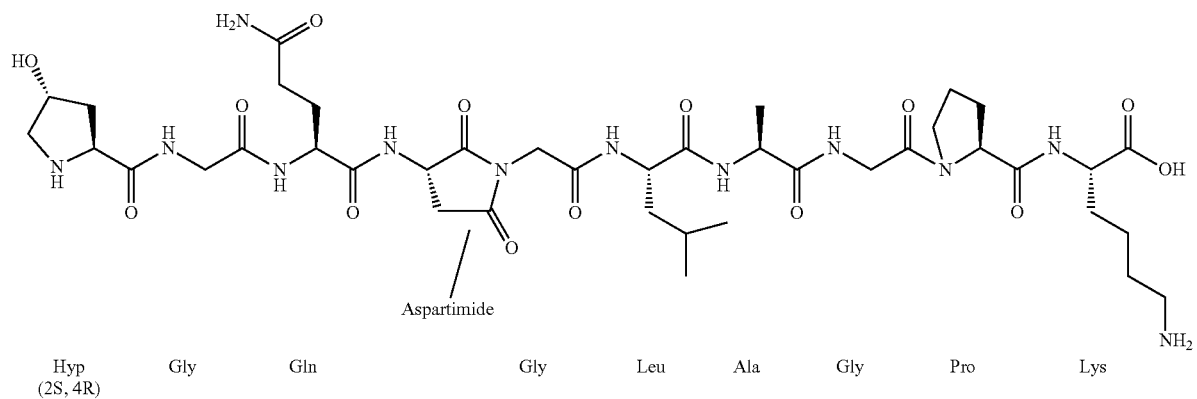

(SEQ ID NO: 100).

Further, still another aspect of the present invention provides a compound represented by Formula 10:

[Formula 10]

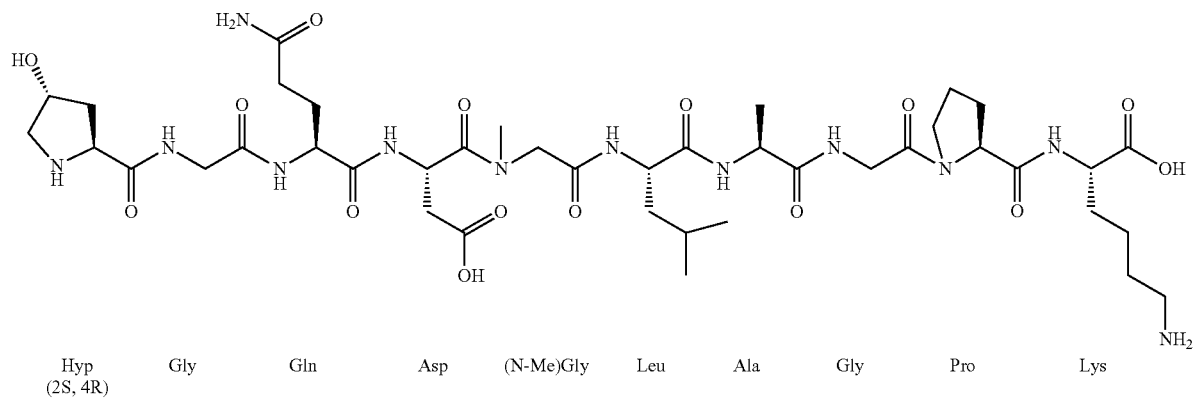

(SEQ ID NO: 102).

In addition, still another aspect of the present invention provides a pharmaceutical composition for treating an eye disease, which comprises the compound or the peptide as an active pharmaceutical ingredient.

Further, still another aspect of the present invention provides a method for treating an eye disease, which comprises administering the compound or the peptide to a subject.

Effects of the Invention

When a novel peptide of the present invention is administered to the eye, it increases the amount of tear secretion and recovers promotes recovery of the damaged cornea. Hence, they can be advantageously used as therapeutic agents for treating eye diseases.

BRIEF DESCRIPTION OF THE DRAWINGS

FIG. 1 is a diagram showing the sequence and characteristics of the peptides prepared according to an embodiment of the present invention.

FIG. 120 is a diagram confirming the molecular weight of YDE-053 prepared according to an embodiment of the present invention through Ion-Mass.

FIG. 121 is a diagram confirming the molecular weight of YDE-054 prepared according to an embodiment of the present invention through Ion-Mass.

FIG. 122 is a diagram confirming the molecular weight of YDE-055 prepared according to an embodiment of the present invention through Ion-Mass.

FIG. 123 is a diagram confirming the molecular weight of YDE-056 prepared according to an embodiment of the present invention through Ion-Mass.

FIG. 124 is a diagram confirming the molecular weight of YDE-057 prepared according to an embodiment of the present invention through Ion-Mass.

FIG. 125 is a diagram confirming the molecular weight of YDE-058 prepared according to an embodiment of the present invention through Ion-Mass.

FIG. 126 is a diagram confirming the molecular weight of YDE-059 prepared according to an embodiment of the present invention through Ion-Mass.

FIG. 127 is a diagram confirming the molecular weight of YDE-060 prepared according to an embodiment of the present invention through Ion-Mass.

FIG. 128 is a diagram confirming the molecular weight of YDE-064 prepared according to an embodiment of the present invention through Ion-Mass.

FIG. 129 is a diagram confirming the molecular weight of YDE-066 prepared according to an embodiment of the present invention through Ion-Mass.

FIG. 130 is a diagram confirming the molecular weight of YDE-072 prepared according to an embodiment of the present invention through Ion-Mass.

FIG. 131 is a diagram confirming the molecular weight of YDE-073 prepared according to an embodiment of the present invention through Ion-Mass.

Figure 132:
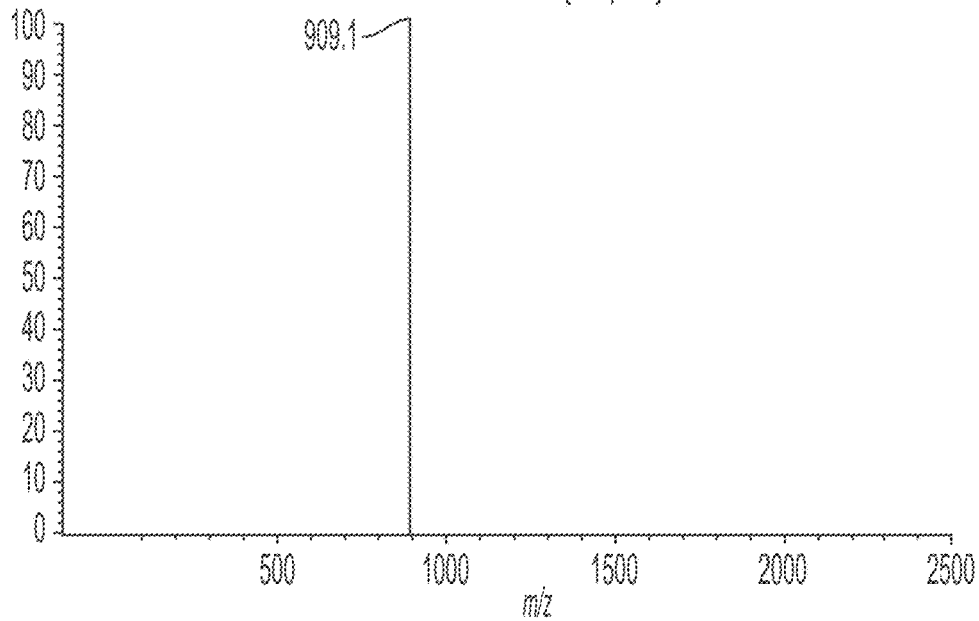

FIG. 132 is a diagram confirming the molecular weight of YDE-074 prepared according to an embodiment of the present invention through Ion-Mass.

Figure 133:
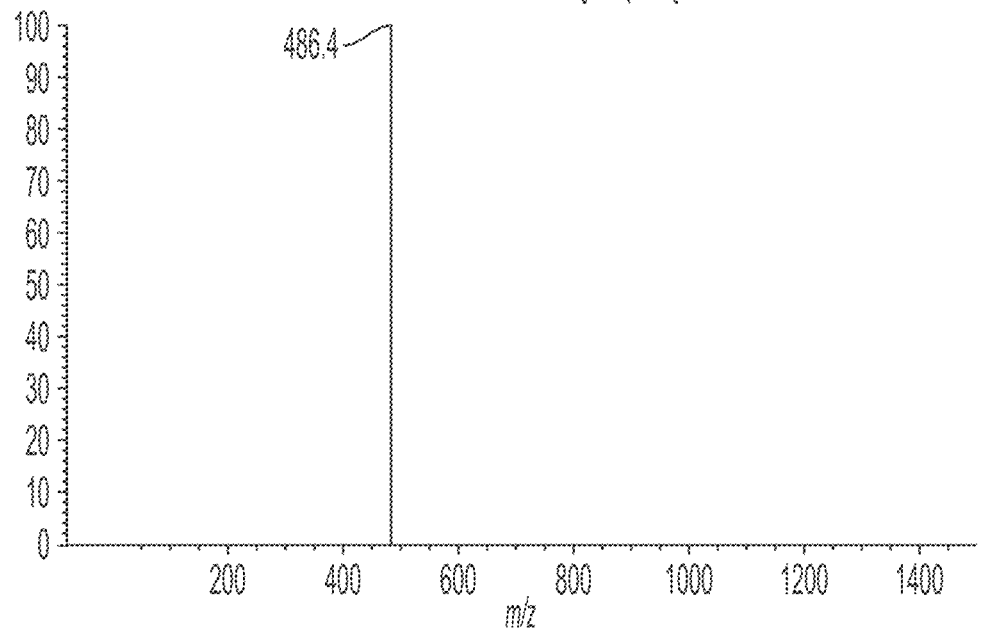

FIG. 133 is a diagram confirming the molecular weight of YDE-075 prepared according to an embodiment of the present invention through Ion-Mass.

Figure 134:
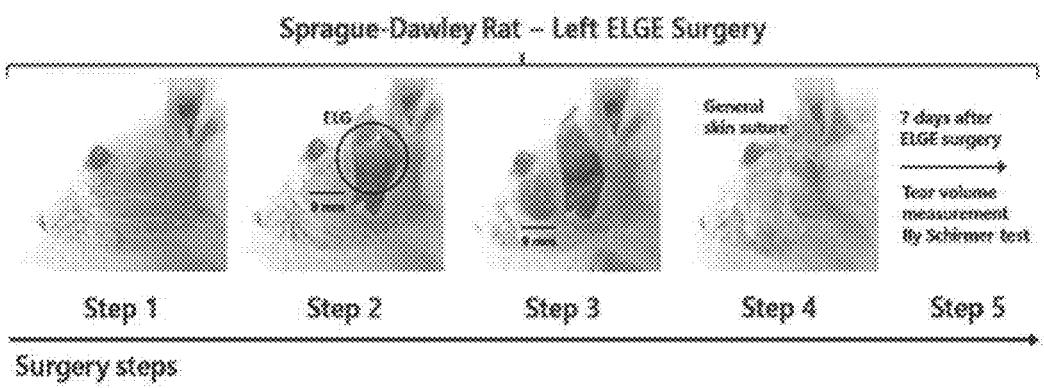

FIG. 134 is a photograph showing a procedure of extra-orbital lacrimal gland excision.

FIG. 135 is a diagram showing a change in the body weight of a rat model whose eyes have been administered with YDE-001 to YDE-028.

FIG. 136 is a diagram showing a change in the body weight of a rat model whose eyes have been administered with YDE-029 to YDE-043.

FIG. 137 is a photograph showing a procedure of administering an agent to the eyes of a rat model.

Figure 138:
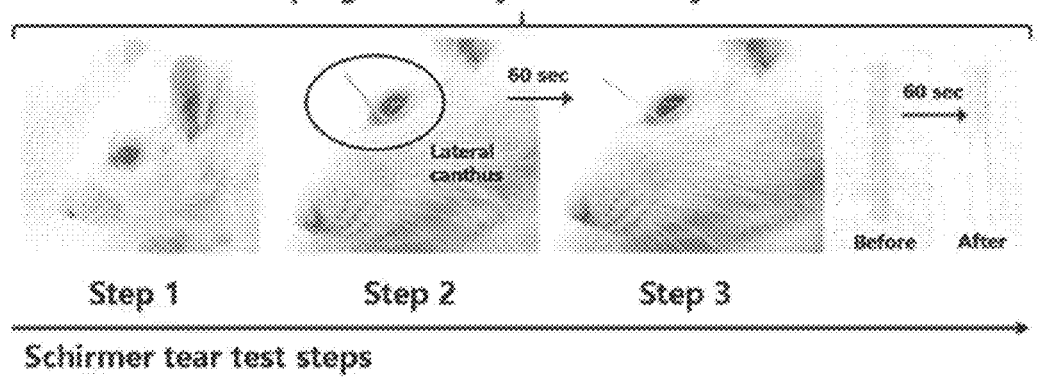

FIG. 138 is a photograph showing a procedure of measuring the amount of tear secretion of a rat model using cobalt chloride paper.

Figure 139:
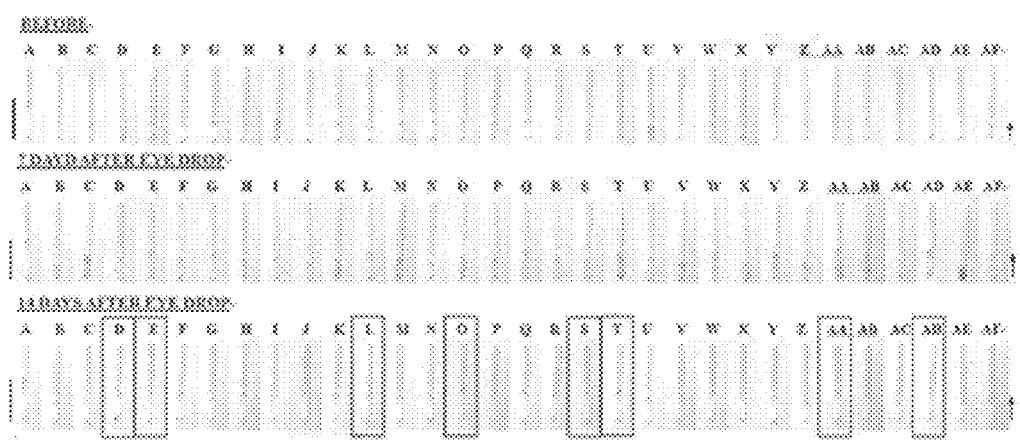

FIG. 139 is a photograph showing the results of measuring the amount of tear secretion of a rat model whose eyes have been administered with YDE-001 to YDE-028 using cobalt chloride paper.

FIG. 140 is a diagram showing the changes in the amount of tear secretion of a rat model whose eyes have been administered with YDE-001 to YDE-028.

Figure 141:
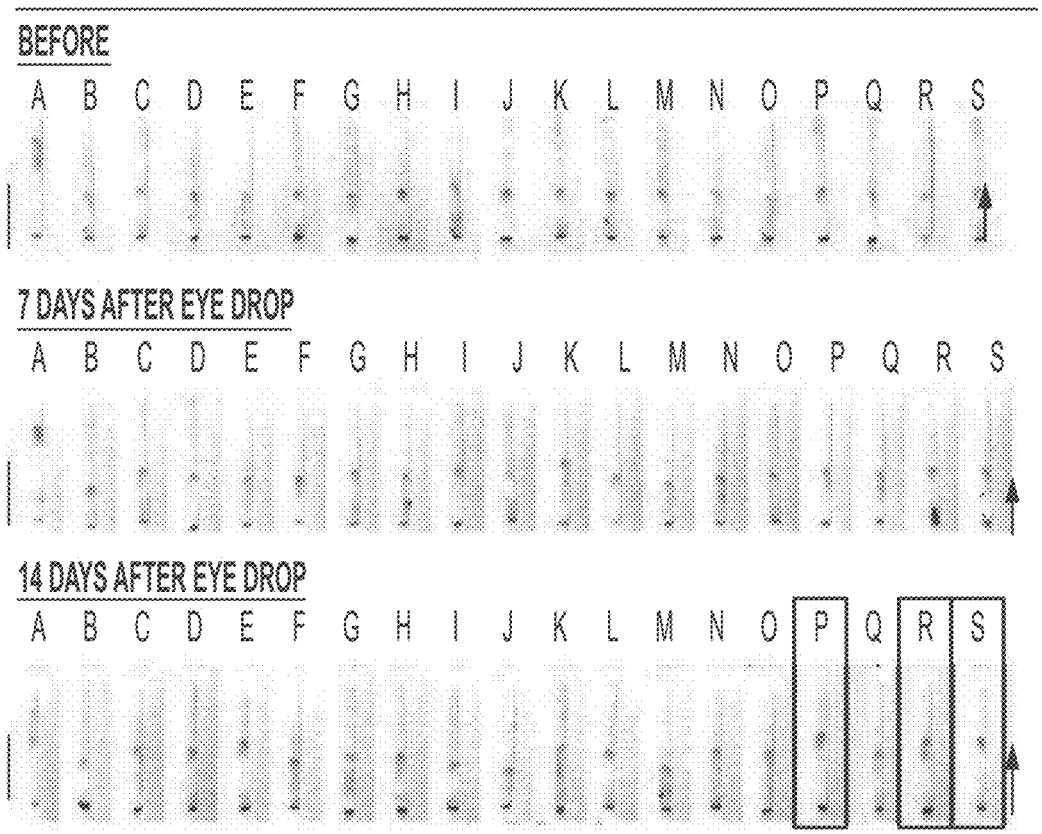

FIG. 141 is a photograph showing the results of measuring the amount of tear secretion of a rat model whose eyes have been administered with YDE-029 to YDE-043 using cobalt chloride paper.

Figures 142, 143:
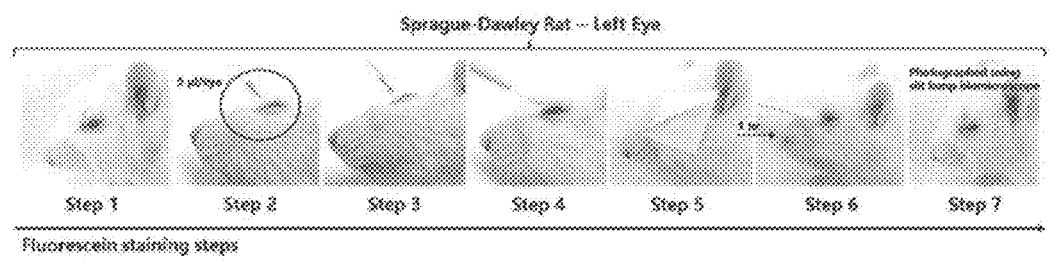

FIG. 142 is a diagram showing the changes in the amount of tear secretion of a rat model whose eyes have been administered with YDE-029 to YDE-043.

FIG. 143 is a photograph showing a procedure of administering a fluorescent substance to the eyes of a rat model for confirming damage to the cornea thereof.

Figure 144:
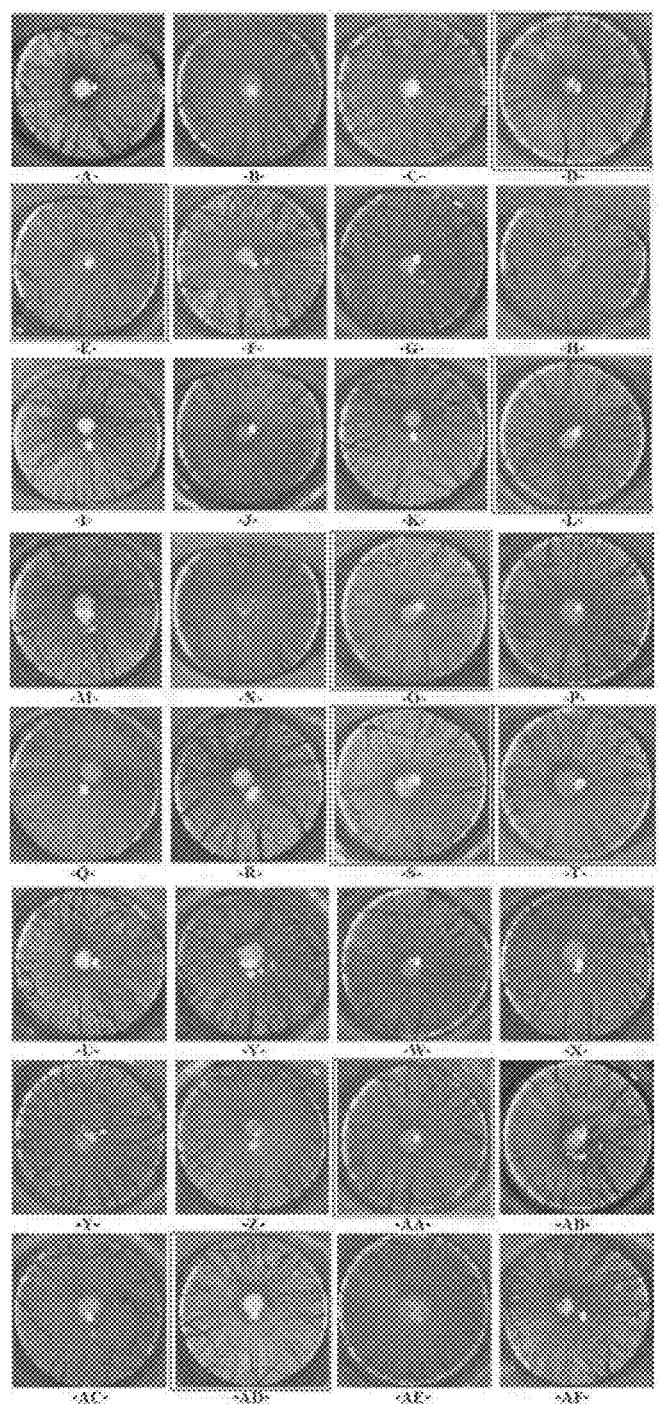

FIG. 144 is a photograph showing the results of measuring damage to the cornea of a rat model whose eyes have been administered with YDE-001 to YDE-028 using a fluorescent substance.

FIG. 145 is a diagram showing the permeability of a fluorescence dye to confirm the recovery of corneal damage of a rat model whose eyes have been administered with YDE-001 to YDE-028.

Figure 146:
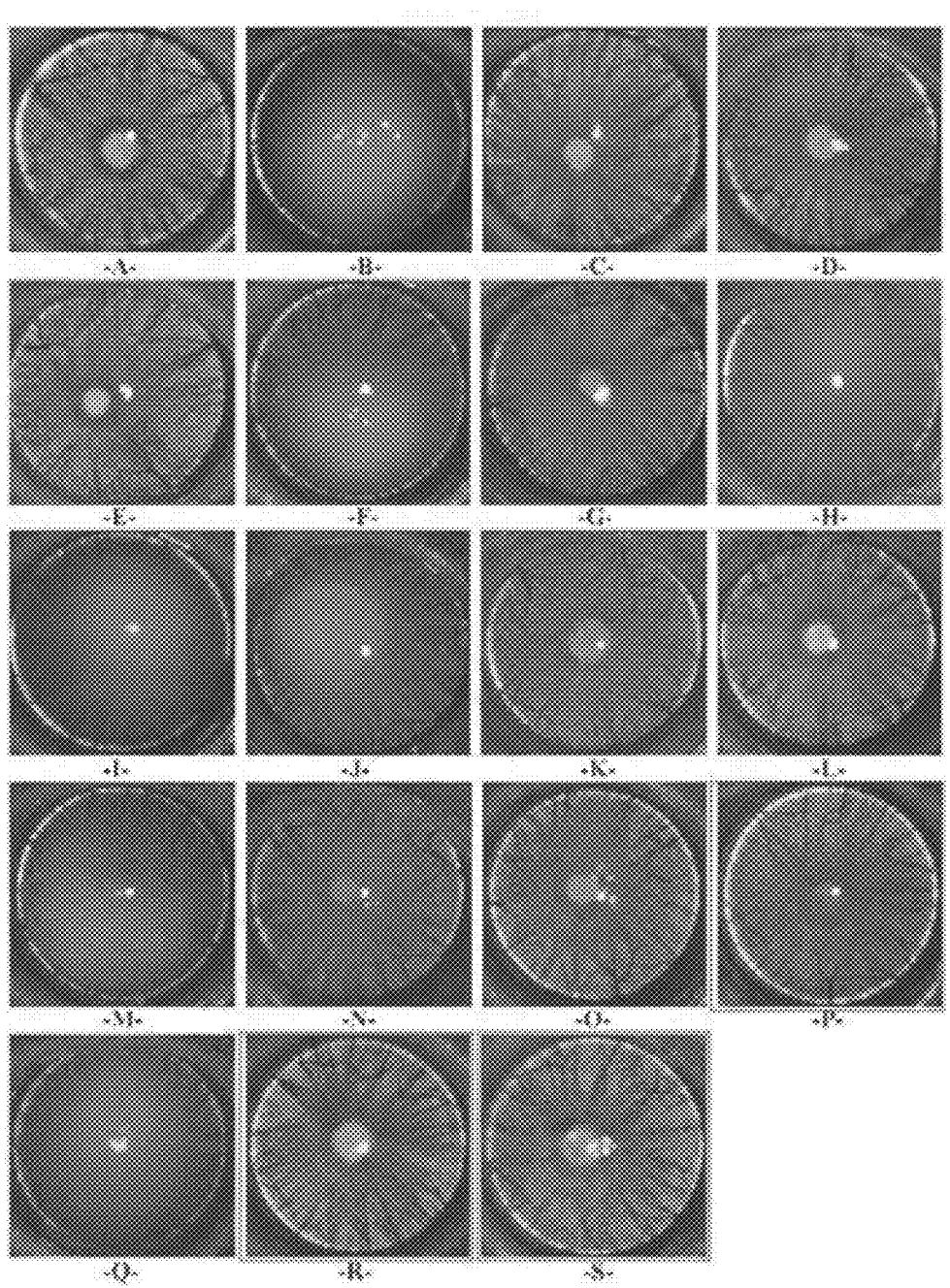

FIG. 146 is a photograph showing the results of measuring damage to the cornea of a rat model whose eyes have been administered with YDE-029 to YDE-043 using a fluorescent substance.

FIG. 147 is a diagram showing the permeability of a fluorescence dye to confirm the recovery of corneal damage of a rat model whose eyes have been administered with YDE-029 to YDE-043.

Figure 148:
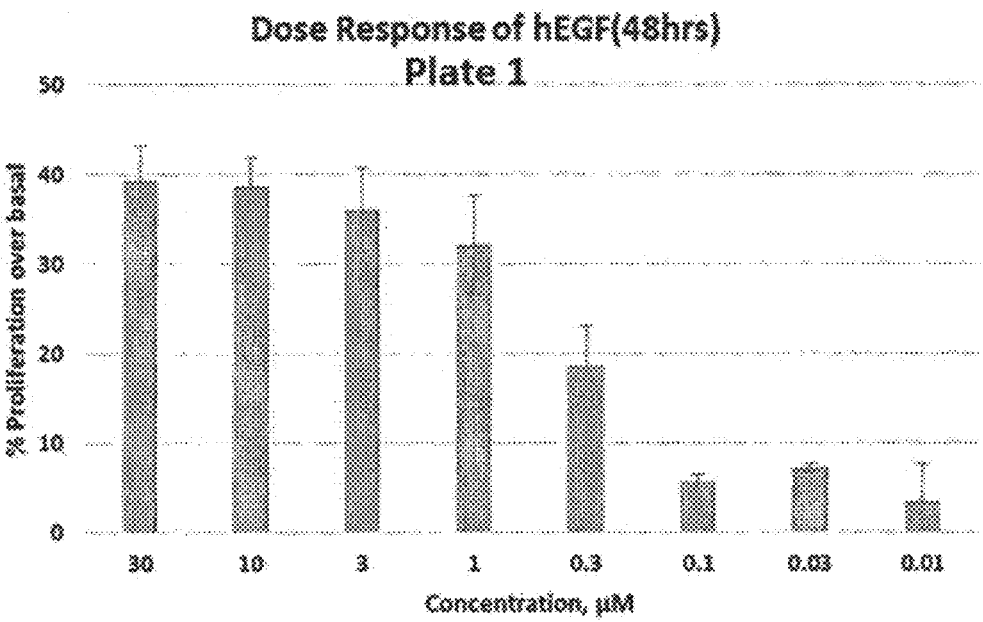

FIG. 148 is a diagram showing the cell growth rate after 48 hours from the treatment of hEGF on human corneal epithelial cells of plate No. 1.

Figure 149:
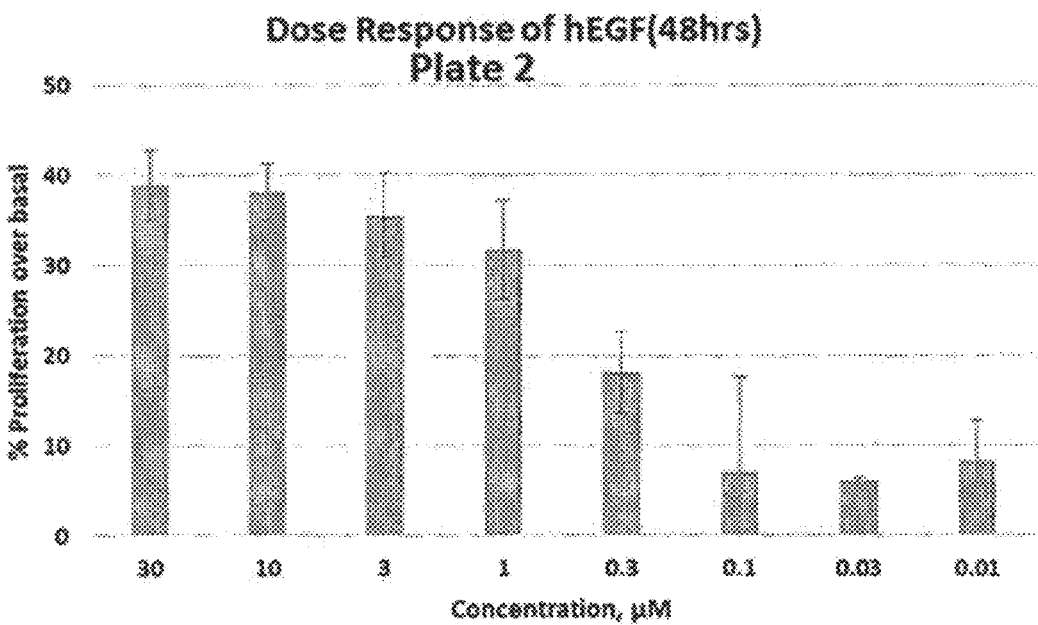

FIG. 149 is a diagram showing the cell growth rate after 48 hours from the treatment of hEGF on human corneal epithelial cells of plate No. 2.

Figure 150:
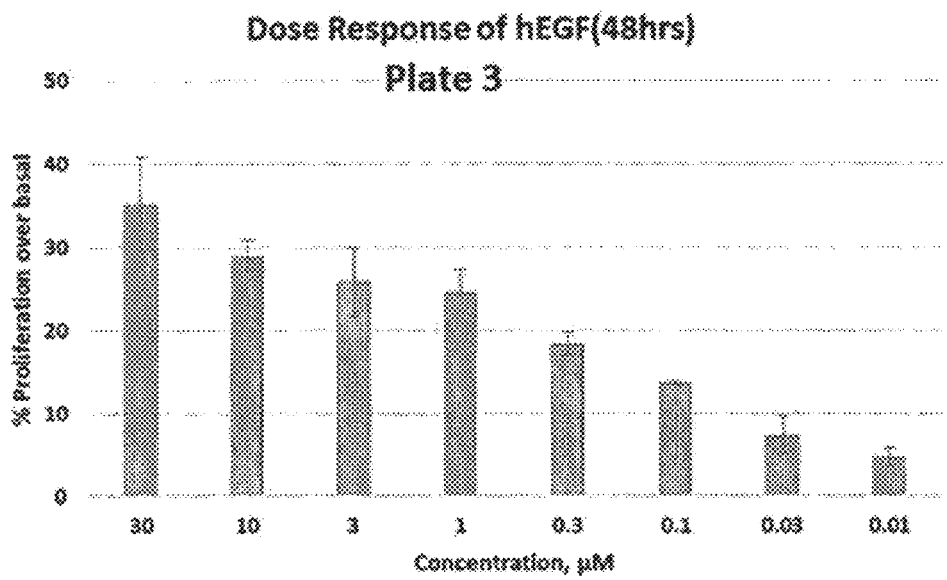

FIG. 150 is a diagram showing the cell growth rate after 48 hours from the treatment of hEGF on human corneal epithelial cells of plate No. 3.

Figure 151:
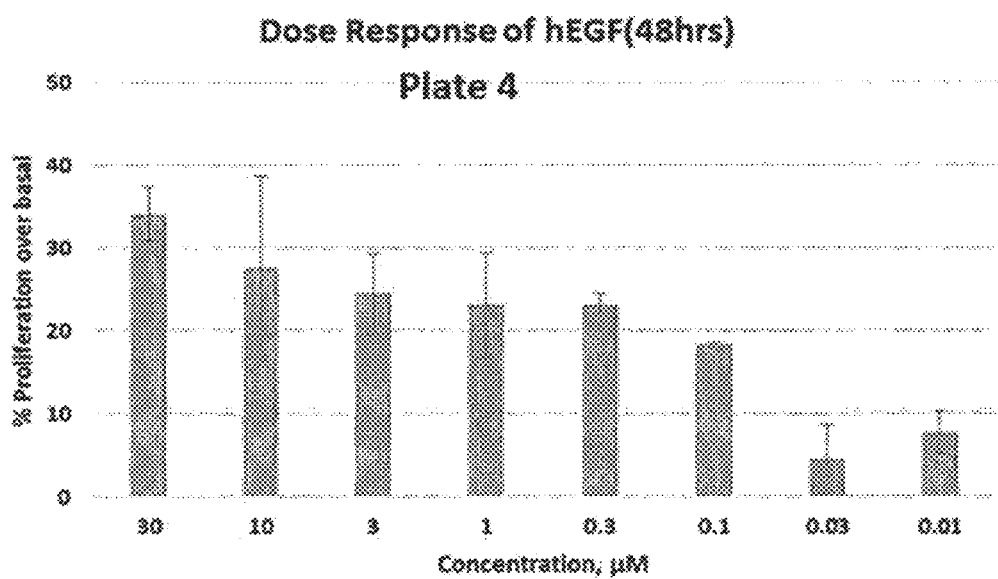

FIG. 151 is a diagram showing the cell growth rate after 48 hours from the treatment of hEGF on human corneal epithelial cells of plate No. 4.

Figure 152:
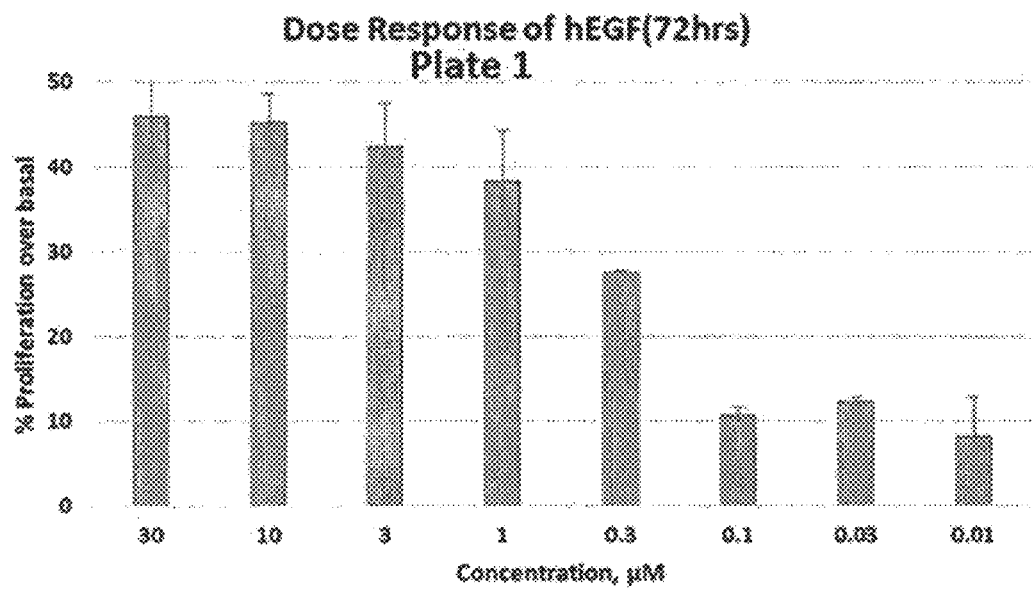

FIG. 152 is a diagram showing the cell growth rate after 72 hours from the treatment of hEGF on human corneal epithelial cells of plate No. 1.

Figure 153:
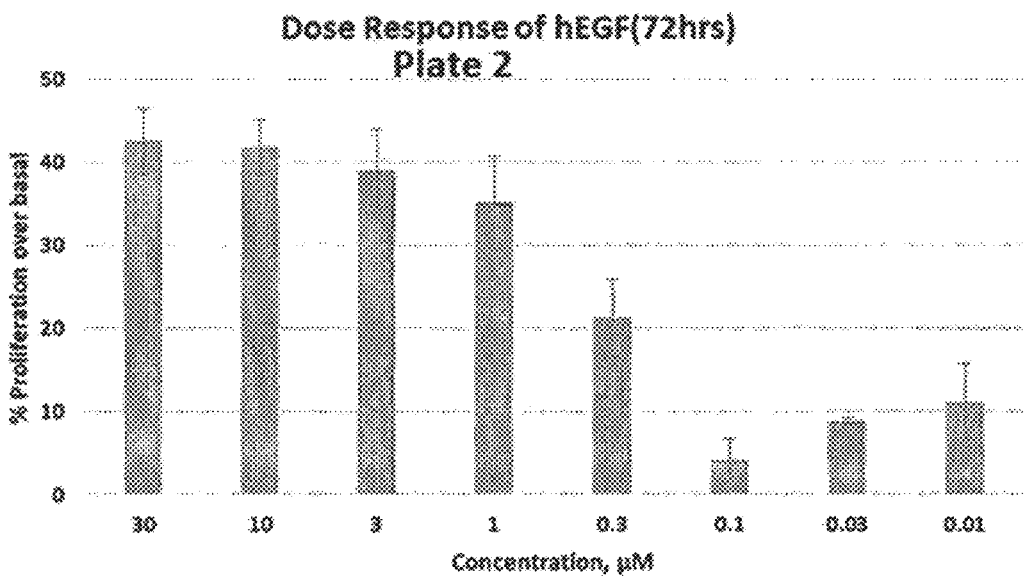

FIG. 153 is a diagram showing the cell growth rate after 72 hours from the treatment of hEGF on human corneal epithelial cells of plate No. 2.

Figure 154:
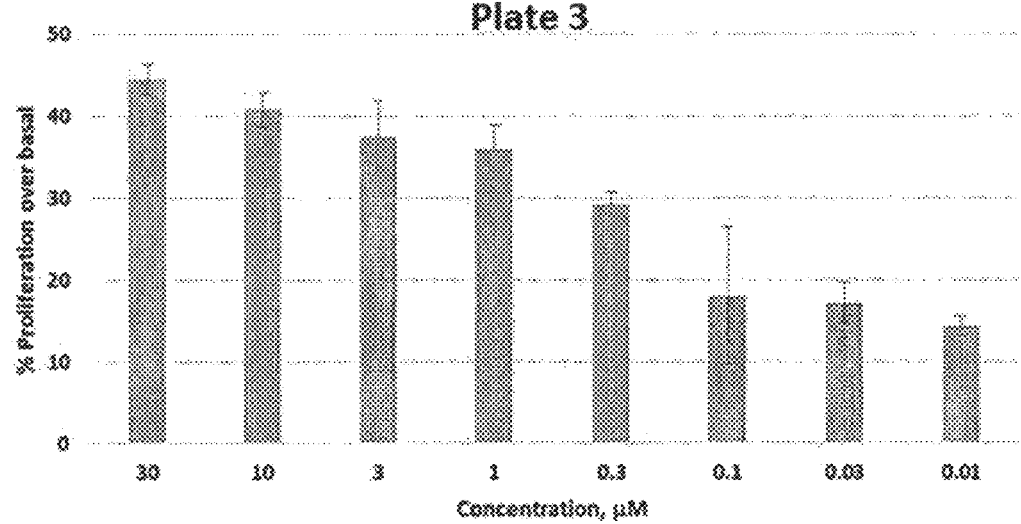

FIG. 154 is a diagram showing the cell growth rate after 72 hours from the treatment of hEGF on human corneal epithelial cells of plate No. 3.

Figure 155:
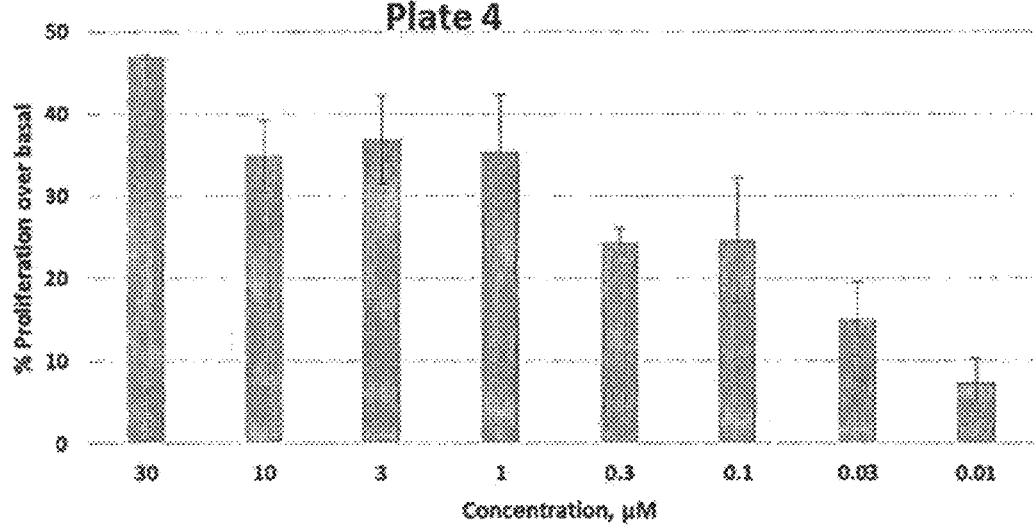

FIG. 155 is a diagram showing the cell growth rate after 48 hours from the treatment of hEGF on human corneal epithelial cells of plate No. 4.

Figure 156:
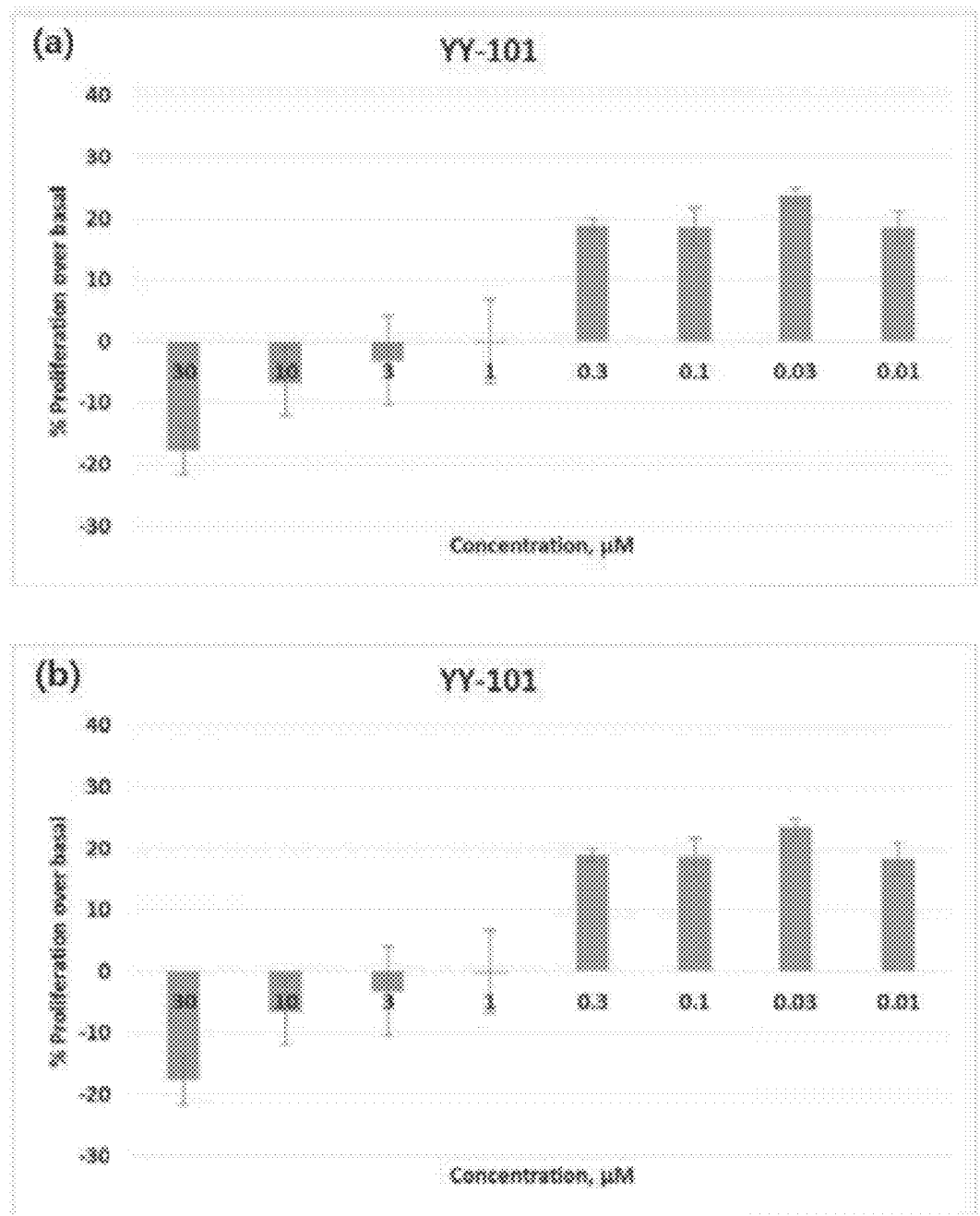

FIG. 156 is a diagram showing the cell growth rate after (a) 48 hours or (b) 72 hours from the treatment of YY-101 on human corneal epithelial cells.

Figure 157:
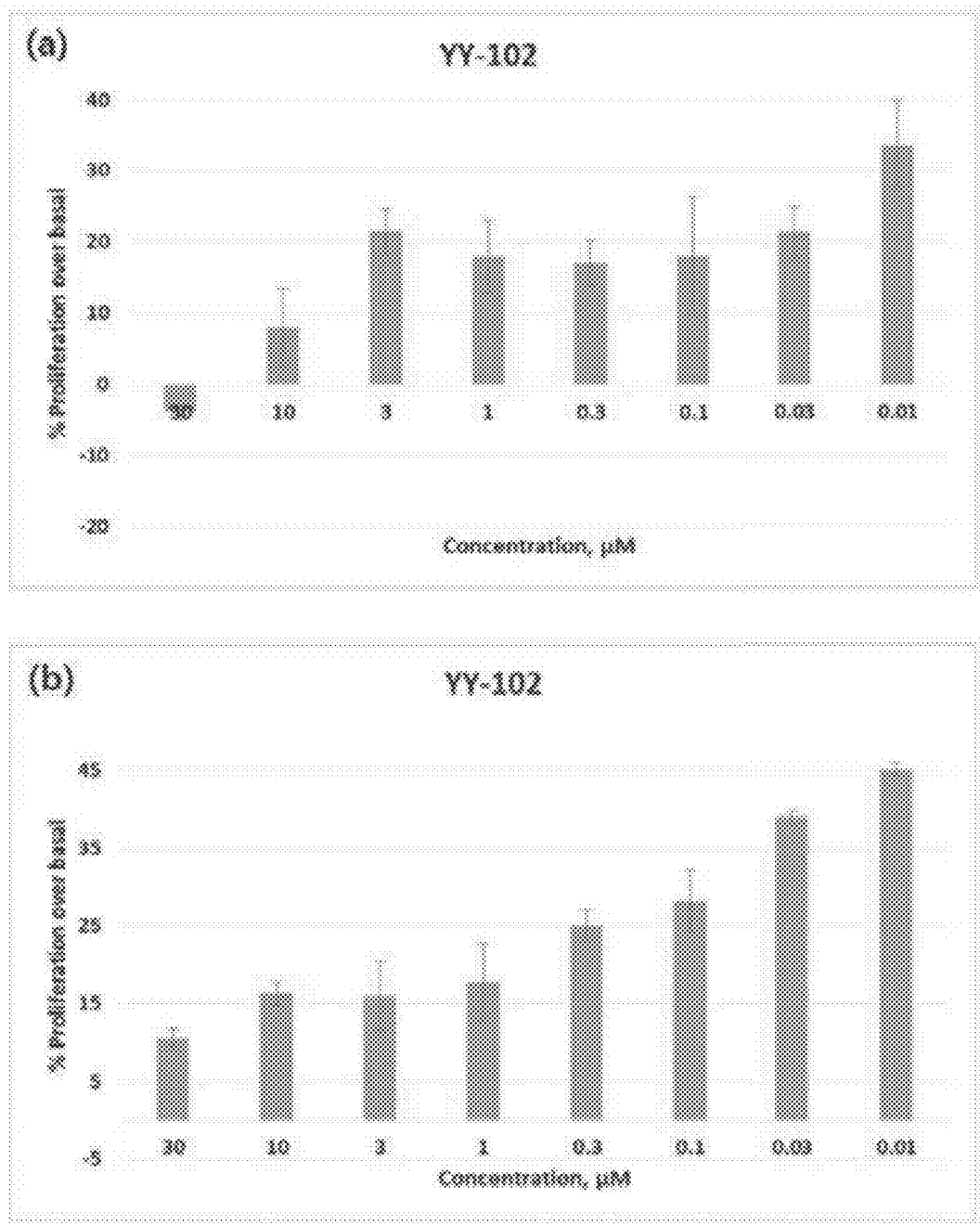

FIG. 157 is a diagram showing the cell growth rate after (a) 48 hours or (b) 72 hours from the treatment of YY-102 on human corneal epithelial cells.

Figure 158:
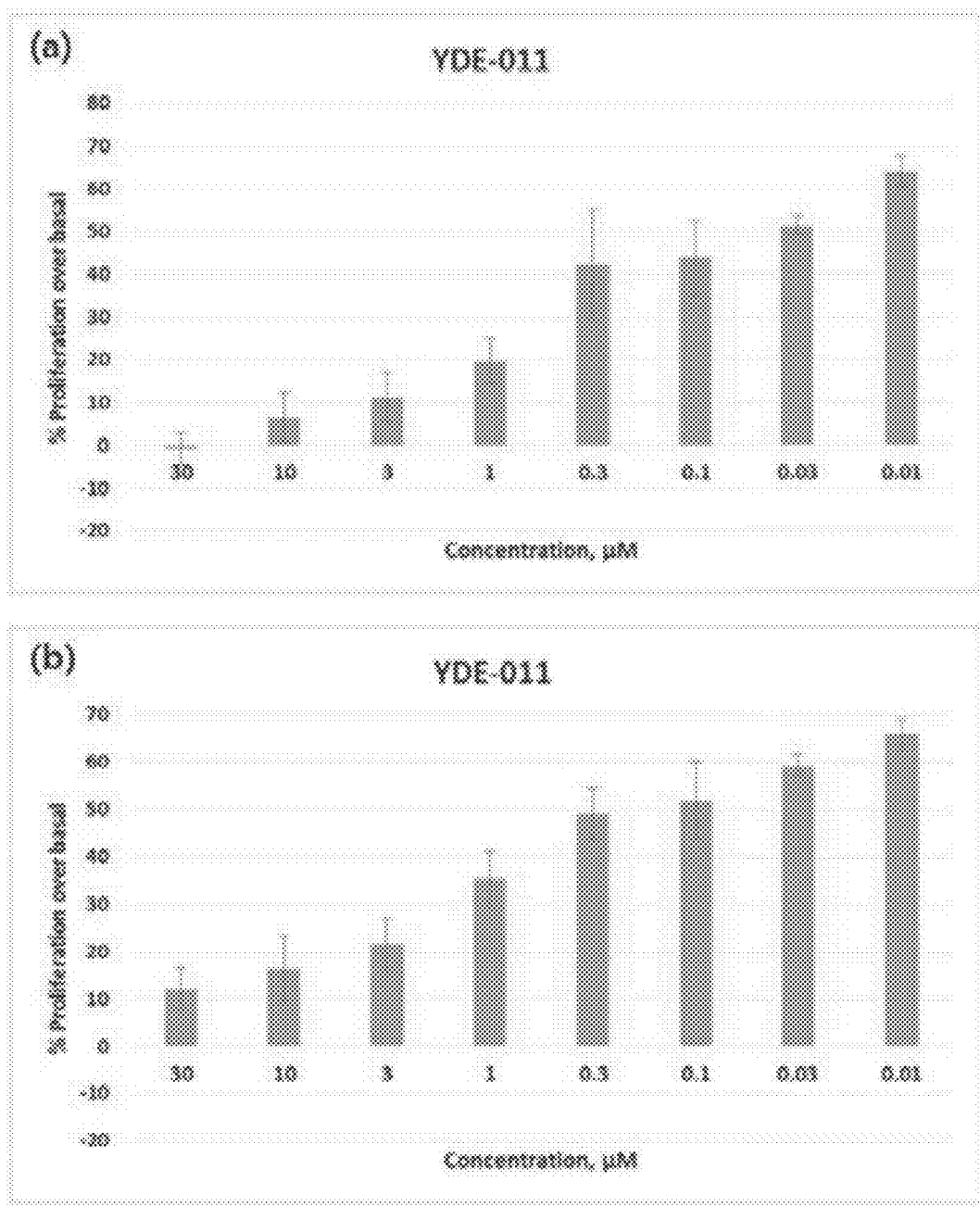

FIG. 158 is a diagram showing the cell growth rate after (a) 48 hours or (b) 72 hours from the treatment of YDE-011 on human corneal epithelial cells.

Figure 159:
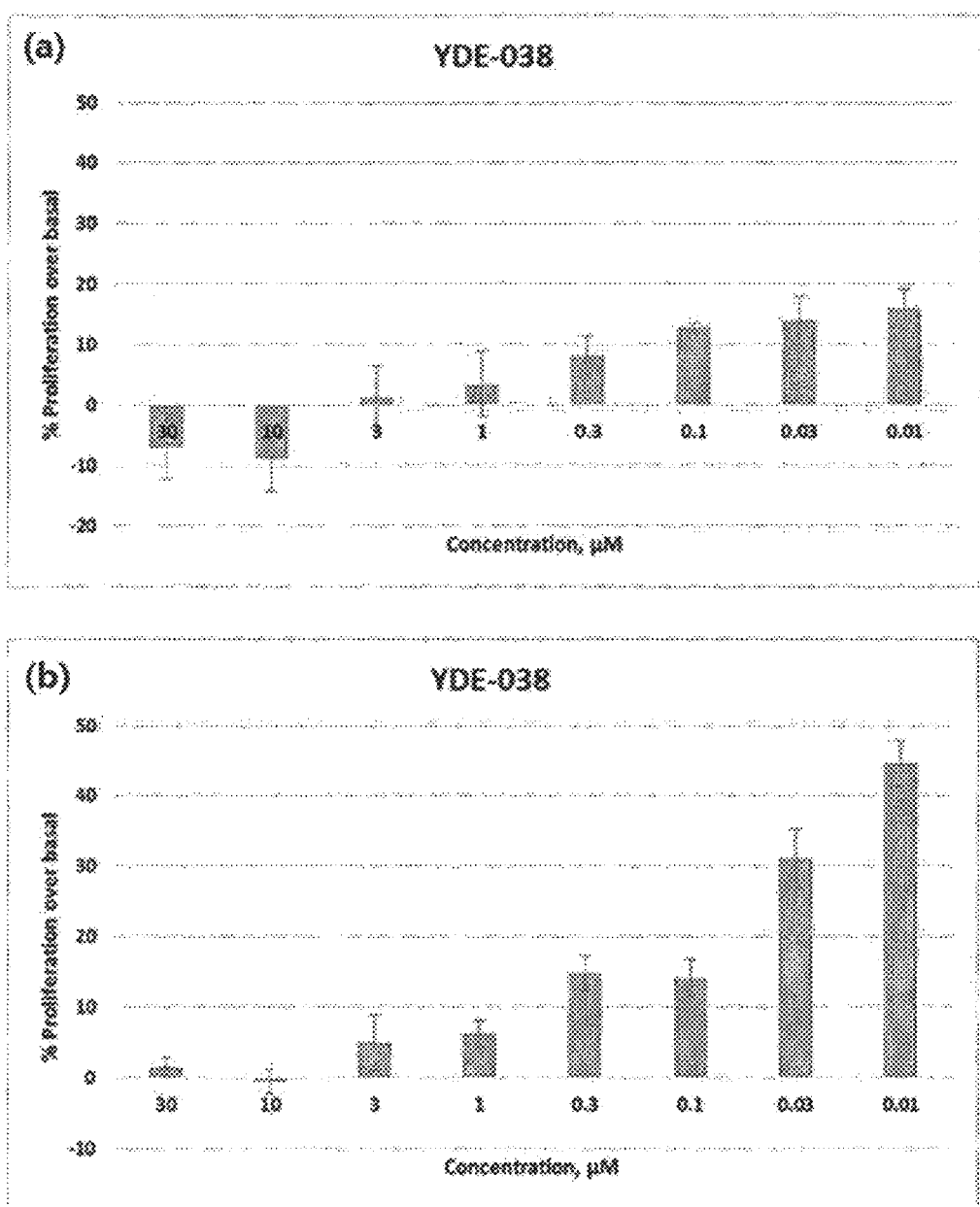

FIG. 159 is a diagram showing the cell growth rate after (a) 48 hours or (b) 72 hours from the treatment of YDE-038 on human corneal epithelial cells.

FIG. 160 is a diagram showing the cell growth rate after (a) 48 hours or (b) 72 hours from the treatment of YDE-042 on human corneal epithelial cells.

FIG. 161 is a diagram showing the cell growth rate after (a) 48 hours or (b) 72 hours from the treatment of YDE-043 on human corneal epithelial cells.

FIG. 162 is a diagram showing the cell growth rate after (a) 48 hours or (b) 72 hours from the treatment of YDE-044 on human corneal epithelial cells.

Figure 163:
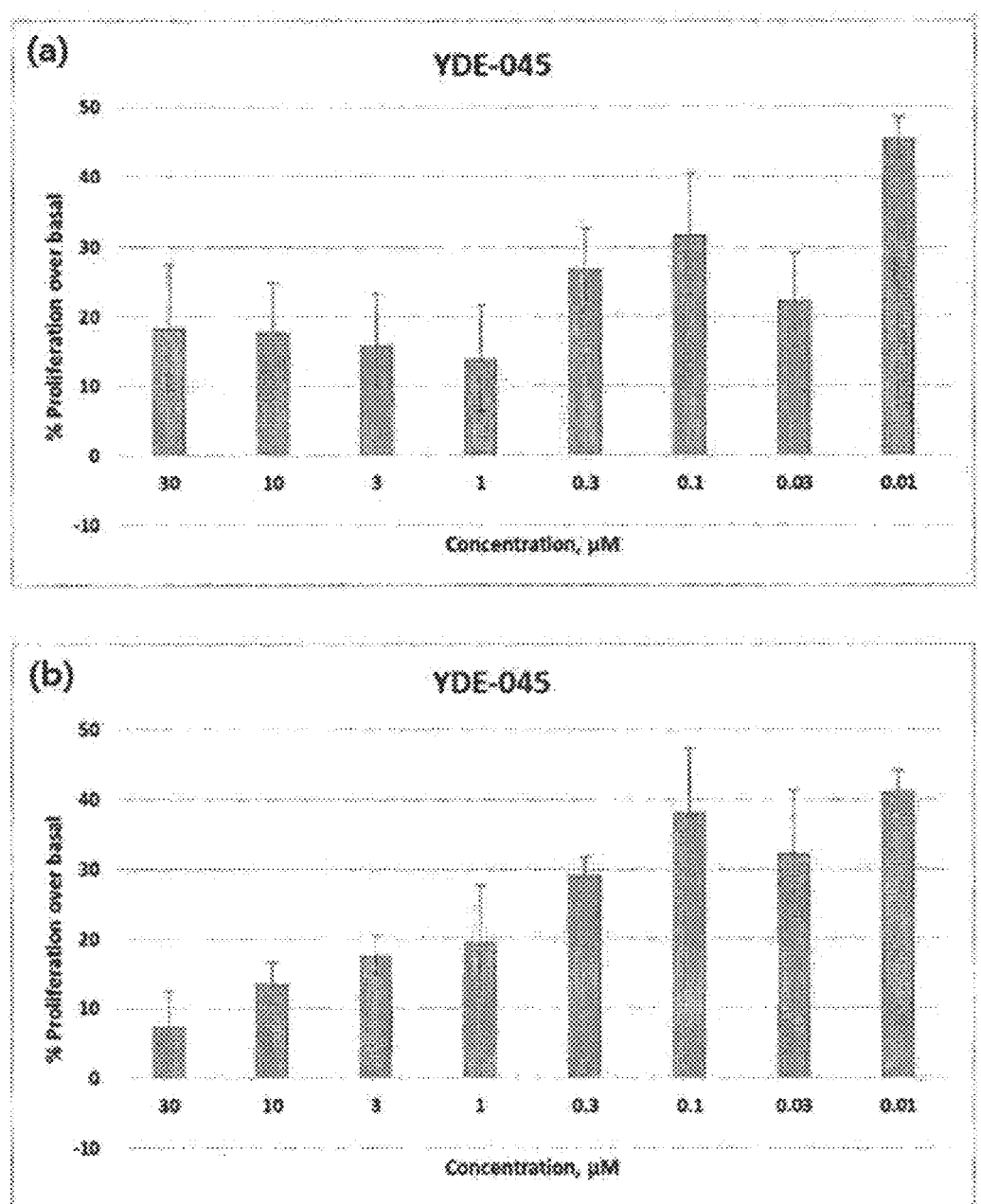

FIG. 163 is a diagram showing the cell growth rate after (a) 48 hours or (b) 72 hours from the treatment of YDE-045 on human corneal epithelial cells.

FIG. 164 is a diagram showing the cell growth rate after (a) 48 hours or (b) 72 hours from the treatment of YDE-049 on human corneal epithelial cells.

FIG. 165 is a diagram showing the cell growth rate after (a) 48 hours or (b) 72 hours from the treatment of YDE-054 on human corneal epithelial cells.

Figure 166:
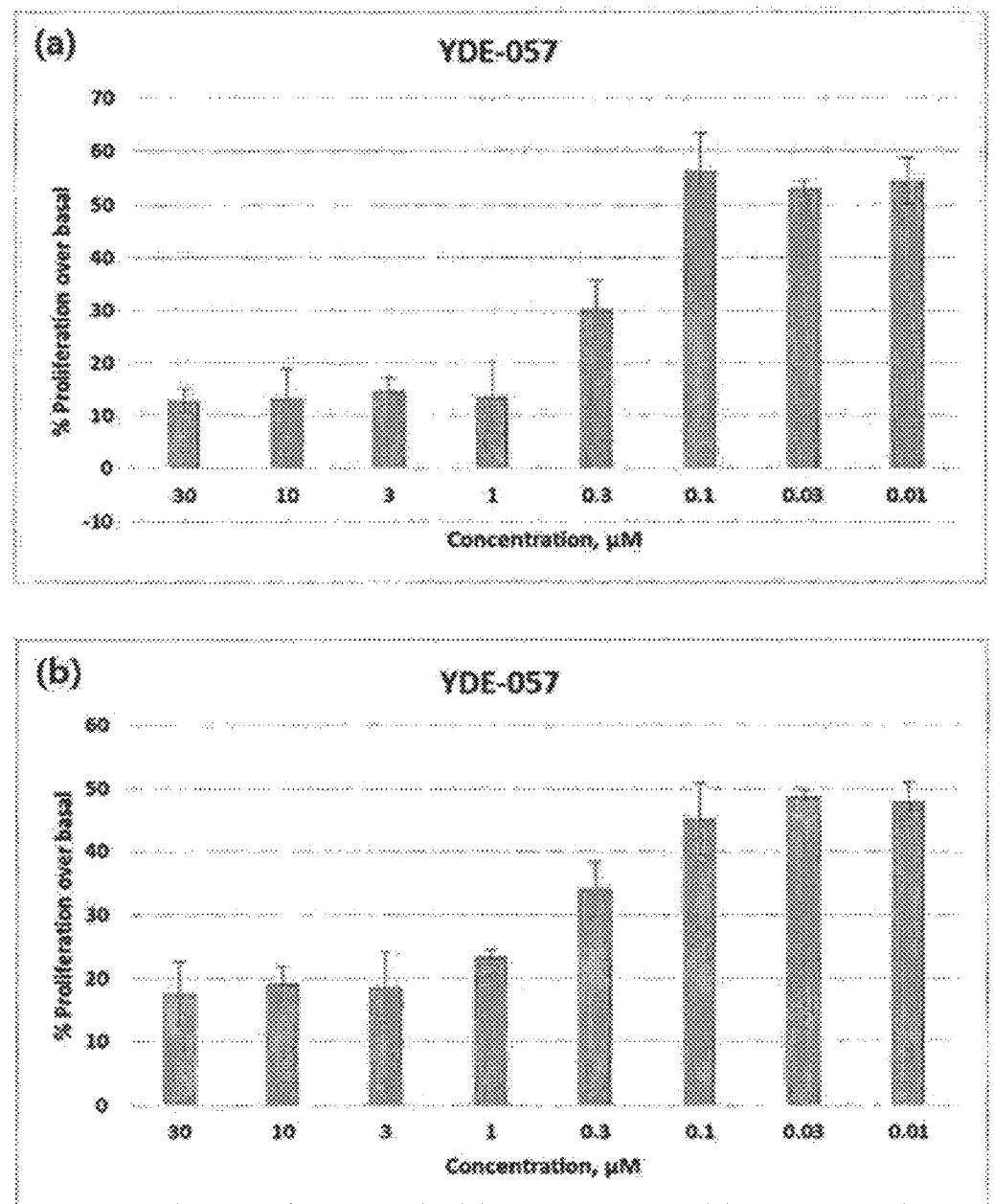

FIG. 166 is a diagram showing the cell growth rate after (a) 48 hours or (b) 72 hours from the treatment of YDE-057 on human corneal epithelial cells.

FIG. 167 is a diagram showing the cell growth rate after (a) 48 hours or (b) 72 hours from the treatment of YDE-058 on human corneal epithelial cells.

Figure 168:
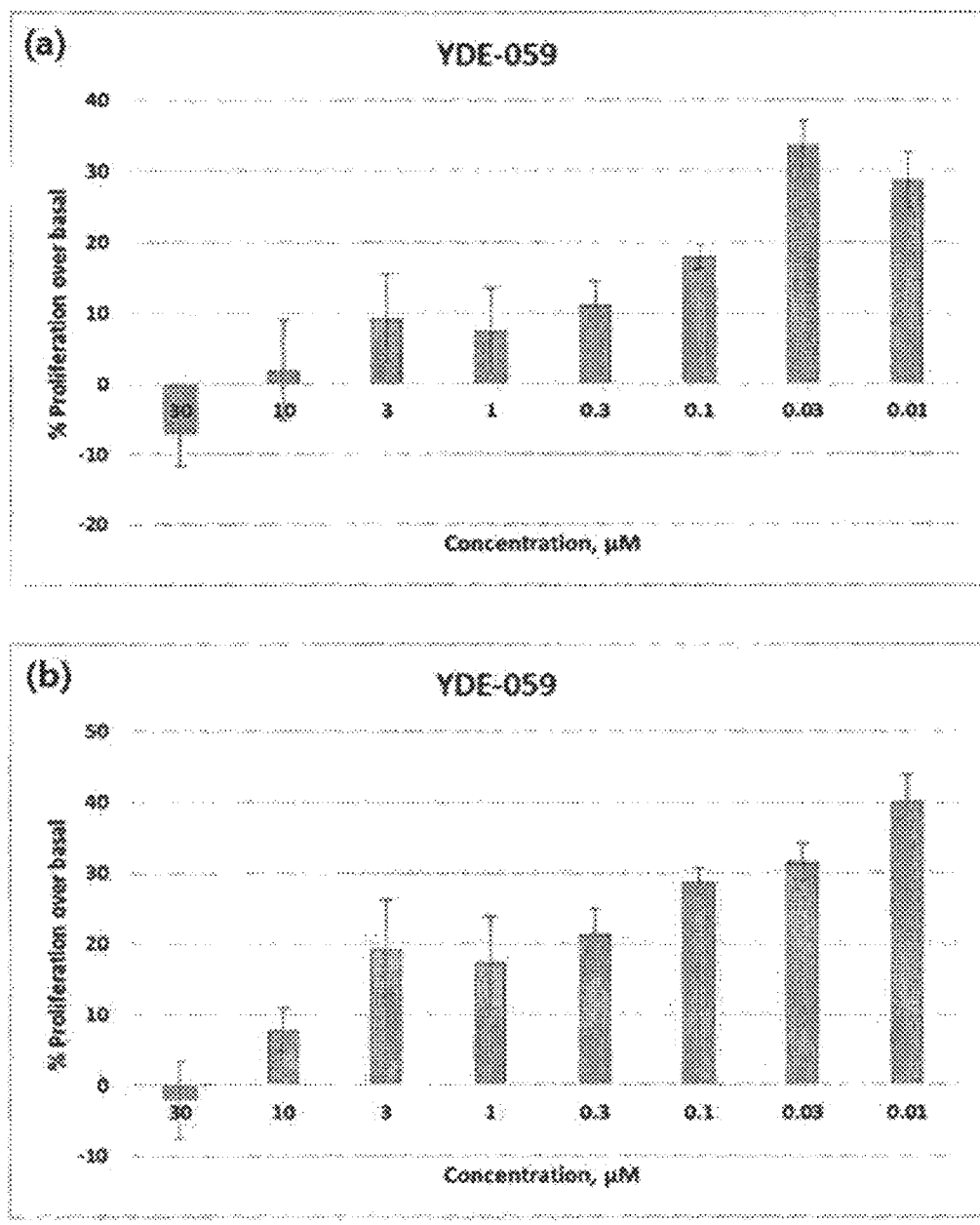

FIG. 168 is a diagram showing the cell growth rate after (a) 48 hours or (b) 72 hours from the treatment of YDE-059 on human corneal epithelial cells.

Figure 169:
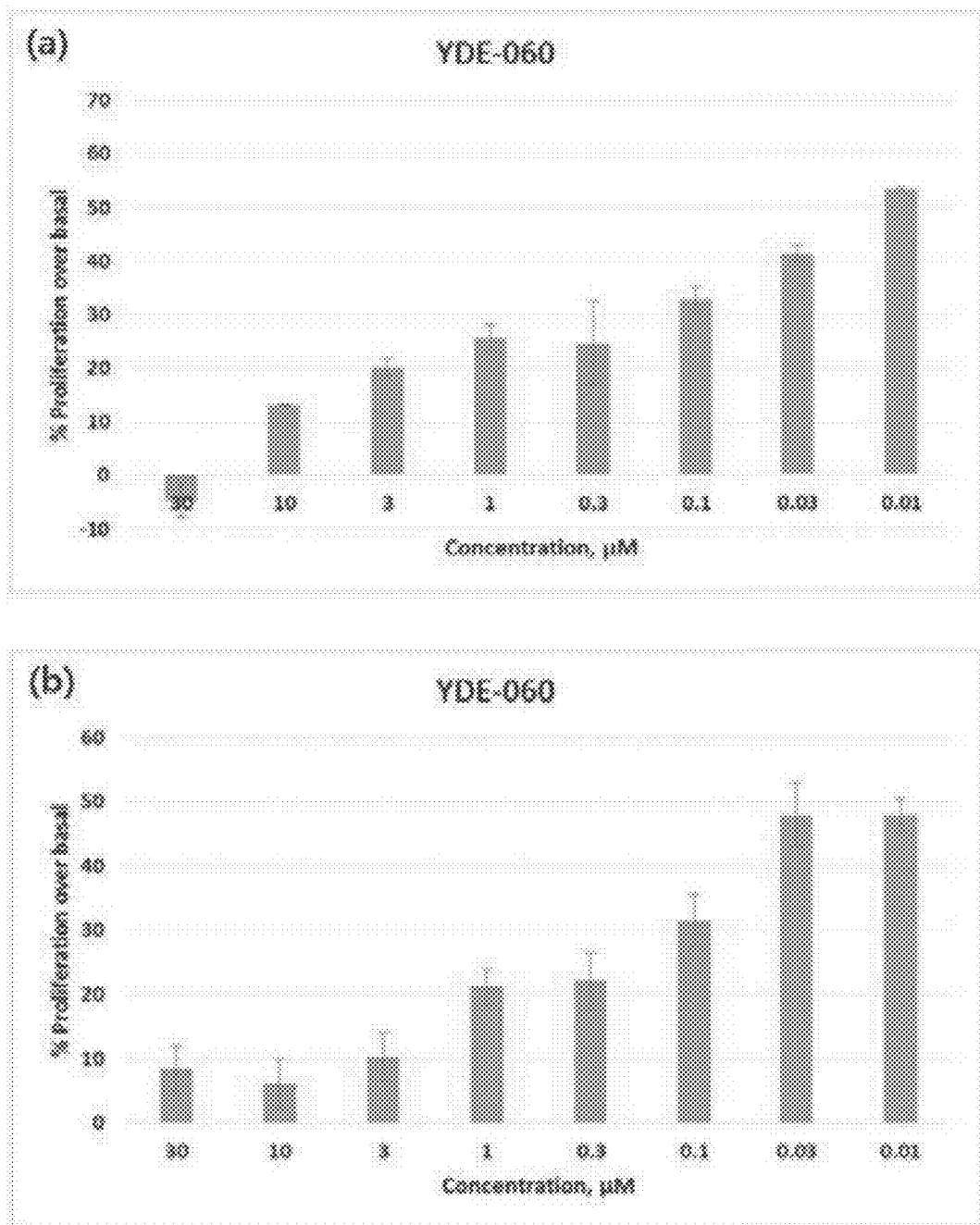

FIG. 169 is a diagram showing the cell growth rate after (a) 48 hours or (b) 72 hours from the treatment of YDE-060 on human corneal epithelial cells.

Figure 170:
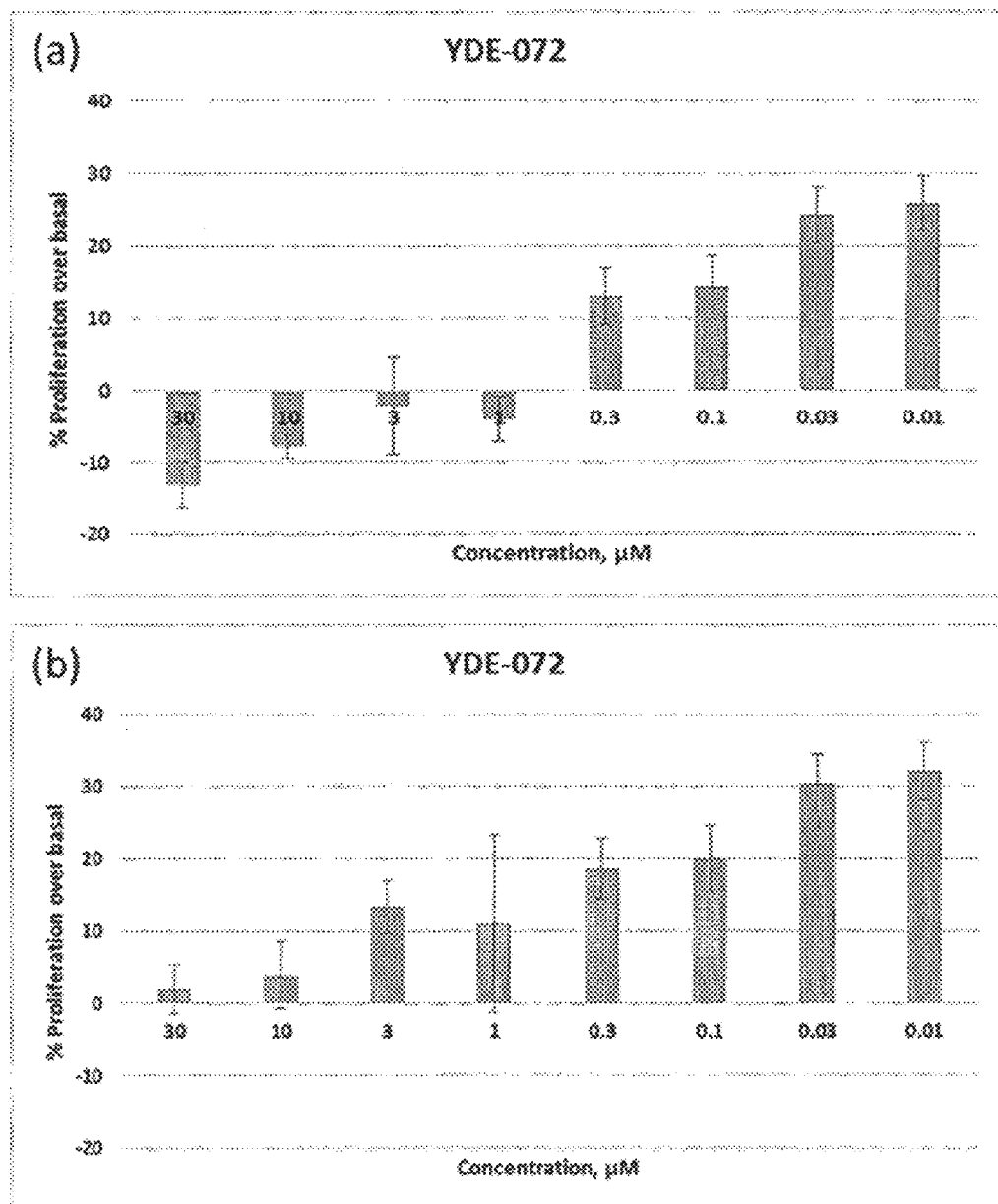

FIG. 170 is a diagram showing the cell growth rate after (a) 48 hours or (b) 72 hours from the treatment of YDE-072 on human corneal epithelial cells.

Figure 171:
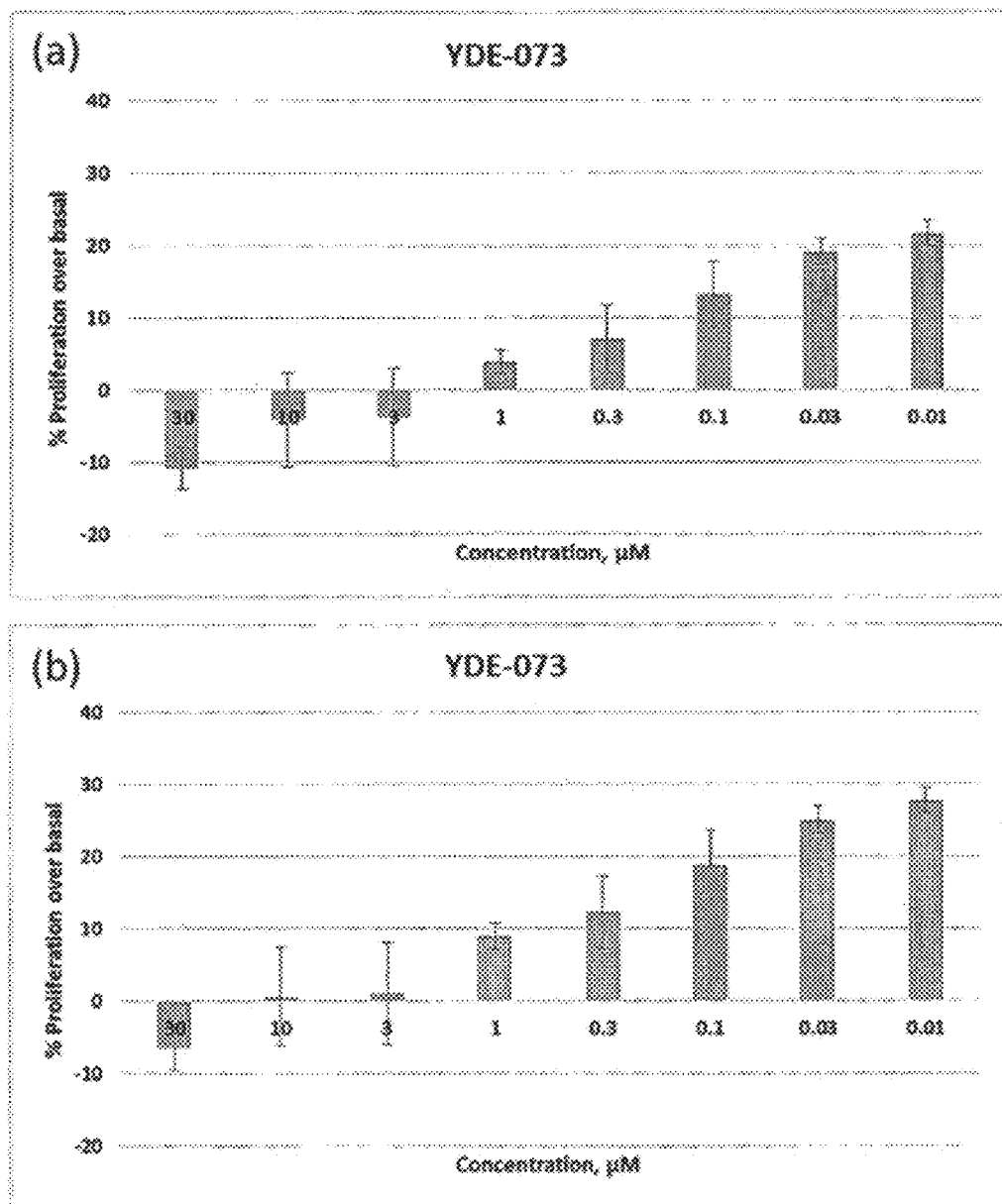

FIG. 171 is a diagram showing the cell growth rate after (a) 48 hours or (b) 72 hours from the treatment of YDE-073 on human corneal epithelial cells.

Figure 172:
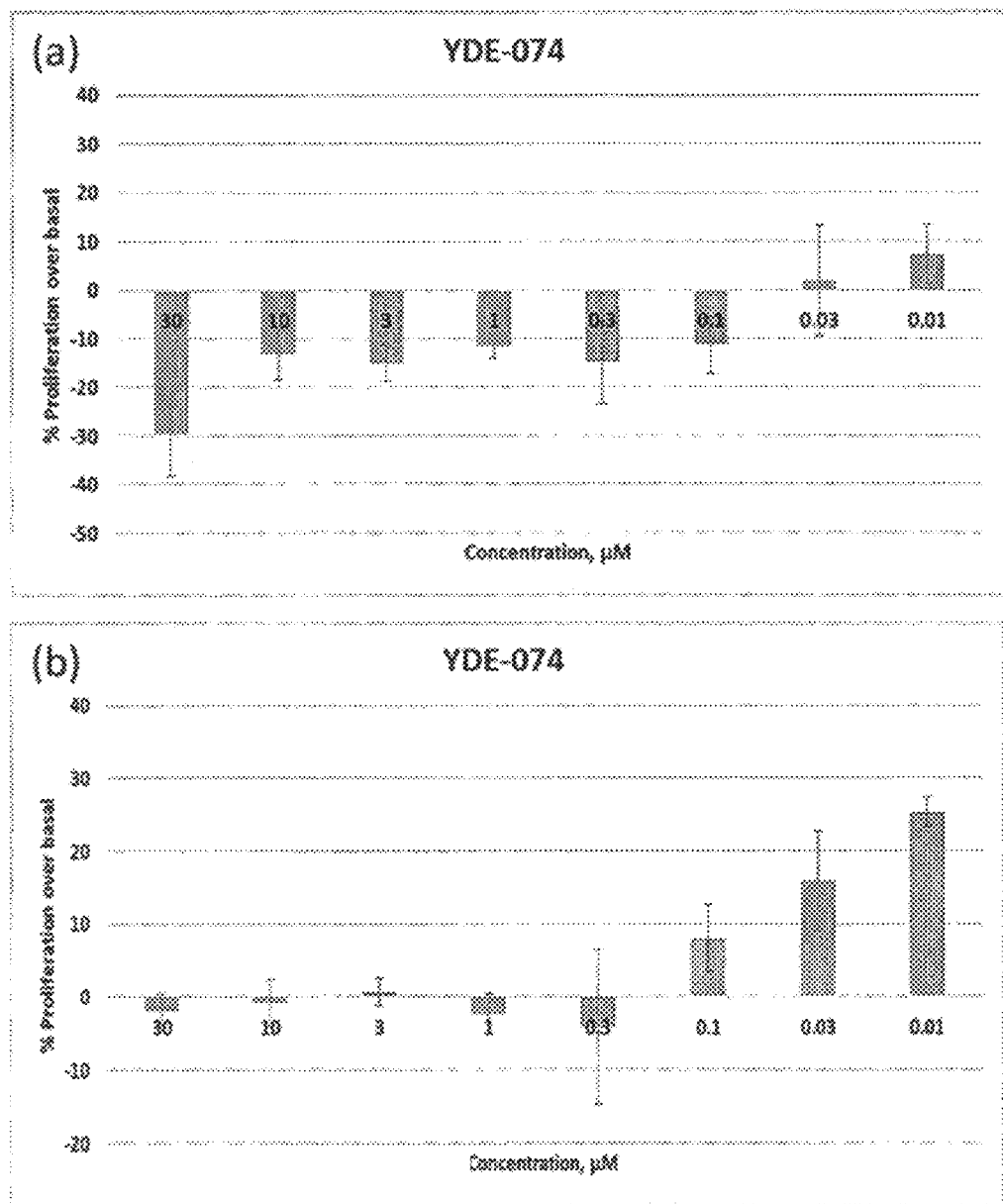

FIG. 172 is a diagram showing the cell growth rate after (a) 48 hours or (b) 72 hours from the treatment of YDE-074 on human corneal epithelial cells.

Figure 173:
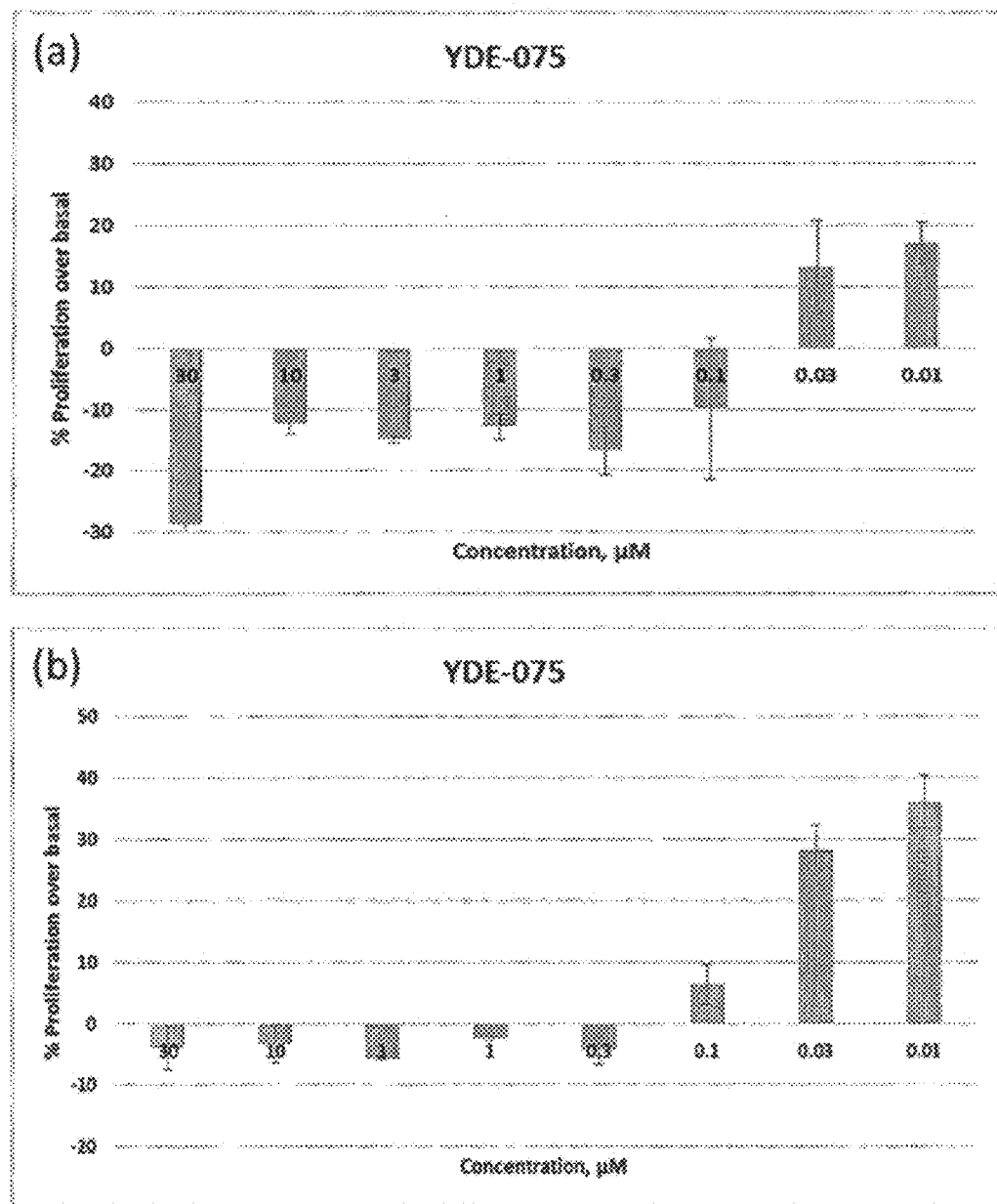

FIG. 173 is a diagram showing the cell growth rate after (a) 48 hours or (b) 72 hours from the treatment of YDE-075 on human corneal epithelial cells.

DETAILED DESCRIPTION OF THE INVENTION

Hereinafter, the present invention will be described in detail.

An aspect of the present invention provides a compound represented by Formula 1.

[Formula 1]

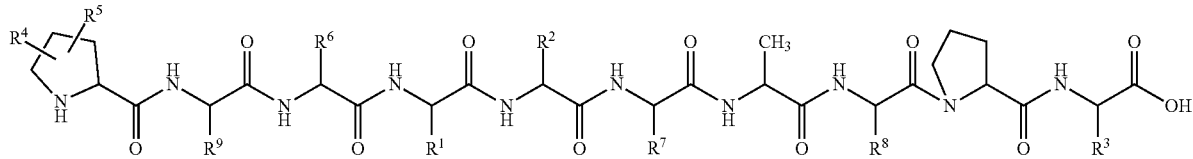

In the above formula,
- $R^1$ to $R^3$ are each independently hydrogen, substituted or unsubstituted $C_{1-6}$ alkyl, substituted or unsubstituted $C_{1-10}$ alkoxy, substituted or unsubstituted $C_{1-10}$ haloalkyl, substituted or unsubstituted $C_{2-10}$ alkenyl, substituted or unsubstituted $C_{2-10}$ alkynyl, substituted or unsubstituted $C_{1-10}$ alkylene, substituted or unsubstituted $C_{1-10}$ alkenylene, substituted or unsubstituted $C_{1-10}$ alkynylene, substituted or unsubstituted $C_{5-12}$ aryl, substituted or unsubstituted $C_{7-12}$ arylalkyl, substituted or unsubstituted $C_{5-14}$ arylalkynyl, substituted or unsubstituted $C_{8-16}$ arylalkenyl, substituted or unsubstituted $C_{3-10}$ heteroalkyl, substituted or unsubstituted $C_{3-10}$ cycloalkyl, substituted or unsubstituted $C_{3-10}$ heterocycloalkyl, or substituted or unsubstituted $C_{5-12}$ heteroaryl, the heteroalkyl, heterocycloalkyl, or heteroaryl containing at least one of N, O, and S,
- the substitution refers to a substitution with one or more non-hydrogen substituents, each non-hydrogen substituent being selected from the group consisting of $-X_1$, $-R_a$, $-O-$, $=O$, $-OR_a$, $-SR_a$, $-S^-$, $-N(R_a)_2$, $-N^+(R_a)_3$, $=NR_a$, $-C(X_1)_3$, $-CN$, $-OCN$, $-SCN$, $-N=C=O$, $-NCS$, $-NO$, $-NO_2$, $=N-OH$, $=N_2$, $-N_3$, $-NHC(=O)R_a$, $-C(=O)R_a$, $-C(=O)NR_aR_a$, $-S(=O)_2O-$, $-S(=O)_2OH$, $-S(=O)_2R_a$, $-OS(=O)_2OR_a$, $-S(=O)_2NR_a$, $-S(=O)R_a$, $-OP(=O)(OR_a)_2$, $-C(=O)R_a$, alkylene-$C(=O)R_a$, $-C(=S)R_a$, $-C(=O)OR_a$, alkylene-$C(=O)OR_a$, $-C(=O)O-$, alkylene-$C(=O)O-$, $-C(=S)OR_a$, $-C(=O)SR_a$, $-C(=S)SR_a$, $-C(=O)NR_aR_a$, alkylene-$C(=O)NR_aR_a$, $-C(=S)NR_aR_a$, and $-C(=NR_a)NR_aR_a$, each $X_1$ is independently selected from F, Cl, Br, or I, each $R_a$ is independently selected from hydrogen, $C_{1-6}$ alkyl, $C_{5-12}$ aryl, $C_{7-12}$ arylalkyl, or heterocycle,
- $R^4$ and $R^5$ are each independently hydrogen, substituted or unsubstituted $C_{1-6}$ alkyl, $-X_2$, $-R_b$, $-O-$, $=O$, $-CH_2OR_b$, or $-OR_b$, $X_2$ is F, Cl, Br, or I, and $R_b$ is H, substituted or unsubstituted $C_{1-6}$ alkyl, substituted or unsubstituted $C_{5-12}$ aryl, substituted or unsubstituted $C_{7-12}$ arylalkyl, or substituted or unsubstituted heterocycle,
- $R^6$ is hydrogen or substituted or unsubstituted $C_{1-6}$ alkyl, the substituent being $-C(=O)NH_2$,
- $R^7$ is hydrogen or $C_{1-6}$ alkyl, and
- $R^8$ and $R^9$ are each independently hydrogen or unsubstituted $C_{1-6}$ alkyl.

In the definition of $R_b$, the substitution refers to a substitution with the non-hydrogen substituent.

According to the convention used in the art,

in the formulae herein is used to denote a bond, where a moiety or a substituent is attached to the nucleus or the backbone structure.

"Alkyl" is a hydrocarbon having primary, secondary, tertiary, and/or cyclic carbon atoms. For example, an alkyl group may have 1 to 20 carbon atoms (i.e., $C_1$-$C_{20}$ alkyl), 1 to 10 carbon atoms (i.e., $C_1$-$C_{10}$ alkyl), or 1 to 6 carbon atoms (i.e., $C_1$-$C_6$ alkyl). Examples of a suitable alkyl group include methyl (Me, $-CH_3$), ethyl (Et, $-CH_2CH_3$), 1-propyl (n-Pr, n-propyl, $-CH_2CH_2CH_3$), 2-propyl (i-Pr, i-propyl, $-CH(CH_3)_2$), 1-butyl (n-Bu, n-butyl, $-CH_2CH_2CH_2CH_3$), 2-methyl-1-propyl (i-Bu, i-butyl, $-CH_2CH(CH_3)_2$), 2-butyl (s-Bu, s-butyl, $-CH(CH_3)CH_2CH_3$), 2-methyl-2-propyl (t-Bu, t-butyl, $-C(CH_3)_3$), 1-pentyl (n-pentyl, $-CH_2CH_2CH_2CH_2CH_3$), 2-pentyl ($-CH(CH_3)CH_2CH_2CH_3$), 3-pentyl ($-CH(CH_2CH_3)_2$), 2-methyl-2-butyl ($-C(CH_3)_2CH_2CH_3$), 3-methyl-2-butyl ($-CH(CH_3)CH(CH_3)_2$), 3-methyl-1-butyl ($-CH_2CH_2CH(CH_3)_2$), 2-methyl-1-butyl ($-CH_2CH(CH_3)CH_2CH_3$), 1-hexyl ($-CH_2CH_2CH_2CH_2CH_2CH_3$), 2-hexyl ($-CH(CH_3)CH_2CH_2CH_2CH_3$), 3-hexyl ($-CH(CH_2CH_3)(CH_2CH_2CH_3)$), 2-methyl-2-pentyl ($-C(CH_3)_2CH_2CH_2CH_3$), 3-methyl-2-pentyl ($-CH(CH_3)CH(CH_3)CH_2CH_3$), 4-methyl-2-pentyl ($-CH(CH_3)CH_2CH(CH_3)_2$), 3-methyl-3-pentyl ($-C(CH_3)(CH_2CH_3)_2$), 2-methyl-3-pentyl ($-CH(CH_2CH_3)CH(CH_3)_2$), 2,3-dimethyl-2-butyl ($-C(CH_3)_2CH(CH_3)_2$), 3,3-dimethyl-2-butyl ($-CH(CH_3)C(CH_3)_3$), and octyl ($-(CH_2)_7CH_3$), but it is not limited thereto.

"Alkoxy" refers to a group having the formula $-O$-alkyl, wherein the alkyl group as defined above is attached to the parent compound via an oxygen atom. The alkyl moiety of the alkoxy group may have 1 to 20 carbon atoms (i.e., $C_1$-$C_{20}$ alkoxy), 1 to 12 carbon atoms (i.e., $C_1$-$C_{12}$ alkoxy), or 1 to 6 carbon atoms (i.e., $C_1$-$C_6$ alkoxy). Examples of a suitable alkoxy group include methoxy ($-O-CH_3$ or $-OMe$), ethoxy ($-OCH_2CH_3$ or $-OEt$), and t-butoxy ($-OC(CH_3)_3$ or $-O$-tBu), but it is not limited thereto.

"Haloalkyl" is an alkyl group in which at least one of the hydrogen atoms of the alkyl group as defined above is substituted by a halogen atom. The alkyl moiety of the haloalkyl group may have 1 to 20 carbon atoms (i.e., $C_1$-$C_{20}$ haloalkyl), 1 to 12 carbon atoms (i.e., $C_1$-$C_{12}$ haloalkyl), or 1 to 6 carbon atoms (i.e., $C_1$-$C_6$ haloalkyl). Examples of a suitable haloalkyl group include $-CF_3$, $-CHF_2$, $-CFH_2$, and $-CH_2CF_3$, but it is not limited thereto.

"Alkenyl" is a hydrocarbon having primary, secondary, tertiary, and/or cyclic carbon atoms, and having at least one unsaturated region, i.e., a carbon-carbon $sp^2$ double bond. For example, an alkenyl group may have 2 to 20 carbon atoms (i.e., $C_2$-$C_{20}$ alkenyl), 2 to 12 carbon atoms (i.e., $C_2$-$C_{12}$ alkenyl), or 2 to 6 carbon atoms (i.e., $C_2$-$C_6$ alkenyl). Examples of a suitable alkenyl group include vinyl (—CH═CH$_2$), allyl (—CH$_2$CH═CH$_2$), cyclopentenyl (—C$_5$H$_7$), and 5-hexenyl (—CH$_2$CH$_2$CH$_2$C$_2$CH═CH$_2$), but it is not limited thereto.

"Alkynyl" is a hydrocarbon having primary, secondary, tertiary, and/or cyclic carbon atoms, and having at least two unsaturated regions, i.e., one carbon-carbon sp triple bond. For example, an alkynyl group may have 2 to 20 carbon atoms (i.e., C$_2$-C$_{20}$ alkynyl), 2 to 12 carbon atoms (i.e., C$_2$-C$_{12}$ alkynyl), or 2 to 6 carbon atoms (i.e., C$_2$-C$_6$ alkynyl). Examples of a suitable alkenyl group include acetylenic (—C≡CH) and propargyl (—CH$_2$C≡CH), but it is not limited thereto.

"Alkylene" refers to a saturated hydrocarbon group that may be branched, straight, or cyclic and has two valencies derived by a removal of two hydrogen atoms from the same carbon atom or two different carbon atoms of a parent alkane. For example, an alkylene group may have 1 to 20 carbon atoms, 1 to 10 carbon atoms, or 1 to 6 carbon atoms. Examples of a typical alkylene radical include methylene (—CH$_2$—), 1,1-ethylene (—CH(CH$_3$)—), 1,2-ethylene (—CH$_2$CH$_2$—), 1,1-propylene (—CH(CH$_2$CH$_3$)—), 1,2-propylene (—CH$_2$CH(CH$_3$)—), 1,3-propylene (—CH$_2$CH$_2$CH$_2$—), and 1,4-butylene (—CH$_2$CH$_2$CH$_2$CH$_2$—), but it is not limited thereto.

"Alkenylene" refers to an unsaturated hydrocarbon group that may be branched, straight, and/or cyclic and has two valencies derived by a removal of two hydrogen atoms from the same carbon atom or two different carbon atoms of a parent alkene. For example, an alkenylene group may have 1 to 20 carbon atoms, 1 to 10 carbon atoms, or 1 to 6 carbon atoms. Examples of a typical alkenylene group include 1,2-ethylene (—CH═CH—), but it is not limited thereto.

"Alkynylene" refers to an unsaturated hydrocarbon group that is branched, straight, and/or cyclic and has two valencies derived by a removal of two hydrogen atoms from the same carbon atom or two different carbon atoms of a parent alkyne. For example, an alkynylene group may have 1 to 20 carbon atoms, 1 to 10 carbon atoms, or 1 to 6 carbon atoms. Examples of a typical alkynylene radical include acetylenylene (—C≡C—), propargylene (—CHa$_2$C≡C—), and 4-pentynylene (—CH$_2$CH$_2$CH$_2$C≡C—), but it is not limited thereto.

"Aryl" refers to an aromatic hydrocarbon group derived by a removal of one hydrogen atom from the six carbon atoms of a parent aromatic ring system. For example, an aryl group may have 6 to 20 carbon atoms, 6 to 14 carbon atoms, or 6 to 12 carbon atoms. Examples of a typical aryl group include a radical derived from benzene (e.g., phenyl), substituted benzene, substituted or unsubstituted naphthalene, substituted or unsubstituted anthracene, substituted or unsubstituted biphenyl, and the like, but it is not limited thereto.

"Arylalkyl" refers to an acyclic alkyl group in which one hydrogen atom bonded to a carbon atom, typically a terminal or other sp3 carbon atom, is substituted by an aryl group. Examples of a typical arylalkyl group include benzyl, 2-phenylethan-1-yl, naphthylmethyl, 2-naphthylethane-1-yl, naphthobenzyl, 2-naphthophenylethane-1-yl, and the like (each of which is substituted or unsubstituted), but it is not limited thereto. An arylalkyl group may have 7 to 20 carbon atoms. For example, the alkyl moiety thereof may have 1 to 6 carbon atoms, and the aryl moiety thereof may have 6 to 14 carbon atoms.

"Arylalkenyl" refers to an acyclic alkenyl radical in which one of the hydrogen atoms bonded to a carbon atom, typically a terminal or sp3 carbon atom although an sp2 carbon atom is also available, is substituted with an aryl radical. The aryl moiety of the arylalkenyl may be, for example, any aryl group described herein, and the alkenyl moiety of the arylalkenyl may comprise, for example, any of the alkenyl groups described herein. An arylalkenyl group may have 8 to 20 carbon atoms. For example, the alkenyl moiety thereof may have 2 to 6 carbon atoms, and the aryl moiety thereof may have 6 to 14 carbon atoms.

"Cycloalkyl" refers to a saturated monocycle or polycycle that comprises only carbon atoms in the ring. A cycloalkyl group may have 3 to 7 carbon atoms as a monocycle, 7 to 12 carbon atoms as a bicycle, and up to about 20 carbon atoms as a polycycle. A monocyclic cycloalkyl has 3 to 6 ring atoms, more typically 5 or 6 ring atoms. A bicyclic cycloalkyl may have 7 to 12 ring atoms arranged in a bicyclo[4,5], [5,5], [5,6], or [6,6] system or 9 to 10 ring atoms arranged in a bicyclo[5,6] or [6,6] system or in a spiro-bonded ring. Non-limiting examples of a monocyclic cycloalkyl include cyclopropyl, cyclobutyl, cyclopentyl, and cyclohexyl (each of which may be substituted or unsubstituted).

"Arylalkynyl" refers to an acyclic alkynyl group in which one of the hydrogen atoms bonded to a carbon atom, typically a terminal or other sp3 carbon atom, although an sp carbon atom may also be used, is substituted by an aryl group. The aryl moiety of the arylalkynyl may be, for example, any aryl group described herein, and the alkynyl moiety of the arylalkynyl may comprise, for example, any of the alkynyl groups described herein. An arylalkynyl group may have 8 to 20 carbon atoms. For example, the alkynyl moiety thereof may have 2 to 6 carbon atoms, and the aryl moiety thereof may have 6 to 14 carbon atoms.

The term "substituted" with respect to alkyl, alkylene, aryl, arylalkyl, heterocyclyl, and the like, for example, "substituted alkyl," "substituted alkylene," "substituted aryl," "substituted arylalkyl," "substituted heterocyclyl," and "substituted carbocyclyl (e.g., substituted cycloalkyl)," means that at least one hydrogen atom of the alkyl, alkylene, aryl, arylalkyl, heterocyclyl, or carbocyclyl (e.g., cycloalkyl) is each independently substituted by a non-hydrogen substituent. Examples of the typical substituent include —X, —R, —O—, ═O, —OR, —SR, —S—, —NR$_2$, —N+R$_3$, ═NR, —C(X)$_3$, —CN, —OCN, —SCN, —N═C═O, —NCS, —NO, —NO$_2$, ═N—OH, ═N$_2$, —N$_3$, —NHC(═O)R, —C(═O)R, —C(═O)NRR, —S(═O)$_2$O—, —S(═O)$_2$OH, —S(═O)$_2$R, —OS(═O)$_2$OR, —S(═O)$_2$NR, —S(═O)R, —OP(═O)(OR)$_2$, —C(═O)R, alkylene-C(═O)R, —C(S)R, —C(═O)OR, alkylene-C(═O)OR, —C(═O)O—, alkylene-C(═O)O—, —C(═S)OR, —C(═O)SR, —C(═S)SR, —C(═O)NRR, alkylene-C(═O)NRR, —C(═S)NRR, and —C(—NR)NRR, wherein X is each independently halogen such as F, Cl, Br, or I, and R is independently H, alkyl, aryl, arylalkyl, or heterocycle, but it is not limited thereto. The alkylene, alkenylene, and alkynylene groups may also be similarly substituted.

Those skilled in the art will understand that when a moiety such as "alkyl," "aryl," "heterocyclyl," and the like is substituted with at least one substituent, they may optionally be referred to as a moiety of "alkylene," "arylene," "heterocyclylene," or the like (that is, at least one hydrogen atom of the parent "alkyl," "aryl," or "heterocyclyl" moiety is substituted by the substituent as described herein). If the moiety of "alkyl," "aryl," "heterocyclyl," or the like is described herein as "substituted" or depicted in the drawings as substituted (or optionally substituted, for example, the number of substituents is 0 or a positive number), the term "alkyl," "aryl," "heterocyclyl," or the like should be understood to be interchangeable with "alkylene," "arylene," "heterocyclylene," or the like.

Those skilled in the art will recognize that the substituents and other moieties of the compound of Formula 1 should be selected so as to provide a compound that is sufficiently stable as a pharmaceutically useful compound that can be formulated into an acceptably stable pharmaceutical composition. The compound of Formula 1 having such stability is to be understood to fall within the scope of the present invention.

"Heteroalkyl" refers to an alkyl group in which at least one carbon atom is substituted by a heteroatom such as O, N, or S. For example, if a carbon atom of the alkyl group attached to a parent molecule is substituted by a heteroatom (e.g., O, N, or S), the resulting heteroalkyl group may be an alkoxy group (e.g., —OCH$_3$), an amine group (e.g., —NHCH$_3$, —N(CH$_3$)$_2$, or the like), or a thioalkyl group (e.g., —SCH$_3$), respectively. If a non-terminal carbon atom of the alkyl group that is not attached to a parent molecule is substituted by a heteroatom (e.g., O, N, or S), the resulting heteroalkyl group may be an alkyl ether (e.g., —CH$_2$CH$_2$—O—CH$_3$ or the like), an alkylamine (e.g., —CH$_2$NHCH$_3$, —CH$_2$N(CH$_3$)$_2$, or the like), or a thioalkyl ether (e.g., —CH$_2$—S—CH$_3$), respectively. If the terminal carbon atom of the alkyl group is substituted by a heteroatom (for example, O, N, or S), the resulting heteroalkyl group may be a hydroxyalkyl group (e.g., —CH$_2$CH$_2$—OH), an aminoalkyl group (e.g., —CH$_2$NH$_2$), or an alkylthiol group (e.g., —CH$_2$CH$_2$—SH), respectively. For example, a heteroalkyl group may have 1 to 20 carbon atoms, 1 to 10 carbon atoms, or 1 to 6 carbon atoms. A C$_1$-C$_6$ heteroalkyl group refers to a heteroalkyl group having 1 to 6 carbon atoms.

The term "heterocycle" or "heterocyclyl" used herein includes those described in the documents such as Paquette, Leo A., Principles of Modern Heterocyclic Chemistry (W. A. Benjamin, New York, 1968), specifically Chapters 1, 3, 4, 6, 7, and 9; The Chemistry of Heterocyclic Compounds, A Series of Monographs (John Wiley & Sons, New York, from 1950 to the present), specifically Volumes 13, 14, 16, 19, and 28; and J. Am. Chem. Soc. (1960) 82:5566, but it is not limited thereto. In a specific embodiment of the present invention, "heterocycle" includes "carbocycle" as defined herein in which at least one (e.g., 1, 2, 3, or 4) carbon atom is substituted by a heteroatom (e.g., O, N, or S). The term "heterocycle" or "heterocyclyl" includes saturated, partially unsaturated, and aromatic rings (i.e., a heteroaromatic ring). Substituted heterocycle, for example, includes a heterocyclic ring substituted with any of the substituents disclosed herein, inclusive of a carbonyl group.

Examples of heterocycles include pyridyl, dihydropyridyl, tetrahydropyridyl(piperidyl), thiazolyl, tetrahydrothiophenyl, sulfur-oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidinyl, pyrrolidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, azocynyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxatinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, phtheridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, isothinoyl, and bis-tetrahydrofuranyl (each of which may be substituted or unsubstituted), but it is not limited thereto.

As an example, a carbon-bonded heterocycle may be bonded at the 2, 3, 4, 5, or 6-position of pyrazine, at the 3, 4, 5, or 6-position of pyridazine, at the 2, 4, 5, or 6-position of pyrimidine, at the 2, 3, 5, or 6-position of pyrazine, at the 2, 3, 4, or 5-position of furan, tetrahydrofuran, thiofuran, thiophene, pyrrole, or tetrahydropyrrole, at the 2, 4, or 5-position of oxazole, imidazole, or thiazole, at the 3, 4, or 5-position of isoxazole, pyrazole, or isothiazole, at the 2 or 3-position of aziridine, at the 2, 3, or 4-position of azetidine, at the 2, 3, 4, 5, 6, 7, or 8-position of quinoline, or at the 1, 3, 4, 5, 6, 7, or 8-position of isoquinoline, but it is not limited thereto. More typically, examples of a carbon-bonded heterocycle include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, and 5-thiazolyl (each of which may be substituted or unsubstituted).

As an example, a nitrogen-bonded heterocycle may be bonded at the 1-position of aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, or 1H-indazole, at the 2-position of isoindole or isoindoline, at the 4-position of morpholine, and at the 9-position of carbazole or β-carboline (each of which may be substituted or unsubstituted), but it is not limited thereto. More typically, examples of a nitrogen-bonded heterocycle include 1-aziridinyl, 1-azetidyl, 1-pyrrolyl, 1-imidazolyl, 1-pyrazolyl, and 1-piperidinyl (each of which may be substituted or unsubstituted).

"Heterocyclylalkyl" refers to an acyclic alkyl radical in which one hydrogen atom bonded to a carbon atom, typically a terminal or sp3 carbon atom, is substituted by a heterocyclyl radical (i.e., a heterocyclyl-alkylene moiety). Examples of a typical heterocyclylalkyl group include heterocyclyl-CH$_2$—, 2-(heterocyclyl)ethan-1-yl, and the like, but it is not limited thereto. The "heterocyclyl" moiety thereof used herein includes those described in the document such as "Principles of Modern Heterocyclic Chemistry" and any heterocyclyl group described above. Those skilled in the art will understand that if the resulting group is chemically stable, the heterocyclyl group may be attached to the alkyl moiety of the heterocyclylalkyl through a carbon-to-carbon bond or a carbon-to-heteroatom bond. A heterocyclylalkyl group may have 2 to 20 carbon atoms. For example, the alkyl moiety of the heterocyclylalkyl group may have 1 to 6 carbon atoms, and the heterocyclyl moiety thereof may have 1 to 14 carbon atoms. Examples of the heterocyclylalkyl include a 5-membered heterocycle containing sulfur, oxygen, and/or nitrogen such as thiazolylmethyl, 2-thiazolylethan-1-yl, imidazolylmethyl, oxazolylmethyl, thiadiazolylmethyl, and the like; and a 6-membered heterocycle containing sulfur, oxygen, and/or nitrogen such as piperidinylmethyl, piperazinylmethyl, morpholinylmethyl, pyridinylmethyl, pyridazylmethyl, pyrimidylmethyl, pyrazinylmethyl, and the like (each of which may be substituted or unsubstituted), but it is not limited thereto.

"Heterocyclylalkenyl" refers to an acyclic alkenyl radical in which one of the hydrogen atoms bonded to a carbon atom, typically a terminal or sp3 carbon atom (although an sp2 carbon atom may also be used), is substituted by a heterocyclyl radical (i.e., a heterocyclyl-alkenylene moiety). The heterocyclyl moiety of the heterocyclylalkenyl group includes those described in the document such as "Principles of Modern Heterocyclic Chemistry" and any heterocyclyl group described herein. The alkenyl moiety of the heterocyclylalkenyl group includes any alkenyl group described herein. Those skilled in the art will understand that if the resulting group is chemically stable, the heterocyclyl group may be attached to the alkenyl moiety of the heterocyclylalkenyl via a carbon-to-carbon bond or a carbon-to-heteroatom bond. A heterocyclylalkenyl group may have 3 to 20 carbon atoms. For example, the alkenyl moiety of the heterocyclylalkenyl group may have 2 to 6 carbon atoms, and the heterocyclyl moiety thereof may have 1 to 14 carbon atoms.

"Heterocyclylalkynyl" refers to an acyclic alkynyl radical in which one of the hydrogen atoms bonded to a carbon atom, typically a terminal or sp3 carbon atom (although an sp carbon atom may also be used), is substituted by a heterocyclyl radical (i.e., a heterocyclyl-alkynylene moiety). The heterocyclyl moiety of the heterocyclylalkynyl group includes those described in the document such as "Principles of Modern Heterocyclic Chemistry" and any heterocyclyl group described herein. The alkynyl moiety of the heterocyclylalkynyl group includes any alkynyl group described herein. Those skilled in the art will understand that if the resulting group is chemically stable, the heterocyclyl group may be attached to the alkynyl moiety of the heterocyclylalkynyl via a carbon-to-carbon bond or a carbon-to-heteroatom bond. A heterocyclylalkynyl group may have 3 to 20 carbon atoms. For example, the alkynyl moiety of the heterocyclylalkynyl group may have 2 to 6 carbon atoms, and the heterocyclyl moiety thereof may have 1 to 14 carbon atoms.

"Heteroaryl" refers to an aromatic heterocyclyl containing at least one heteroatom in the ring. Non-limiting examples of a suitable heteroatom that may be contained in the aromatic ring include oxygen, sulfur, and nitrogen. Non-limiting examples of a heteroaryl ring include all of those enumerated in the definition of "heterocyclyl" herein, inclusive of pyridinyl, pyrrolyl, oxazolyl, indolyl, isoindolyl, furinyl, furanyl, thienyl, benzofuranyl, benzothiophenyl, carbazolyl, imidazolyl, thiazolyl, isoxazolyl, pyrazolyl, isothiazolyl, quinolyl, isoquinolyl, pyridazyl, pyrimidyl, pyrazyl, and the like (each of which may be substituted or unsubstituted).

"Carbocycle" or "carbocyclyl" refers to a saturated, partially unsaturated, or aromatic ring having 3 to 7 carbon atoms as a monocycle, 7 to 12 carbon atoms as a bicycle, and up to about 20 carbon atoms as a polycycle. A monocyclic carbocycle has 3 to 6 ring atoms, more typically 5 or 6 ring atoms. A bicyclic carbocycle has 7 to 12 ring atoms arranged in a bicyclo[4,5], [5,5], [5,6], or [6,6] system or 9 to 10 ring atoms arranged in a bicyclo[5,6] or [6,6] system. Examples of a monocyclic or bicyclic carbocycle include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, phenyl, and naphthyl (each of which may be substituted or unsubstituted).

"Acyl" refers to —C(=O)-alkyl, —C(=O)-carbocycle (which is substituted or unsubstituted), and —C(=O)-heterocycle (which is substituted or unsubstituted), wherein the alkyl, carbocycle, or heterocycle moiety is as defined herein. Non-limiting examples of "acyl" include —C(=O)CH$_3$, —C(=O)CH$_2$CH$_3$, —C(=O)CH(CH$_3$)$_2$, —C(=O)C(CH$_3$)$_3$, —C(=O)-phenyl (which is substituted or unsubstituted), —C(=O)-cyclopropyl (which is substituted or unsubstituted), —C(=O)-cyclobutyl (which is substituted or unsubstituted), —C(=O)-cyclopentyl (which is substituted or unsubstituted), —C(=O)-cyclohexyl (which is substituted or unsubstituted), and —C(=O)-pyridyl (which is substituted or unsubstituted).

"Arylheteroalkyl" refers to a heteroalkyl as defined herein, wherein a hydrogen atom (which may be attached to either a carbon atom or a heteroatom) is substituted by an aryl group as defined herein. If the resulting group is chemically stable, the aryl group may be attached to a carbon atom of the heteroalkyl group or the heteroatom of the heteroalkyl group. For example, an arylheteroalkyl group may have a formula of -alkylene-O-aryl, -alkylene-O-alkylene-aryl, -alkylene-NH-aryl, -alkylene-NH-alkylene-aryl, -alkylene-S-aryl, -alkylene-S-alkylene-aryl, or the like. In addition, any alkylene moiety in the above formulae may be further substituted with any of the substituents defined or exemplified herein.

"Heteroarylalkyl" refers to an alkyl group as defined herein, wherein a hydrogen atom is substituted by a heteroaryl group as defined herein. Non-limiting examples of heteroarylalkyl include —CH$_2$-pyridinyl, —CH$_2$-pyrrolyl, —CH$_2$-oxazolyl, —CH$_2$-indolyl, —CH$_2$-isoindolyl, —CH$_2$-furinyl, —CH$_2$-furanyl, —CH$_2$-thienyl, —CH$_2$-benzofuranyl, —CH$_2$-benzothiophenyl, —CH$_2$-carbazolyl, —CH$_2$-imidazolyl, —CH$_2$— thiazolyl, —CH$_2$-isoxazolyl, —CH$_2$-pyrazolyl, —CH$_2$-isothiazolyl, —CH$_2$-quinolyl, —CH$_2$-isoquinolyl, —CH$_2$-pyridazyl, —CH$_2$-pyrimidyl, —CH$_2$-pyrazyl, —CH(CH$_3$)-pyridinyl, —CH(CH$_3$)-pyrrolyl, —CH(CH$_3$)-oxazolyl, —CH(CH$_3$)-indolyl, —CH(CH$_3$)-isoindolyl, —CH(CH$_3$)-furinyl, —CH(CH$_3$)-furanyl, —CH(CH$_3$)-thienyl, —CH(CH$_3$)-benzofuranyl, —CH(CH$_3$)-benzothiophenyl, —CH(CH$_3$)-carbazolyl, —CH(CH$_3$)-imidazolyl, —CH(CH$_3$)-thiazolyl, —CH(CH$_3$)-isoxazolyl, —CH(CH$_3$)-pyrazolyl, —CH(CH$_3$)-isothiazolyl, —CH(CH$_3$)-quinolyl, —CH(CH$_3$)-isoquinolyl, —CH(CH$_3$)-pyridazyl, —CH(CH$_3$)-pyrimidyl, —CH(CH$_3$)-pyrazyl, and the like.

"Silyloxy" refers to the group —O—SiR$_3$, wherein R comprises alkyl, aryl (which is substituted or unsubstituted), heteroaryl (which is substituted or unsubstituted), or a combination thereof. Non-limiting examples of silyloxy include —O—Si(CH$_3$)$_3$, —O—Si(CH$_3$)$_2$tBu, —O—Si(tBu)$_2$CH$_3$, —O—Si(tBu)$_3$, —O—Si(CH$_3$)$_2$Ph, —O—Si(Ph)$_2$CH$_3$, and —O—Si(Ph)$_3$.

The term "optionally substituted" refers to a particular moiety (e.g., an optionally substituted aryl group) of the compound of Formula 1 that has one, two, or more substituents.

The term "ester thereof" refers to any ester of a compound wherein any —COOH functional group of the molecule is substituted to a —COOR functional group or any —OH functional group of the molecule is substituted to a —C(=O)OR. Here, the R moiety of the ester may be any carbon-containing group that forms a stable ester moiety, which includes, but is not limited to, alkyl, alkenyl, alkynyl, cycloalkyl, cycloalkylalkyl, aryl, arylalkyl, heterocyclyl, heterocyclylalkyl, and substituted derivatives thereof. Examples of the ester may also include an ester such as those described above of a "tautomeric enol" as described below.

In the present invention, the compound represented by the above Formula 1 may be an optical isomer type L or D.

The compound represented by the above Formula 1 may be represented by Formula 1-1 when $R^2$ is H, $R^3$ is $R^4$ is —OH, $R^5$ is H, $R^6$ is
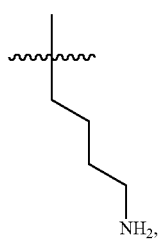 [SMILES: *CCCCN]
$R^7$ is
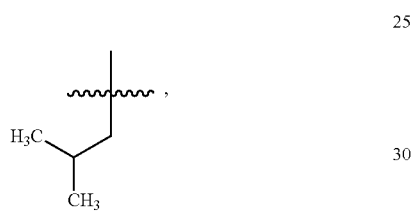
$R^8$ is H, and $R^9$ is H. Further, the compound represented by the following Formula 1-1 may be an optical isomer type L or D.
[Formula 1-1]
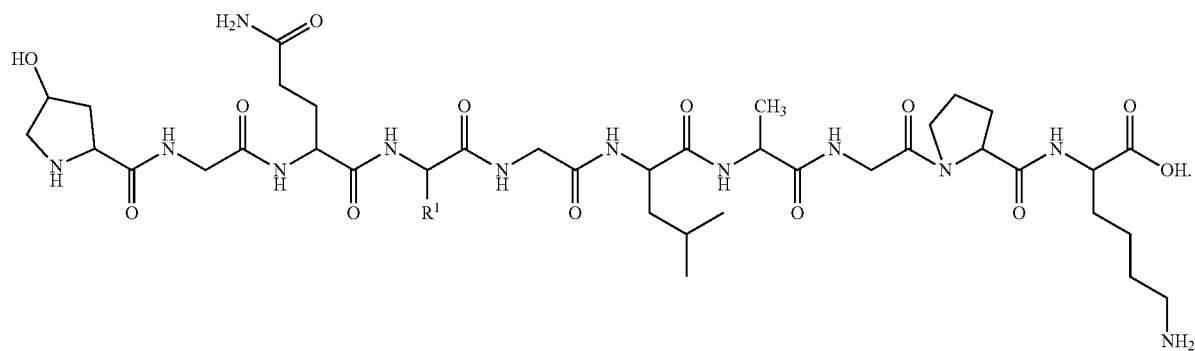
$R^1$ may be one selected from the group consisting of substituted or unsubstituted $C_{1-6}$ alkyl,
-continued
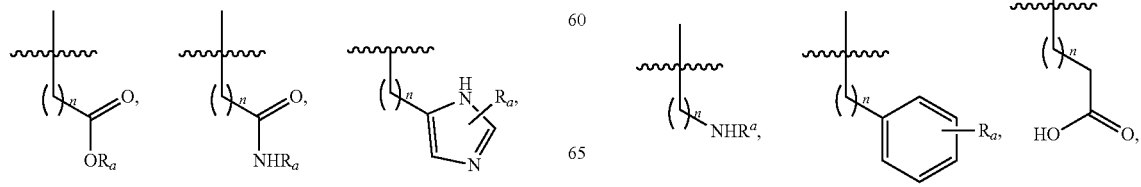

23
-continued
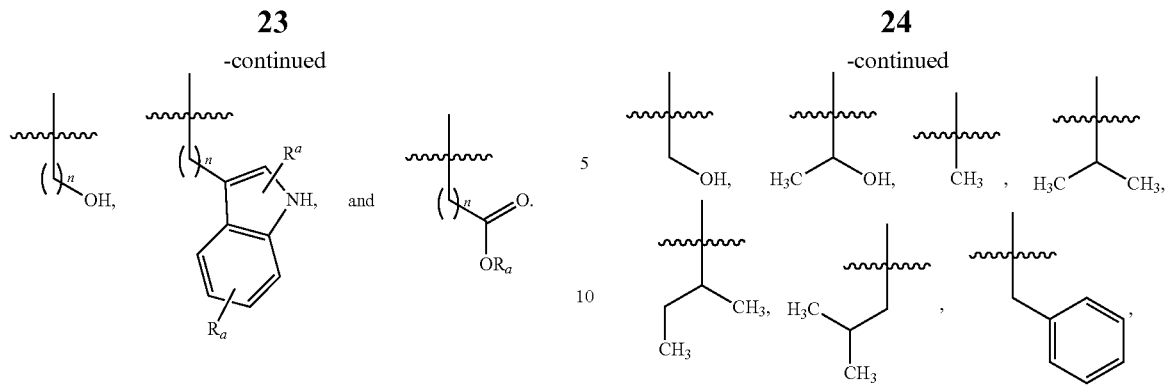
Here, n may be an integer of 1 to 10, but it is not limited thereto. $R_a$ may be hydrogen or $C_{1-6}$ alkyl.
Specifically, $R^1$ may be one selected from the group consisting of
24
-continued
More specifically, the compound may be a compound described in Table 1 below.
TABLE 1
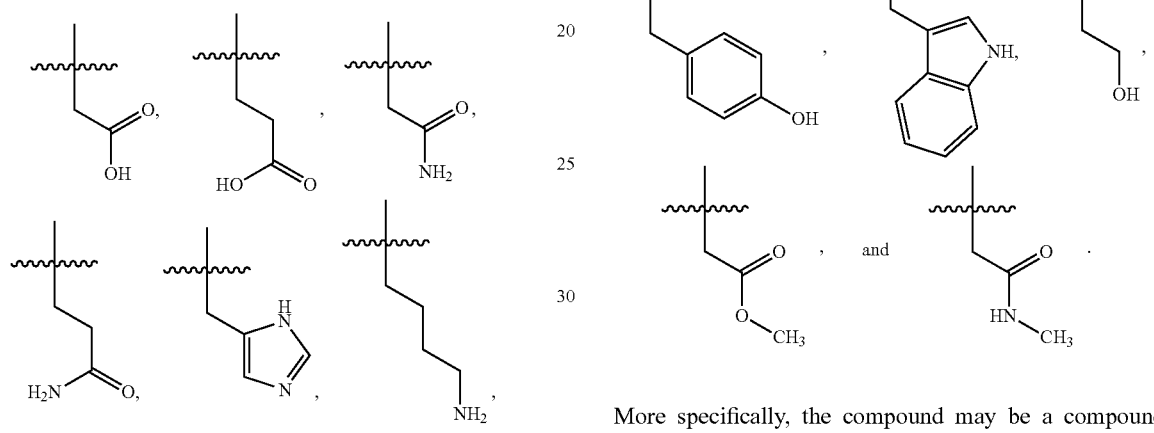
| YDE-001 | | | | | | | | | SEQ ID NO: 1 |
|---|---|---|---|---|---|---|---|---|---|
| Hyp (2S,4R) | Gly | Gln | Glu | Gly | Leu | Ala | Gly | Pro | Lys |
| YDE-002 | | | | | | | | | SEQ ID NO: 2 |
|---|---|---|---|---|---|---|---|---|---|
| Hyp (2S,4R) | Gly | Gln | Asn | Gly | Leu | Ala | Gly | Pro | Lys |

TABLE 1-continued
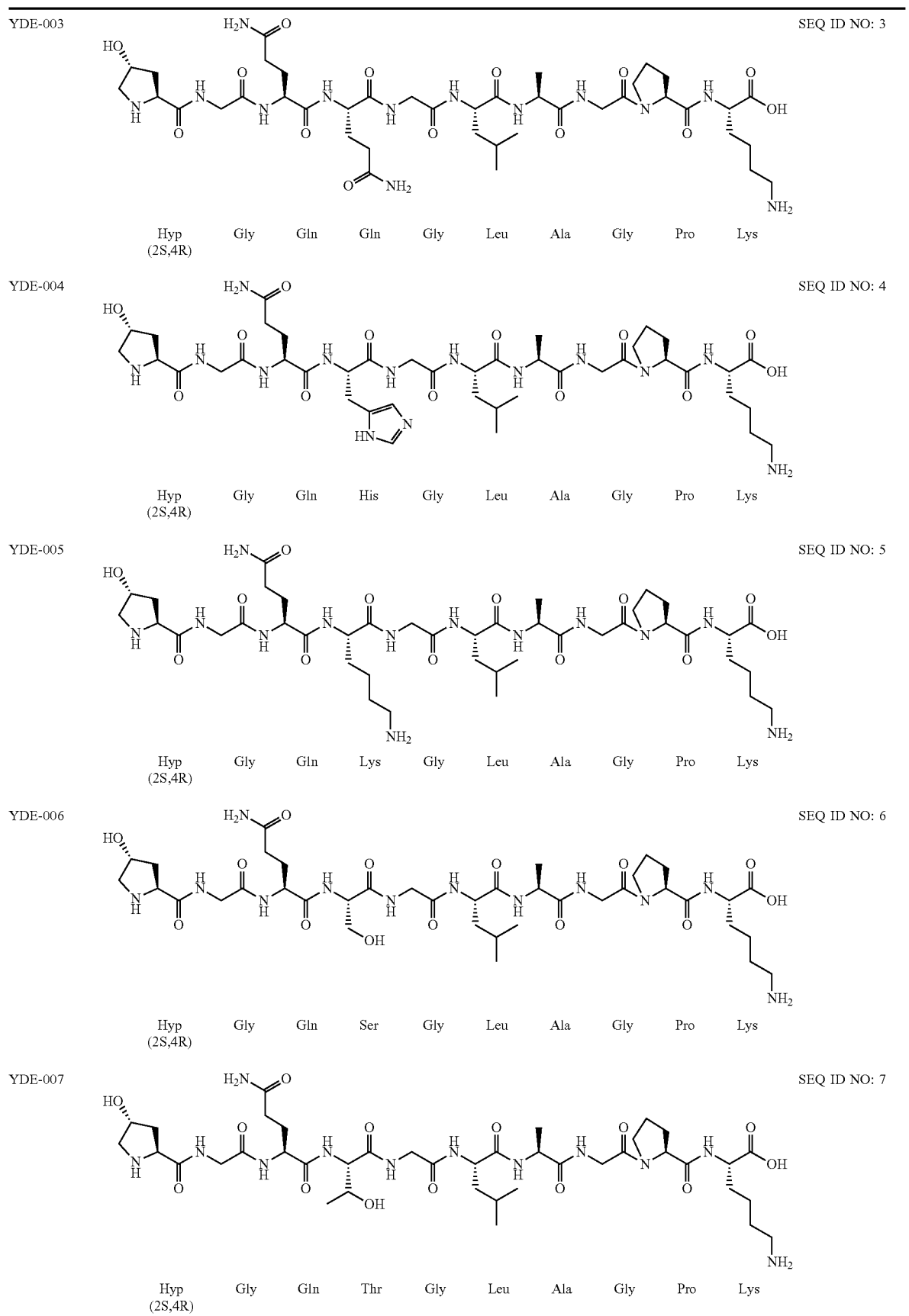

TABLE 1-continued
YDE-008  SEQ ID NO: 8
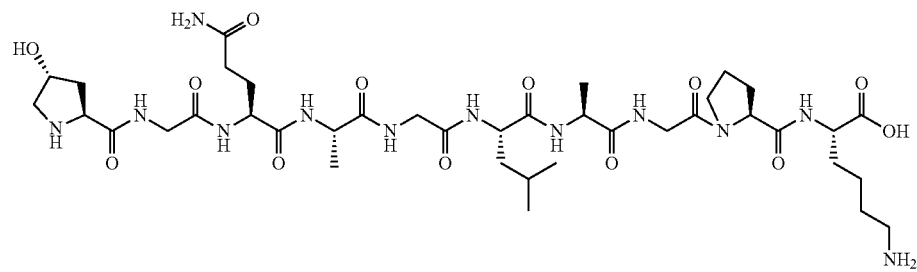
| Hyp (2S,4R) | Gly | Gln | Ala | Gly | Leu | Ala | Gly | Pro | Lys |
YDE-009  SEQ ID NO: 9
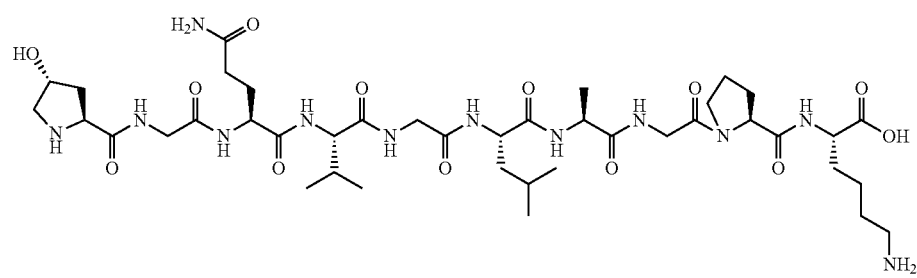
| Hyp (2S,4R) | Gly | Gln | Val | Gly | Leu | Ala | Gly | Pro | Lys |
YDE-010  SEQ ID NO: 10
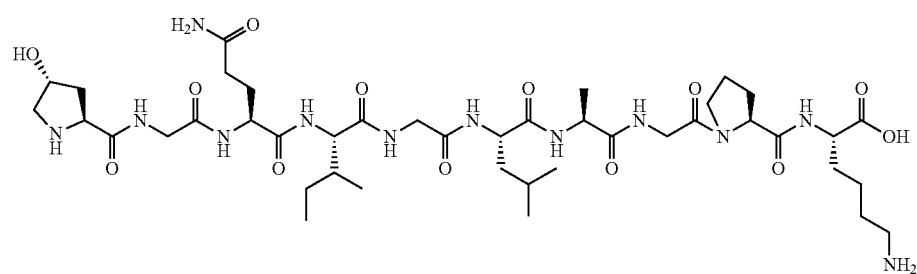
| Hyp (2S,4R) | Gly | Gln | Ile | Gly | Leu | Ala | Gly | Pro | Lys |
YDE-011  SEQ ID NO: 11
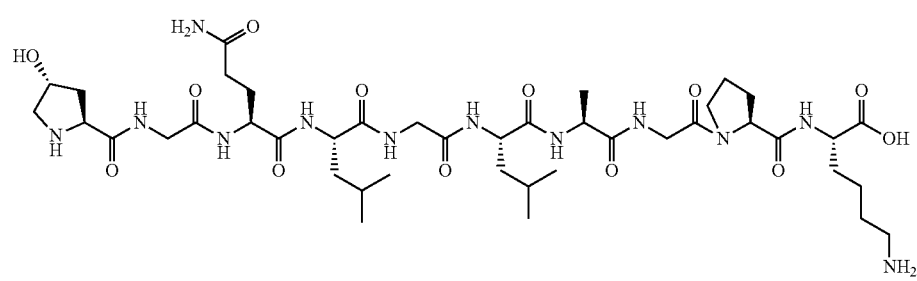
| Hyp (2S,4R) | Gly | Gln | Leu | Gly | Leu | Ala | Gly | Pro | Lys |

TABLE 1-continued
YDE-012  SEQ ID NO: 12
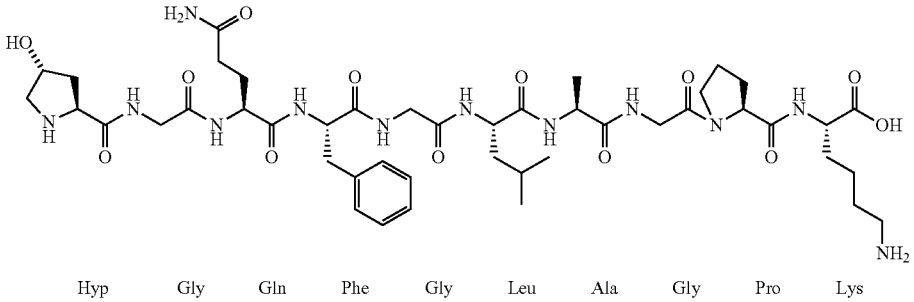
| Hyp (2S,4R) | Gly | Gln | Phe | Gly | Leu | Ala | Gly | Pro | Lys |
YDE-013  SEQ ID NO: 13
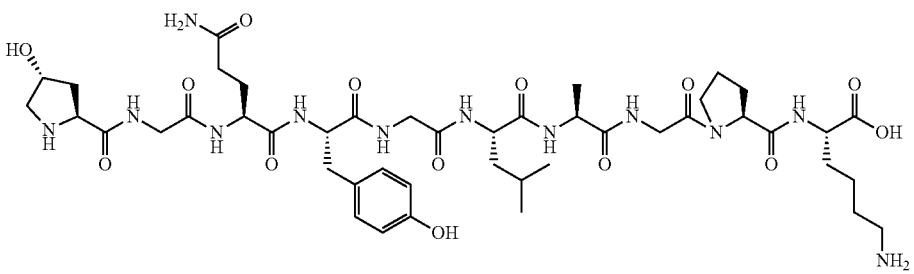
| Hyp (2S,4R) | Gly | Gln | Tyr | Gly | Leu | Ala | Gly | Pro | Lys |
YDE-014  SEQ ID NO: 14
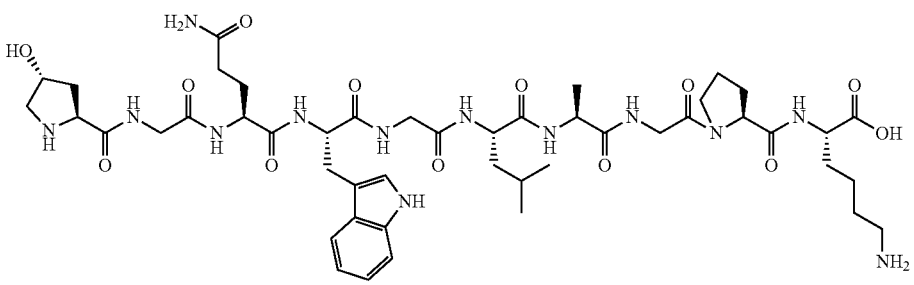
| Hyp (2S,4R) | Gly | Gln | Trp | Gly | Leu | Ala | Gly | Pro | Lys |
YDE-026  SEQ ID NO: 15
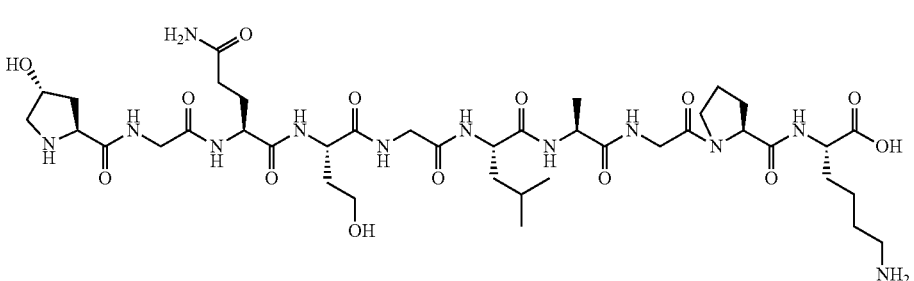
| Hyp (2S,4R) | Gly | Gln | Homo-Ser | Gly | Leu | Ala | Gly | Pro | Lys |

TABLE 1-continued
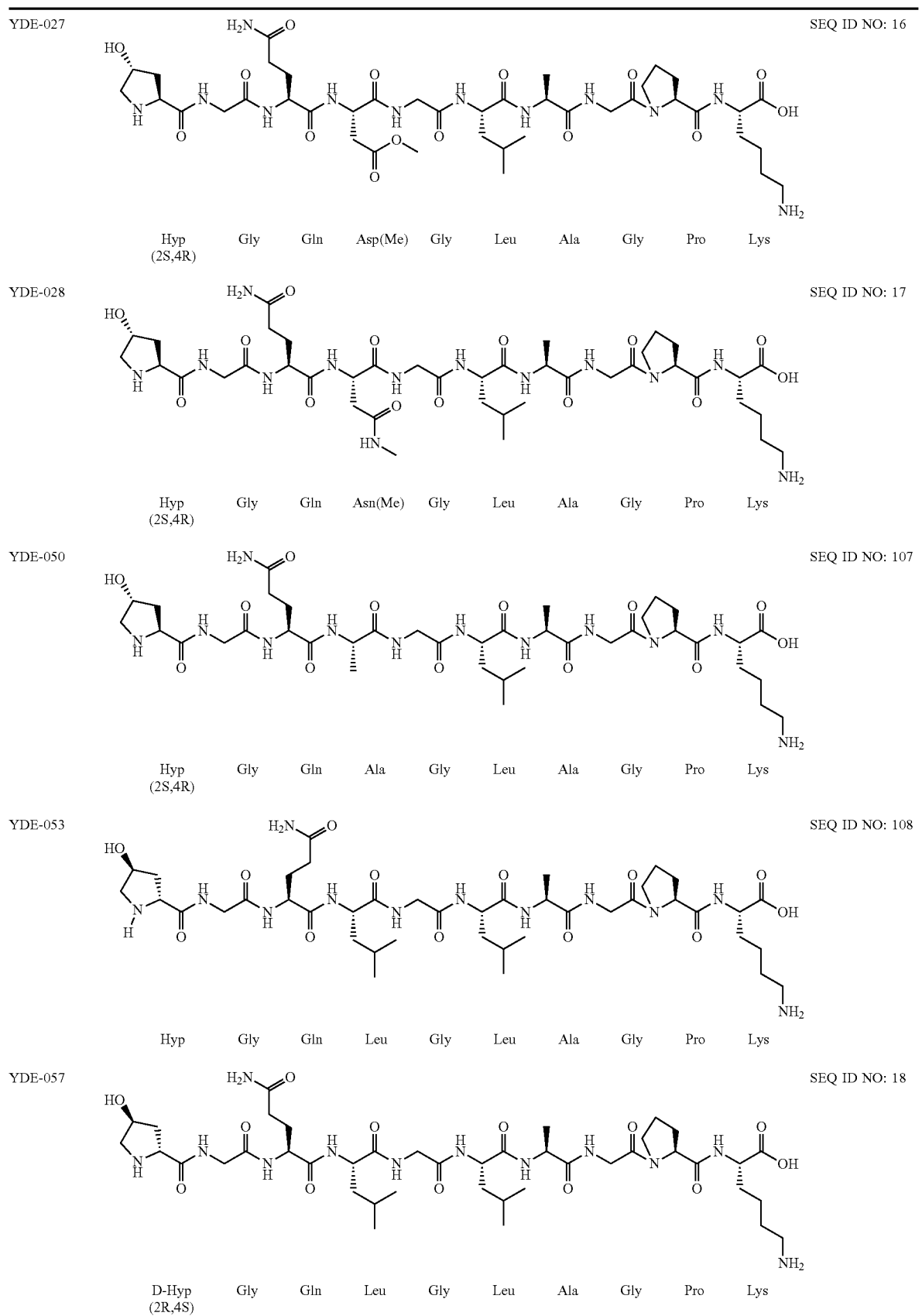
YDE-027 SEQ ID NO: 16
Hyp(2S,4R) Gly Gln Asp(Me) Gly Leu Ala Gly Pro Lys
YDE-028 SEQ ID NO: 17
Hyp(2S,4R) Gly Gln Asn(Me) Gly Leu Ala Gly Pro Lys
YDE-050 SEQ ID NO: 107
Hyp(2S,4R) Gly Gln Ala Gly Leu Ala Gly Pro Lys
YDE-053 SEQ ID NO: 108
Hyp Gly Gln Leu Gly Leu Ala Gly Pro Lys
YDE-057 SEQ ID NO: 18
D-Hyp(2R,4S) Gly Gln Leu Gly Leu Ala Gly Pro Lys TABLE 1-continued

YDE-058  SEQ ID NO: 19

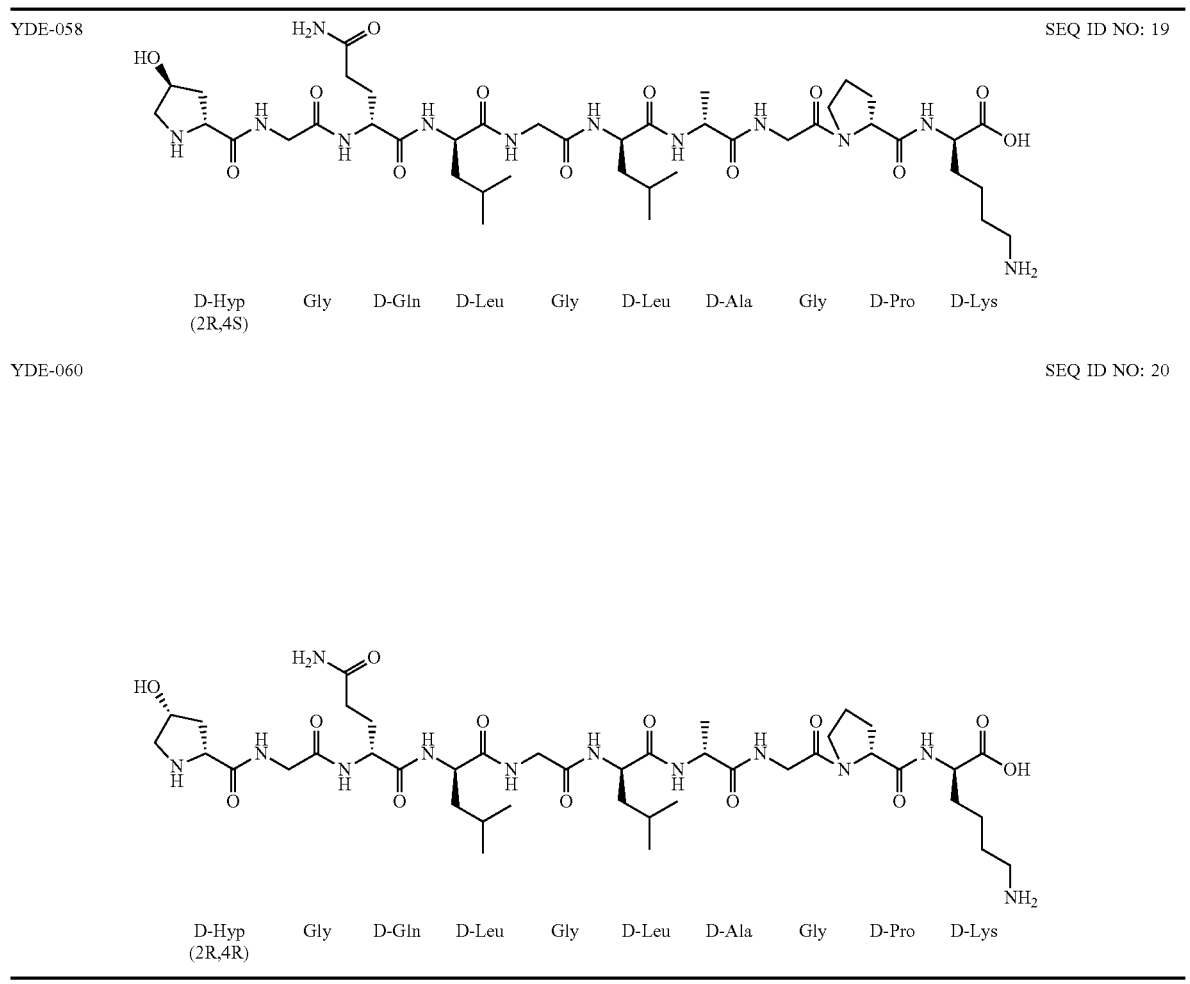

| D-Hyp (2R,4S) | Gly | D-Gln | D-Leu | Gly | D-Leu | D-Ala | Gly | D-Pro | D-Lys |

YDE-060  SEQ ID NO: 20

| D-Hyp (2R,4R) | Gly | D-Gln | D-Leu | Gly | D-Leu | D-Ala | Gly | D-Pro | D-Lys |

The compound represented by the above Formula 1 may be represented by Formula 1-2 when $R^1$ is

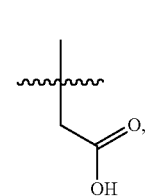 [SMILES: *CC(=O)O]

$R^3$ is

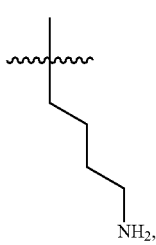 [SMILES: *CCCCN]

$R^4$ is —OH, $R^5$ is H, $R^6$ is

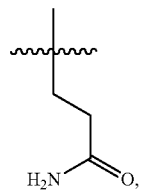

$R^7$ is

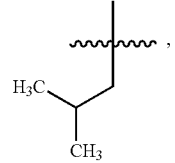

$R^8$ is H, and $R^9$ is H. Further, the compound represented by the following Formula 1-2 may be an optical isomer type L or D.

[Formula 1-2]

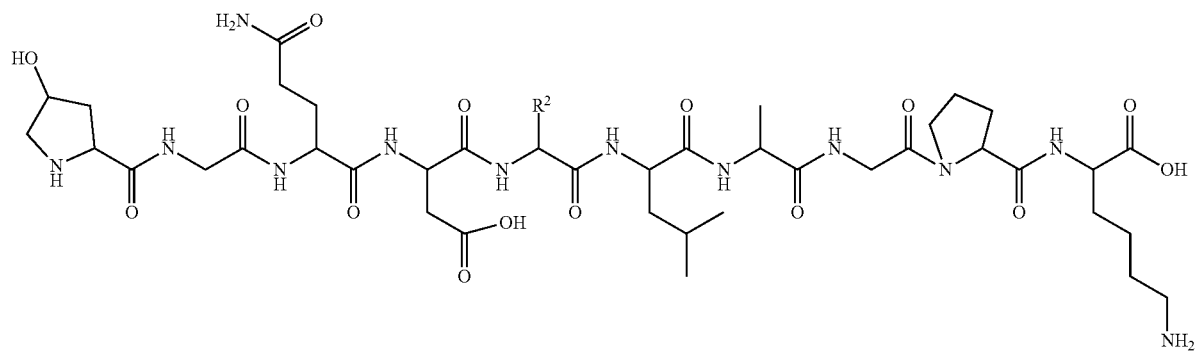

In addition, R² may be one selected from the group consisting of hydrogen, substituted or unsubstituted $C_{1-6}$ alkyl,

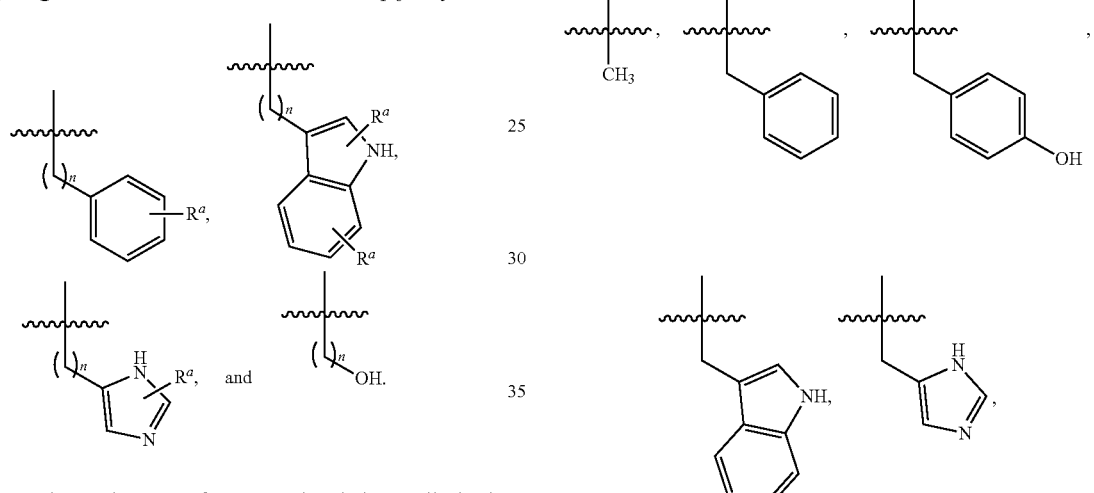

Here, n may be an integer of 1 to 10, but it is not limited thereto. $R_a$ may be hydrogen or $C_{1-6}$ alkyl.

Specifically, R² may be one selected from the group consisting of

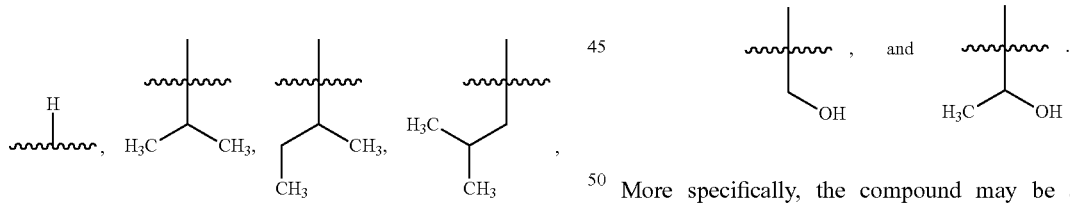

More specifically, the compound may be a compound described in Table 2 below.

TABLE 2

| YDE-015 | | | | | | | | | | SEQ ID NO: 21 |
|---|---|---|---|---|---|---|---|---|---|---|
| 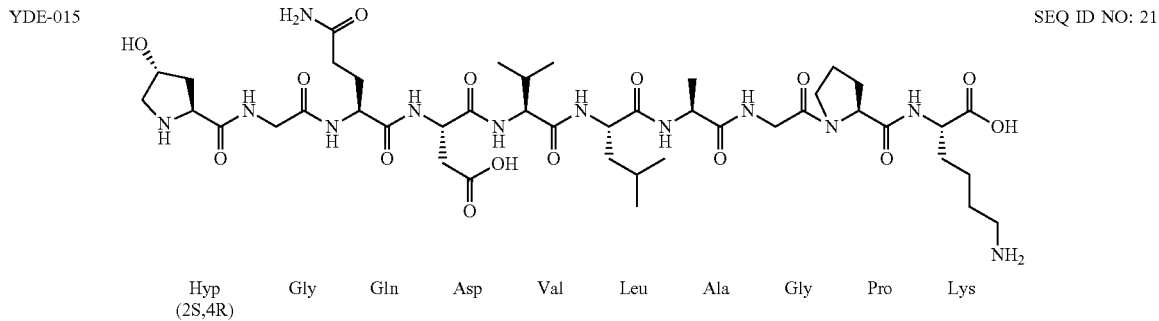 | | | | | | | | | | |
| Hyp (2S,4R) | Gly | Gln | Asp | Val | Leu | Ala | Gly | Pro | Lys | |

TABLE 2-continued
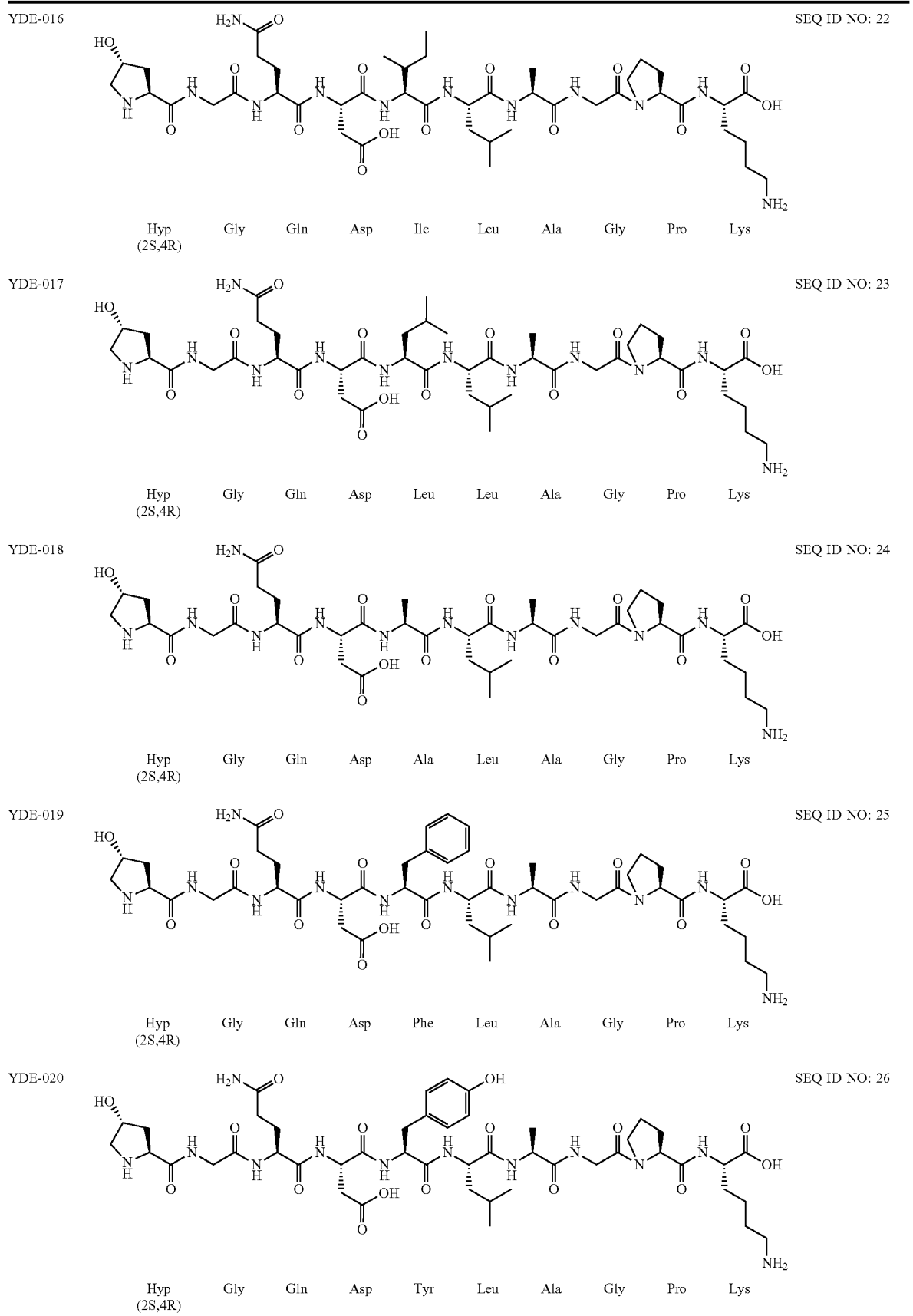

TABLE 2-continued
YDE-021  SEQ ID NO: 27
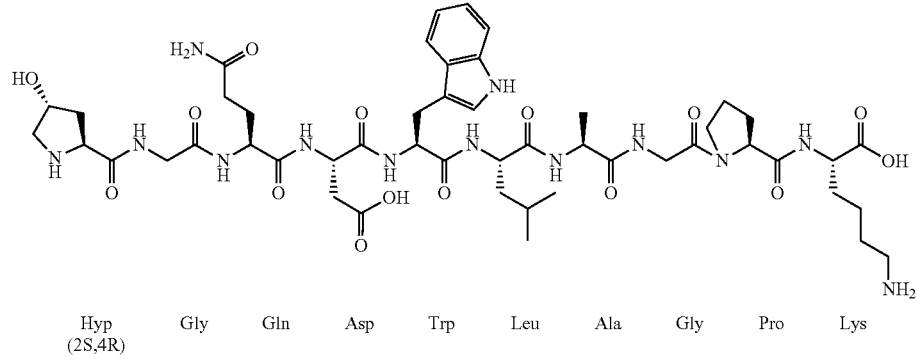 [SMILES: CC(C)C[C@H](NC(=O)[C@H](Cc1c[nH]c2ccccc12)NC(=O)[C@H](CC(=O)O)NC(=O)[C@H](CCC(N)=O)NC(=O)CNC(=O)[C@@H]1C[C@@H](O)CN1)C(=O)N[C@@H](C)C(=O)NCC(=O)N1CCC[C@H]1C(=O)N[C@@H](CCCCN)C(=O)O]
| Hyp (2S,4R) | Gly | Gln | Asp | Trp | Leu | Ala | Gly | Pro | Lys |
YDE-022  SEQ ID NO: 28
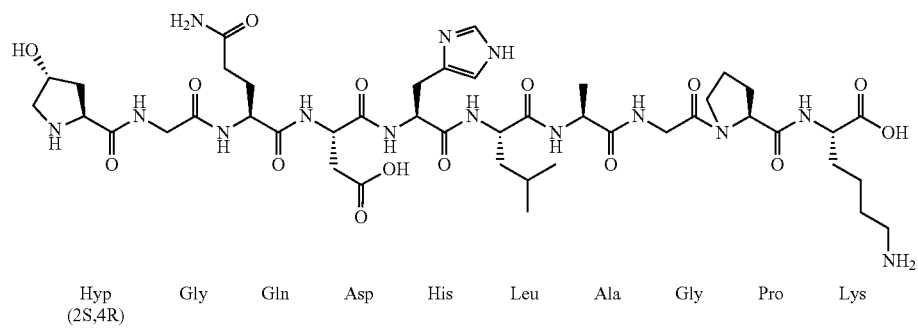 [SMILES: CC(C)C[C@H](NC(=O)[C@H](Cc1c[nH]cn1)NC(=O)[C@H](CC(=O)O)NC(=O)[C@H](CCC(N)=O)NC(=O)CNC(=O)[C@@H]1C[C@@H](O)CN1)C(=O)N[C@@H](C)C(=O)NCC(=O)N1CCC[C@H]1C(=O)N[C@@H](CCCCN)C(=O)O]
| Hyp (2S,4R) | Gly | Gln | Asp | His | Leu | Ala | Gly | Pro | Lys |
YDE-023  SEQ ID NO: 29
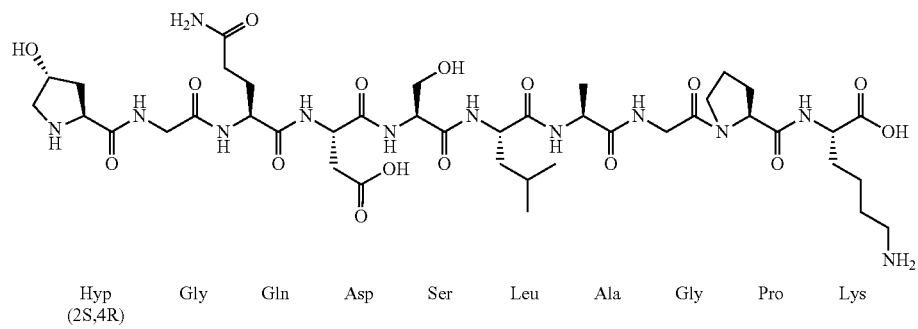 [SMILES: CC(C)C[C@H](NC(=O)[C@H](CO)NC(=O)[C@H](CC(=O)O)NC(=O)[C@H](CCC(N)=O)NC(=O)CNC(=O)[C@@H]1C[C@@H](O)CN1)C(=O)N[C@@H](C)C(=O)NCC(=O)N1CCC[C@H]1C(=O)N[C@@H](CCCCN)C(=O)O]
| Hyp (2S,4R) | Gly | Gln | Asp | Ser | Leu | Ala | Gly | Pro | Lys |
YDE-024  SEQ ID NO: 30
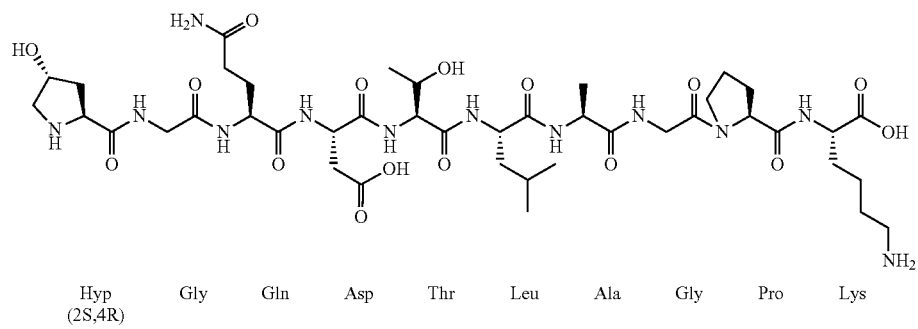 [SMILES: CC(C)C[C@H](NC(=O)[C@@H](NC(=O)[C@H](CC(=O)O)NC(=O)[C@H](CCC(N)=O)NC(=O)CNC(=O)[C@@H]1C[C@@H](O)CN1)C(C)O)C(=O)N[C@@H](C)C(=O)NCC(=O)N1CCC[C@H]1C(=O)N[C@@H](CCCCN)C(=O)O]
| Hyp (2S,4R) | Gly | Gln | Asp | Thr | Leu | Ala | Gly | Pro | Lys |

The compound represented by the above Formula 1 may be represented by Formula 1-3 when $R^3$ is
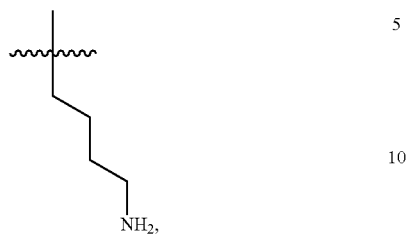
$R^4$ is —OH, $R^5$ is H, $R^6$ is
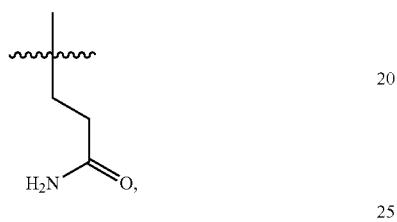
$R^7$ is
$R^8$ is H, and $R^9$ is H. Further, the compound represented by the following Formula 1-3 may be an optical isomer type L or D.
[Formula 1-3]
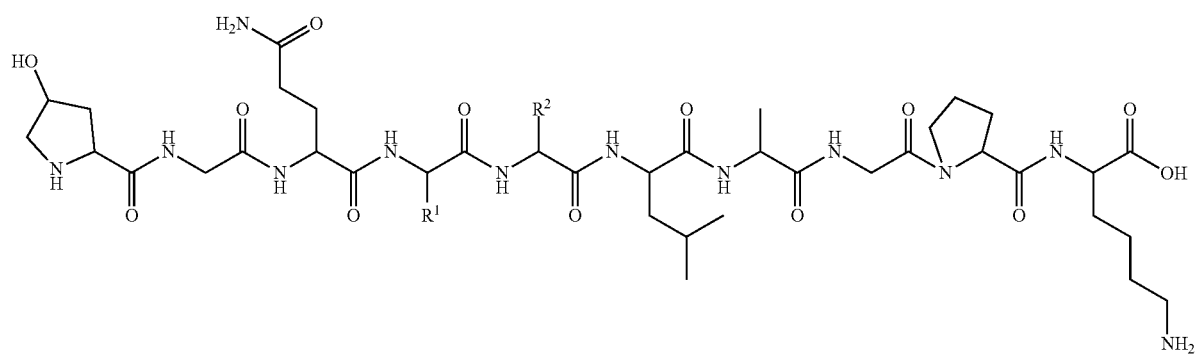

$R^1$ may be $C_{1-6}$ alkyl. Specifically, $R^1$ may be

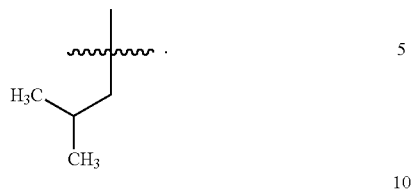

$R^2$ may be $C_{1-6}$ alkyl. Specifically, $R^2$ may be

More specifically, the compound may be a compound described in Table 3 below.

TABLE 3

| YDE-051 | | | | | | | | | | SEQ ID NO: 32 |
|---|---|---|---|---|---|---|---|---|---|---|
| | Hyp (2S,4R) | Gly | Gln | Leu | Ala | Leu | Ala | Gly | Pro | Lys |

The compound represented by the above Formula 1 may be represented by Formula 1-4 when $R^1$ is

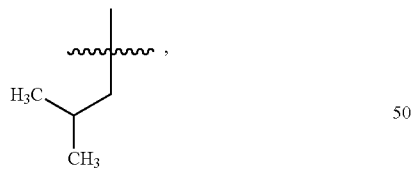

$R^2$ is H, $R^4$ is —OH, $R^5$ is H, $R^6$ is

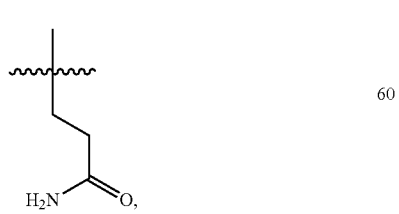

$R^7$ is $R^8$ is H, and $R^9$ is H. Further, the compound represented by the following Formula 1-4 may be an optical isomer type L or D.

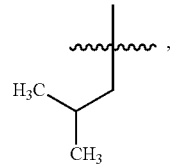

[Formula 1-4]

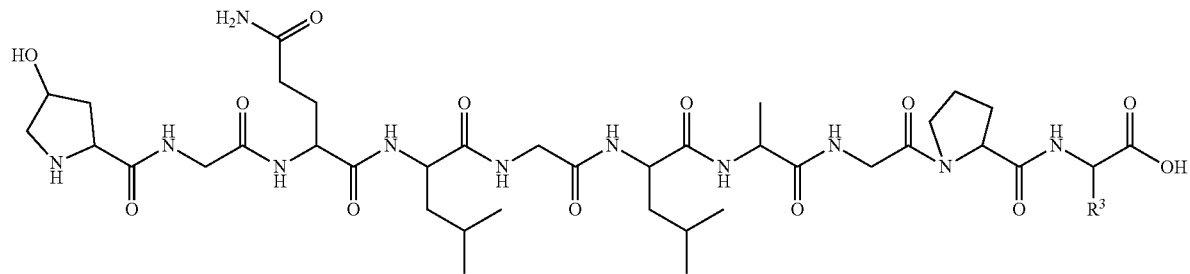

$R^3$ may be one selected from the group consisting of substituted or unsubstituted $C_{1-6}$ alkyl

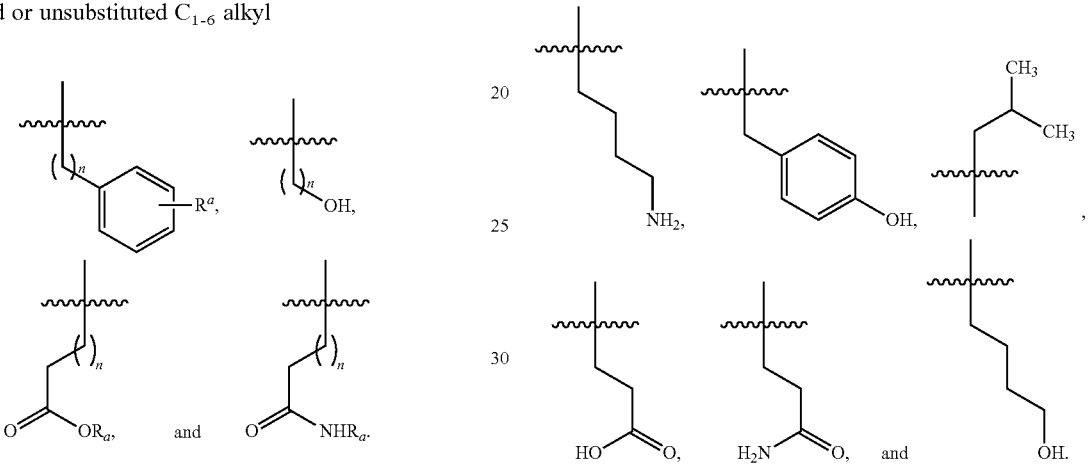

Here, n may be an integer of 1 to 10, but it is not limited thereto. $R_a$ may be hydrogen or $C_{1-6}$ alkyl.

Specifically, $R^3$ may be one selected from the group consisting of,

More specifically, the compound may be a compound described in Table 4 below.

TABLE 4

| YDE-029 | 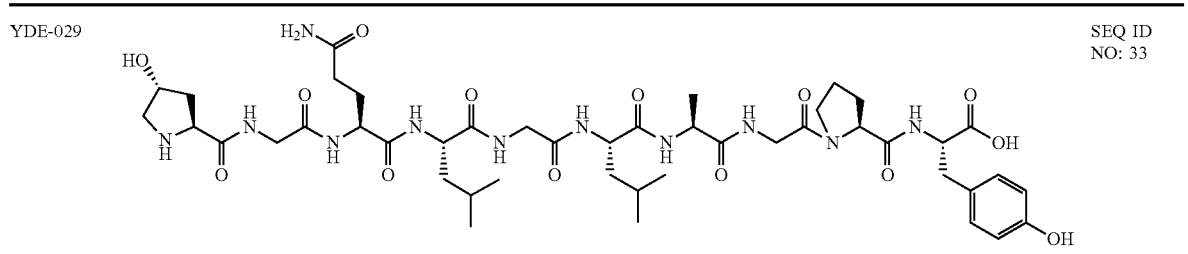 | SEQ ID NO: 33 |
|---|---|---|
| | Hyp (2S,4R)　Gly　Gln　Leu　Gly　Leu　Ala　Gly　Pro　Tyr | |
| YDE-030 | 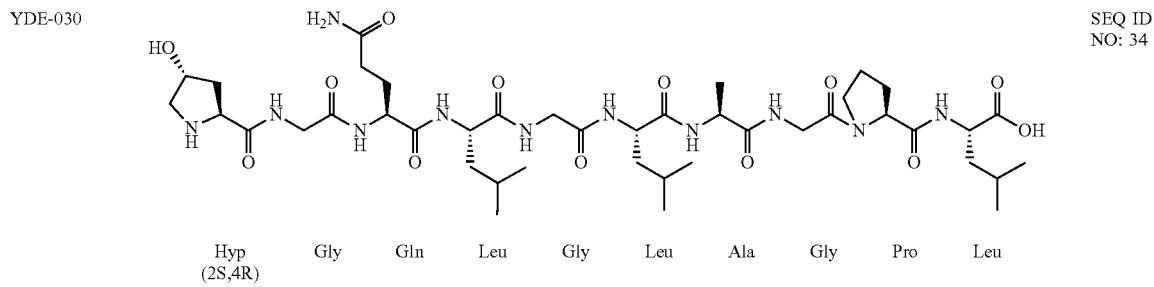 | SEQ ID NO: 34 |
| | Hyp (2S,4R)　Gly　Gln　Leu　Gly　Leu　Ala　Gly　Pro　Leu | |

TABLE 4-continued
YDE-031 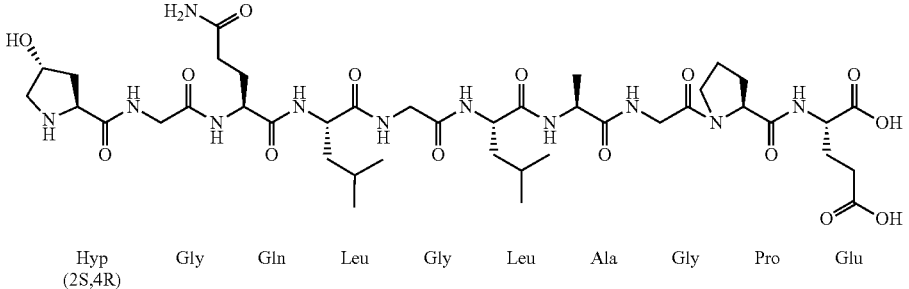 [SMILES: CC(C)C[C@H](NC(=O)CNC(=O)[C@H](CC(C)C)NC(=O)[C@H](CCC(N)=O)NC(=O)CNC(=O)[C@@H]1C[C@@H](O)CN1)C(=O)N[C@@H](C)C(=O)NCC(=O)N1CCC[C@H]1C(=O)N[C@@H](CCC(=O)O)C(=O)O]
| Hyp (2S,4R) | Gly | Gln | Leu | Gly | Leu | Ala | Gly | Pro | Glu |
SEQ ID NO: 35
YDE-032 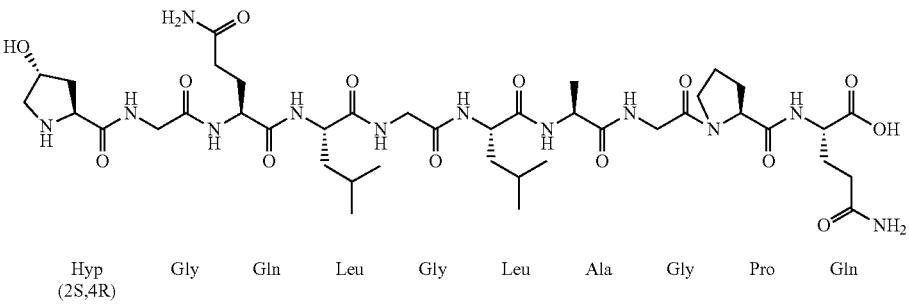 [SMILES: CC(C)C[C@H](NC(=O)CNC(=O)[C@H](CC(C)C)NC(=O)[C@H](CCC(N)=O)NC(=O)CNC(=O)[C@@H]1C[C@@H](O)CN1)C(=O)N[C@@H](C)C(=O)NCC(=O)N1CCC[C@H]1C(=O)N[C@@H](CCC(N)=O)C(=O)O]
| Hyp (2S,4R) | Gly | Gln | Leu | Gly | Leu | Ala | Gly | Pro | Gln |
SEQ ID NO: 36
YDE-033 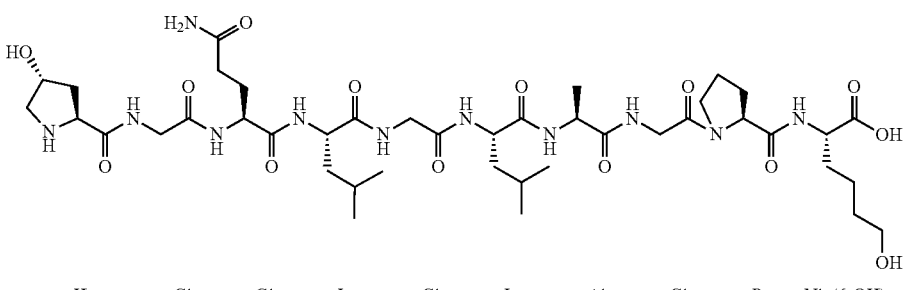
| Hyp (2S,4R) | Gly | Gln | Leu | Gly | Leu | Ala | Gly | Pro | Nle(6-OH) |
SEQ ID NO: 37
YDE-056 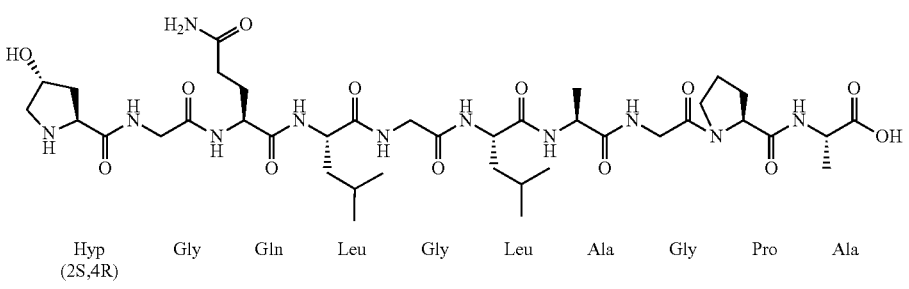 [SMILES: CC(C)C[C@H](NC(=O)CNC(=O)[C@H](CC(C)C)NC(=O)[C@H](CCC(N)=O)NC(=O)CNC(=O)[C@@H]1C[C@@H](O)CN1)C(=O)N[C@@H](C)C(=O)NCC(=O)N1CCC[C@H]1C(=O)N[C@@H](C)C(=O)O]
| Hyp (2S,4R) | Gly | Gln | Leu | Gly | Leu | Ala | Gly | Pro | Ala |
SEQ ID NO: 38
YDE-073 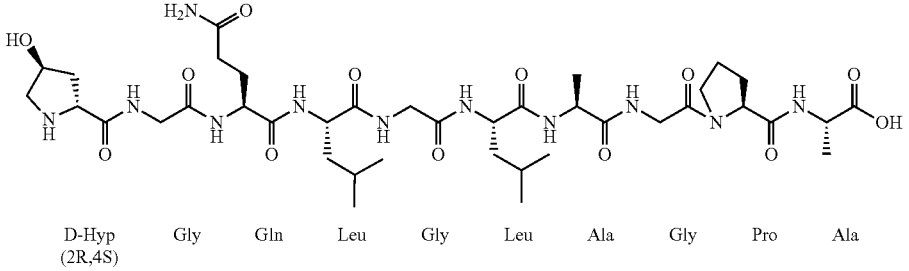 [SMILES: CC(C)C[C@H](NC(=O)CNC(=O)[C@H](CC(C)C)NC(=O)[C@H](CCC(N)=O)NC(=O)CNC(=O)[C@H]1C[C@H](O)CN1)C(=O)N[C@@H](C)C(=O)NCC(=O)N1CCC[C@H]1C(=O)N[C@@H](C)C(=O)O]
| D-Hyp (2R,4S) | Gly | Gln | Leu | Gly | Leu | Ala | Gly | Pro | Ala |
SEQ ID NO: 39

The compound represented by the above Formula 1 may be represented by Formula 1-5 when $R^1$ is
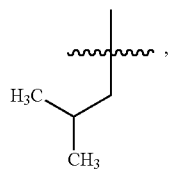
$R^2$ is H, $R^3$ is
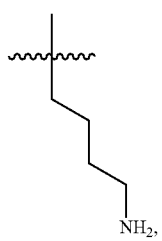 [SMILES: *CCCCN]
$R^6$ is
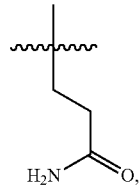
$R^7$ is
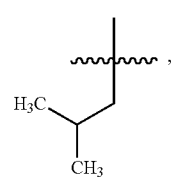
$R^8$ is H, and $R^9$ is H. Further, the compound represented by the following Formula 1-5 may be an optical isomer type L or D.
[Formula 1-5]
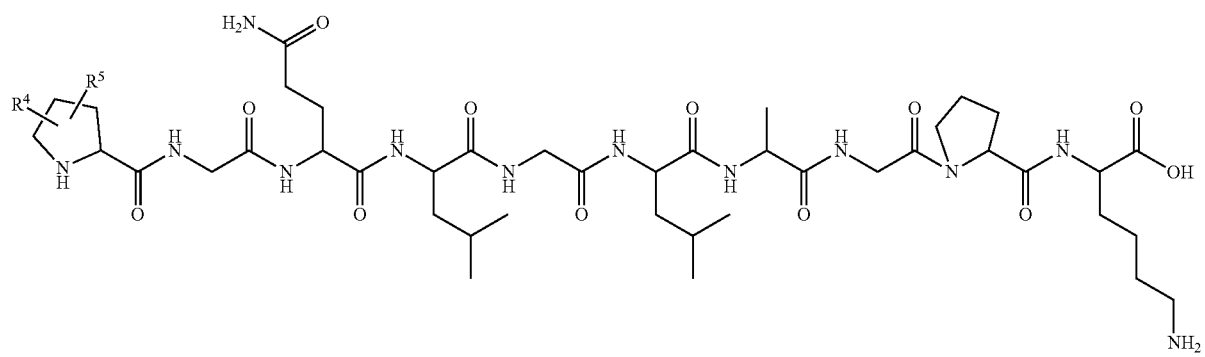

$R^4$ and $R^5$ may be each independently one selected from the group consisting of substituted or unsubstituted $C_{1-6}$ alkyl, $-OR_b$, $=O$, $-CH_2OR_b$, and $-X_2$. Here, $X_2$ may be independently halogen such as F, Cl, Br, or I. $R_b$ may be hydrogen or $C_{1-6}$ alkyl.

Specifically, $R^4$ may be one selected from the group consisting of H, $-OH$, $=O$, $-CH_2OR_b$, and F; in such event, $R^5$ may be H. Further, $R^4$ may be $CH_3$; in such event, $R^5$ may be $CH_3$.

More specifically, the compound may be a compound described in Table 5 below.

TABLE 5

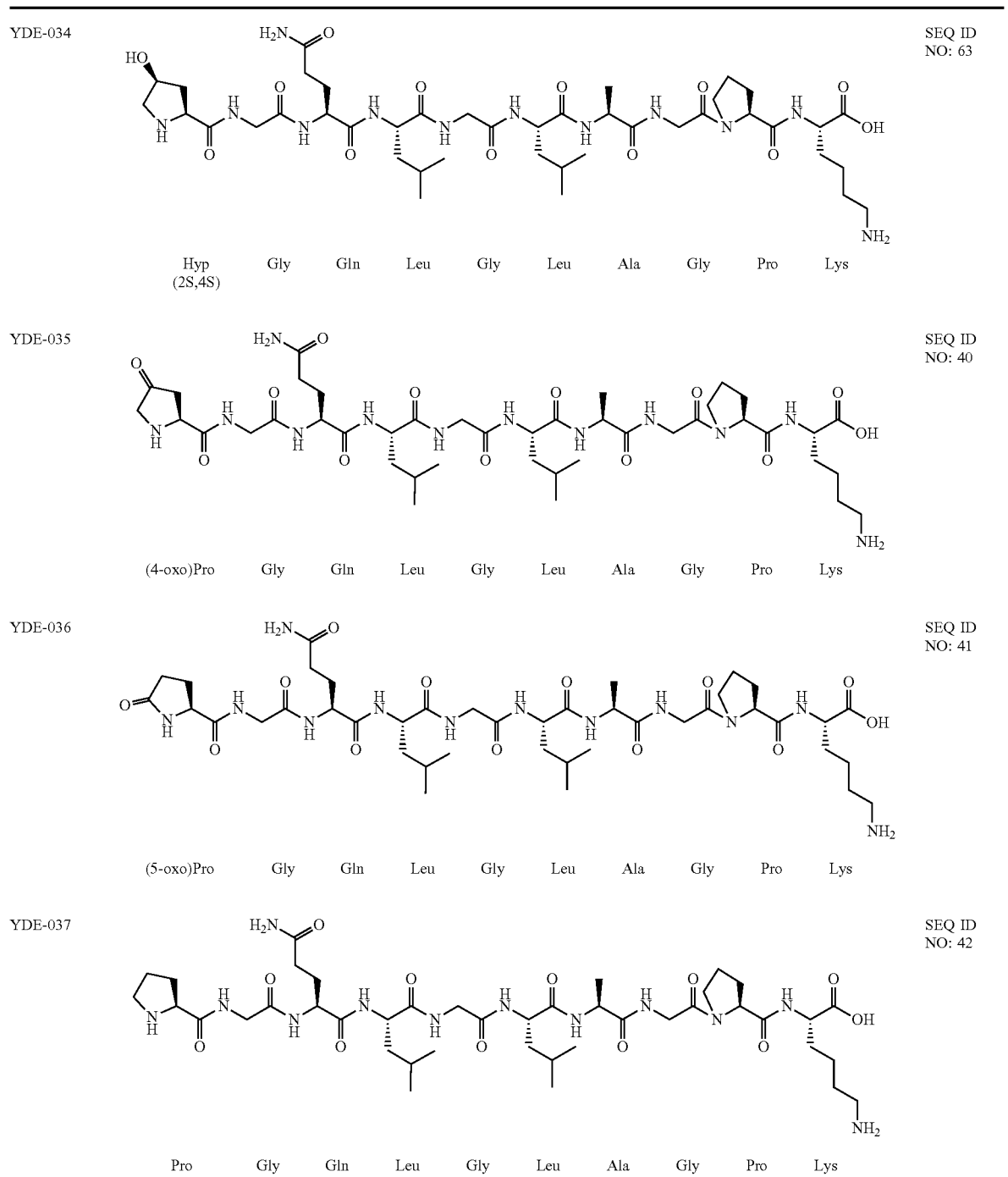

TABLE 5-continued

YDE-038

(4-hydroxyMe)Pro (4R) — Gly — Gln — Leu — Gly — Leu — Ala — Gly — Pro — Lys

SEQ ID NO: 43

YDE-039

(4-Fluoro)Pro (4R) — Gly — Gln — Leu — Gly — Leu — Ala — Gly — Pro — Lys

SEQ ID NO: 44

YDE-040

(4-Dimethyl)Pro — Gly — Gln — Leu — Gly — Leu — Ala — Gly — Pro — Lys

SEQ ID NO: 45

YDE-044

(4-Me)Pro (4R) — Gly — Gln — Leu — Gly — Leu — Ala — Gly — Pro — Lys

SEQ ID NO: 46

TABLE 5-continued
| YDE-045 | | | | | | | | | | SEQ ID NO: 47 |
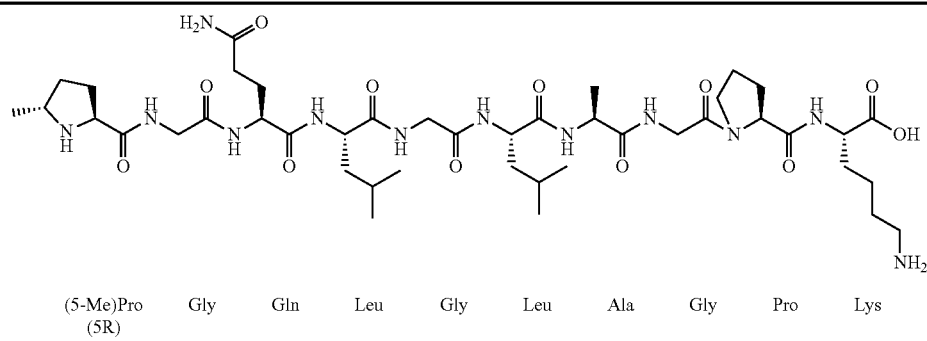
| (5-Me)Pro (5R) | Gly | Gln | Leu | Gly | Leu | Ala | Gly | Pro | Lys |
The compound represented by the above Formula 1 may be represented by Formula 1-6 when $R^2$ is H, $R^3$ is
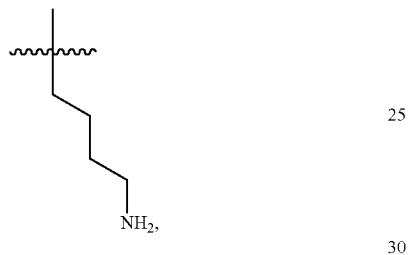
$R^4$ is —OH, $R^5$ is H, $R^7$ is
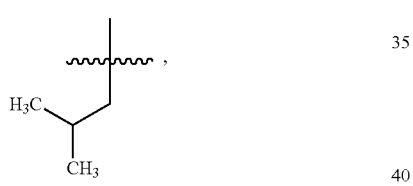
$R^7$ is H, and $R^9$ is H. Further, the compound represented by the following Formula 1-6 may be an optical isomer type L or D.
[Formula 1-6]
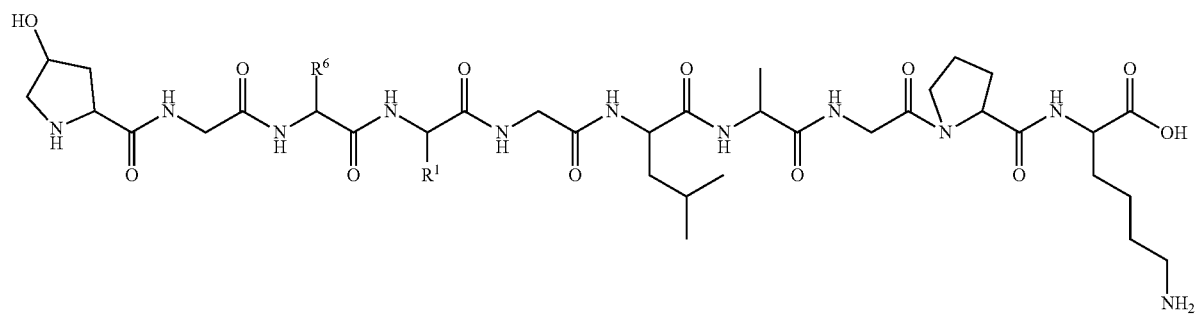

$R^1$ may be $C_{1-6}$ alkyl. Specifically, $R^1$ may be

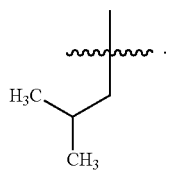

$R^6$ may be substituted or unsubstituted $C_{1-6}$ alkyl, wherein the substituent may be $-C(=O)NH_2$. Specifically, $R^6$ may be

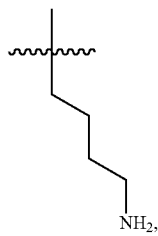 [SMILES: *CCCCN]

More specifically, the compound may be a compound described in Table 6 below.

TABLE 6

| YDE-049 | 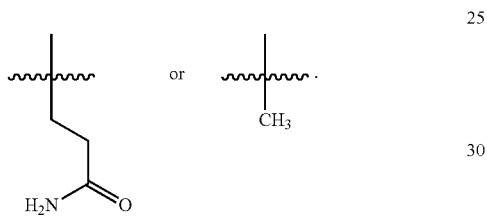 | SEQ ID NO: 48 |
|---|---|---|
| | Hyp (2S,4R)　Gly　Ala　Leu　Gly　Leu　Ala　Gly　Pro　Lys | |

The compound represented by the above Formula 1 may be represented by Formula 1-7 when $R^2$ is H, $R^3$ is

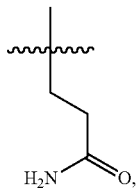 [SMILES: *CCC(N)=O]

$R^4$ is $-OH$, $R^5$ is H, $R^6$ is $R^8$ is H, and $R^9$ is H. Further, the compound represented by the following Formula 1-7 may be an optical isomer type L or D.

[Formula 1-7]
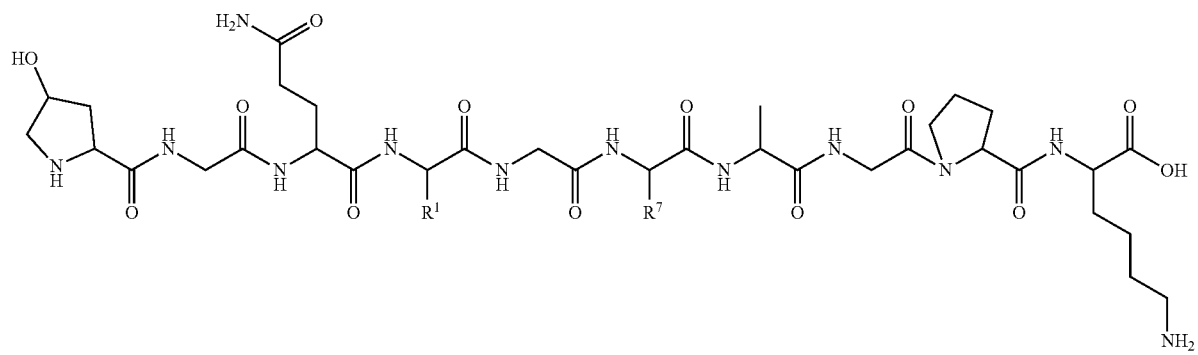
R¹ may be $C_{1-6}$ alkyl. Specifically, R¹ may be
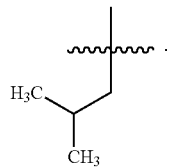
R⁷ may be unsubstituted $C_{1-6}$ alkyl. Specifically, R⁷ may be
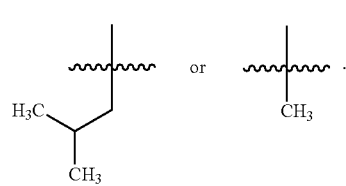
More specifically, the compound may be a compound described in Table 7 below.
TABLE 7
| YDE-052 | | | | | | | | | | SEQ ID NO: 49 |
|---|---|---|---|---|---|---|---|---|---|---|
| | 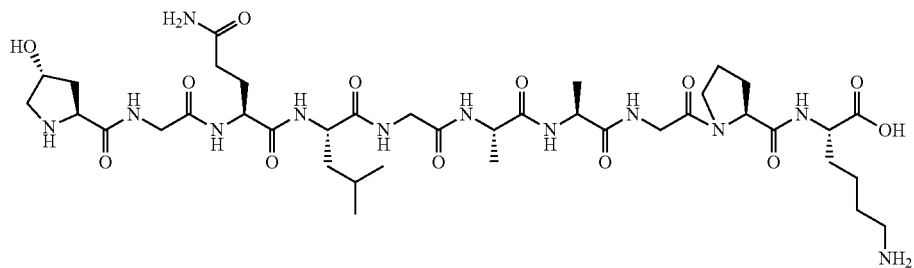 | | | | | | | | | |
| | Hyp (2S, 4R) | Gly | Gln | Leu | Gly | Ala | Ala | Gly | Pro | Lys |

The compound represented by the above Formula 1 may be represented by Formula 1-8 when $R^2$ is H, $R^3$ is
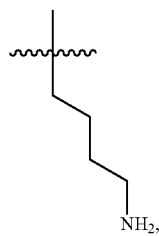
$R^4$ is —OH, $R^5$ is H, $R^6$ is
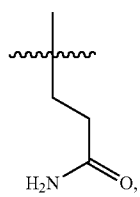 [SMILES: *CCC(N)=O]
$R^7$ is
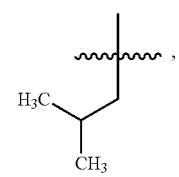
and $R^9$ is H. Further, the compound represented by the following Formula 1-8 may be an optical isomer type L or D.
[Formula 1-8]
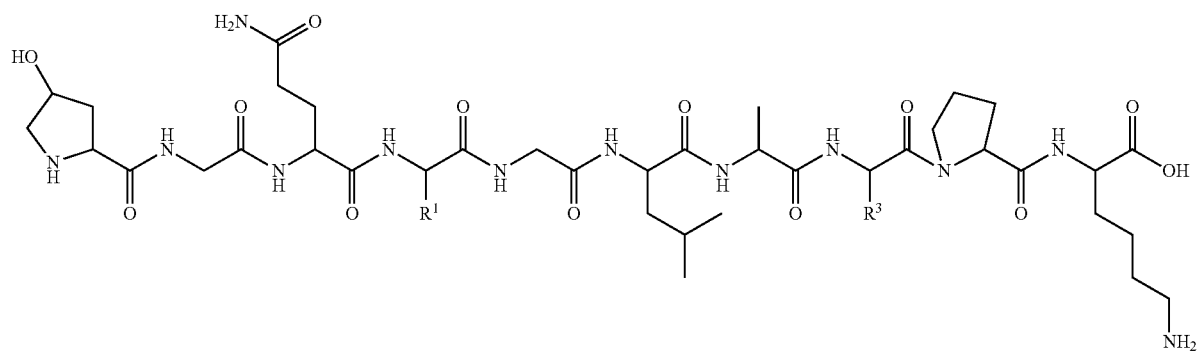

$R^1$ may be $C_{1-6}$ alkyl. Specifically, $R^1$ may be

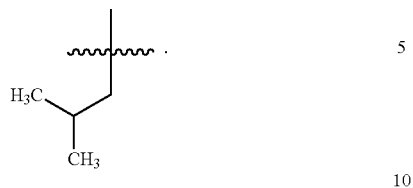

$R^8$ may be hydrogen or $C_{1-6}$ alkyl. Specifically, $R^8$ may be

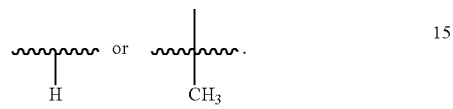

More specifically, the compound may be a compound described in Table 8 below.

TABLE 8

| YDE-054 | SEQ ID NO: 50 |
|---|---|
| 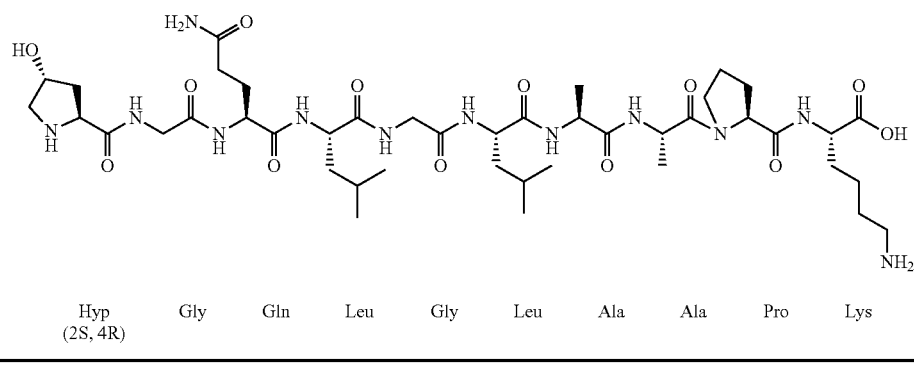 | |
| Hyp (2S, 4R)　Gly　Gln　Leu　Gly　Leu　Ala　Ala　Pro　Lys | |

The compound represented by the above Formula 1 may be represented by Formula 1-9 when $R^2$ is H, $R^3$ is

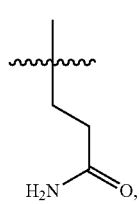

$R^4$ is —OH, $R^5$ is H, $R^6$ is $R^7$ is

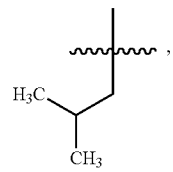 [SMILES: *CC(C)C ; ","]

and $R^8$ is H. Further, the compound represented by the following Formula 1-9 may be an optical isomer type L or D.

[Formula 1-9]
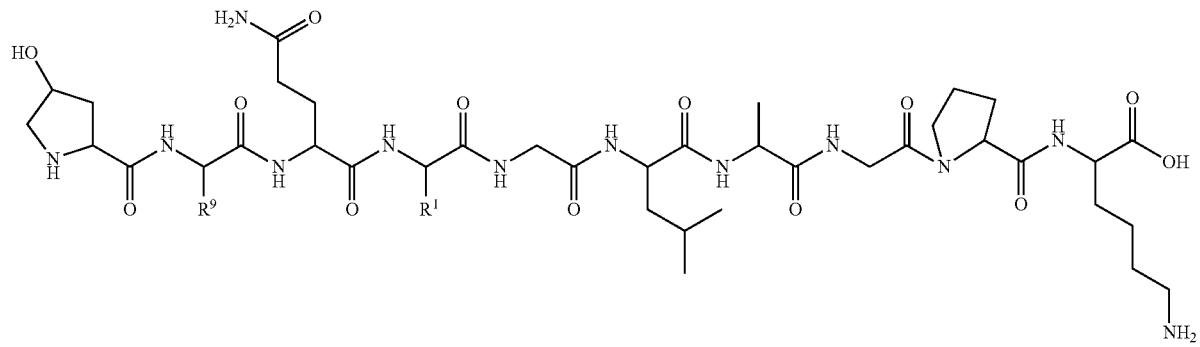
$R^1$ may be $C_{1-6}$ alkyl. Specifically, $R^1$ may be
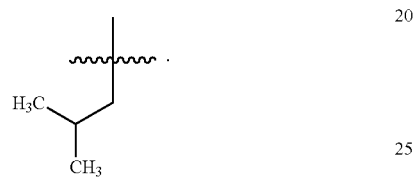
$R^9$ may be hydrogen or $C_{1-6}$ alkyl. Specifically, $R^9$ may be
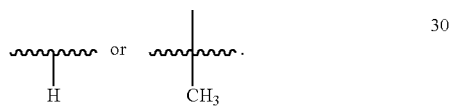
More specifically, the compound may be a compound described in Table 9 below.
TABLE 9
| YDE-048 | SEQ ID NO: 51 |
[structure image]
| Hyp (2S, 4R) | Ala | Gln | Leu | Gly | Leu | Ala | Gly | Pro | Lys |
| YDE-072 | SEQ ID NO: 53 |
[structure image]
| D-Hyp (2R,4S) | Ala | Gln | Leu | Gly | Leu | Ala | Gly | Pro | Lys |

The compound represented by the above Formula 1 may be represented by Formula 1-10 when $R^2$ is H, $R^4$ is —OH, $R^5$ is H, $R^6$ is

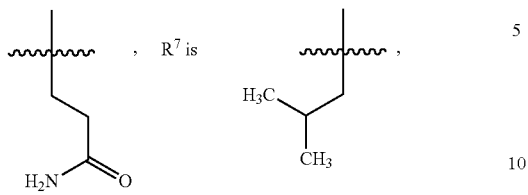

and $R^8$ is H. Further, the compound represented by the following Formula 1-10 may be an optical isomer type L or D.

[Formula 1-10]

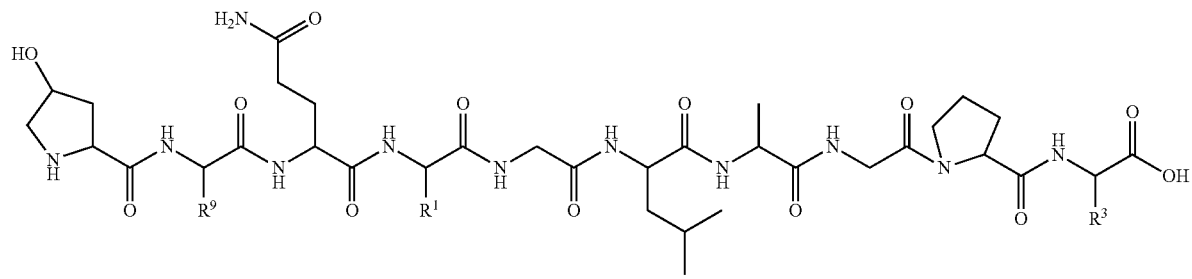

$R^1$ may be $C_{1-6}$ alkyl. Specifically, $R^1$ may be

In such event, $R^3$ may be $C_{1-6}$ alkyl. Specifically, $R^3$ may be

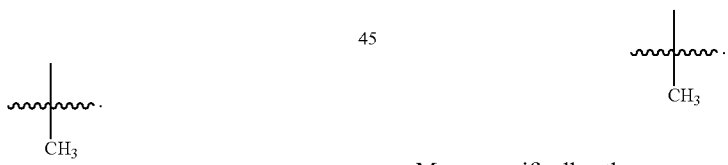

In such event, $R^9$ may be $C_{1-6}$ alkyl. Specifically, $R^9$ may be

More specifically, the compound may be a compound described in Table 10 below.

TABLE 10

| YDE-074 | | | | | | | | | | SEQ ID NO: 52 |
|---|---|---|---|---|---|---|---|---|---|---|
| 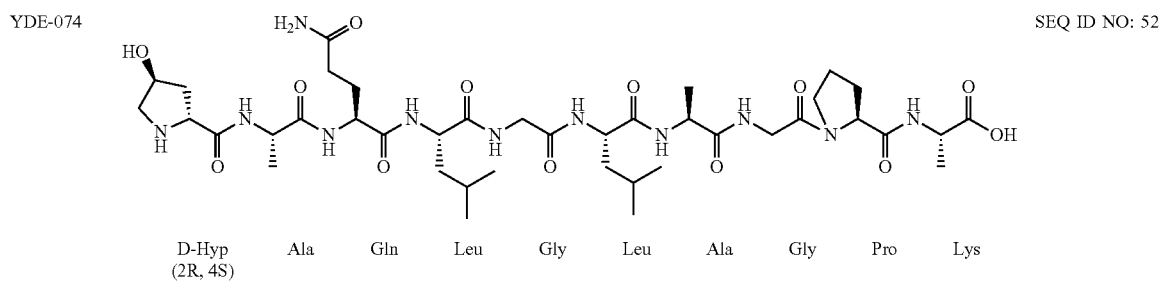 | | | | | | | | | | |
| | D-Hyp (2R, 4S) | Ala | Gln | Leu | Gly | Leu | Ala | Gly | Pro | Lys |

The compounds represented by the above Formulae 1-1 to 1-10 may be any one selected from the group consisting of HyP-Gly-Gln-Glu-Gly-Leu-Ala-Gly-Pro-Lys (SEQ ID NO: 1), HyP-Gly-Gln-Asn-Gly-Leu-Ala-Gly-Pro-Lys (SEQ ID NO: 2), HyP-Gly-Gln-Gln-Gly-Leu-Ala-Gly-Pro-Lys (SEQ ID NO: 3), HyP-Gly-Gln-His-Gly-Leu-Ala-Gly-Pro-Lys (SEQ ID NO: 4), HyP-Gly-Gln-Lys-Gly-Leu-Ala-Gly-Pro-Lys (SEQ ID NO: 5), HyP-Gly-Gln-Ser-Gly-Leu-Ala-Gly-Pro-Lys (SEQ ID NO: 6), HyP-Gly-Gln-Thr-Gly-Leu-Ala-Gly-Pro-Lys (SEQ ID NO: 7), HyP-Gly-Gln-Ala-Gly-Leu-Ala-Gly-Pro-Lys (SEQ ID NO: 8), HyP-Gly-Gln-Val-Gly-Leu-Ala-Gly-Pro-Lys (SEQ ID NO: 9), HyP-Gly-Gln-Ile-Gly-Leu-Ala-Gly-Pro-Lys (SEQ ID NO: 10), HyP-Gly-Gln-Leu-Gly-Leu-Ala-Gly-Pro-Lys (SEQ ID NO: 11), HyP-Gly-Gln-Phe-Gly-Leu-Ala-Gly-Pro-Lys (SEQ ID NO: 12), HyP-Gly-Gln-Tyr-Gly-Leu-Ala-Gly-Pro-Lys (SEQ ID NO: 13), HyP-Gly-Gln-Trp-Gly-Leu-Ala-Gly-Pro-Lys (SEQ ID NO: 14), HyP-Gly-Gln-Ser(Homo)-Gly-Leu-Ala-Gly-Pro-Lys (SEQ ID NO: 15), HyP-Gly-Gln-Asp(Me)-Gly-Leu-Ala-Gly-Pro-Lys (SEQ ID NO: 16), HyP-Gly-Gln-Asn(Me)-Gly-Leu-Ala-Gly-Pro-Lys (SEQ ID NO: 17), $_D$-HyP(2R,4S)-Gly-Gln-Leu-Gly-Leu-Ala-Gly-Pro-Lys (SEQ ID NO: 18), D-Hyp(2R,4S)-Gly-$_D$-Gln-$_D$-Leu-Gly-$_D$-Leu-$_D$-Ala-Gly-$_D$-Pro-$_D$-Lys (SEQ ID NO: 19), $_D$-Hyp(2R, 4R)-Gly-$_D$-Gln-$_D$-Leu-Gly-$_D$-Leu-$_D$-Ala-Gly-$_D$-Pro-$_D$-Lys (SEQ ID NO: 20), HyP-Gly-Gln-Asp-Val-Leu-Ala-Gly-Pro-Lys (SEQ ID NO: 21), HyP-Gly-Gln-Asp-Ile-Leu-Ala-Gly-Pro-Lys (SEQ ID NO: 22), HyP-Gly-Gln-Asp-Leu-Leu-Ala-Gly-Pro-Lys (SEQ ID NO: 23), HyP-Gly-Gln-Asp-Ala-Leu-Ala-Gly-Pro-Lys (SEQ ID NO: 24), HyP-Gly-Gln-Asp-Phe-Leu-Ala-Gly-Pro-Lys (SEQ ID NO: 25), HyP-Gly-Gln-Asp-Tyr-Leu-Ala-Gly-Pro-Lys (SEQ ID NO: 26), HyP-Gly-Gln-Asp-Trp-Leu-Ala-Gly-Pro-Lys (SEQ ID NO: 27), HyP-Gly-Gln-Asp-His-Leu-Ala-Gly-Pro-Lys (SEQ ID NO: 28), HyP-Gly-Gln-Asp-Ser-Leu-Ala-Gly-Pro-Lys (SEQ ID NO: 29), HyP-Gly-Gln-Asp-Thr-Leu-Ala-Gly-Pro-Lys (SEQ ID NO: 30), HyP-Gly-Gln-Leu-Ala-Leu-Ala-Gly-Pro-Lys (SEQ ID NO: 32), HyP-Gly-Gln-Leu-Gly-Leu-Ala-Gly-Pro-Tyr (SEQ ID NO: 33), HyP-Gly-Gln-Leu-Gly-Leu-Ala-Gly-Pro-Leu (SEQ ID NO: 34), HyP-Gly-Gln-Leu-Gly-Leu-Ala-Gly-Pro-Glu (SEQ ID NO: 35), HyP-Gly-Gln-Leu-Gly-Leu-Ala-Gly-Pro-Gln (SEQ ID NO: 36), HyP-Gly-Gln-Leu-Gly-Leu-Ala-Gly-Pro-Nle(6-OH) (SEQ ID NO: 37), HyP-Gly-Gln-Leu-Gly-Leu-Ala-Gly-Pro-Ala (SEQ ID NO: 38), $_D$-HyP(2R, 4S)-Gly-Gln-Leu-Gly-Leu-Ala-Gly-Pro-Ala (SEQ ID NO: 39), Hyp(2S, 4S)-Gly-Gln-Leu-Gly-Leu-Ala-Gly-Pro-Lys (SEQ ID NO: 63), (4-oxo)Pro-Gly-Gln-Leu-Gly-Leu-Ala-Gly-Pro-Lys (SEQ ID NO: 40), (5-oxo)Pro-Gly-Gln-Leu-Gly-Leu-Ala-Gly-Pro-Lys (SEQ ID NO: 41), Pro-Gly-Gln-Leu-Gly-Leu-Ala-Gly-Pro-Lys (SEQ ID NO: 42), (4-hydroxyMe)Pro-Gly-Gln-Leu-Gly-Leu-Ala-Gly-Pro-Lys (SEQ ID NO: 43), (4-Fluoro)Pro-Gly-Gln-Leu-Gly-Leu-Ala-Gly-Pro-Lys (SEQ ID NO: 44), (4-Dimethyl)Pro-Gly-Gln-Leu-Gly-Leu-Ala-Gly-Pro-Lys (SEQ ID NO: 45), (4-Me)Pro-Gly-Gln-Leu-Gly-Leu-Ala-Gly-Pro-Lys (SEQ ID NO: 46), (5-Me)Pro-Gly-Gln-Leu-Gly-Leu-Ala-Gly-Pro-Lys (SEQ ID NO: 47), Hyp-Ala-Leu-Gly-Leu-Ala-Gly-Pro-Lys (SEQ ID NO: 48), Hyp-Gly-Gln-Leu-Gly-Ala-Ala-Gly-Pro-Lys (SEQ ID NO: 49), Hyp-Gly-Gln-Leu-Gly-Leu-Ala-Ala-Pro-Lys (SEQ ID NO: 50), Hyp-Ala-Gln-Leu-Gly-Leu-Ala-Gly-Pro-Lys (SEQ ID NO: 51), $_D$-Hyp(2R, 4S)-Ala-Gln-Leu-Gly-Leu-Ala-Gly-Pro-Lys (SEQ ID NO: 53) and $_D$-Hyp(2R, 4S)-Ala-Gln-Leu-Gly-Leu-Ala-Gly-Pro-Ala (SEQ ID NO: 52).

Another aspect of the present invention provides a peptide having an amino acid sequence represented by HyP-Gly-Gln-Xaa-Gly-Leu-Ala-Gly-Pro-Lys (SEQ ID NO: 120). Here, Xaa may be one selected from the group consisting of Glu, Asn, Gln, His, Lys, Ser, Thr, Ala, Val, Ile, Leu, Phe, Tyr, Trp, homo-Ser, Asp(Me), and Asn(Me).

The peptide may be a variant of a collagen type II α1-derived peptide. The collagen type II α1 may be isolated from the extracellular matrix derived from animal chondrocytes.

The term "peptide" used in the present invention refers to a compound in which two or more amino acids are linked by a peptide bond. Further, it is classified into dipeptide, tripeptide, tetrapeptide, and the like according to the number of constituent amino acids. An oligopeptide has about 10 or fewer peptide bonds, and a polypeptide has a plurality of peptide bonds. In addition, a peptide in the present invention includes a mutated peptide in which its amino acid residue is substituted.

The term "HyP" used in the present invention refers to an amino acid called hydroxyproline, in which a hydroxyl group (—OH) is bonded to the carbon atom at the 4-position of proline. HyP has a structure of $C_5H_9NO_3$ and may be represented by the following Formula 2.

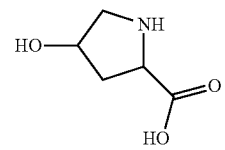

[Formula 2]

HyP may include all isomers. In addition, HyP may be an isomer represented by the stereochemistry of "2S,4R" unless otherwise specified.

The term "2S,4R" is represented by R and S that indicate a stereochemical configuration of a chiral molecule. A typical chiral molecule has a chiral center such as an asymmetric carbon atom. Since the chiral center has four different substituent groups (or substitution atoms), their priority is determined by a predetermined procedure. Once the order of the four substituents is determined by (1), (2), (3), and (4), the lowest order substituent (4) is placed farthest away from the eye direction, and the remaining substituents are arranged from the higher order to the lower order. R (or rectus in Latin, right) indicate the arrangement in which the sequence of (1) to (2) to (3) turns right. S (or sinister, left) indicates the arrangement in which this sequence turns left.

The term "homo-Ser" used in the present invention is called homoserine and refers to an α-amino acid having a hydroxyl group in the side chain. Homo-Ser is not an amino acid that constitutes a protein and is an intermediate present in the biosynthesis of threonine and methionine in microorganisms and plants. Homo-Ser may have the following Formula 3.

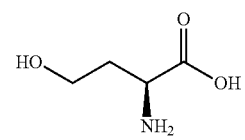

[Formula 3]

The term "Asp(Me)" used in the present invention indicates an amino acid in which the hydrogen atom of the hydroxyl group (OH) bonded to the carbon atom at the 4-position of aspartic acid is substituted by a methyl group (CH₃). Asp(Me) may have the following Formula 4.

[Formula 4]

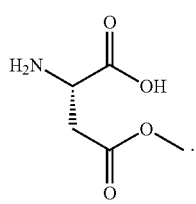

The term "Asn(Me)" used in the present invention indicates an amino acid in which the hydrogen atom of the amine group (NH₂) bonded to the carbon atom at the 4-position of asparagine is substituted by a methyl group (CH₃). Asn(Me) may have the following Formula 5.

[Formula 5]

In addition, still another aspect of the present invention provides a peptide having an amino acid sequence represented by HyP-Gly-Gln-Asp-Xaa-Leu-Ala-Gly-Pro-Lys (SEQ ID NO 121). Here, Xaa may be one selected from the group consisting of Val, Ile, Leu, Ala, Phe, Tyr, Trp, Ser, Thr, and (N-Me)Gly.

The term "(N-Me)Gly" used in the present invention indicates an amino acid in which the hydrogen atom of the amine group (NH₂) bonded to the carbon atom at the 2-position of glycine is substituted by a methyl group (CH₃). (N-Me)Gly may have the following Formula 6.

[Formula 6]

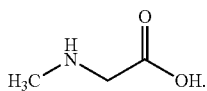

Still another aspect of the present invention provides a peptide having an amino acid sequence represented by HyP-Gly-Gln-Leu-Gly-Leu-Ala-Gly-Pro-Xaa (SEQ ID NO 122). Here, Xaa may be one selected from the group consisting of Tyr, Leu, Glu, Gln, Ala, and Nle(6-OH).

The term "Nle(6-OH)" used in the present invention refers to an amino acid in which a hydroxyl group (—OH) is bonded to the carbon atom at the 6-position of norleucine. Nle(6-OH) has a structure of C₅H₁₁NO₃ and may be represented by the following Formula 7.

[Formula 7]

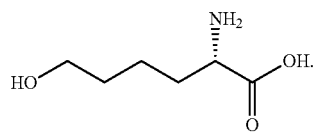

Still another aspect of the present invention provides a peptide having an amino acid sequence represented by PD-Gly-Gln-Leu-Gly-Leu-Ala-Gly-Pro-Lys (SEQ ID NO 123). Here, PD may be any one selected from the group consisting of the following formulae.

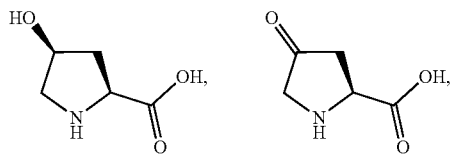

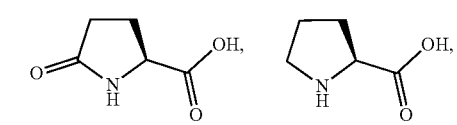

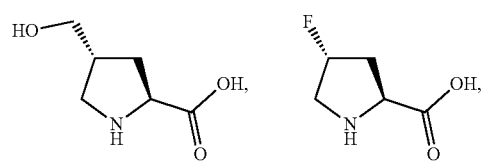

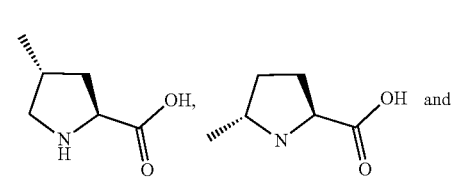

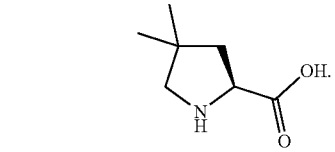

Still another aspect of the present invention provides a peptide having any one amino acid sequence selected from the group consisting of Ala-Gly-Gln-Leu-Gly-Leu-Ala-Gly-Pro-Lys (SEQ ID NO: 54), Hyp-Gly-Gln-Leu-Gly-Leu-Ala-Gly-Ala-Lys (SEQ ID NO: 55), HyP-Gly-Gln-Leu-Gly-Leu-Ala (SEQ ID NO: 56), HyP-Gly-Gln-Glu-Gly-Leu-Gly (SEQ ID NO: 57), HyP-Gly-Gln-Leu-Gly-Leu (SEQ ID NO: 58), D-HyP(2R, 4S)-Gly-D-Gln-D-Leu-Gly-D-Leu (SEQ ID NO: 59), HyP-Gly-Gln-Leu-Gly (SEQ ID NO: 60), HyP-Gly-Gln-D-Leu-Gly (SEQ ID NO: 61), and $_D$-HyP(2R, 4S)-Gly-Gln-Leu-Gly (SEQ ID NO: 62).

Still another aspect of the present invention provides a compound represented by Formula 8.

[Formula 8]

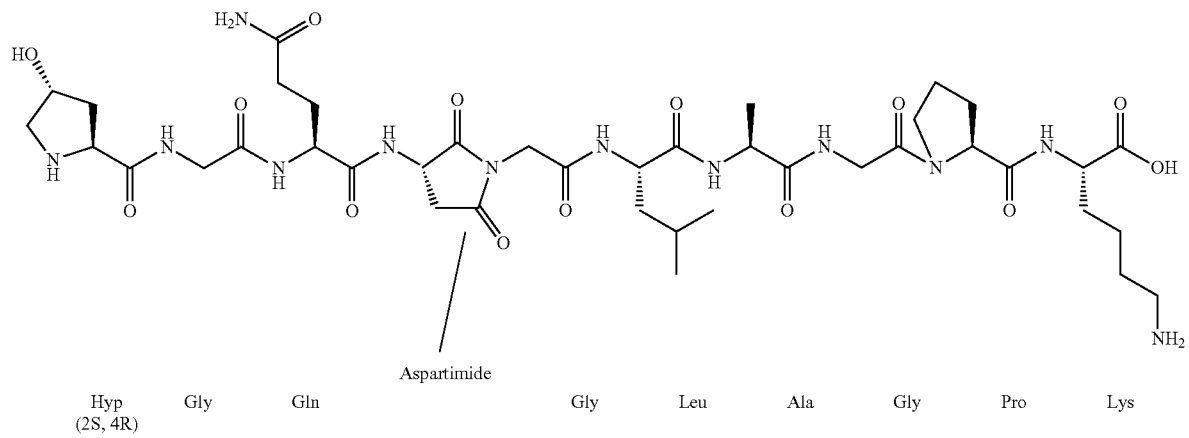

| Hyp (2S, 4R) | Gly | Gln | Aspartimide | Gly | Leu | Ala | Gly | Pro | Lys |

The compound represented by the above Formula 8 indicates a compound in which Asp is modified to Aspartimide by a dehydration condensation reaction of the hydroxyl group (—OH) bonded to the carbon atom at the 4-position of Asp in the amino acid sequence represented by HyP-Gly-Gln-Asp-Gly-Leu-Ala-Gly-Pro-Lys (SEQ ID NO: 124) with the Asp-Gly peptide bond.

The modified compound may be a compound represented by the following Formula 9.

[Formula 9]

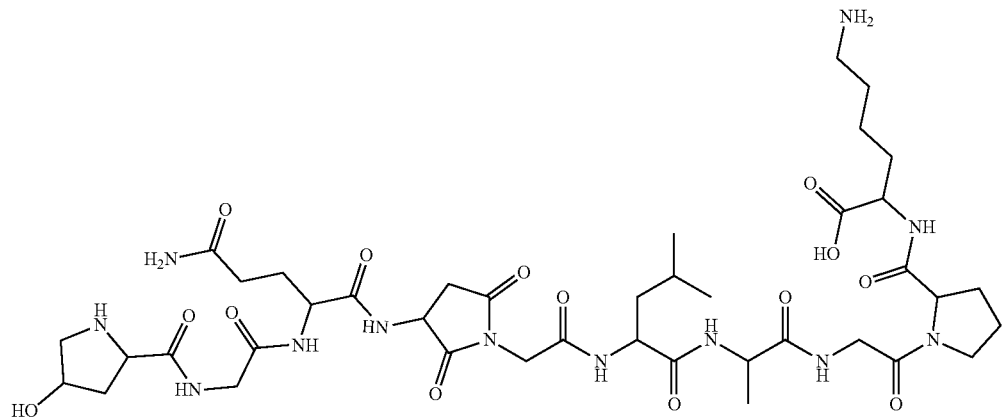

(SEQ ID NO: 101).

Still another aspect of the present invention provides a compound represented by Formula 10.

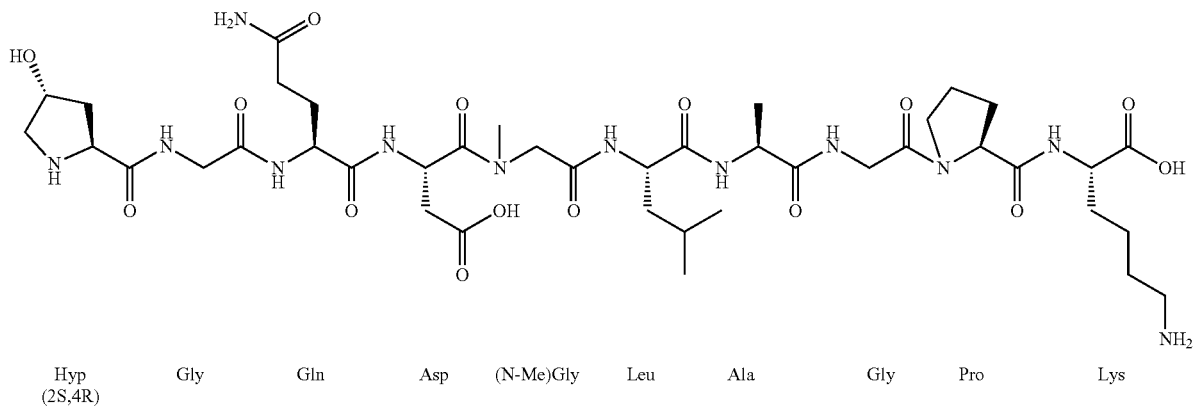

[Formula 10]

Hyp (2S,4R) — Gly — Gln — Asp — (N-Me)Gly — Leu — Ala — Gly — Pro — Lys (SEQ ID NO: 31).

The compound represented by Formula 10 may be a compound represented by the amino acid sequence of SEQ ID NO: 31.

Further, the present invention provides a pharmaceutical composition for treating an eye disease, which comprises the compound or the peptide as an active pharmaceutical ingredient.

Specifically, the eye disease may be one selected from the group consisting of retinopathy, keratitis, dry-macular degeneration, wet-macular degeneration, dry eye syndrome, keratoconjunctival epithelium disorder, proliferative vitreoretinopathy, pigmentary retinopathy, diabetic retinopathy, retinopathy of prematurity, retinopathy of immaturity, proliferative retinopathy, ischemic retinopathy, epidemic keratoconjunctivitis, atopic keratitis, superior limbic keratitis, pterygium keratitis sicca, phlyctenular keratoconjunctivitis, scleritis, corneal transplant rejection, choroidal neovascularization, neovascular glaucoma, ischemic optic neuropathy, retrolental fibroplasias, diabetic macula, neovascular iris disease, erythrosis, myopia, Von Hippel-Lindau syndrome, ocular histoplasmosis, central retinal vein occlusion, Sjogren syndrome and Stevens-Johnson syndrome. Preferably, the eye disease may be one selected from the group consisting of retinopathy, keratitis, macular degeneration, dry eye syndrome and keratoconjunctival epithelium disorder.

The keratoconjunctival epithelium disorder may be due to post-operative surgery, drug, trauma or contact lens wear.

Specifically, the composition for treating an eye disease, which comprises the compound or the peptide as an active pharmaceutical ingredient, may further comprise at least one additive selected from the group consisting of a carrier, an excipient, a disintegrant, a sweetener, a coating agent, a swelling agent, a lubricant, a slip agent, a flavor, an antioxidant, a buffer, a bacteriostat, a diluent, a dispersant, a surfactant, and a binder. Specifically, a formulation for parenteral administration may be a sterilized aqueous solution, a non-aqueous solution, a suspension, an emulsion, a lyophilized preparation, a suppository, or the like.

Still another aspect of the present invention provides a method for treating an eye disease, which comprises administering the compound or the peptide to a subject.

The dose of the compound or the peptide may be adjusted depending on such various factors as the kind of the disease, the severity of the disease, the kinds and amounts of the active pharmaceutical ingredient and other ingredients contained in the pharmaceutical composition, the type of the formulation, the age, body weight, general health condition, sex, and diet of the patient, the time and the route of administration, the duration of treatment, and the drugs concurrently used.

However, for the desired effect, the effective amount of the compound or the peptide contained in the pharmaceutical composition may be 0.0001 μg/day to 100 μg/day. In such event, the administration may be carried out once a day, or divided into several doses. Specifically, the concentration of the compound or the peptide contained in the pharmaceutical composition may be 1000 μM to 0.001 μM. Also, the concentration of the compound or the peptide contained in the pharmaceutical composition may be 100 μM to 0.005 μM or 50 μM to 0.02 μM.

In addition, if necessary, the concentration of the compound or the peptide contained in the pharmaceutical composition may be 30 μM to 1 μM. Further, the concentration of the compound or the peptide contained in the pharmaceutical composition may be 0.01 μM to 1 μM.

In addition, the subject may be a mammal, particularly a human. The administration route may be appropriately selected by a person skilled in the art in consideration of the administration method, the volume and viscosity of the body fluid, and the like. Specifically, the administration may be carried out through any one route selected from the group consisting of an application, intravenous, intraarterial, intraperitoneal, intramuscular, intrasternal, percutaneous, intranasal, inhalation, topical, rectal, oral, intraocular, and intradermal. In particular, it may preferably be applied to the eye for use as an eye drop.

Still another aspect of the present invention provides the use of the compound or the peptides for the treatment of an eye disease.

Still another aspect of the present invention provides the use of the compound or the peptides for the preparation of a pharmaceutical composition for treating an eye disease.

Hereinafter, the present invention is explained in more detail by the following working examples. However, the following working examples are intended to further illustrate the present invention. The scope of the present invention is not limited thereby.

Working Example 1: Preparation of YDE Derivatives

A protein analysis of the extracellular matrix derived from animal chondrocytes was performed in Baek's group of Center of Biomedical Mass Spectrometry (Diatech Korea Co., Ltd., Seoul, Korea). Proline-GQDGLAGPK (P-GQDG-LAGPK) (SEQ ID NO 104), which is a part of the amino acid sequence of the collagen type II α1 protein, was obtained through the above protein analysis. YDE-001 to YDE-075 peptides were synthesized by ANYGEN (Gwangju, Korea) by substituting a part of the above peptide (FIG. 1 and Table 11).

Figure 2:
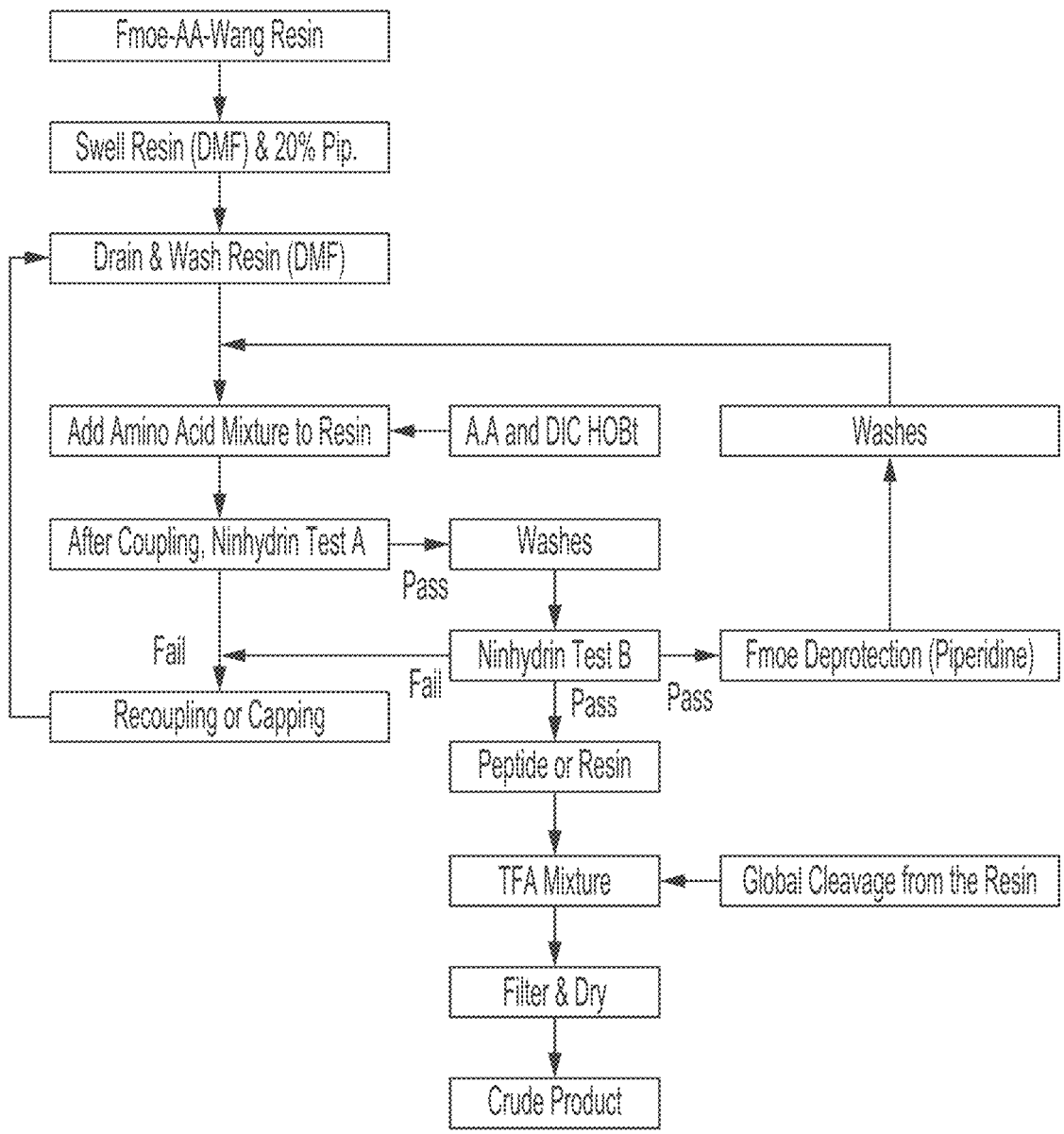
FIG. 2 is a diagram showing a process for synthesizing the peptides prepared according to an embodiment of the present invention.
Figure 3:
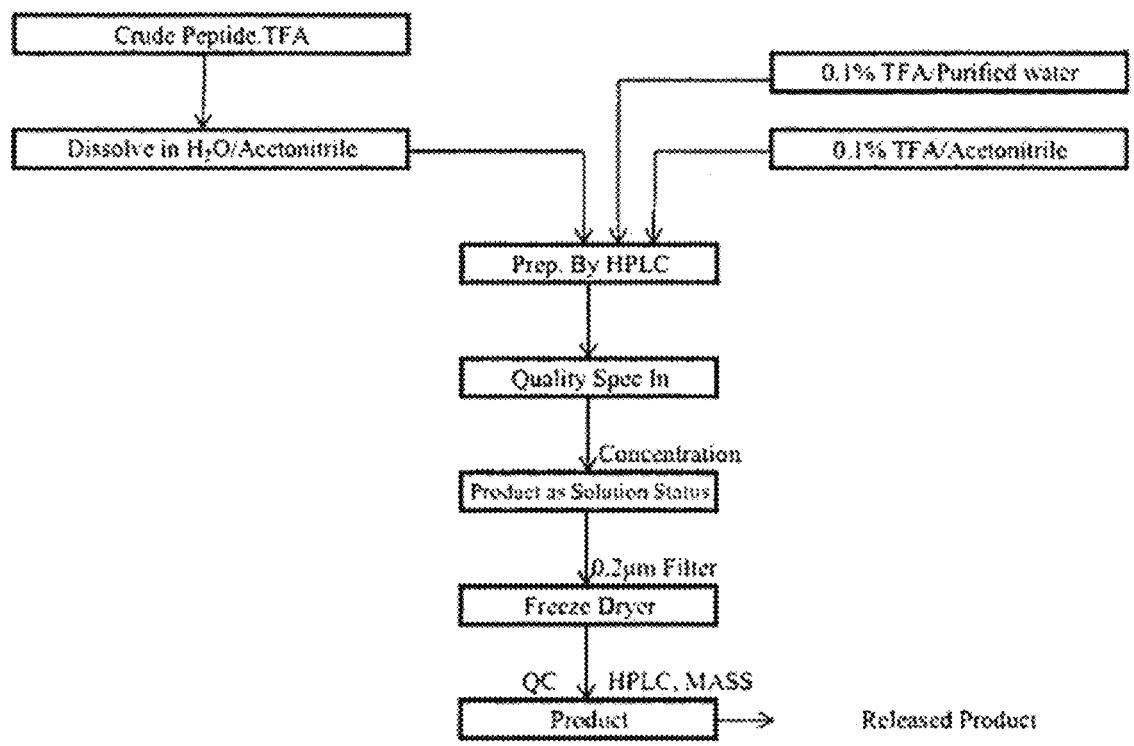
FIG. 3 is a diagram showing a purification procedure of the peptides prepared according to an embodiment of the present invention.

The process for synthesizing the YDE-001 to YDE-075 peptides and the purification procedure thereof conducted by ANYGEN were depicted in FIGS. 2 and 3.

TABLE 11

| No. | Chemical structure | SEQ ID NO. |
|---|---|---|
| YY-101 | Hyp(2S,4R) – Gly – Gln – Asp – Gly – Leu – Ala – Gly – Pro – Lys | SEQ ID NO: 105 |
| YY-102 | Hyp(2S,4R) – Gly – Gln – Aspatimide – Gly – Leu – Ala – Gly – Pro – Lys | SEQ ID NO: 106 |
| YDE-001 | Hyp(2S,4R) – Gly – Gln – Glu – Gly – Leu – Ala – Gly – Pro – Lys | SEQ ID NO: 1 |

TABLE 11-continued

| No. | Chemical structure | SEQ ID NO. |
|---|---|---|
| YDE-002 | Hyp(2S,4R) - Gly - Gln - Asn - Gly - Leu - Ala - Gly - Pro - Lys | SEQ ID NO: 2 |
| YDE-003 | Hyp(2S,4R) - Gly - Gln - Gln - Gly - Leu - Ala - Gly - Pro - Lys | SEQ ID NO: 3 |
| YDE-004 | Hyp(2S,4R) - Gly - Gln - His - Gly - Leu - Ala - Gly - Pro - Lys | SEQ ID NO: 4 |
| YDE-005 | Hyp(2S,4R) - Gly - Gln - Lys - Gly - Leu - Ala - Gly - Pro - Lys | SEQ ID NO: 5 |

TABLE 11-continued
| No. | Chemical structure | SEQ ID NO. |
|---|---|---|
| YDE-006 | 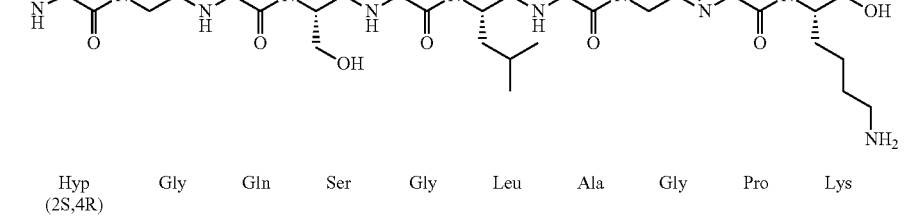 Hyp(2S,4R) — Gly — Gln — Ser — Gly — Leu — Ala — Gly — Pro — Lys | SEQ ID NO: 6 |
| YDE-007 | 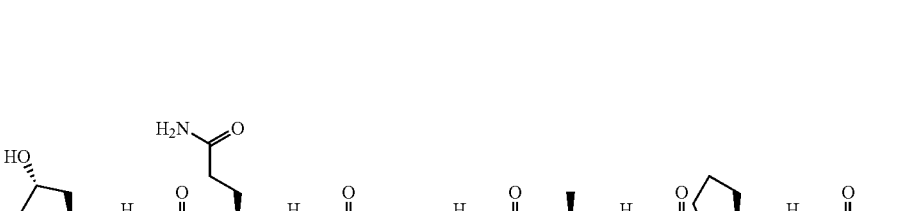 Hyp(2S,4R) — Gly — Gln — Thr — Gly — Leu — Ala — Gly — Pro — Lys | SEQ ID NO: 7 |
| YDE-008 | 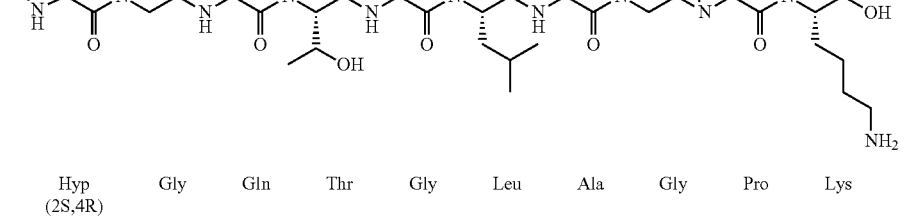 Hyp(2S,4R) — Gly — Gln — Ala — Gly — Leu — Ala — Gly — Pro — Lys | SEQ ID NO: 8 |
| YDE-009 | 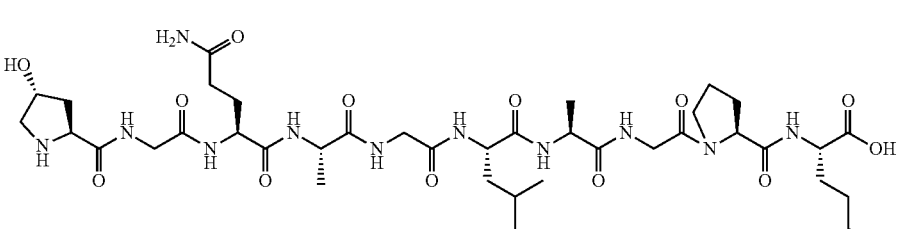 Hyp(2S,4R) — Gly — Gln — Val — Gly — Leu — Ala — Gly — Pro — Lys | SEQ ID NO: 9 |

TABLE 11-continued

| No. | Chemical structure | SEQ ID NO. |
|---|---|---|
| YDE-010 | Hyp(2S,4R) - Gly - Gln - Ile - Gly - Leu - Ala - Gly - Pro - Lys | SEQ ID NO: 10 |
| YDE-011 | Hyp(2S,4R) - Gly - Gln - Leu - Gly - Leu - Ala - Gly - Pro - Lys | SEQ ID NO: 11 |
| YDE-012 | Hyp(2S,4R) - Gly - Gln - Phe - Gly - Leu - Ala - Gly - Pro - Lys | SEQ ID NO: 12 |
| YDE-013 | Hyp(2S,4R) - Gly - Gln - Tyr - Gly - Leu - Ala - Gly - Pro - Lys | SEQ ID NO: 13 |

TABLE 11-continued
| No. | Chemical structure | SEQ ID NO. |
|---|---|---|
| YDE-014 | 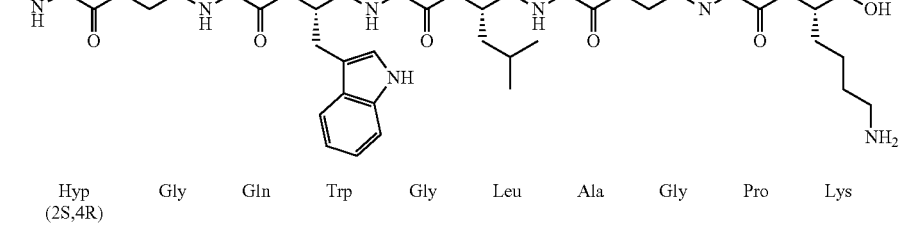 Hyp(2S,4R) Gly Gln Trp Gly Leu Ala Gly Pro Lys | SEQ ID NO: 14 |
| YDE-015 | 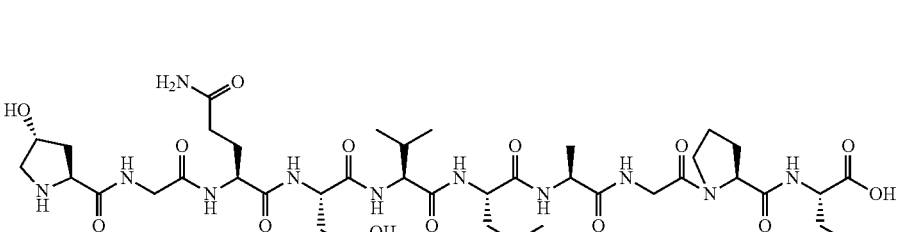 Hyp(2S,4R) Gly Gln Asp Val Leu Ala Gly Pro Lys | SEQ ID NO: 21 |
| YDE-016 | 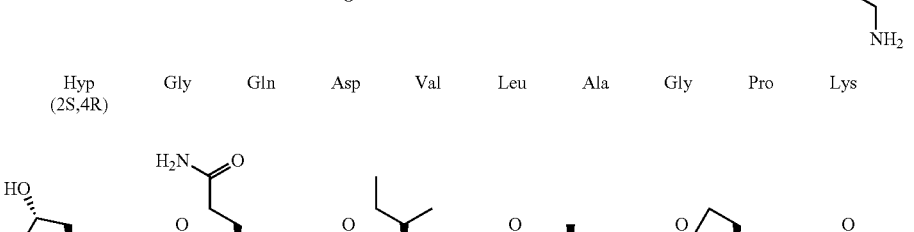 Hyp(2S,4R) Gly Gln Asp Ile Leu Ala Gly Pro Lys | SEQ ID NO: 22 |
| YDE-017 | 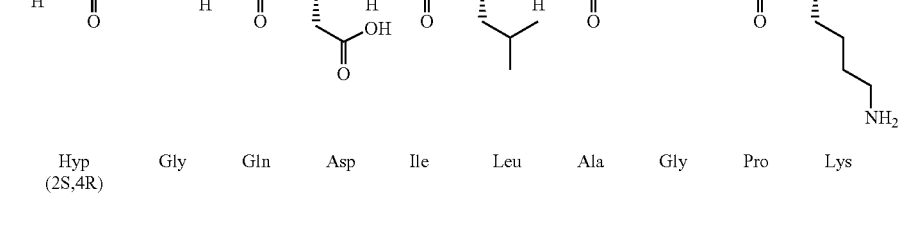 Hyp(2S,4R) Gly Gln Asp Leu Leu Ala Gly Pro Lys | SEQ ID NO: 23 |

TABLE 11-continued
| No. | Chemical structure | SEQ ID NO. |
|---|---|---|
| YDE-018 | 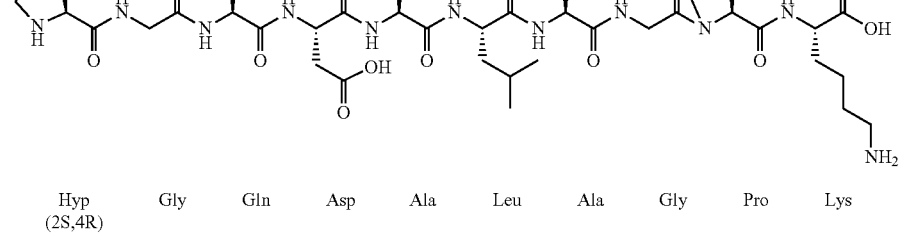<br>Hyp (2S,4R) — Gly — Gln — Asp — Ala — Leu — Ala — Gly — Pro — Lys | SEQ ID NO: 24 |
| YDE-019 | 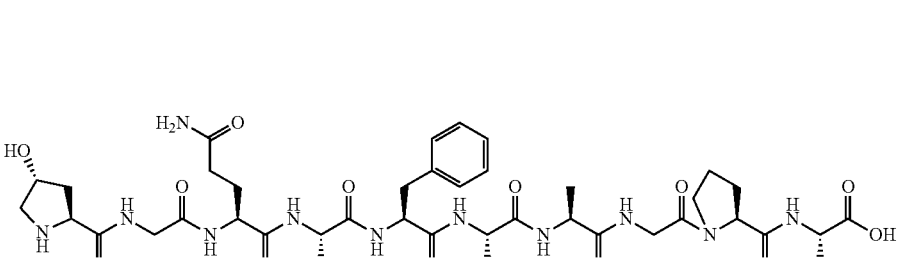<br>Hyp (2S,4R) — Gly — Gln — Asp — Phe — Leu — Ala — Gly — Pro — Lys | SEQ ID NO: 25 |
| YDE-020 | 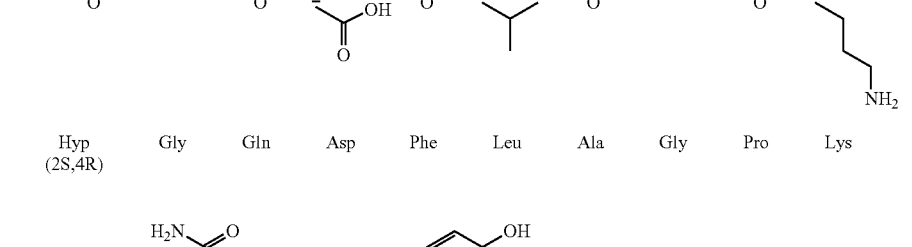<br>Hyp (2S,4R) — Gly — Gln — Asp — Tyr — Leu — Ala — Gly — Pro — Lys | SEQ ID NO: 26 |
| YDE-021 | 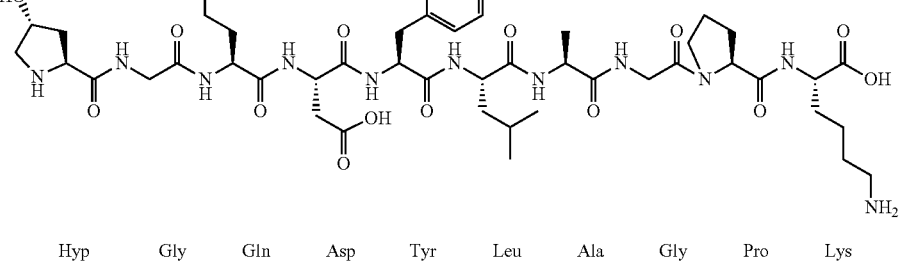<br>Hyp (2S,4R) — Gly — Gln — Asp — Trp — Leu — Ala — Gly — Pro — Lys | SEQ ID NO: 27 |

TABLE 11-continued
| No. | Chemical structure | SEQ ID NO. |
|---|---|---|
| YDE-022 | 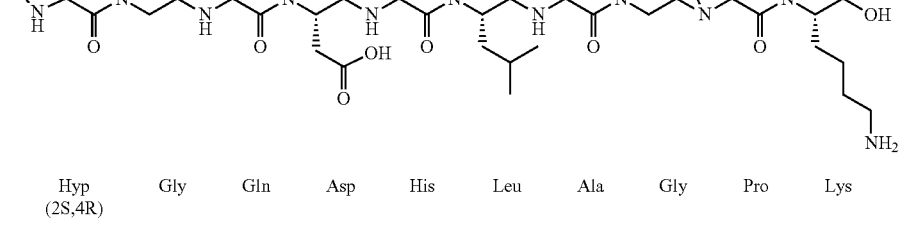<br>Hyp(2S,4R) Gly Gln Asp His Leu Ala Gly Pro Lys | SEQ ID NO: 28 |
| YDE-023 | 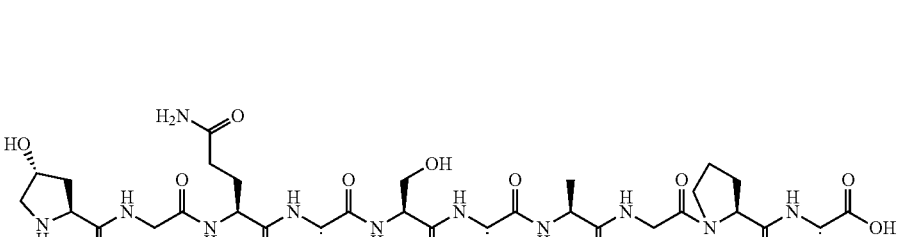<br>Hyp(2S,4R) Gly Gln Asp Ser Leu Ala Gly Pro Lys | SEQ ID NO: 29 |
| YDE-024 | 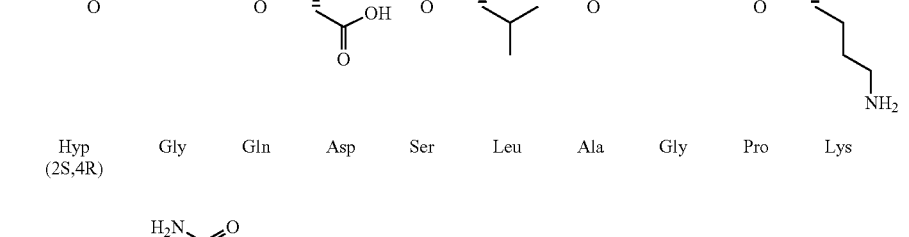<br>Hyp(2S,4R) Gly Gln Asp Thr Leu Ala Gly Pro Lys | SEQ ID NO: 30 |
| YDE-025 | 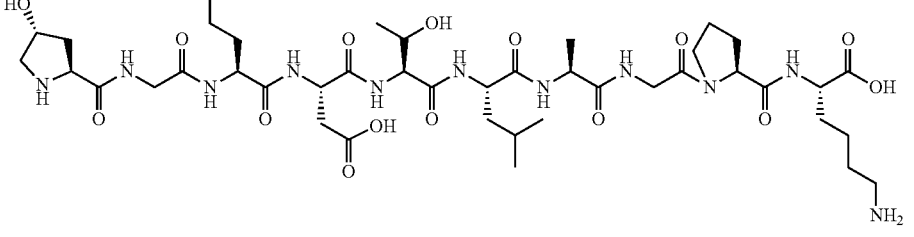<br>Hyp(2S,4R) Gly Gln Asp (Me)Gly Leu Ala Gly Pro Lys | SEQ ID NO: 31 |

TABLE 11-continued

| No. | Chemical structure | SEQ ID NO. |
|---|---|---|
| YDE-026 | Hyp(2S,4R) — Gly — Gln — Homo-Ser — Gly — Leu — Ala — Gly — Pro — Lys | SEQ ID NO: 15 |
| YDE-027 | Hyp(2S,4R) — Gly — Gln — Asp(Me) — Gly — Leu — Ala — Gly — Pro — Lys | SEQ ID NO: 16 |
| YDE-028 | Hyp(2S,4R) — Gly — Gln — Asn(Me) — Gly — Leu — Ala — Gly — Pro — Lys | SEQ ID NO: 17 |
| YDE-029 | Hyp(2S,4R) — Gly — Gln — Leu — Gly — Leu — Ala — Gly — Pro — Tyr | SEQ ID NO: 33 |
| YDE-030 | Hyp(2S,4R) — Gly — Gln — Leu — Gly — Leu — Ala — Gly — Pro — Leu | SEQ ID NO: 34 |

TABLE 11-continued

| No. | Chemical structure | SEQ ID NO. |
|---|---|---|
| YDE-031 | Hyp(2S,4R) - Gly - Gln - Leu - Gly - Leu - Ala - Gly - Pro - Glu | SEQ ID NO: 35 |
| YDE-032 | Hyp(2S,4R) - Gly - Gln - Leu - Gly - Leu - Ala - Gly - Pro - Gln | SEQ ID NO: 36 |
| YDE-033 | Hyp(2S,4R) - Gly - Gln - Leu - Gly - Leu - Ala - Gly - Pro - Nle(6-OH) | SEQ ID NO: 37 |
| YDE-034 | Hyp(2S,4S) - Gly - Gln - Leu - Gly - Leu - Ala - Gly - Pro - Lys | SEQ ID NO: 63 |

TABLE 11-continued
| No. | Chemical structure | SEQ ID NO. |
|---|---|---|
| YDE-035 | 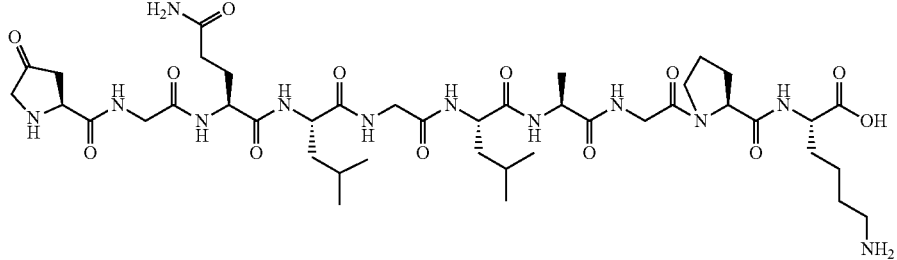<br>(4-oxo)Pro Gly Gln Leu Gly Leu Ala Gly Pro Lys | SEQ ID NO: 40 |
| YDE-036 | 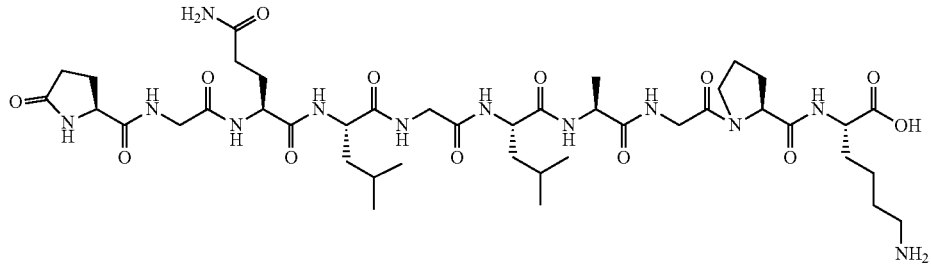<br>(5-oxo)Pro Gly Gln Leu Gly Leu Ala Gly Pro Lys | SEQ ID NO: 41 |
| YDE-037 | 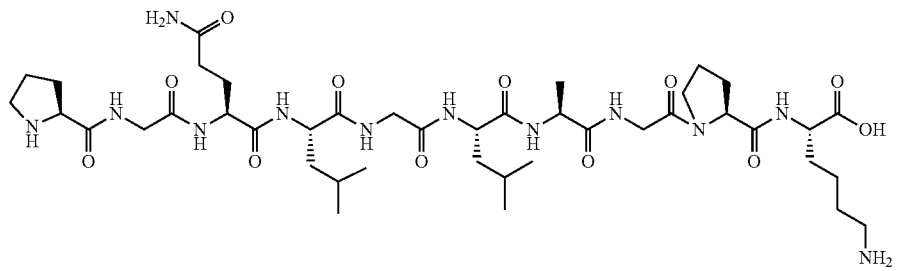<br>Pro Gly Gln Leu Gly Leu Ala Gly Pro Lys | SEQ ID NO: 42 |
| YDE-038 | 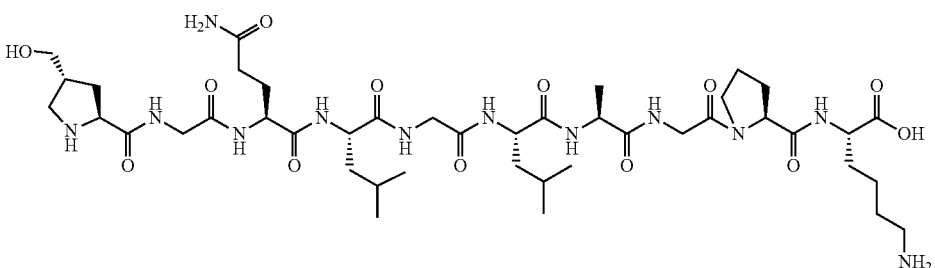<br>(4-hydroxyMe)Pro Gly Gln Leu Gly Leu Ala Gly Pro Lys<br>(4R) | SEQ ID NO: 43 |
| YDE-039 | 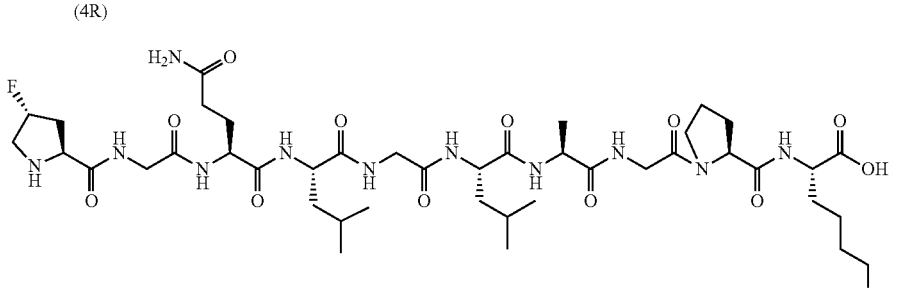<br>(4-Fluoro)Pro Gly Gln Leu Gly Leu Ala Gly Pro Lys<br>(4R) | SEQ ID NO: 44 |

TABLE 11-continued

| No. | Chemical structure | SEQ ID NO. |
|---|---|---|
| YDE-040 | (4-Dimethyl)Pro – Gly – Gln – Leu – Gly – Leu – Ala – Gly – Pro – Lys | SEQ ID NO: 45 |
| YDE-041 | Hyp(2S,4R) – Gly – Gln – Leu – Gly – Leu – Ala | SEQ ID NO: 56 |
| YDE-042 | Hyp(2S,4R) – Gly – Gln – Leu – Gly – Leu | SEQ ID NO: 58 |
| YDE-043 | Hyp(2S,4R) – Gly – Gln – Leu – Gly | SEQ ID NO: 60 |
| YDE-044 | (4-Me)Pro(4R) – Gly – Gln – Leu – Gly – Leu – Ala – Gly – Pro – Lys | SEQ ID NO: 46 |

TABLE 11-continued
| No. | Chemical structure | SEQ ID NO. |
|---|---|---|
| YDE-045 | 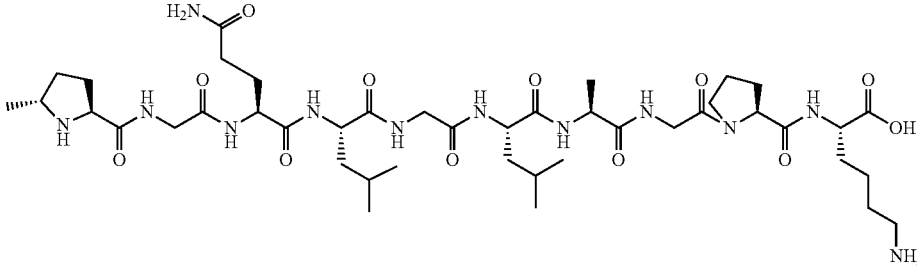<br>(5-Me)Pro (5R) — Gly — Gln — Leu — Gly — Leu — Ala — Gly — Pro — Lys | SEQ ID NO: 48 |
| YDE-047 | 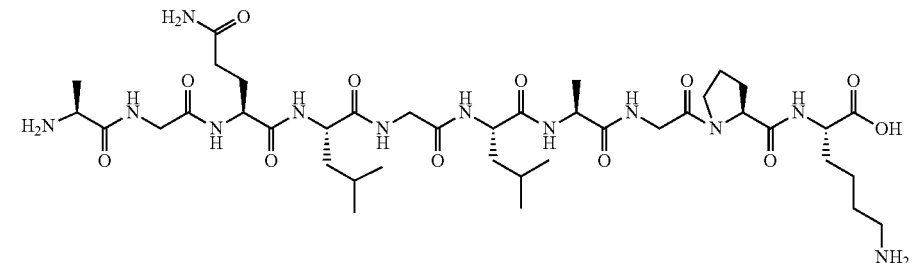<br>Ala — Gly — Gln — Leu — Gly — Leu — Ala — Gly — Pro — Lys | SEQ ID NO: 54 |
| YDE-048 | 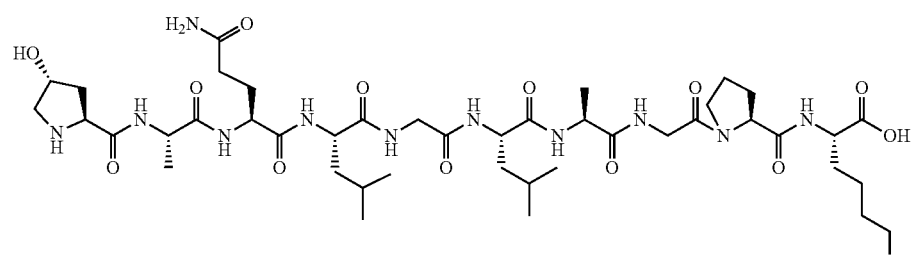<br>Hyp (2S, 4R) — Ala — Gln — Leu — Gly — Leu — Ala — Gly — Pro — Lys | SEQ ID NO: 51 |
| YDE-049 | 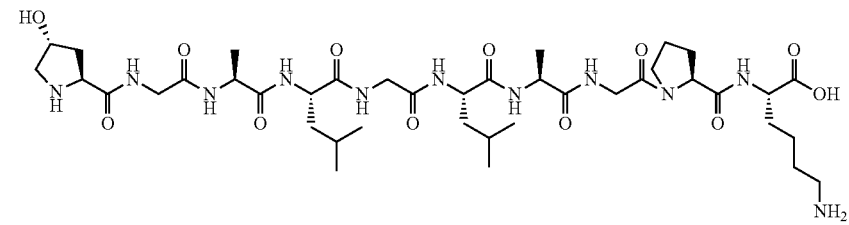<br>Hyp (2S, 4R) — Gly — Ala — Leu — Gly — Leu — Ala — Gly — Pro — Lys | SEQ ID NO: 48 |

TABLE 11-continued
| No. | Chemical structure | SEQ ID NO. |
|---|---|---|
| YDE-050 | 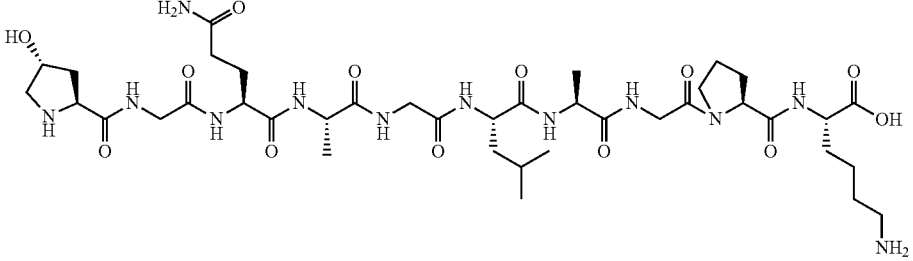<br>Hyp (2S, 4R)  Gly  Gln  Ala  Gly  Leu  Ala  Gly  Pro  Lys | SEQ ID NO: 107 |
| YDE-051 | 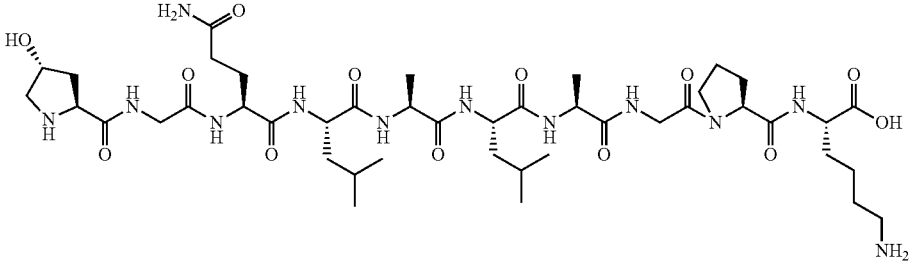<br>Hyp (2S, 4R)  Gly  Gln  Leu  Ala  Leu  Ala  Gly  Pro  Lys | SEQ ID NO: 32 |
| YDE-052 | 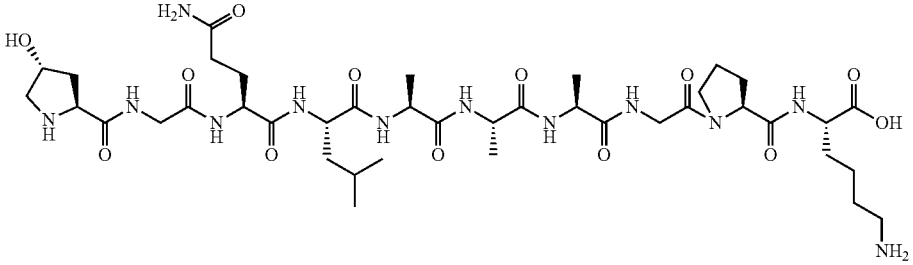<br>Hyp (2S, 4R)  Gly  Gln  Leu  Gly  Ala  Ala  Gly  Pro  Lys | SEQ ID NO: 49 |
| YDE-053 | 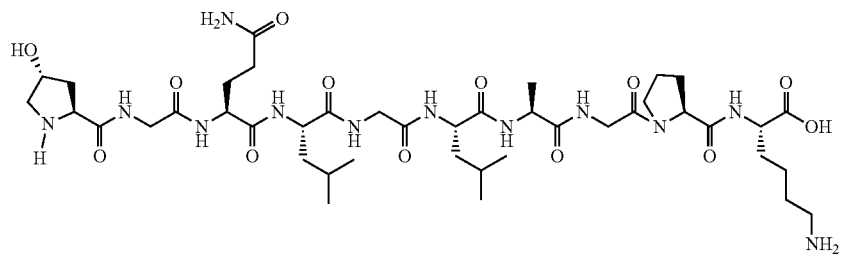<br>Hyp  Gly  Gln  Leu  Gly  Leu  Ala  Gly  Pro  Lys | SEQ ID NO: 108 |

TABLE 11-continued
| No. | Chemical structure | SEQ ID NO. |
|---|---|---|
| YDE-054 | 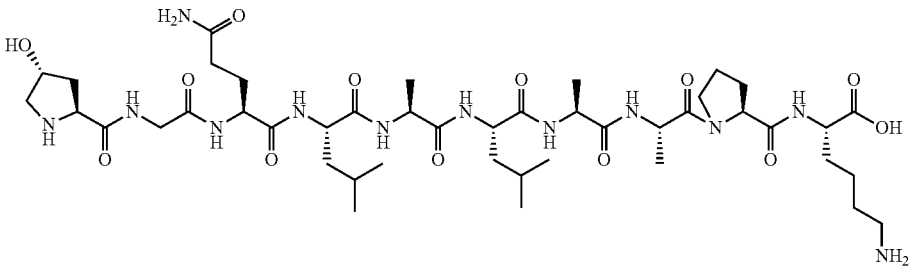 Hyp (2S, 4R) — Gly — Gln — Leu — Gly — Leu — Ala — Ala — Pro — Lys | SEQ ID NO: 50 |
| YDE-055 | 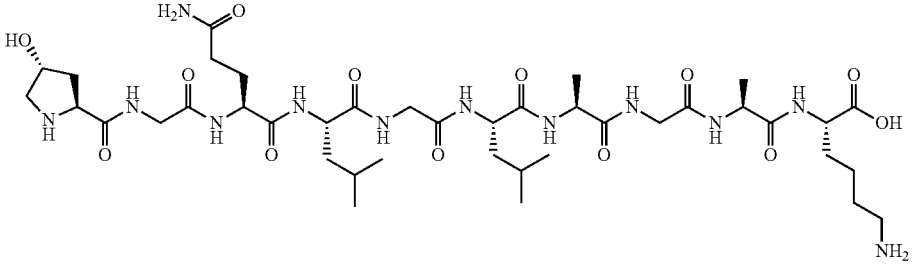 Hyp (2S, 4R) — Gly — Gln — Leu — Gly — Leu — Ala — Gly — Pro — Lys | SEQ ID NO: 55 |
| YDE-056 | 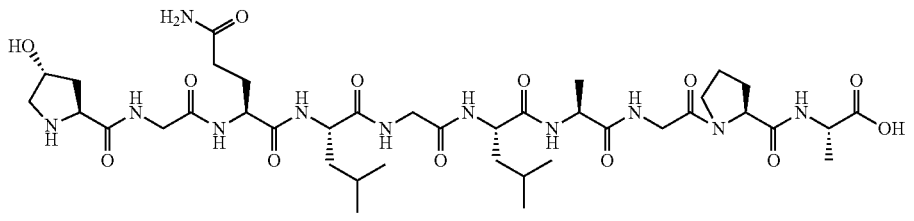 Hyp (2S, 4R) — Gly — Gln — Leu — Gly — Leu — Ala — Gly — Pro — Ala | SEQ ID NO: 38 |
| YDE-057 | 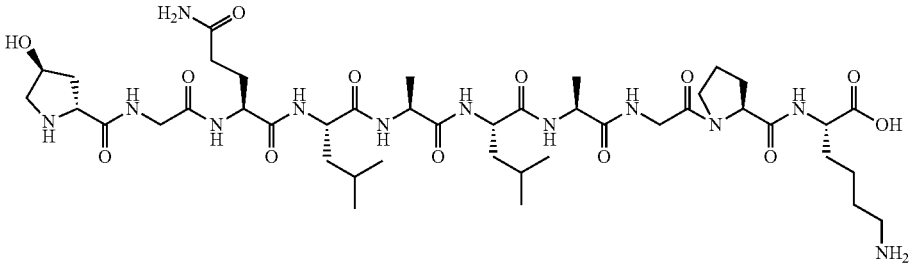 D-Hyp (2R, 4S) — Gly — Gln — Leu — Gly — Leu — Ala — Gly — Pro — Lys | SEQ ID NO: 18 |

TABLE 11-continued

| No. | Chemical structure | SEQ ID NO. |
|---|---|---|
| YDE-058 | D-Hyp (2R, 4S) — Gly — D-Gln — D-Leu — Gly — D-Leu — D-Ala — Gly — D-Pro — D-Lys | SEQ ID NO: 19 |
| YDE-059 | Hyp (2S,4R) — Gly — Gln — Glu — Gly — Lys — Gly (amide bond between Glu and Lys) | SEQ ID NO: 57 |
| YDE-060 | D-Hyp (2R, 4R) — Gly — D-Gln — D-Leu — Gly — D-Leu — D-Ala — Gly — D-Pro — D-Lys | SEQ ID NO: 20 |
| YDE-064 | D-Hyp (2R,4S) — Gly — D-Gln — D-Leu — Gly — D-Leu | SEQ ID NO: 59 |
| YDE-066 | Hyp (2S,4R) — Gly — Gln — D-Leu — Gly | SEQ ID NO: 61 |

TABLE 11-continued

| No. | Chemical structure | SEQ ID NO. |
|---|---|---|
| YDE-072 | D-Hyp (2R,4S) – Ala – Gln – Leu – Gly – Leu – Ala – Gly – Pro – Lys | SEQ ID NO: 53 |
| YDE-073 | D-Hyp (2R,4S) – Gly – Gln – Leu – Gly – Leu – Ala – Gly – Pro – Ala | SEQ ID NO: 39 |
| YDE-074 | D-Hyp (2R,4S) – Ala – Gln – Leu – Gly – Leu – Ala – Gly – Pro – Ala | SEQ ID NO: 52 |
| YDE-075 | D-Hyp (2R,4S) – Gly – Gln – Leu – Gly | SEQ ID NO: 62 |

Experimental Example 1: Analysis of YDE Derivatives

Figure 4:
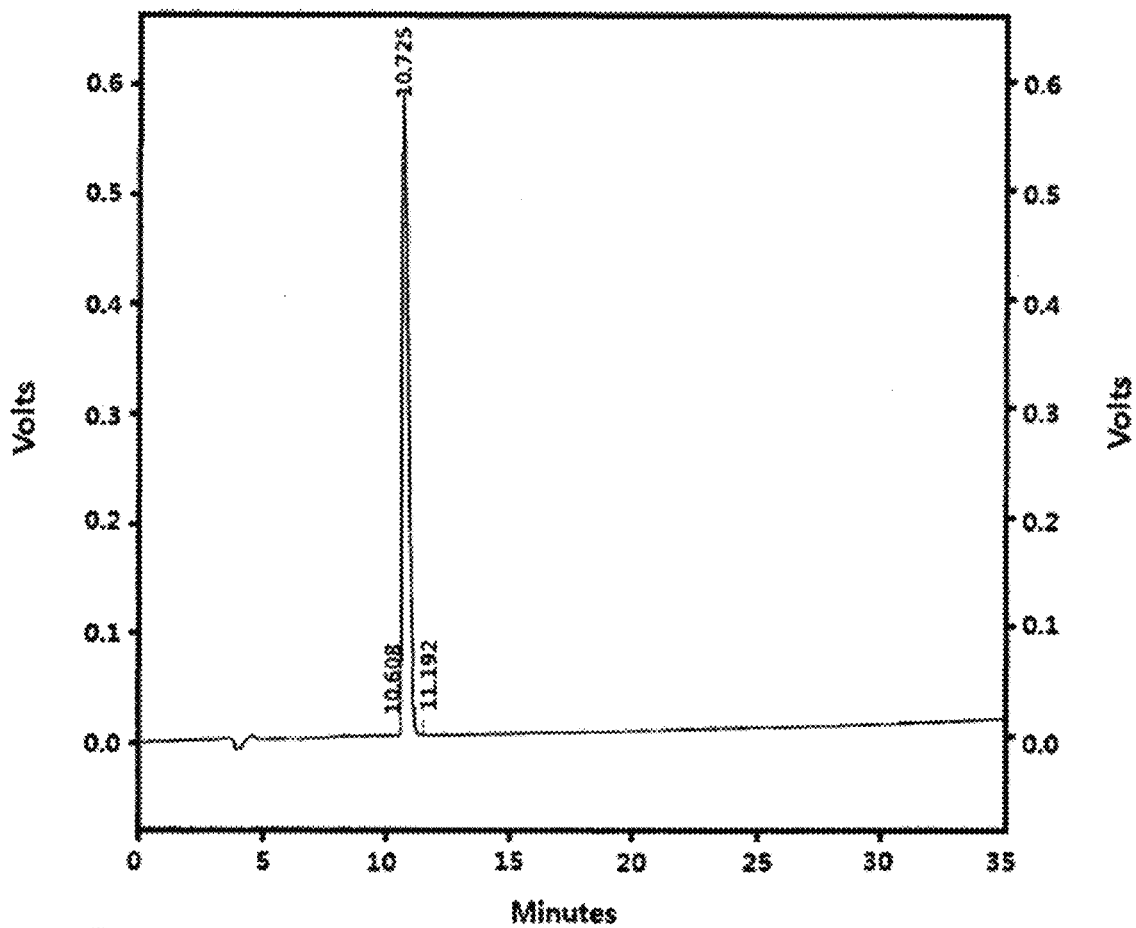
FIG. 4 is a diagram confirming the purity of YDE-001 prepared according to an embodiment of the present invention through HPLC.
Figure 5:
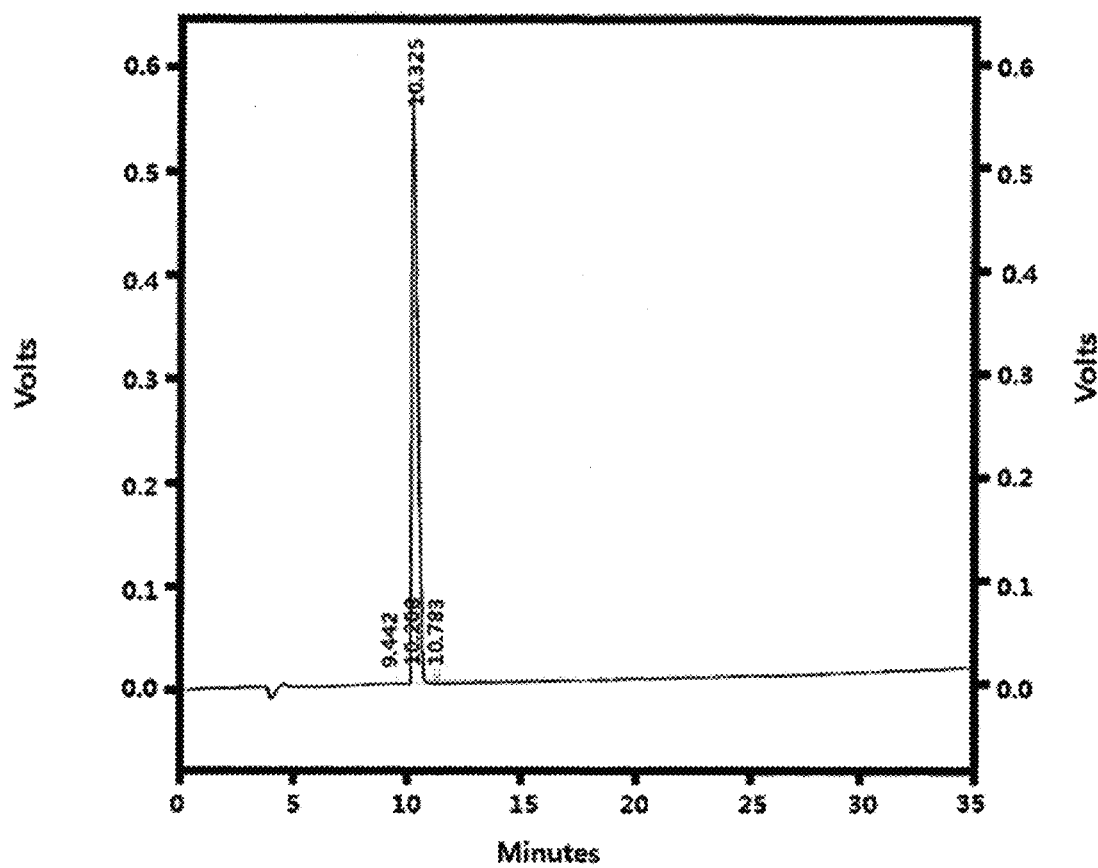
FIG. 5 is a diagram confirming the purity of YDE-002 prepared according to an embodiment of the present invention through HPLC.
Figure 6:
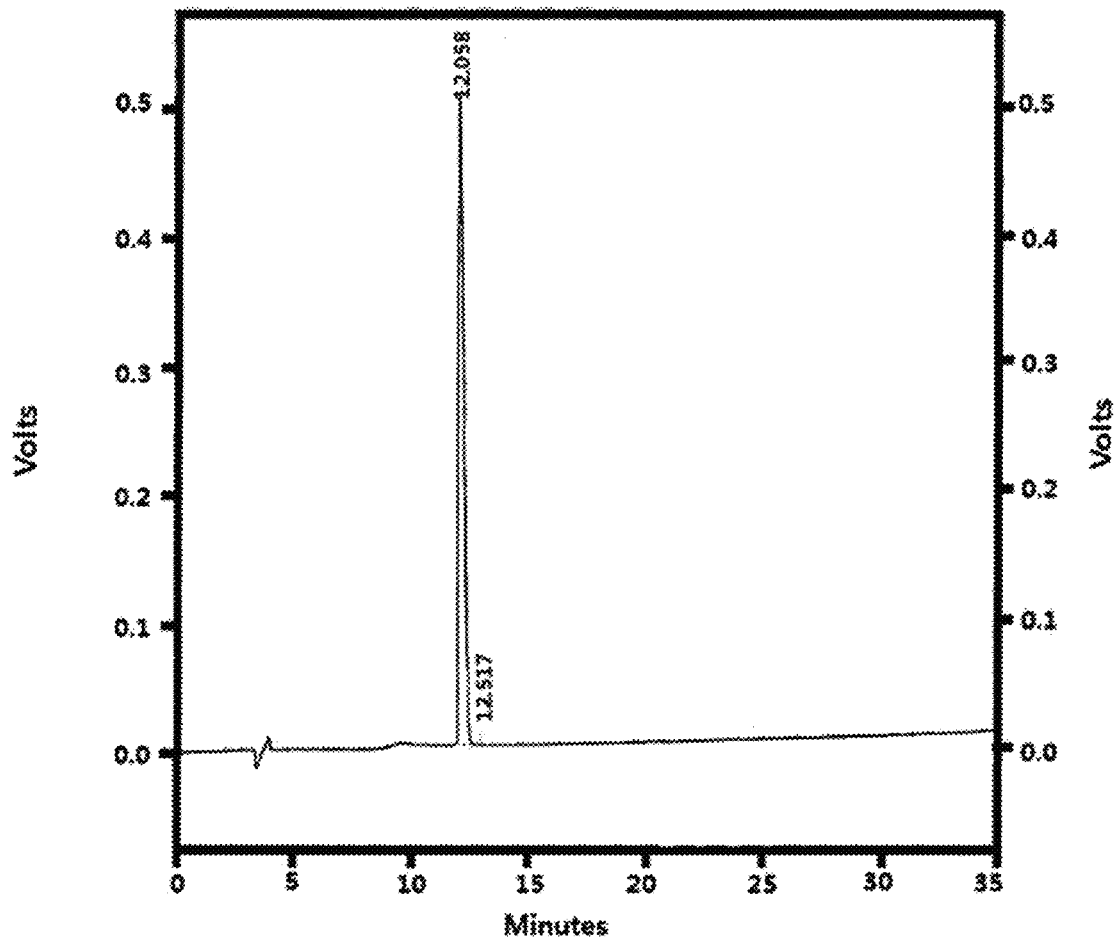
FIG. 6 is a diagram confirming the purity of YDE-003 prepared according to an embodiment of the present invention through HPLC.
Figure 7:
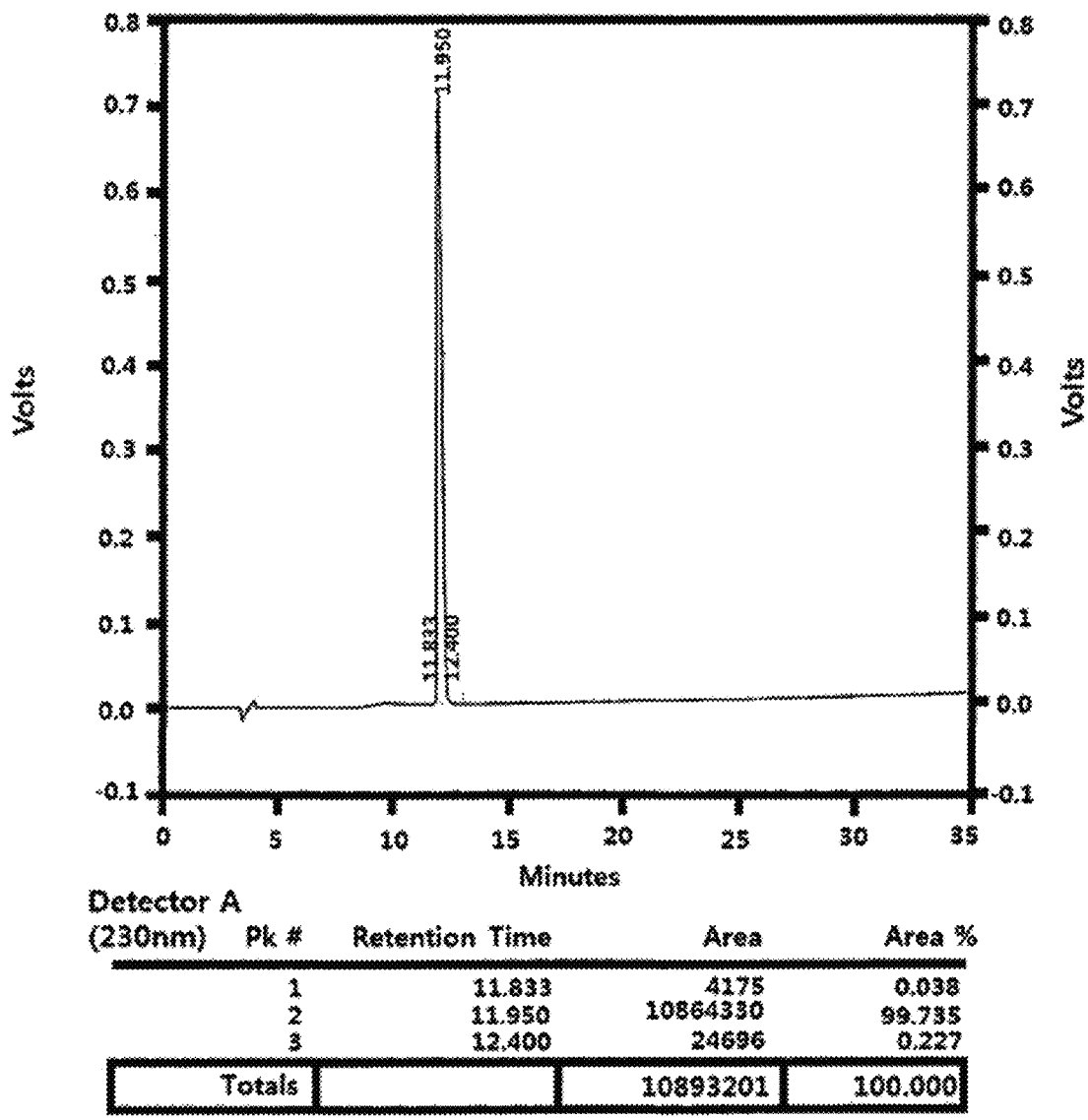
FIG. 7 is a diagram confirming the purity of YDE-004 prepared according to an embodiment of the present invention through HPLC.
Figure 8:
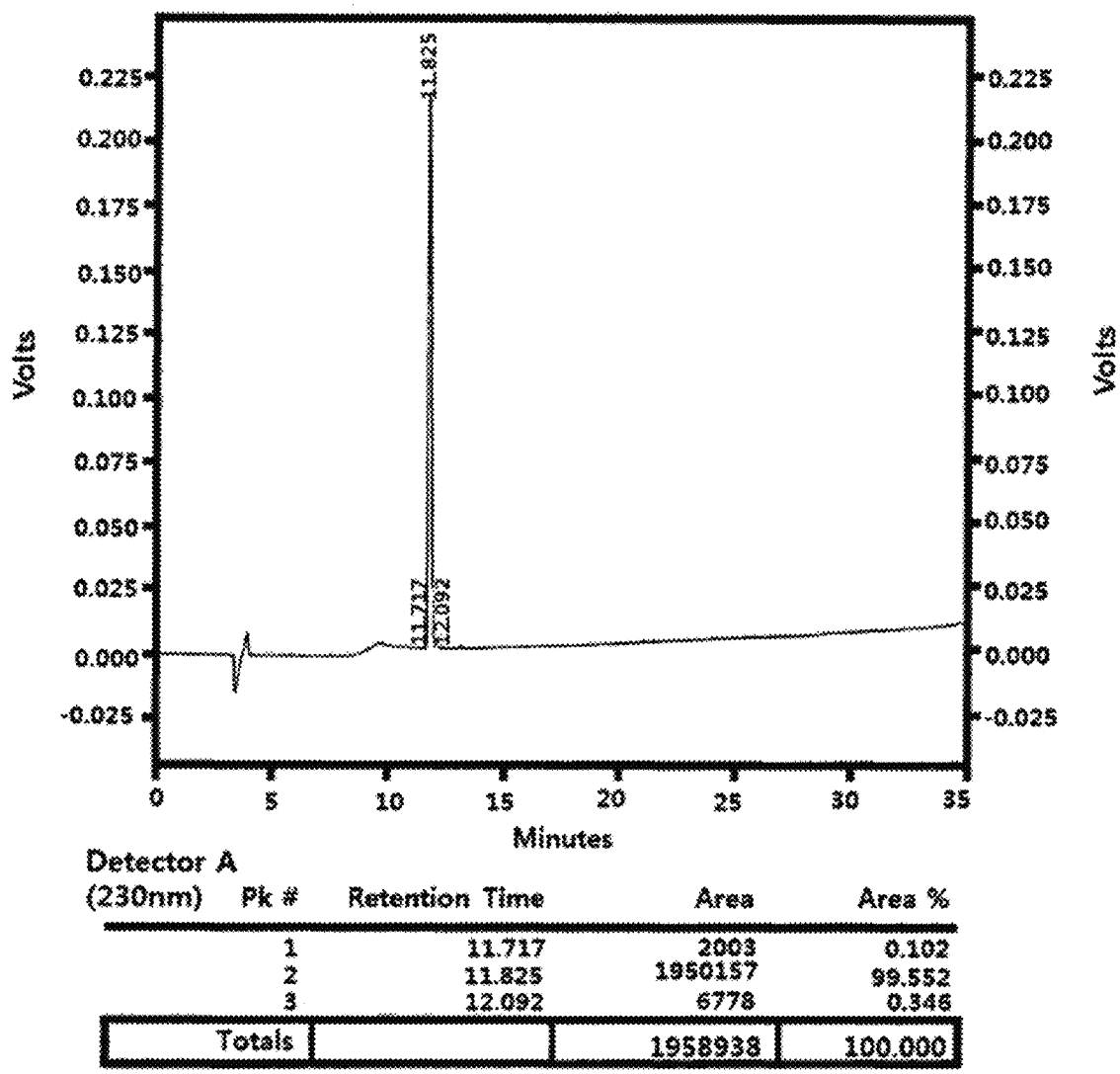
FIG. 8 is a diagram confirming the purity of YDE-005 prepared according to an embodiment of the present invention through HPLC.
Figure 9:
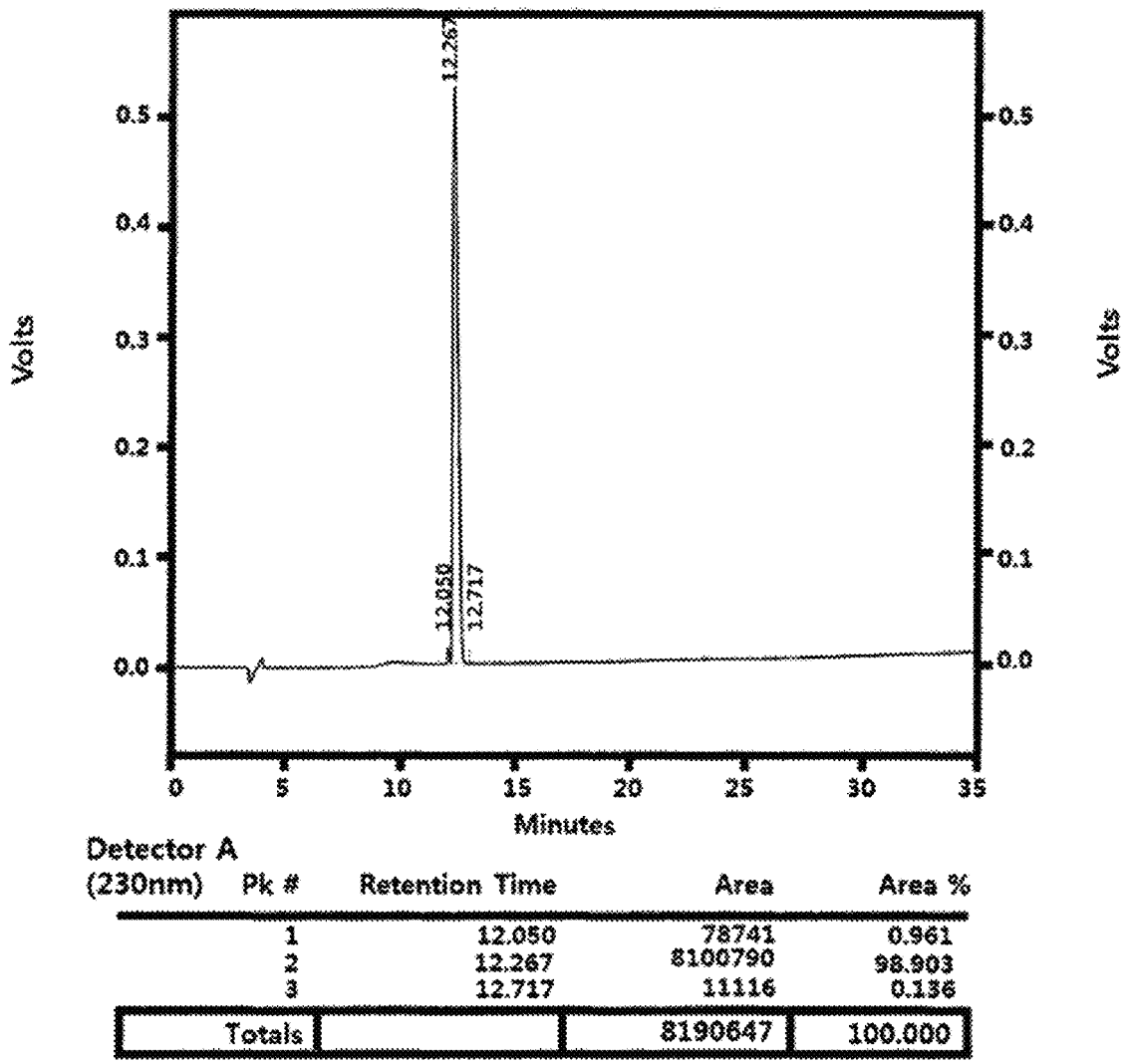
FIG. 9 is a diagram confirming the purity of YDE-006 prepared according to an embodiment of the present invention through HPLC.
Figure 10:
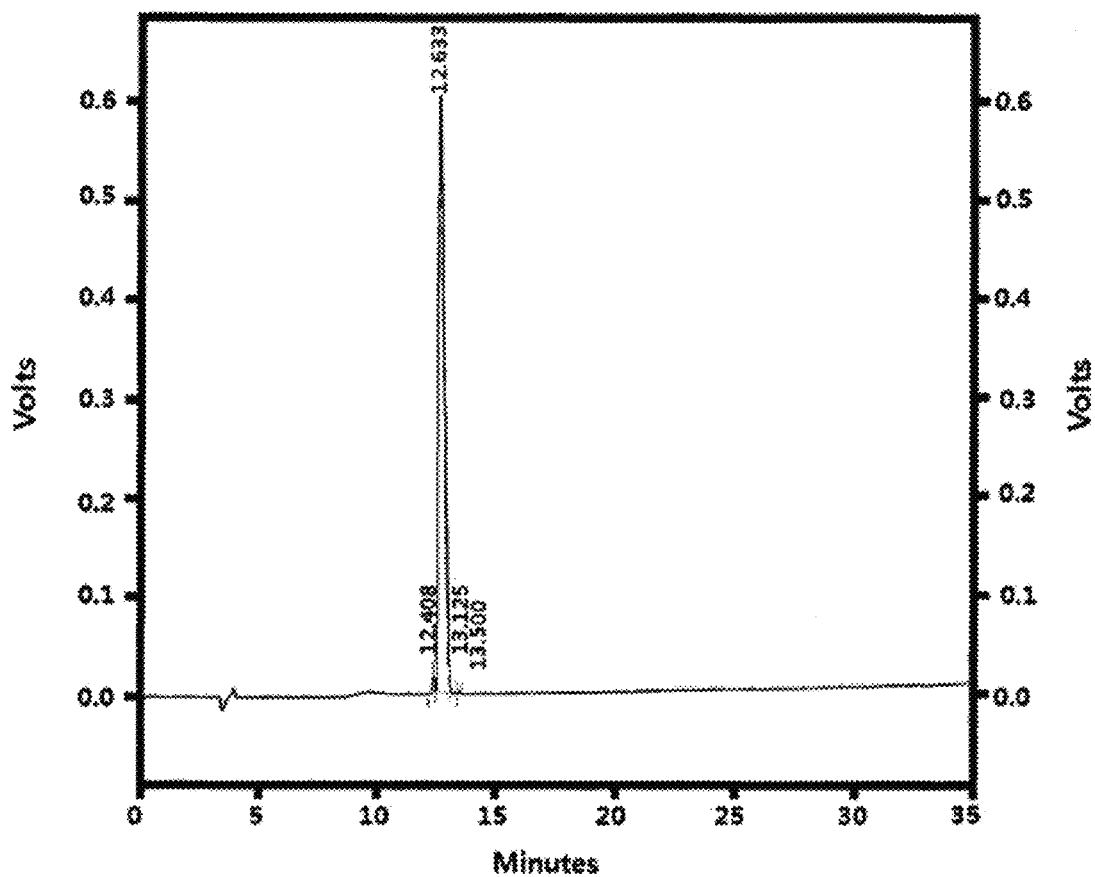
FIG. 10 is a diagram confirming the purity of YDE-007 prepared according to an embodiment of the present invention through HPLC.
Figure 11:
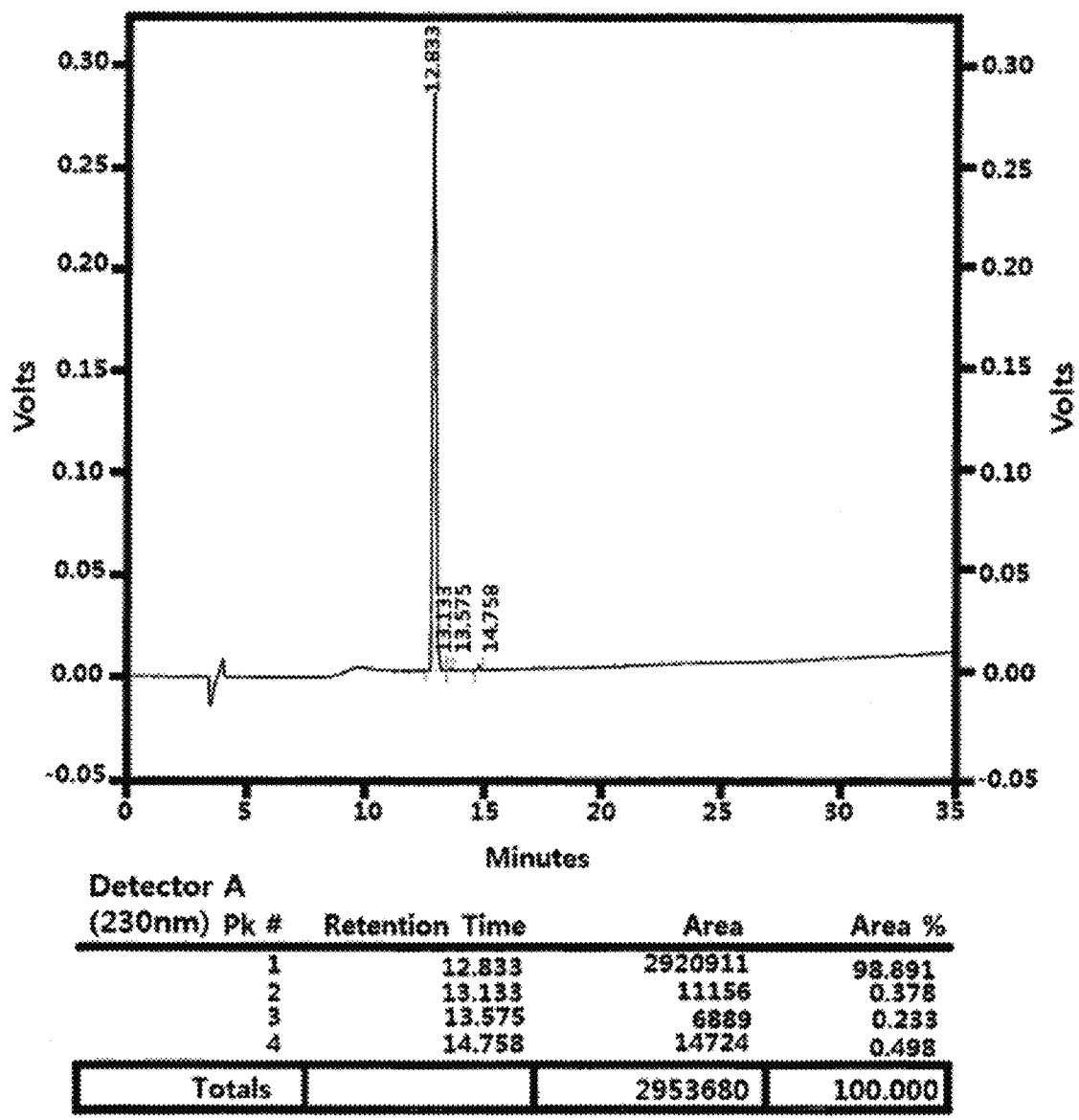
FIG. 11 is a diagram confirming the purity of YDE-008 prepared according to an embodiment of the present invention through HPLC.
Figure 12:
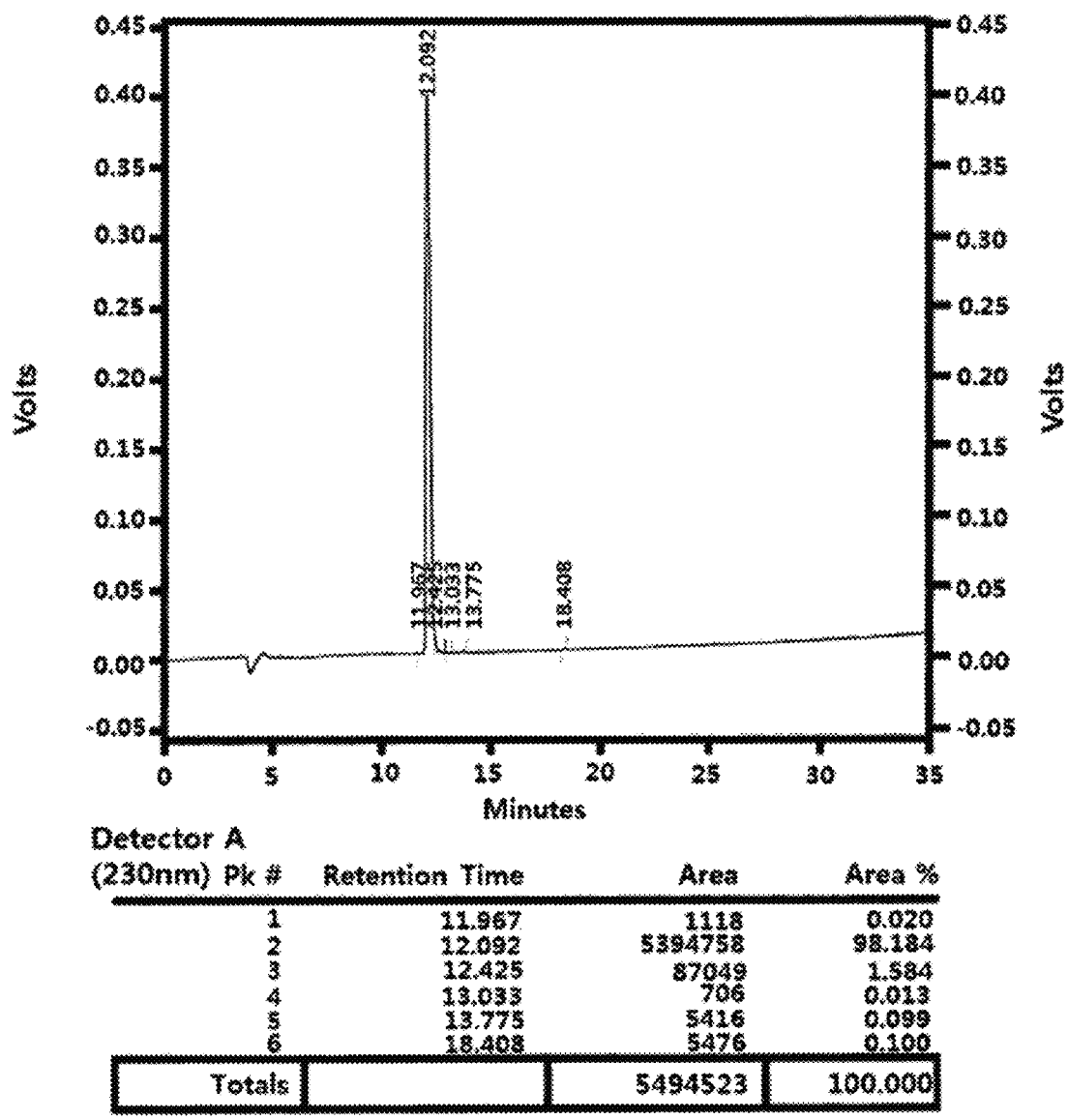
FIG. 12 is a diagram confirming the purity of YDE-009 prepared according to an embodiment of the present invention through HPLC.
Figure 13:
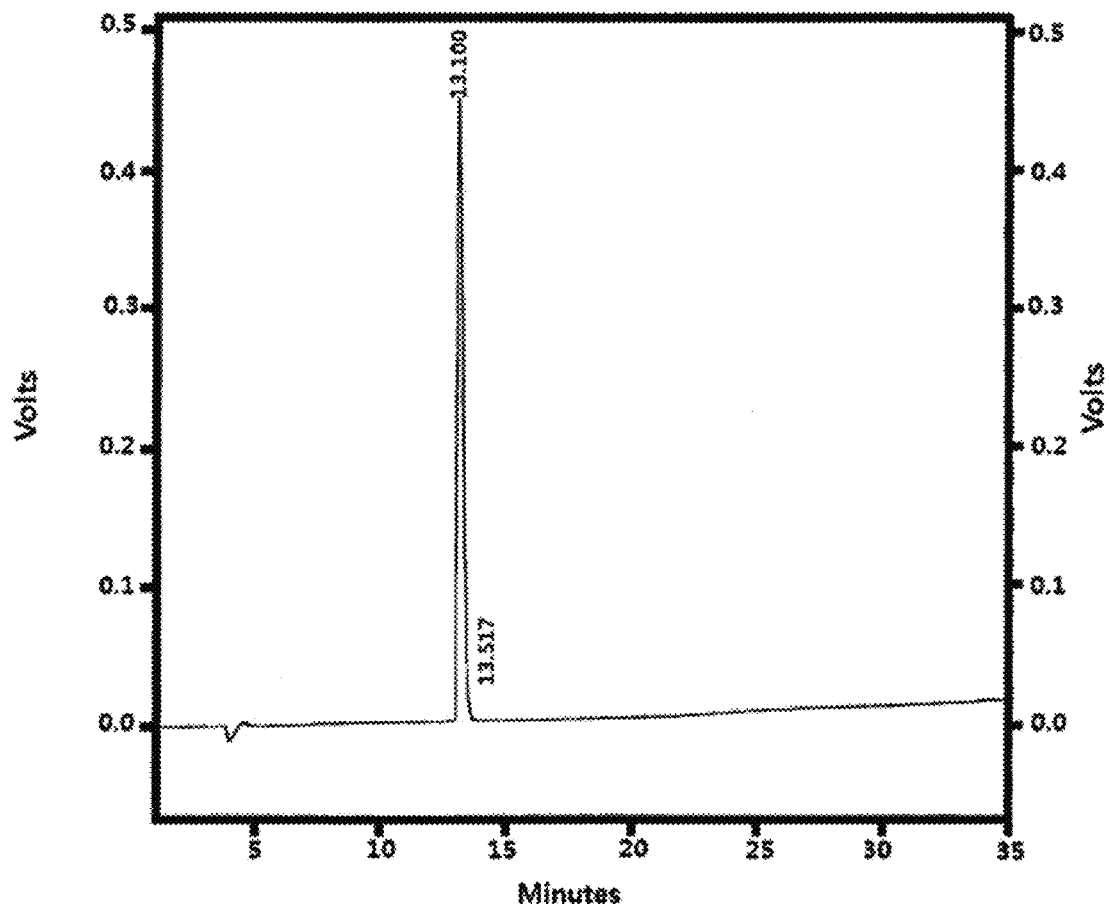
FIG. 13 is a diagram confirming the purity of YDE-010 prepared according to an embodiment of the present invention through HPLC.
Figure 14:
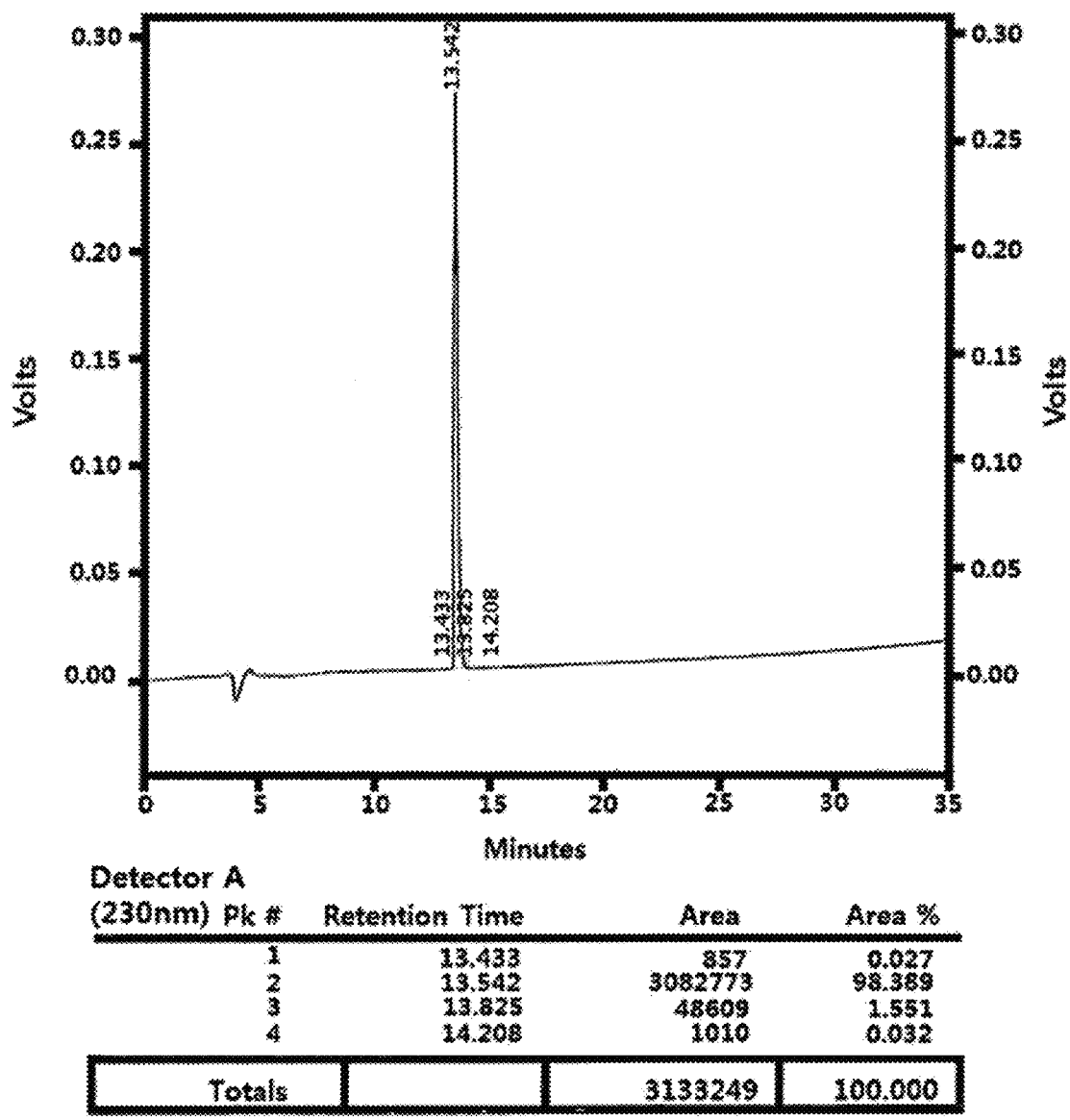
FIG. 14 is a diagram confirming the purity of YDE-011 prepared according to an embodiment of the present invention through HPLC.
Figure 15:
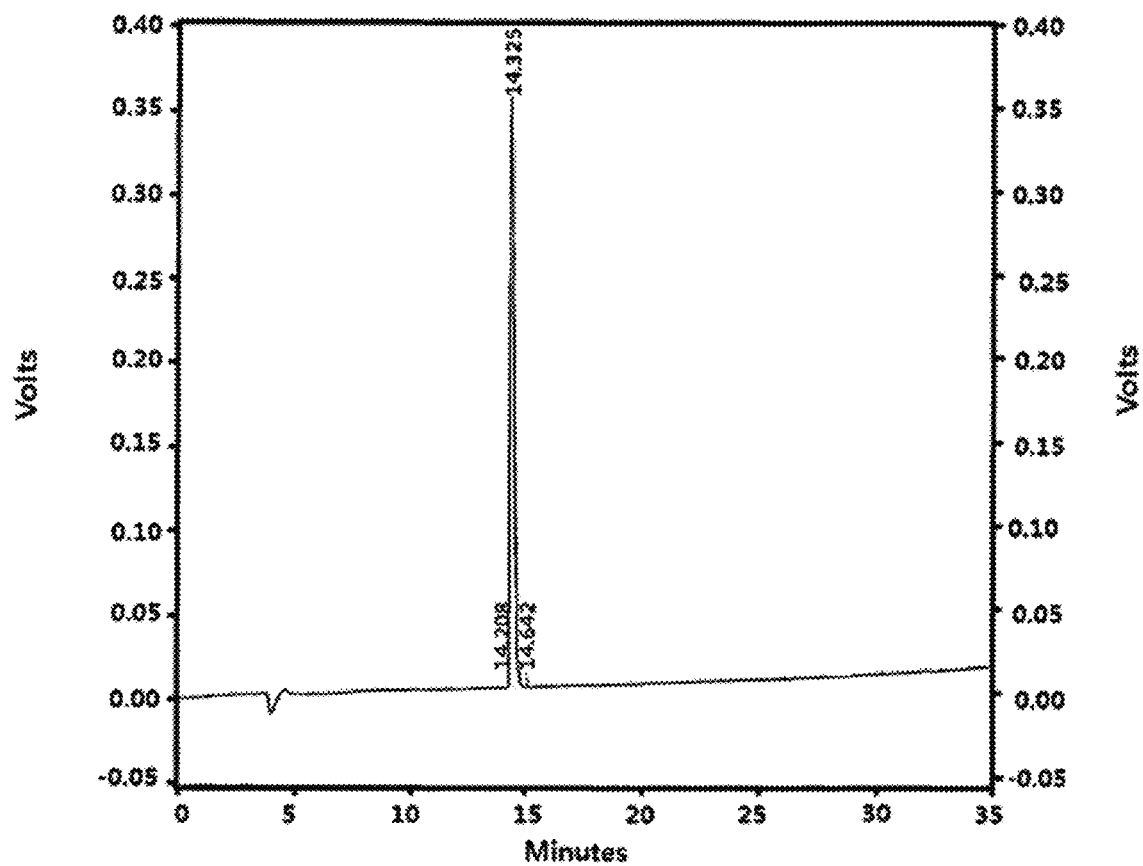
FIG. 15 is a diagram confirming the purity of YDE-012 prepared according to an embodiment of the present invention through HPLC.
Figure 16:
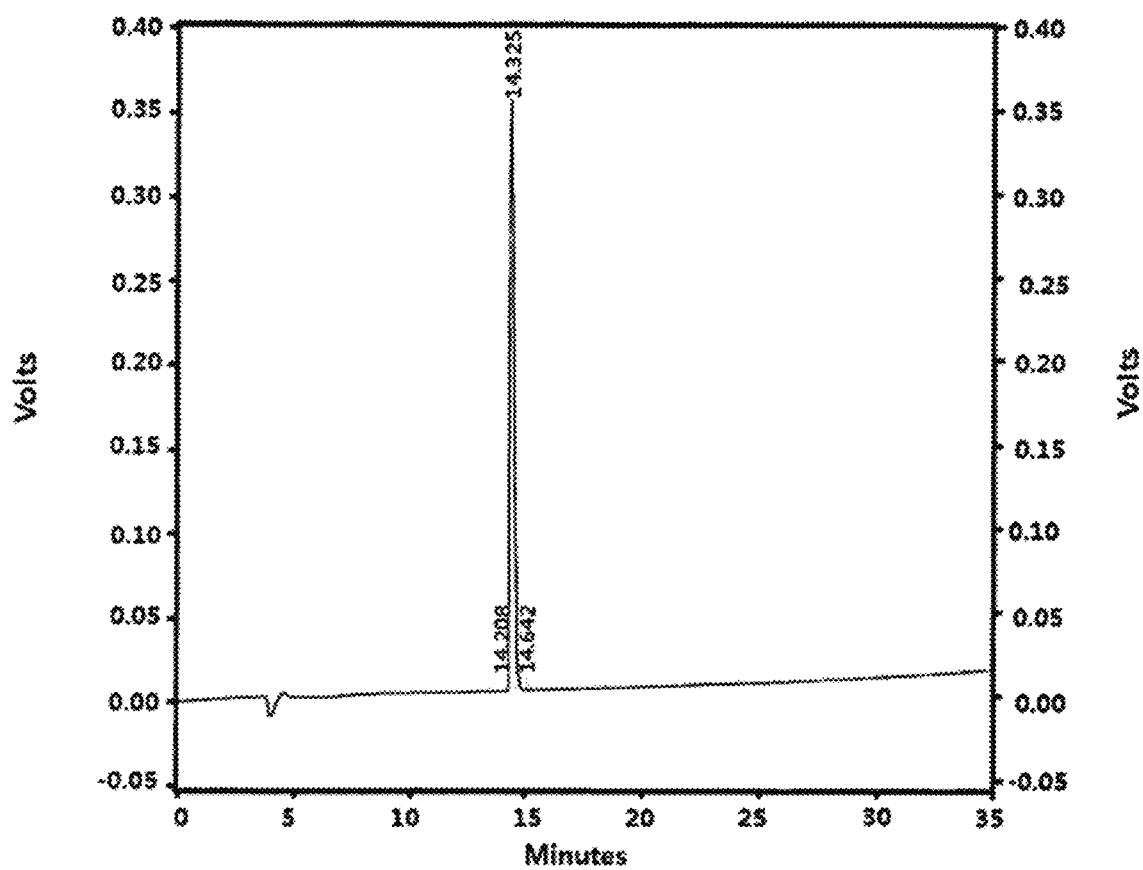
FIG. 16 is a diagram confirming the purity of YDE-012 prepared according to an embodiment of the present invention through HPLC.
Figure 17:
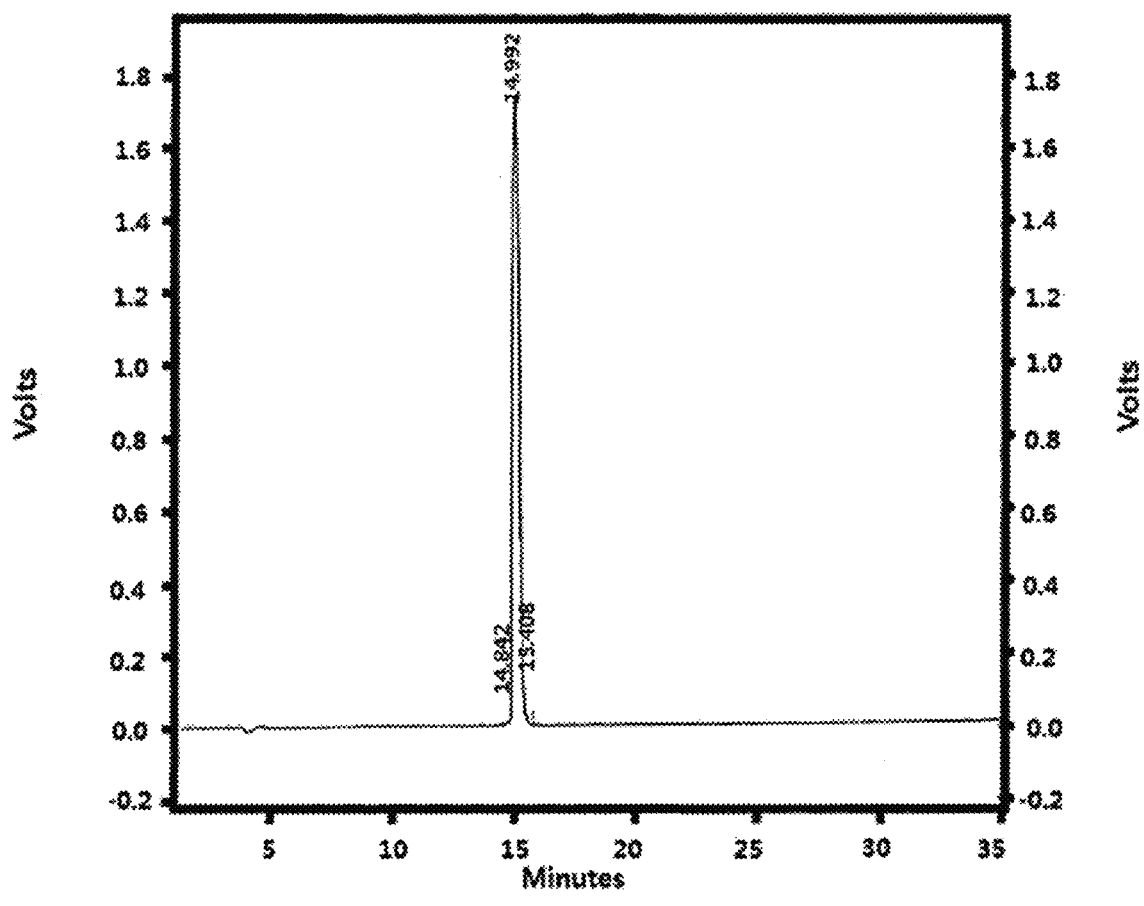
FIG. 17 is a diagram confirming the purity of YDE-014 prepared according to an embodiment of the present invention through HPLC.
Figure 18:
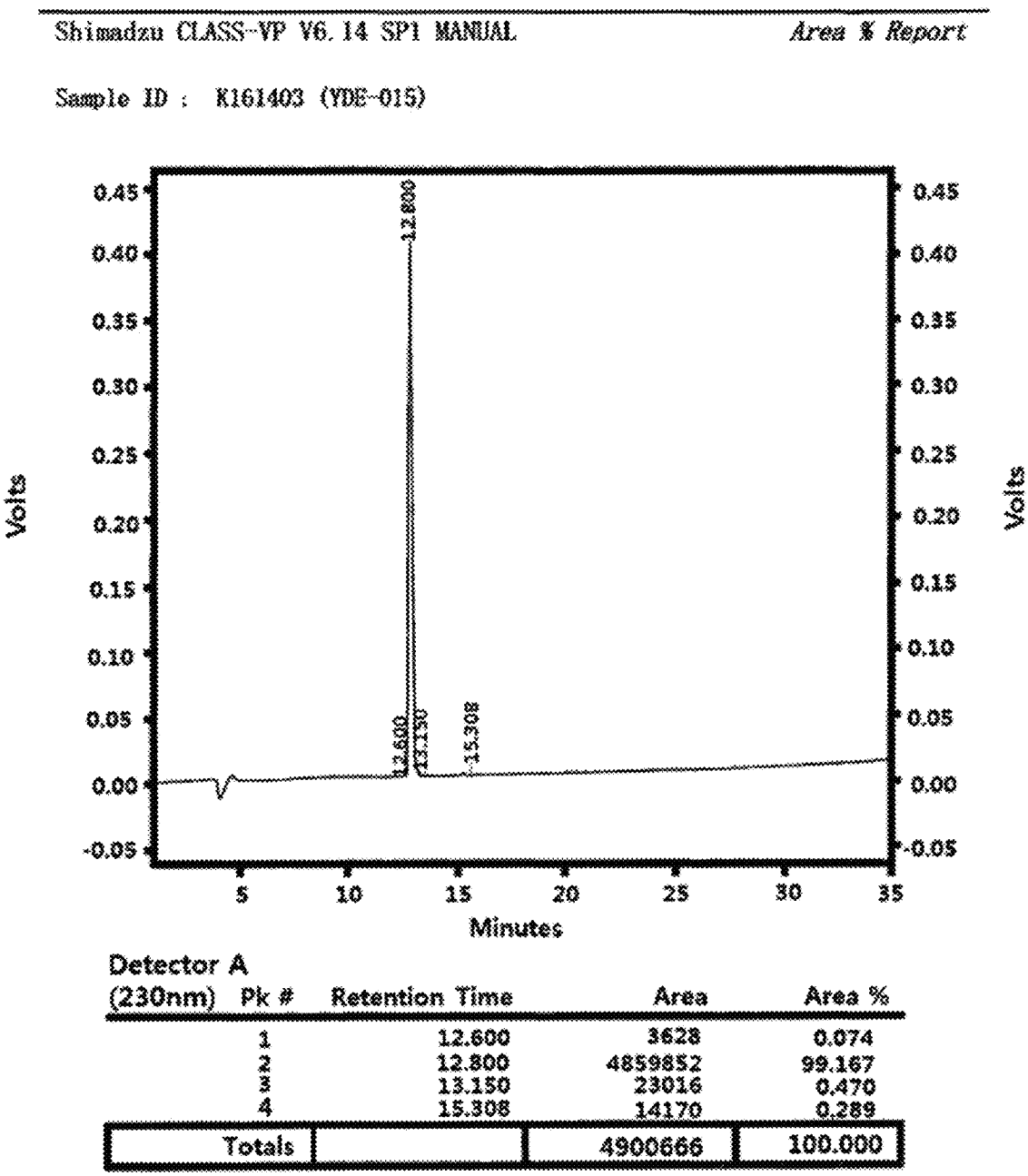
FIG. 18 is a diagram confirming the purity of YDE-015 prepared according to an embodiment of the present invention through HPLC.
Figure 19:
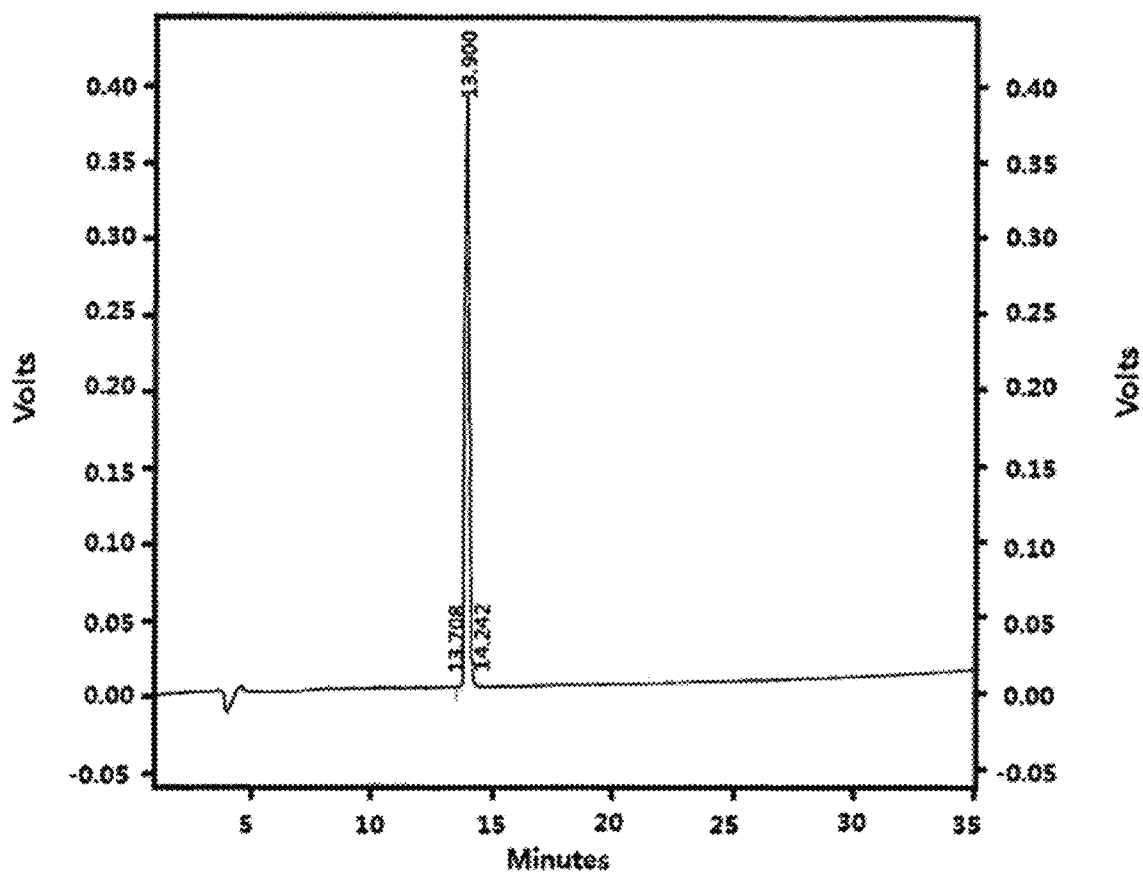
FIG. 19 is a diagram confirming the purity of YDE-016 prepared according to an embodiment of the present invention through HPLC.
Figure 20:
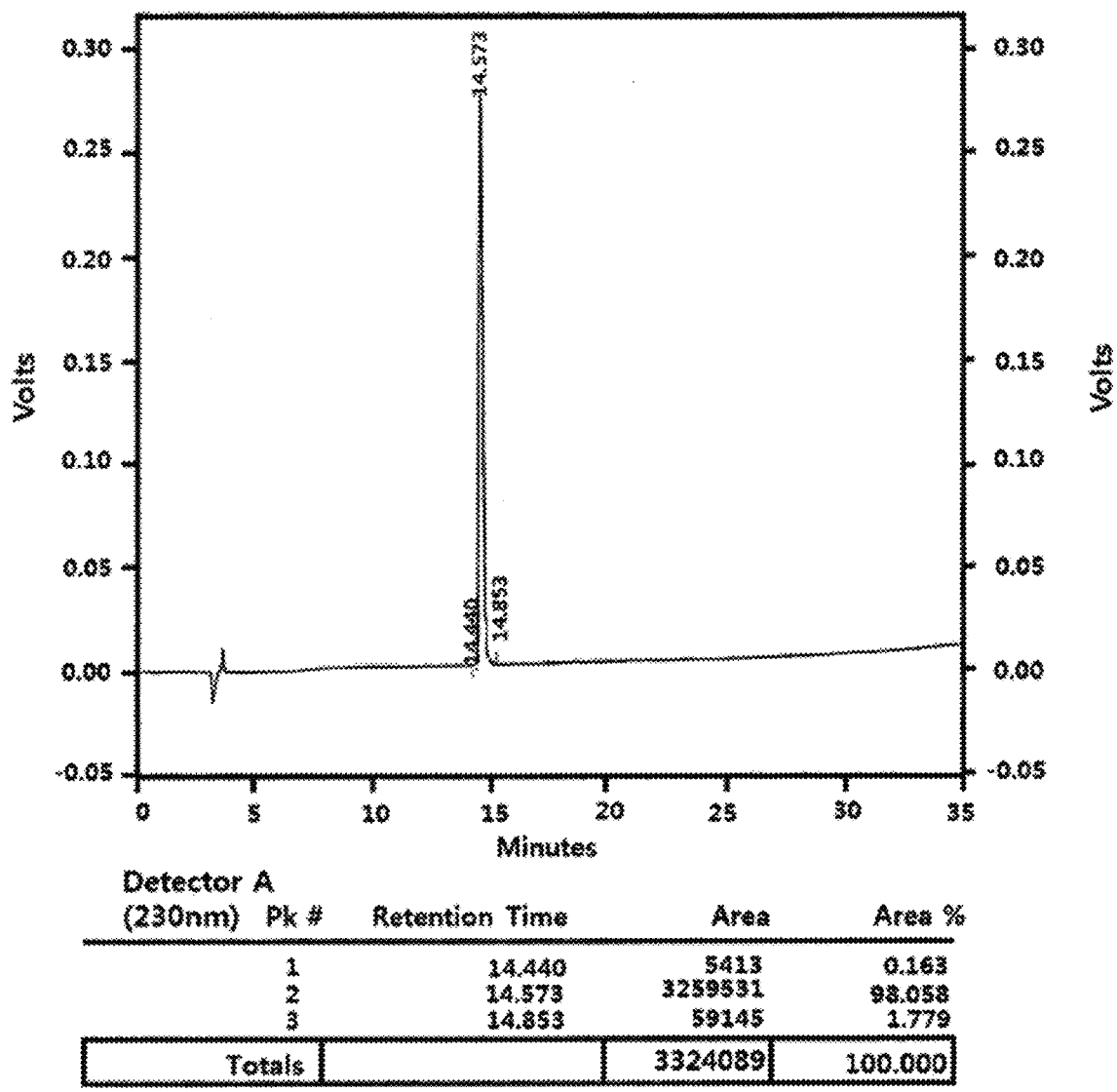
FIG. 20 is a diagram confirming the purity of YDE-017 prepared according to an embodiment of the present invention through HPLC.
Figure 21:
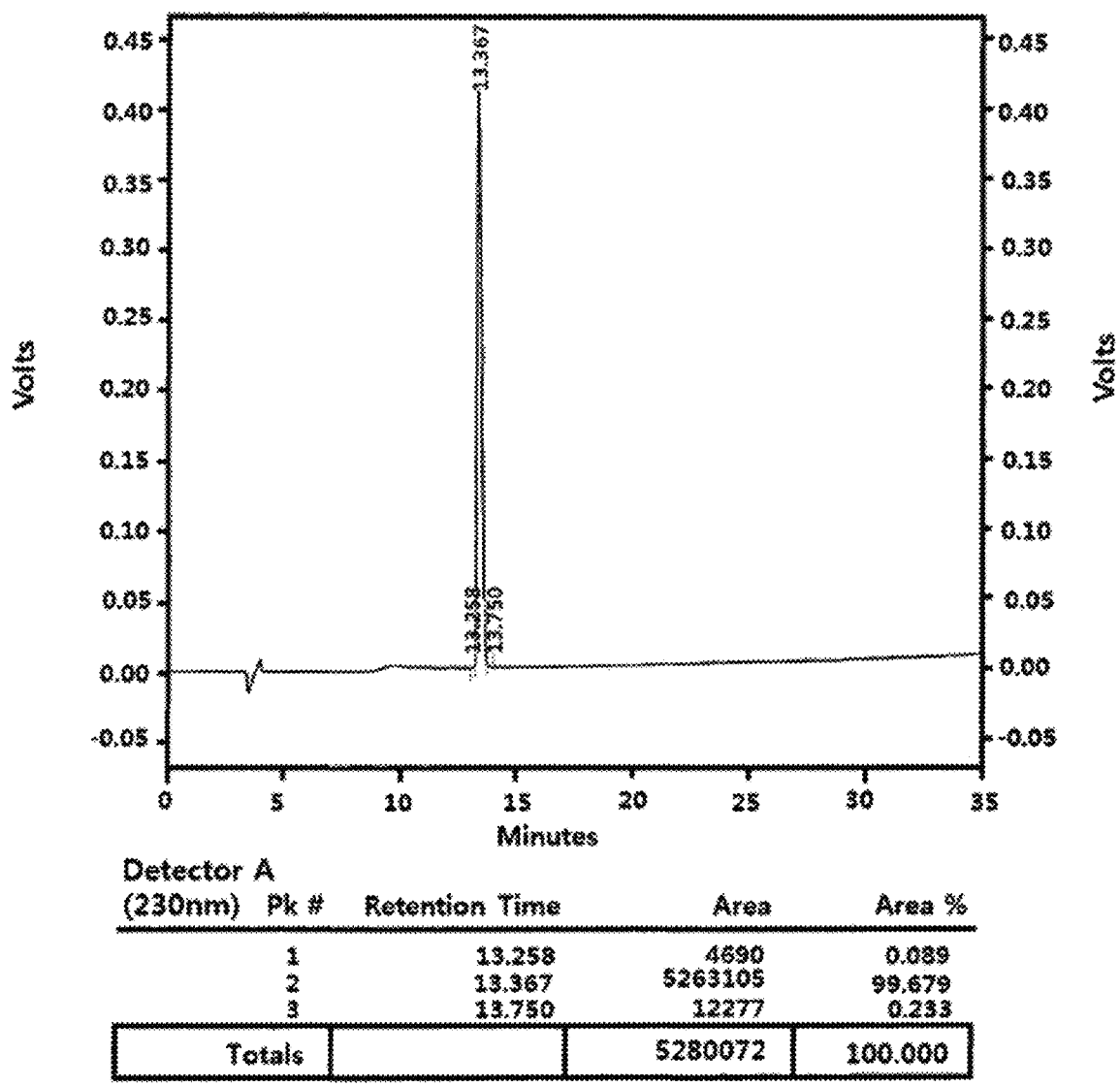
FIG. 21 is a diagram confirming the purity of YDE-018 prepared according to an embodiment of the present invention through HPLC.
Figure 22:
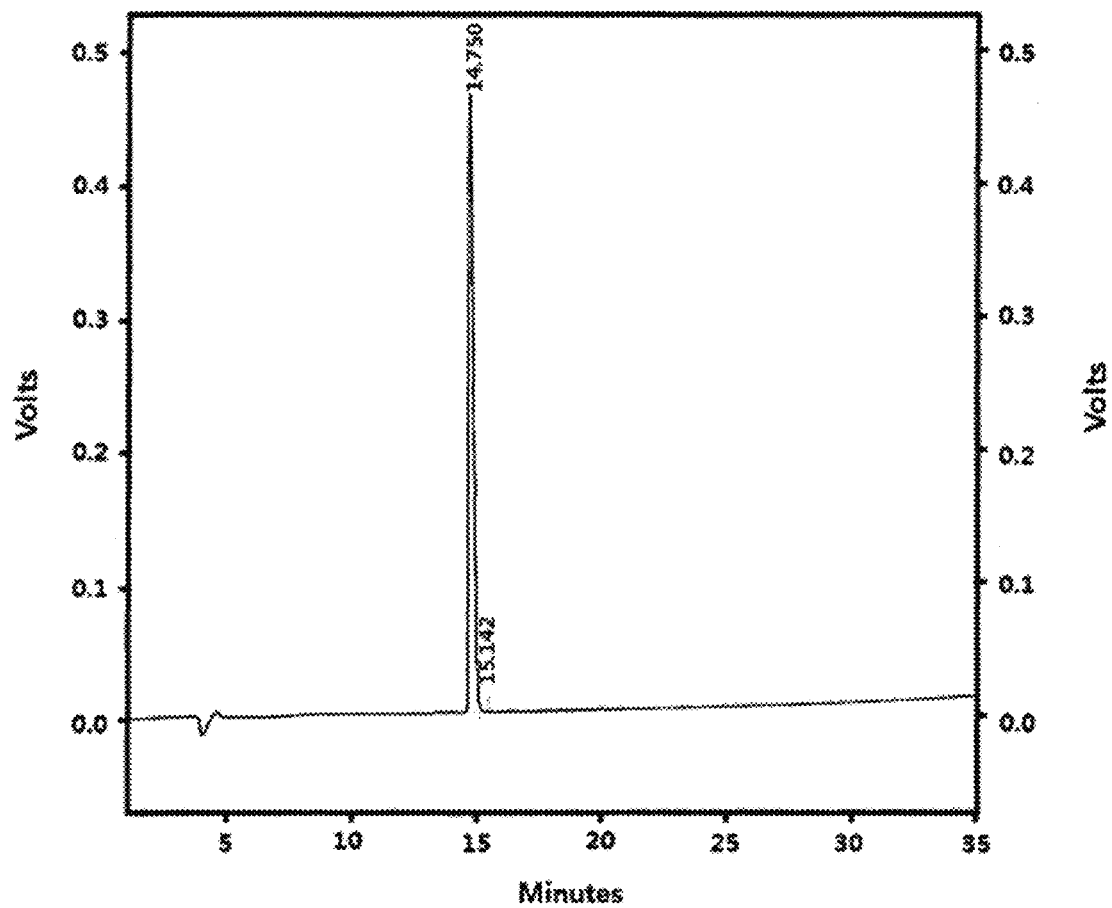
FIG. 22 is a diagram confirming the purity of YDE-019 prepared according to an embodiment of the present invention through HPLC.
Figure 23:
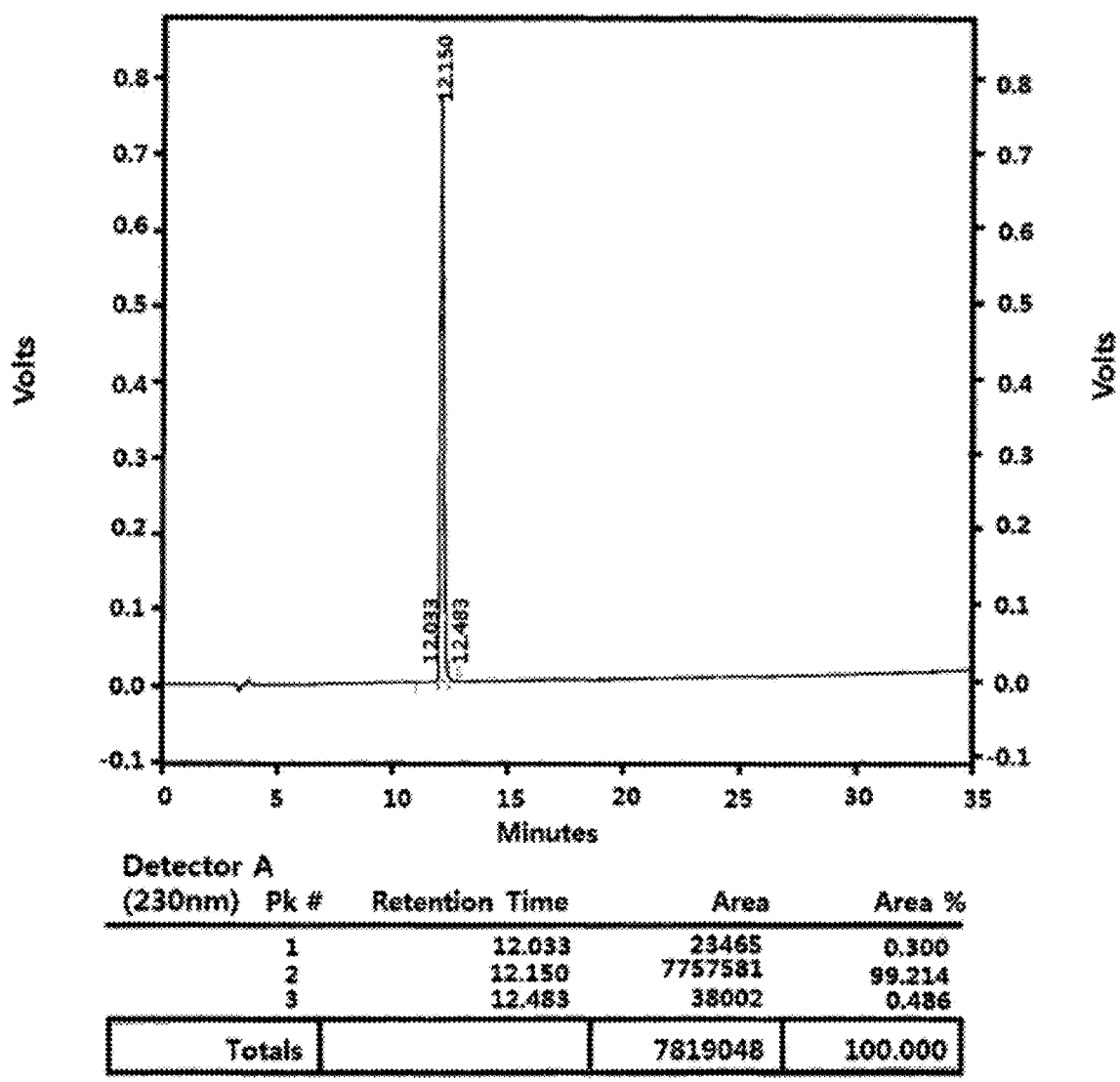
FIG. 23 is a diagram confirming the purity of YDE-020 prepared according to an embodiment of the present invention through HPLC.
Figure 24:
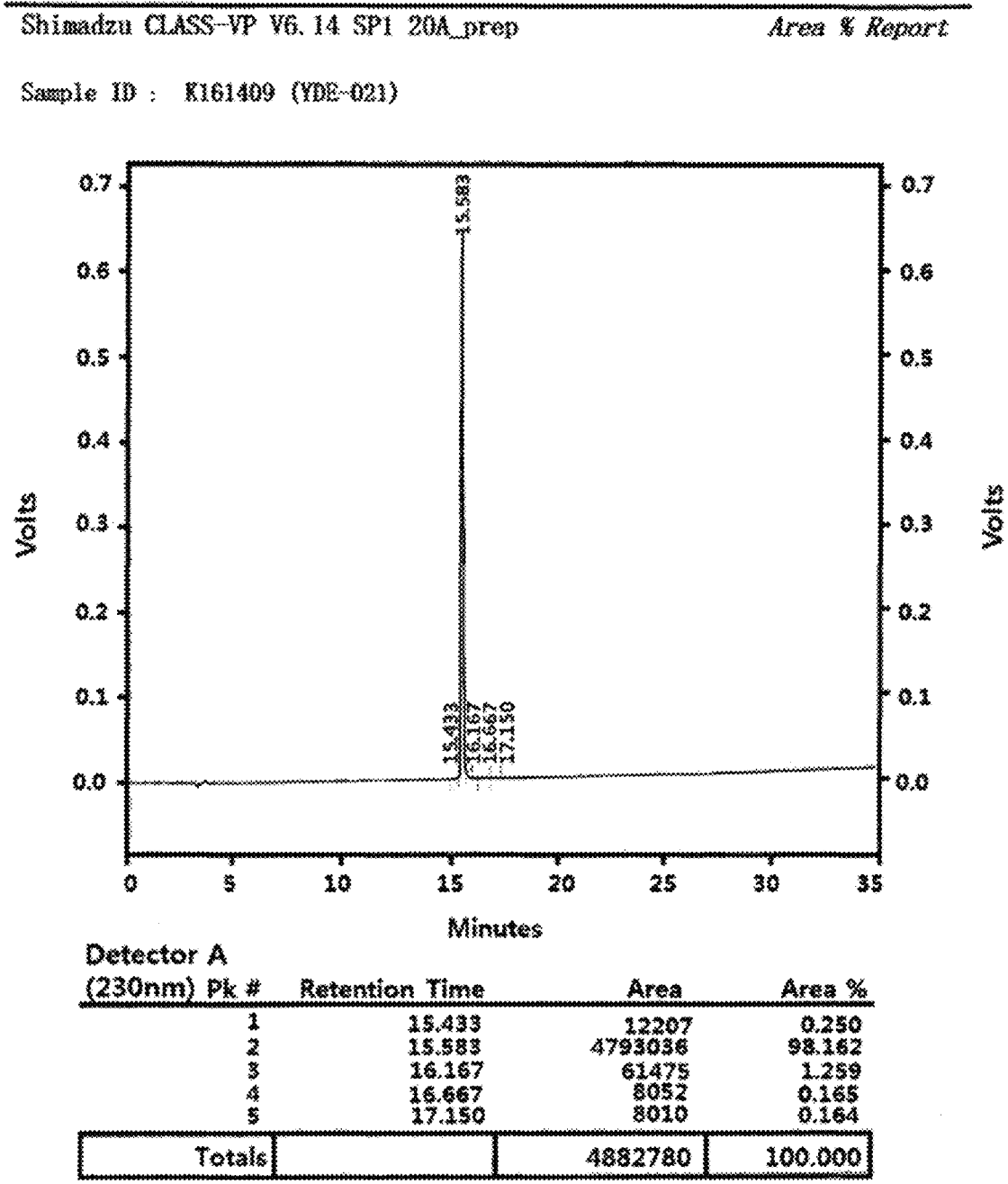
FIG. 24 is a diagram confirming the purity of YDE-021 prepared according to an embodiment of the present invention through HPLC.
Figure 25:
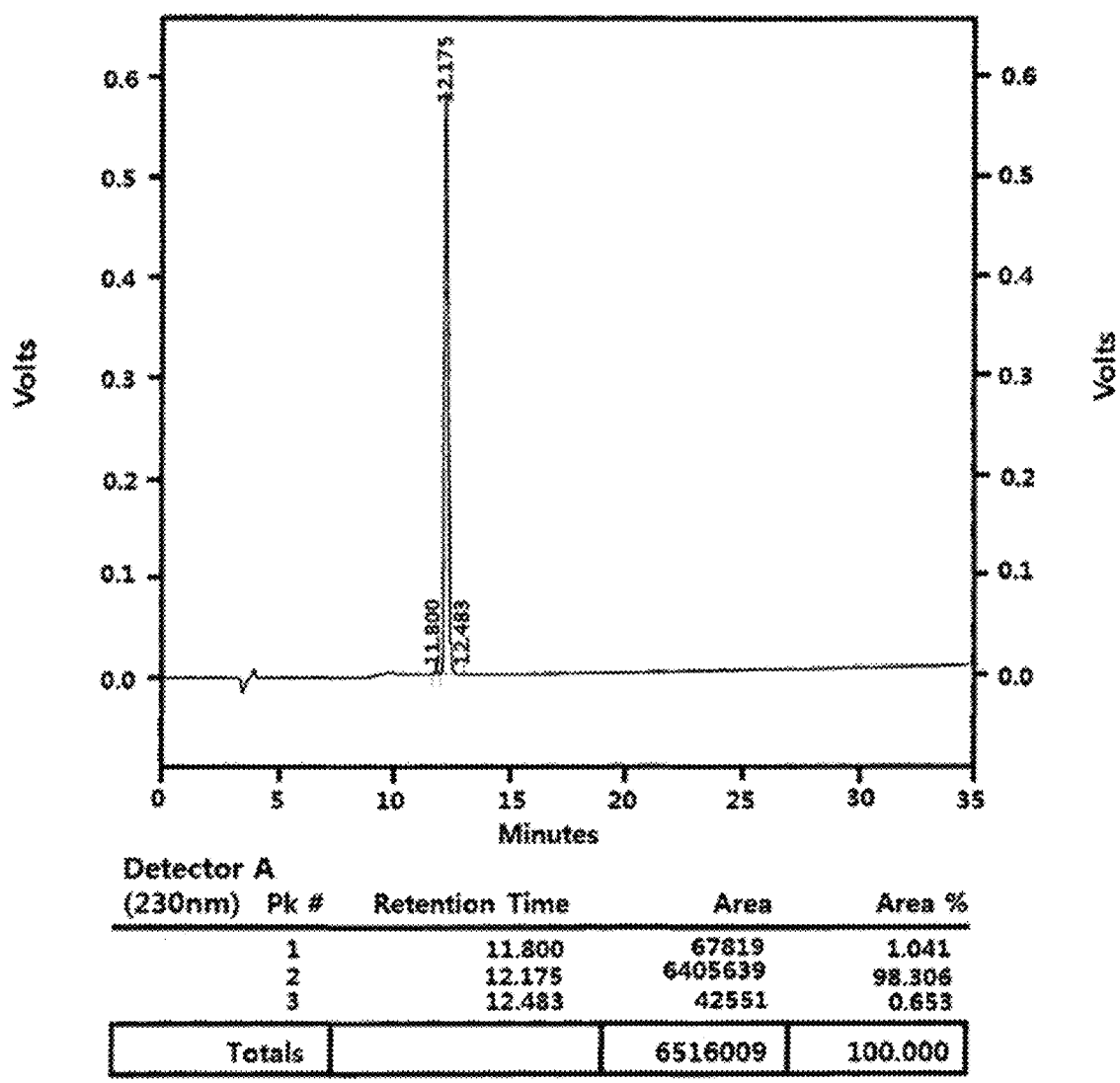
FIG. 25 is a diagram confirming the purity of YDE-022 prepared according to an embodiment of the present invention through HPLC.
Figure 26:
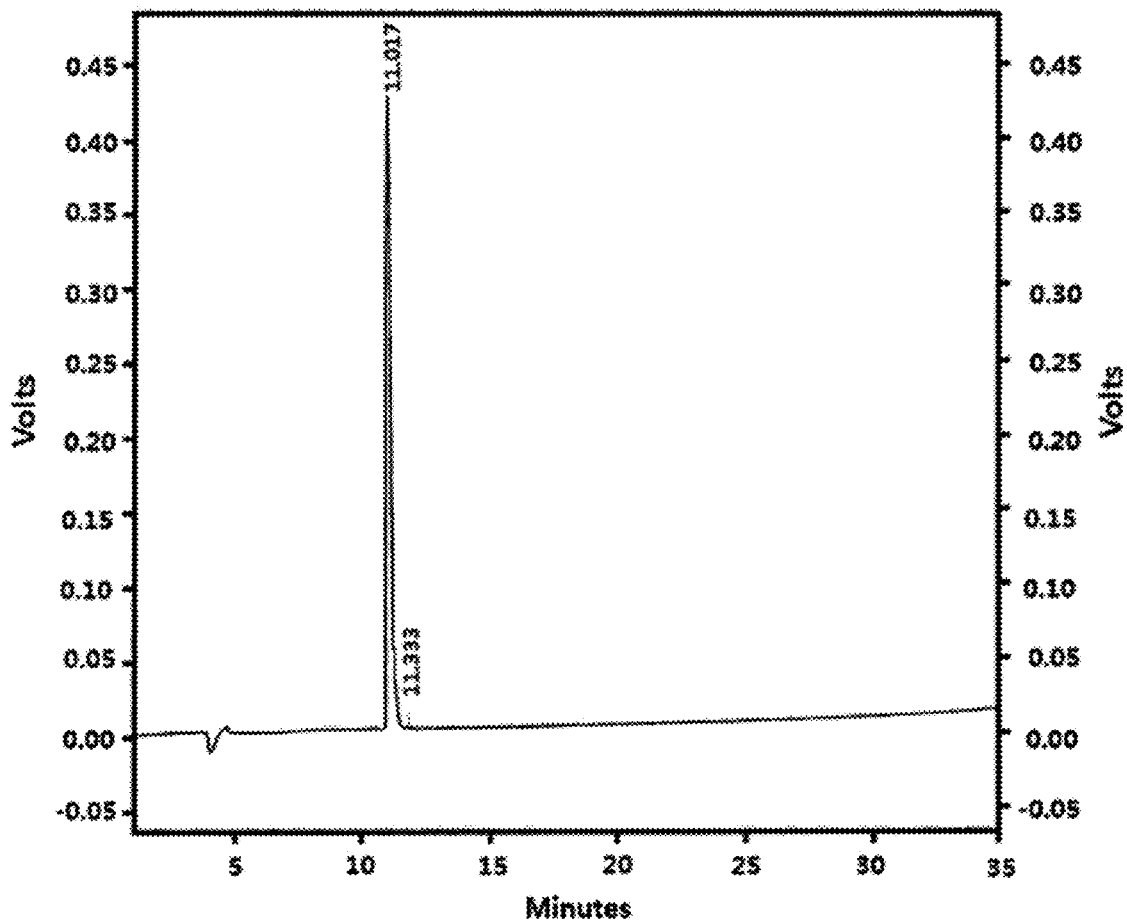
FIG. 26 is a diagram confirming the purity of YDE-023 prepared according to an embodiment of the present invention through HPLC.
Figure 27:
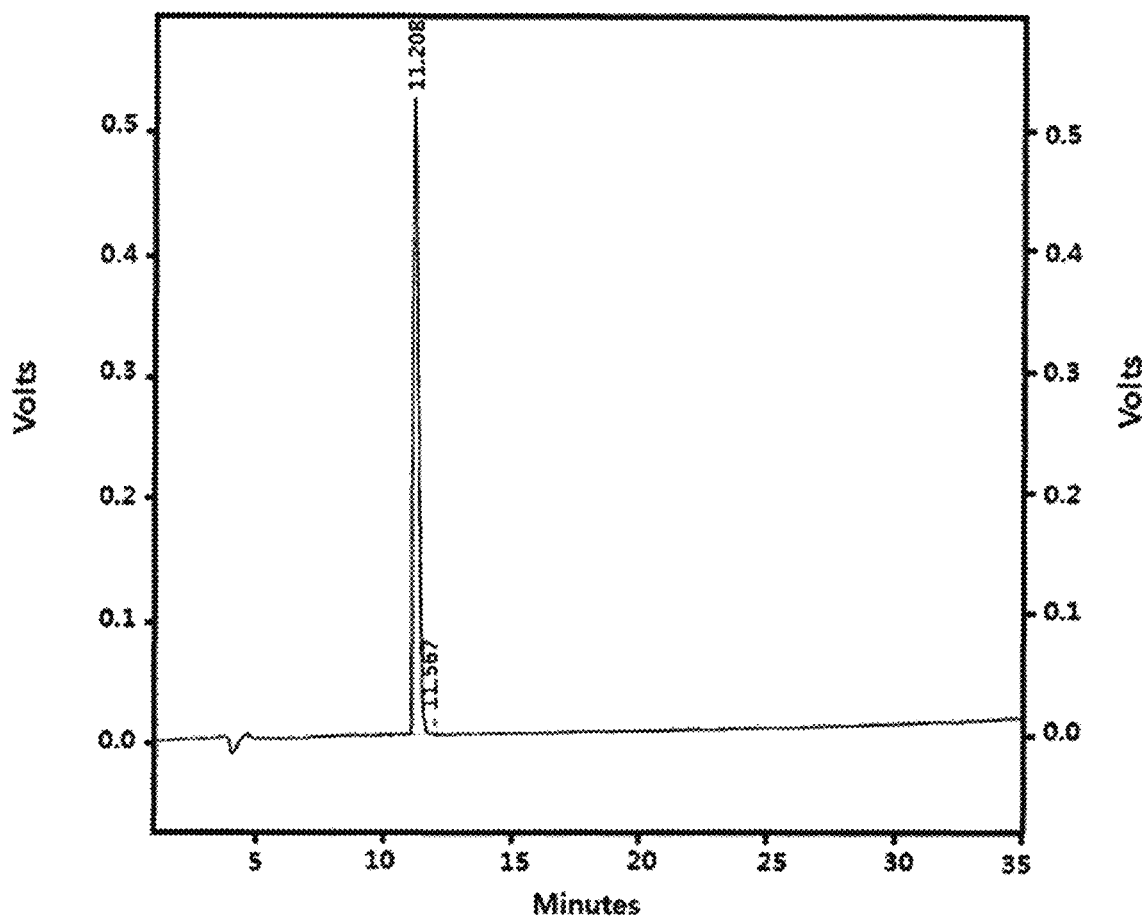
FIG. 27 is a diagram confirming the purity of YDE-024 prepared according to an embodiment of the present invention through HPLC.
Figure 28:
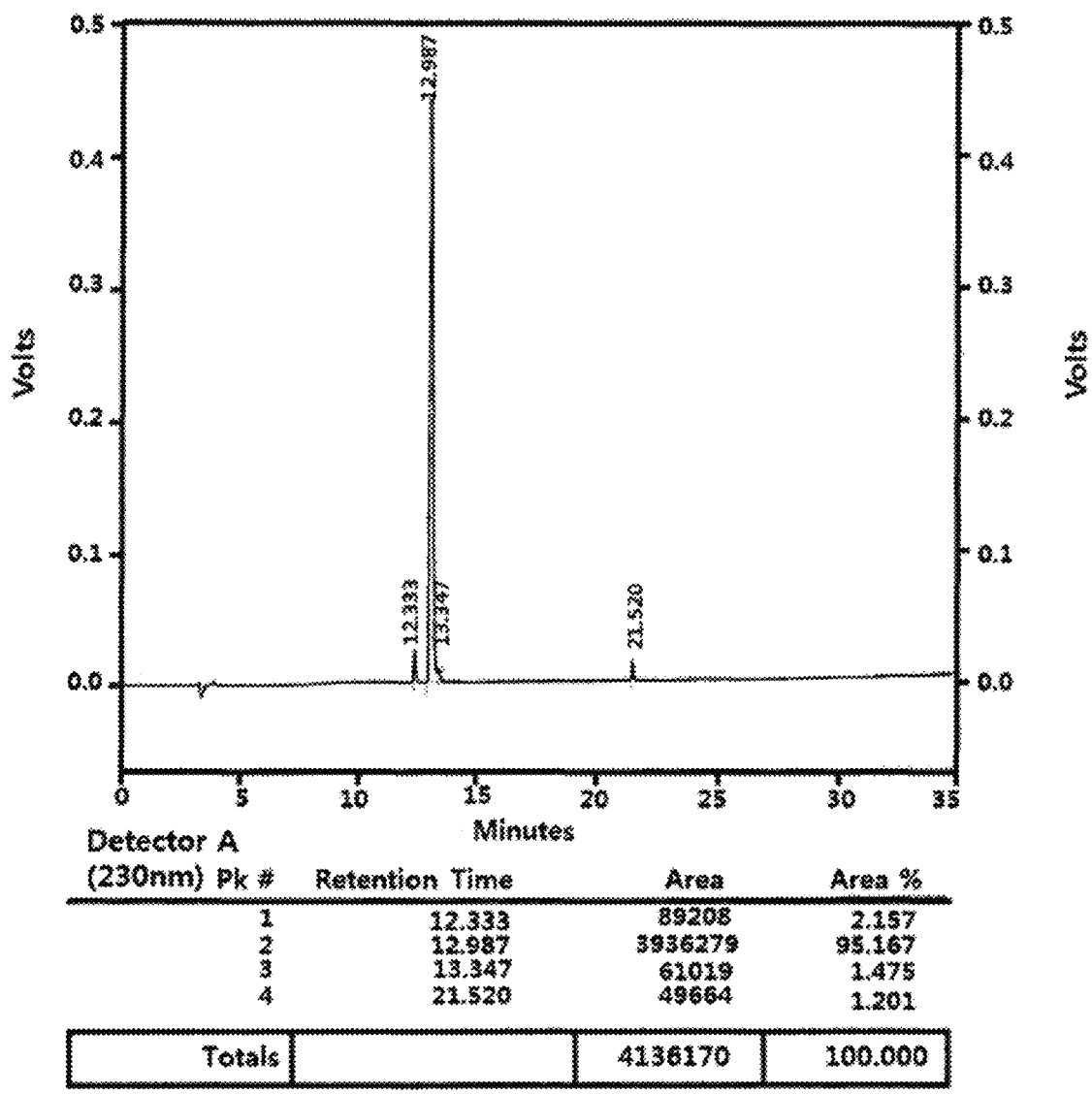
FIG. 28 is a diagram confirming the purity of YDE-025 prepared according to an embodiment of the present invention through HPLC.
Figure 29:
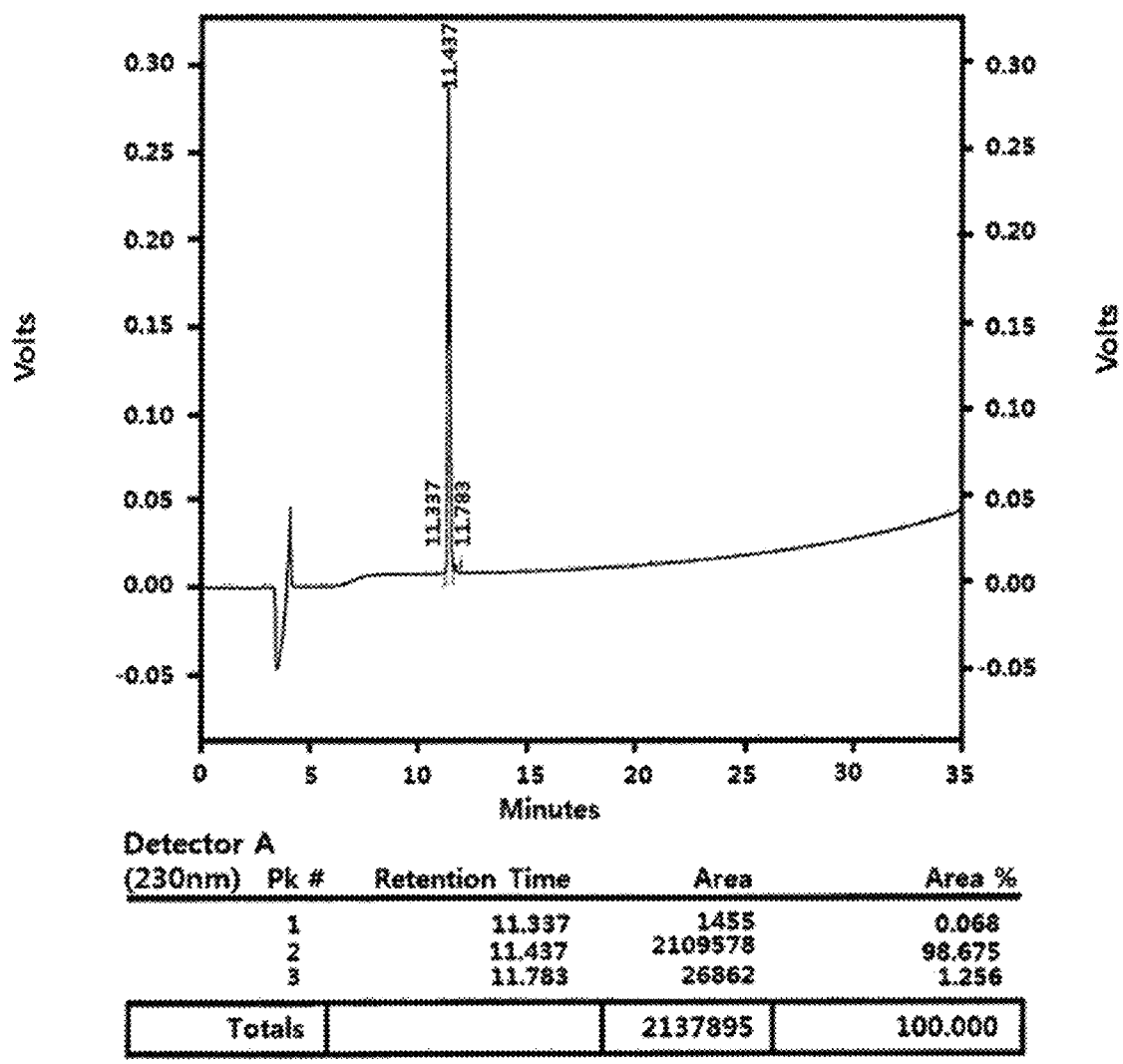
FIG. 29 is a diagram confirming the purity of YDE-026 prepared according to an embodiment of the present invention through HPLC.
Figure 30:
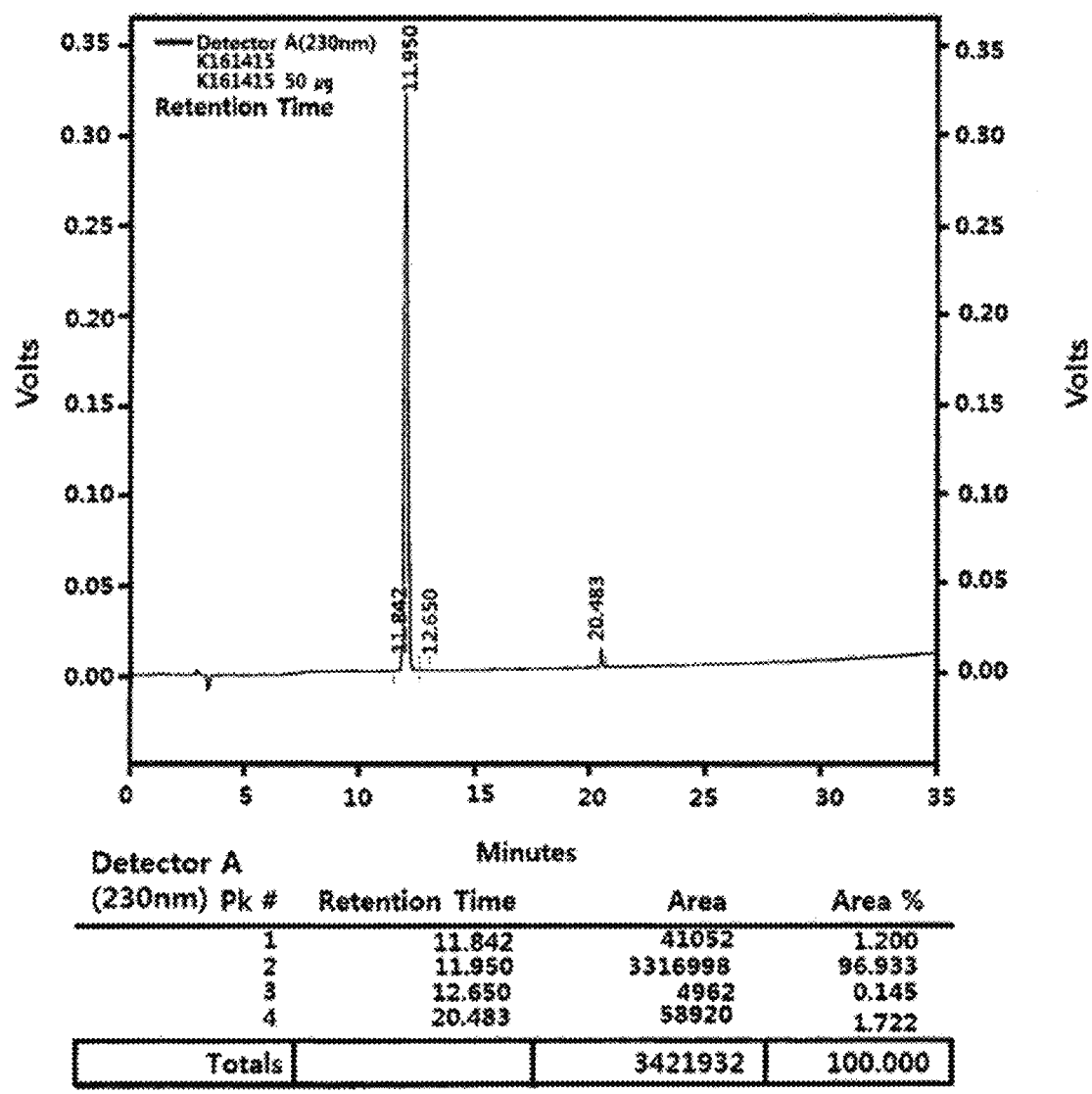
FIG. 30 is a diagram confirming the purity of YDE-027 prepared according to an embodiment of the present invention through HPLC.
Figure 31:
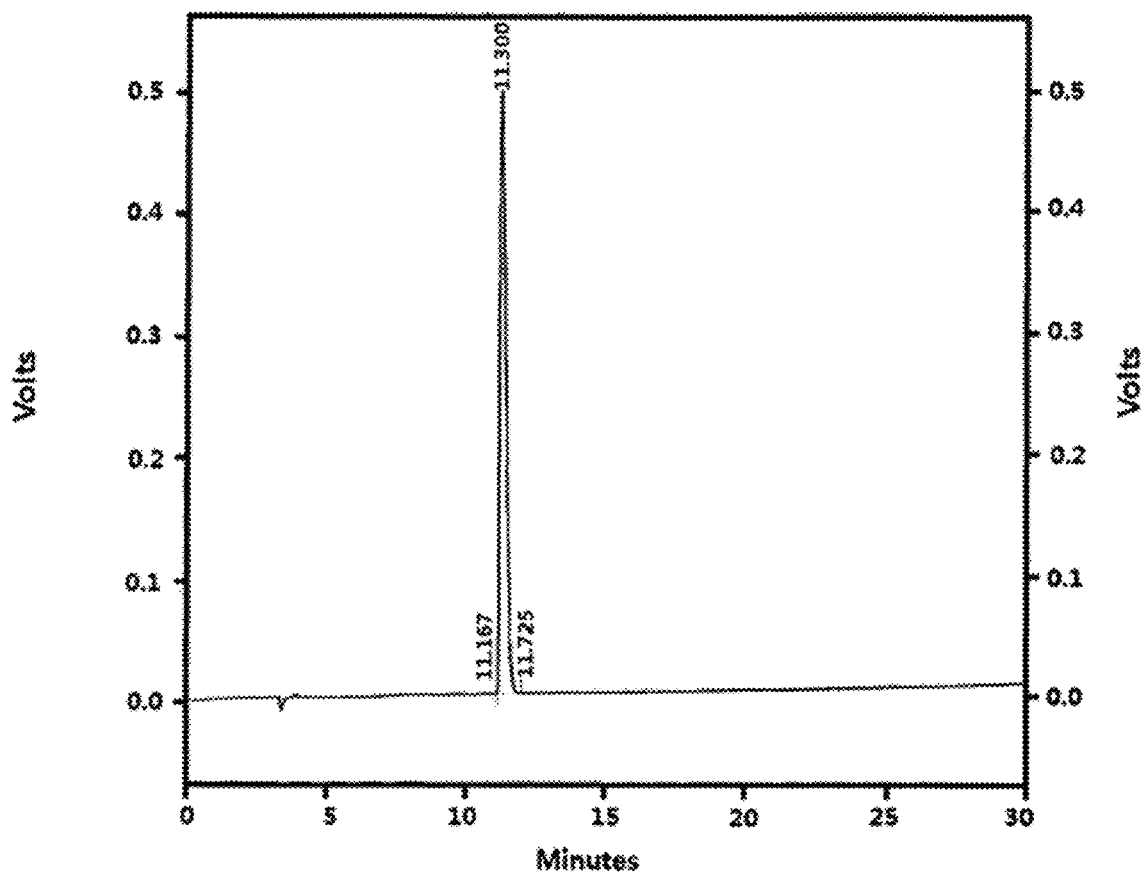
FIG. 31 is a diagram confirming the purity of YDE-028 prepared according to an embodiment of the present invention through HPLC.
Figure 32:
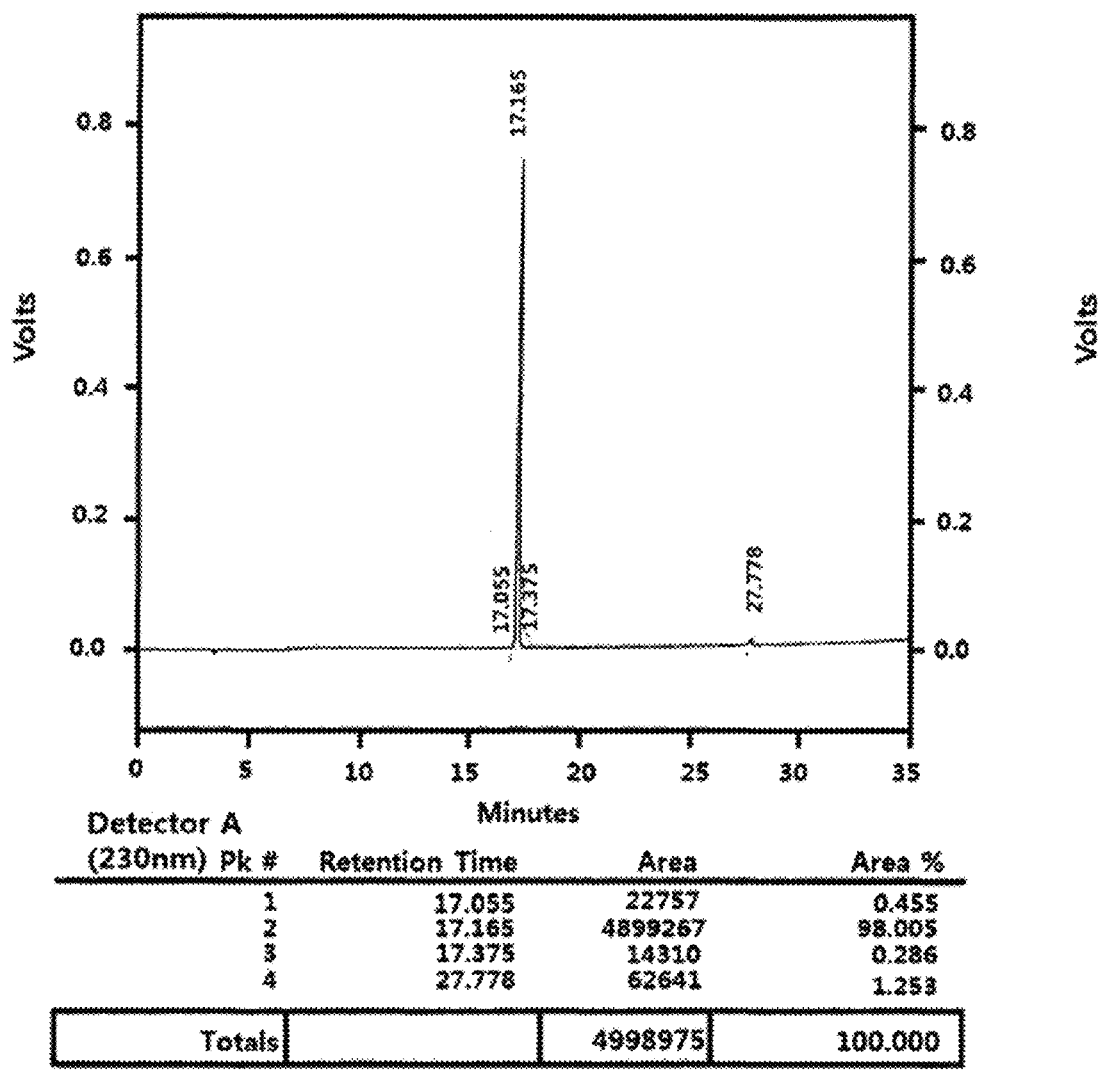
FIG. 32 is a diagram confirming the purity of YDE-029 prepared according to an embodiment of the present invention through HPLC.
Figure 33:
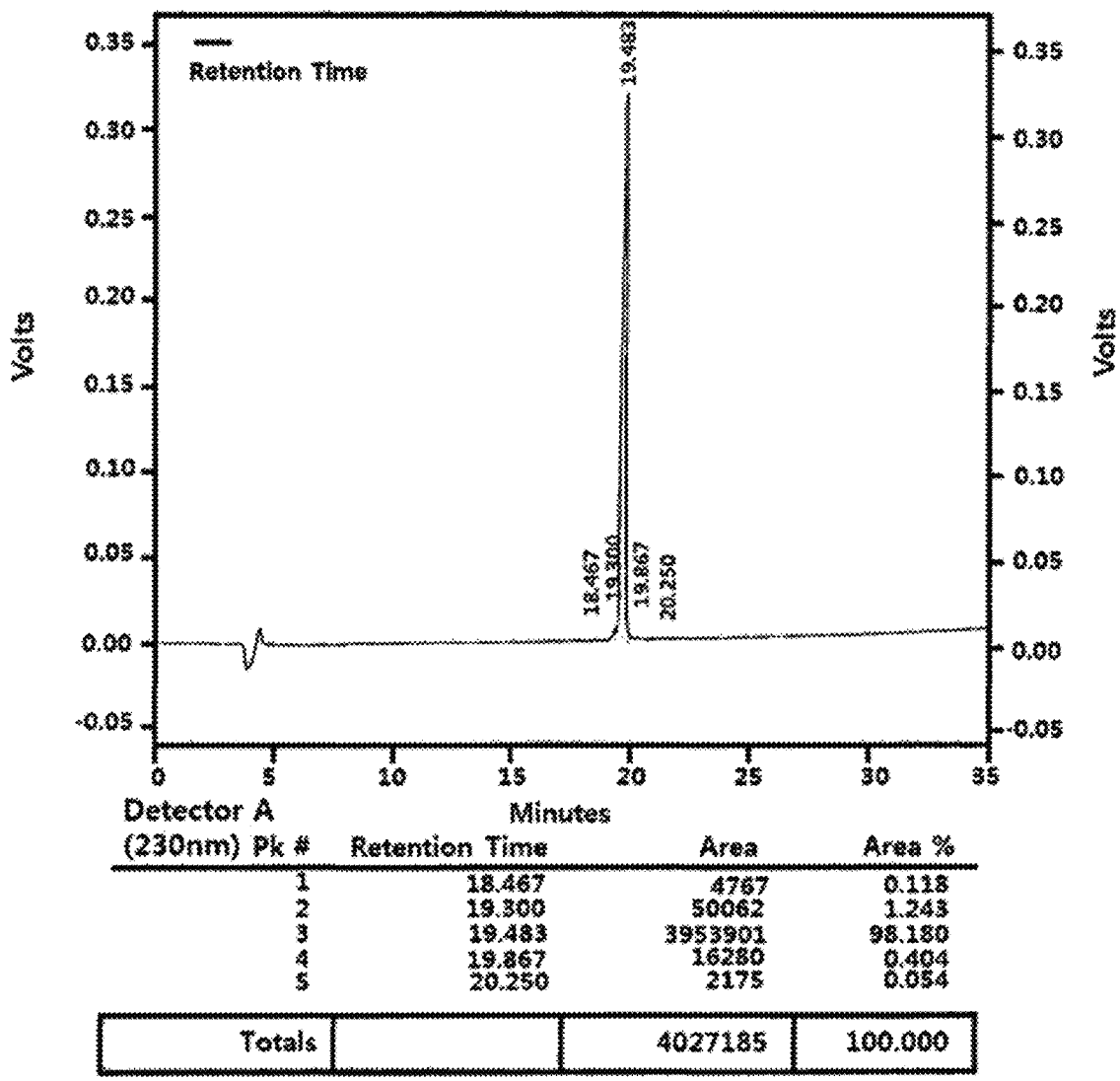
FIG. 33 is a diagram confirming the purity of YDE-030 prepared according to an embodiment of the present invention through HPLC.
Figure 34:
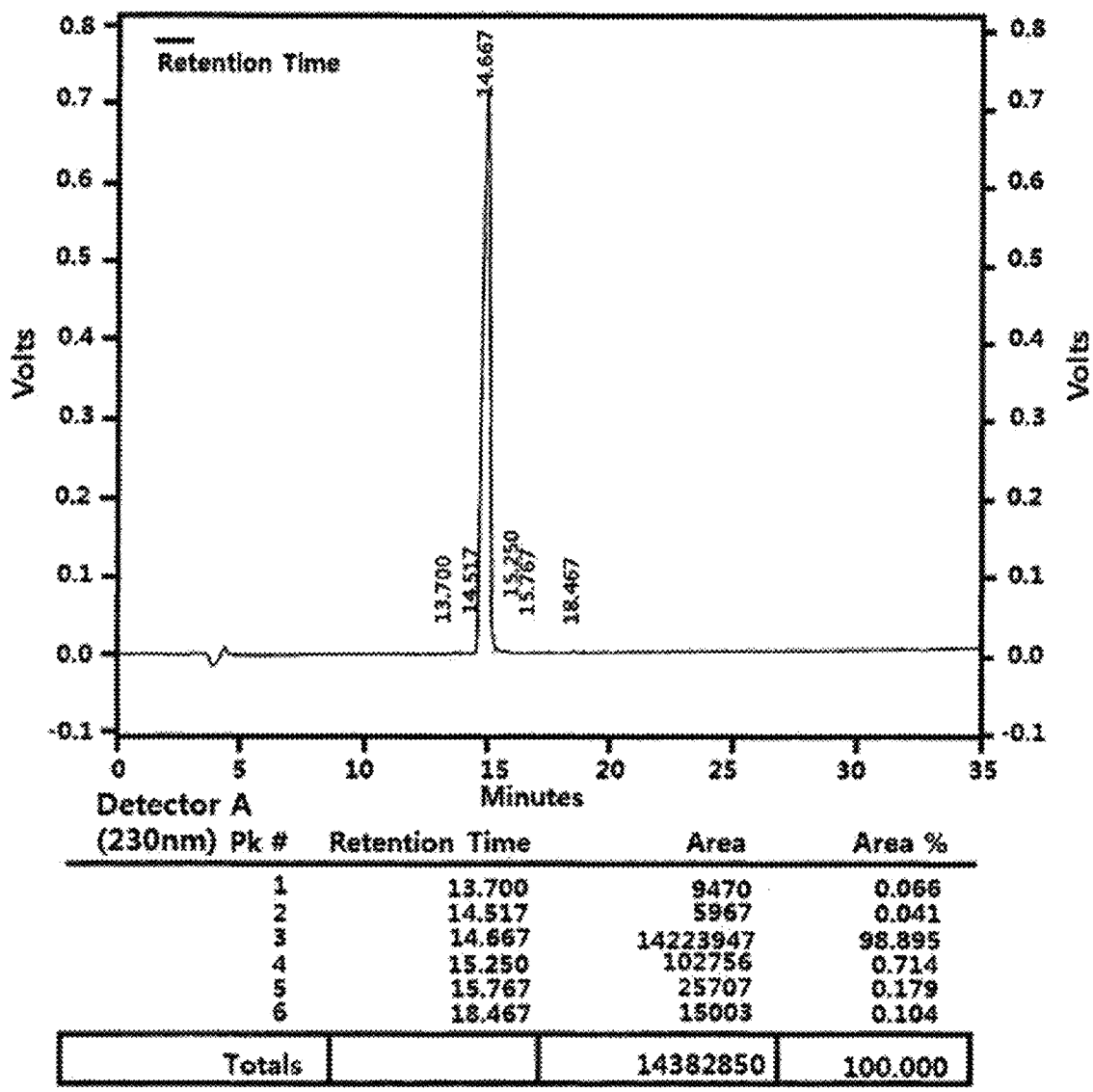
FIG. 34 is a diagram confirming the purity of YDE-031 prepared according to an embodiment of the present invention through HPLC.
Figure 35:
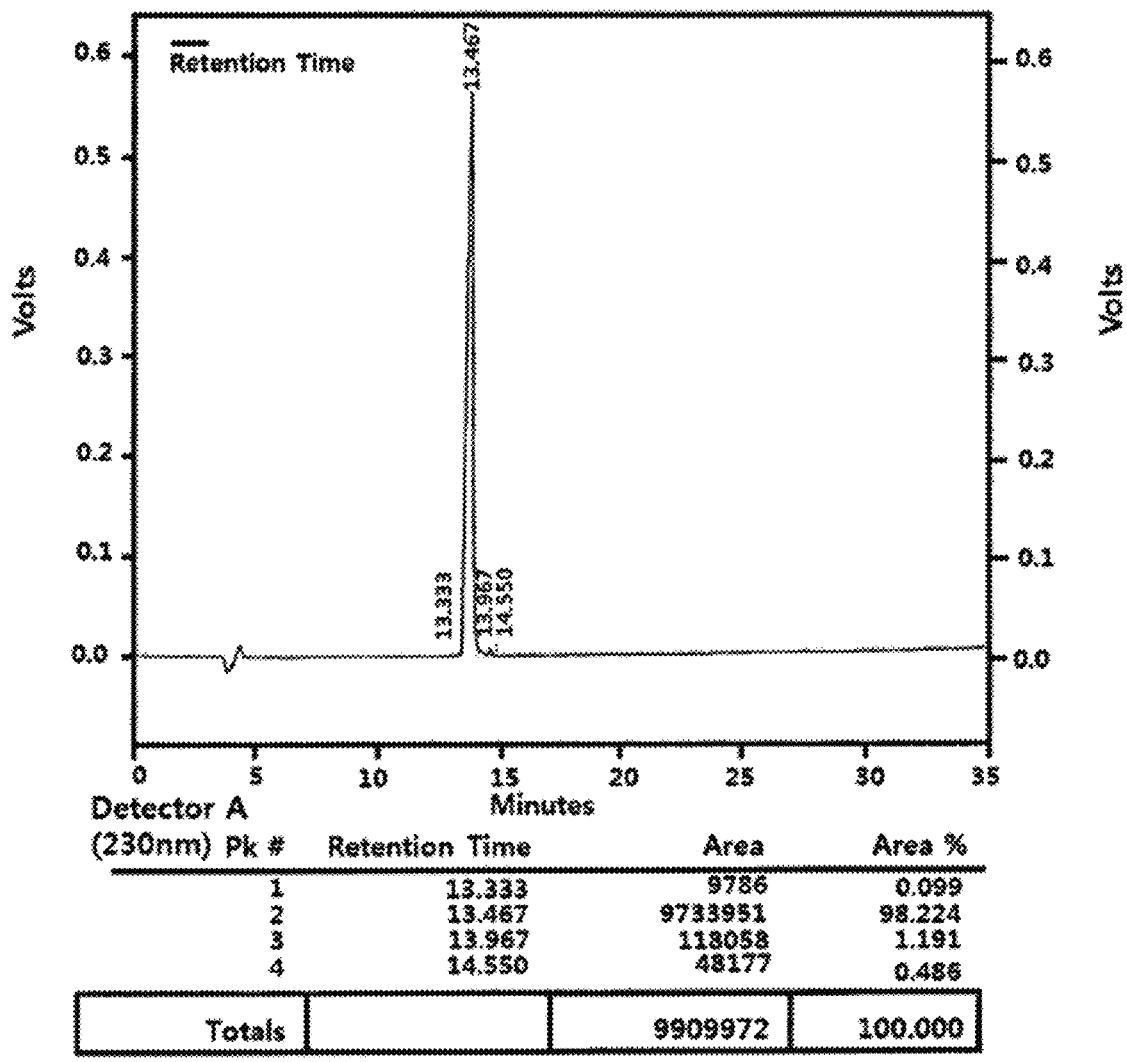
FIG. 35 is a diagram confirming the purity of YDE-032 prepared according to an embodiment of the present invention through HPLC.
Figure 36:
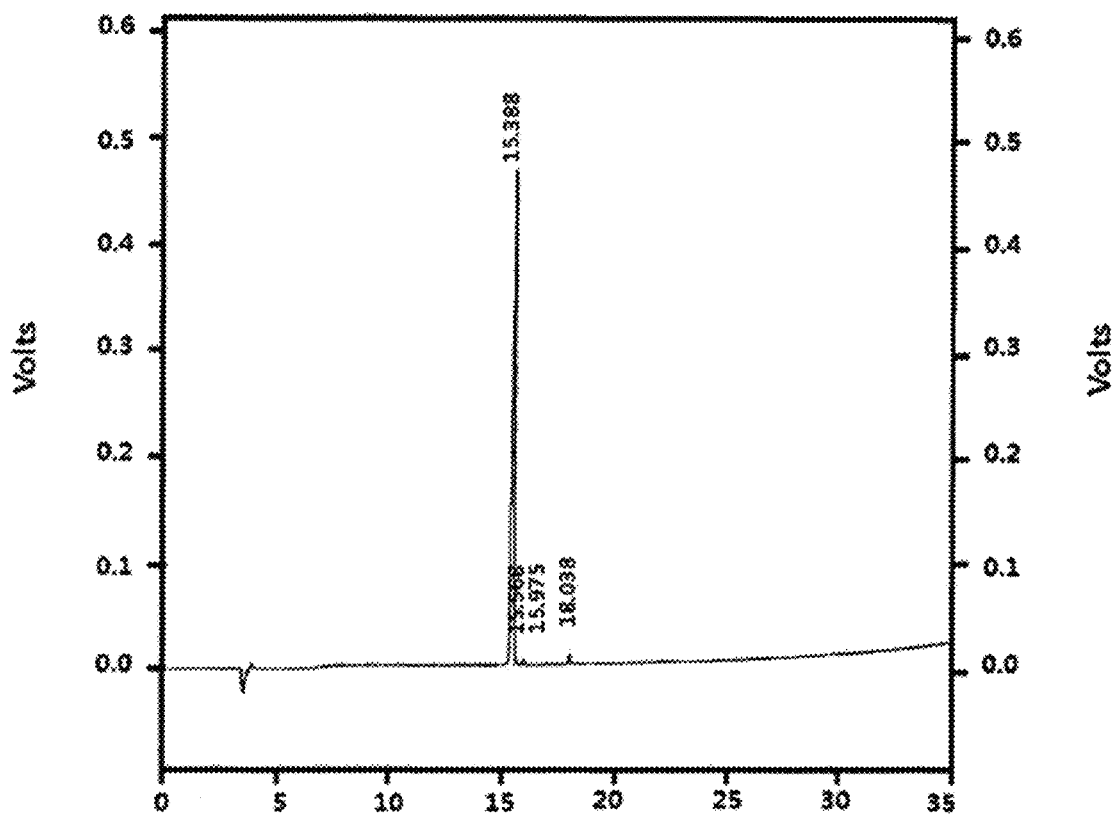
FIG. 36 is a diagram confirming the purity of YDE-033 prepared according to an embodiment of the present invention through HPLC.
Figure 37:
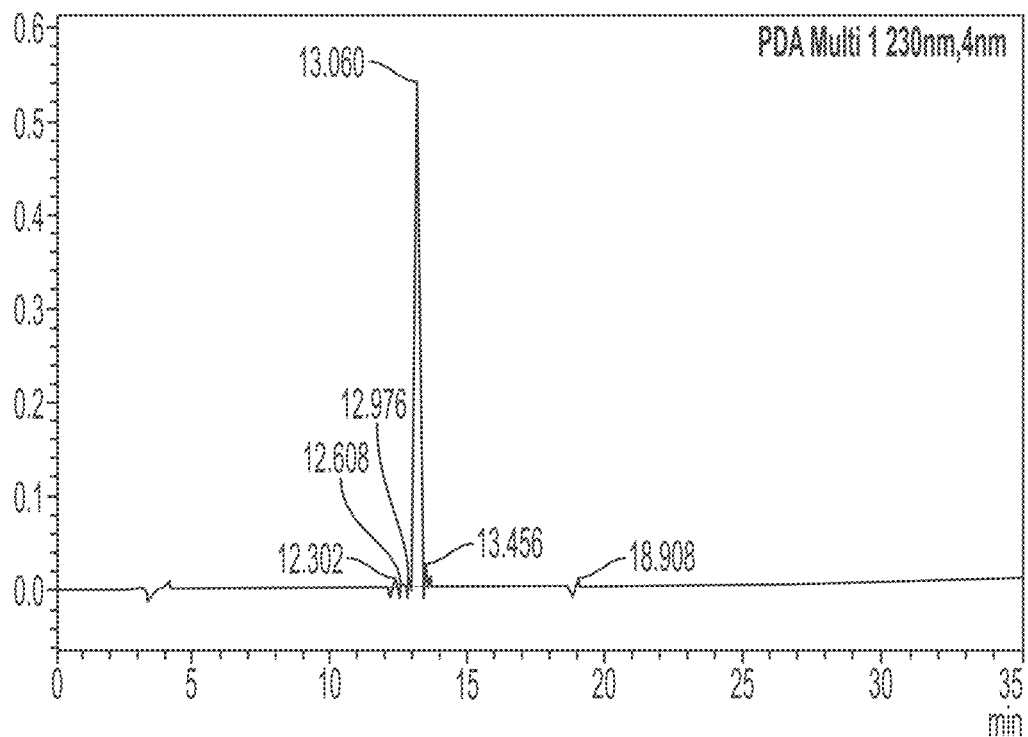
FIG. 37 is a diagram confirming the purity of YDE-034 prepared according to an embodiment of the present invention through HPLC.
Figure 38:
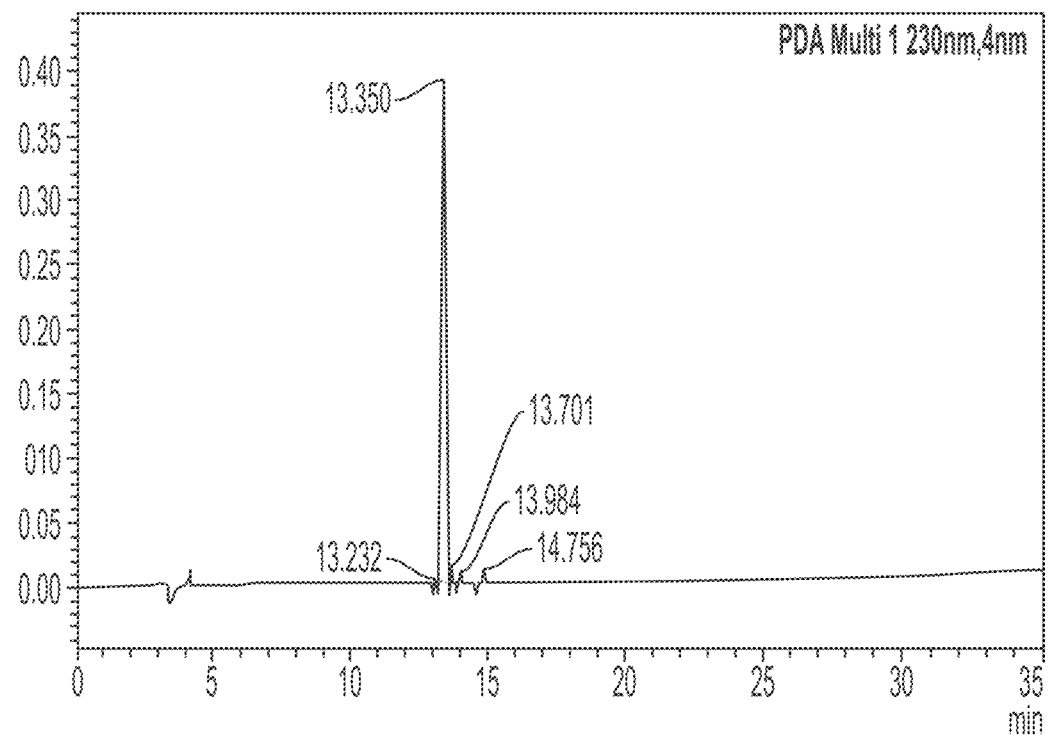
FIG. 38 is a diagram confirming the purity of YDE-035 prepared according to an embodiment of the present invention through HPLC.
Figure 39:
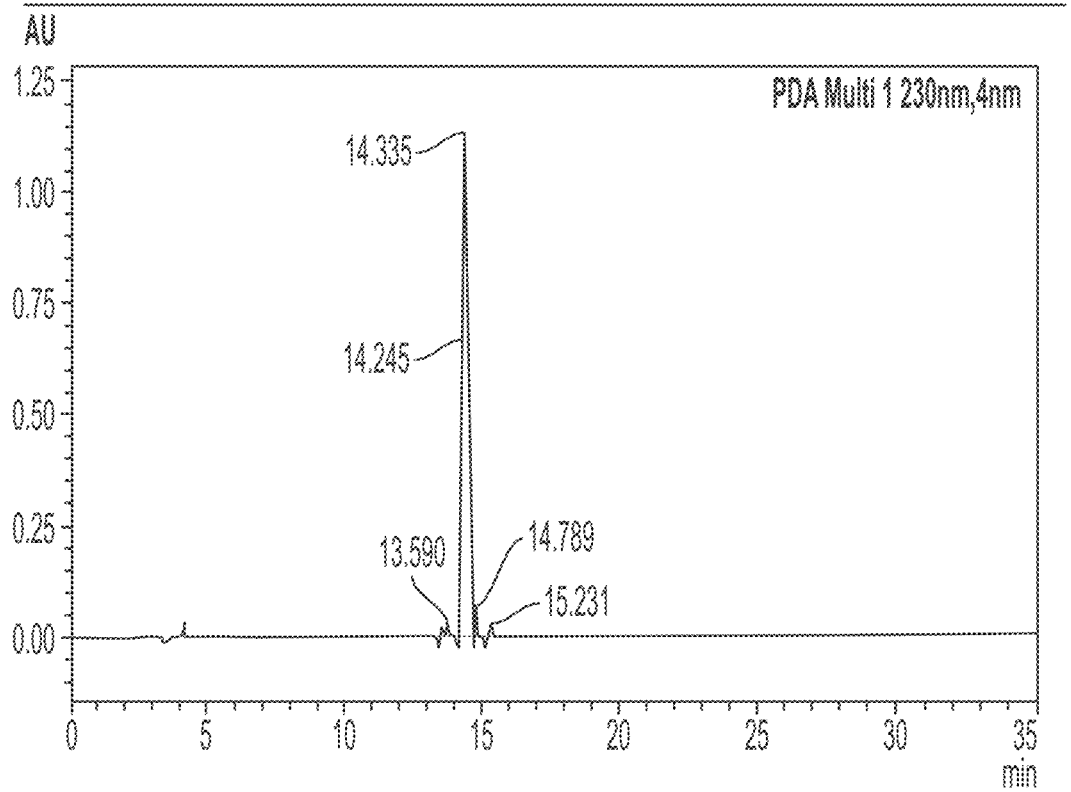
FIG. 39 is a diagram confirming the purity of YDE-036 prepared according to an embodiment of the present invention through HPLC.
Figure 40:
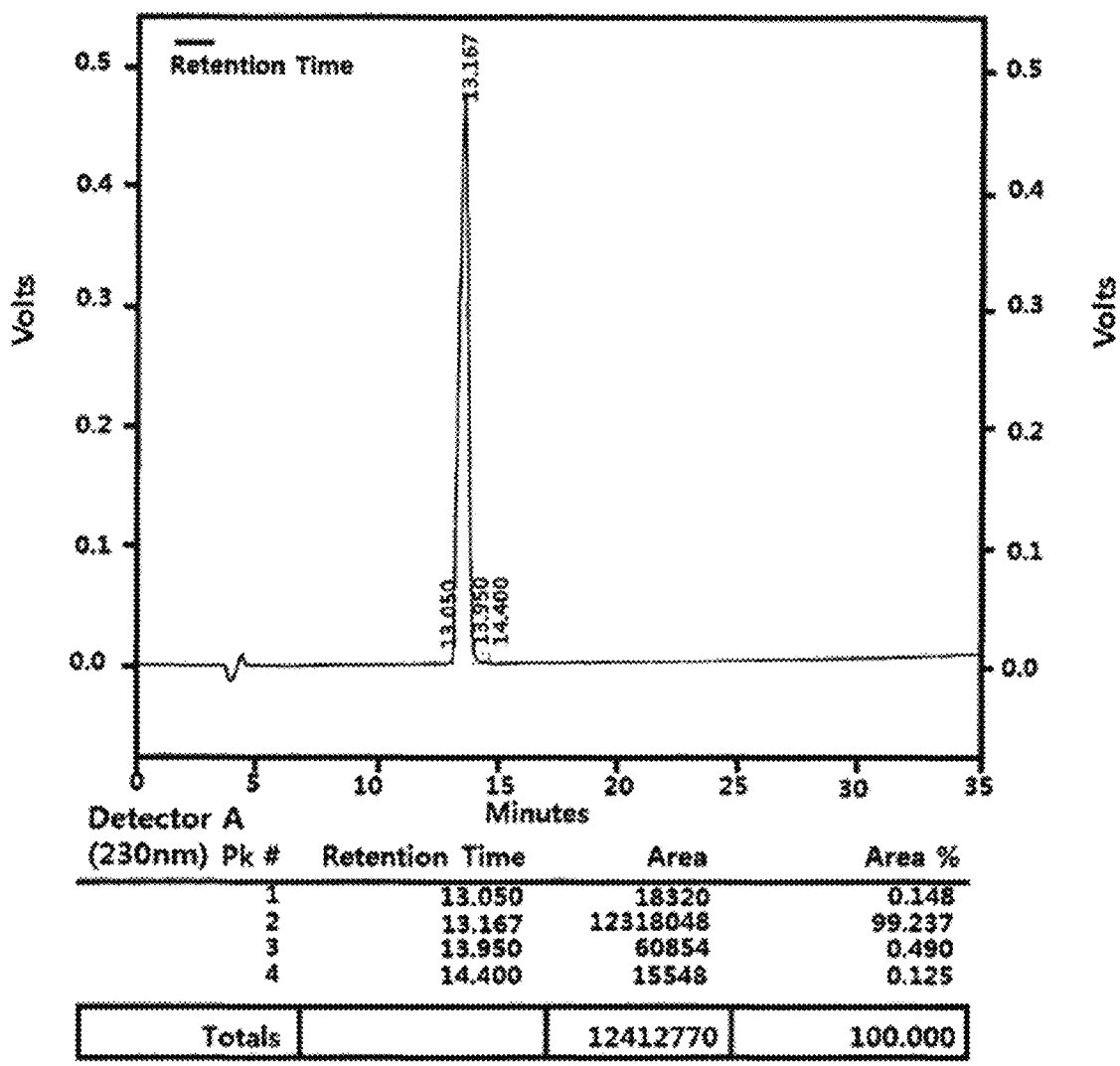
FIG. 40 is a diagram confirming the purity of YDE-037 prepared according to an embodiment of the present invention through HPLC.
Figure 41:
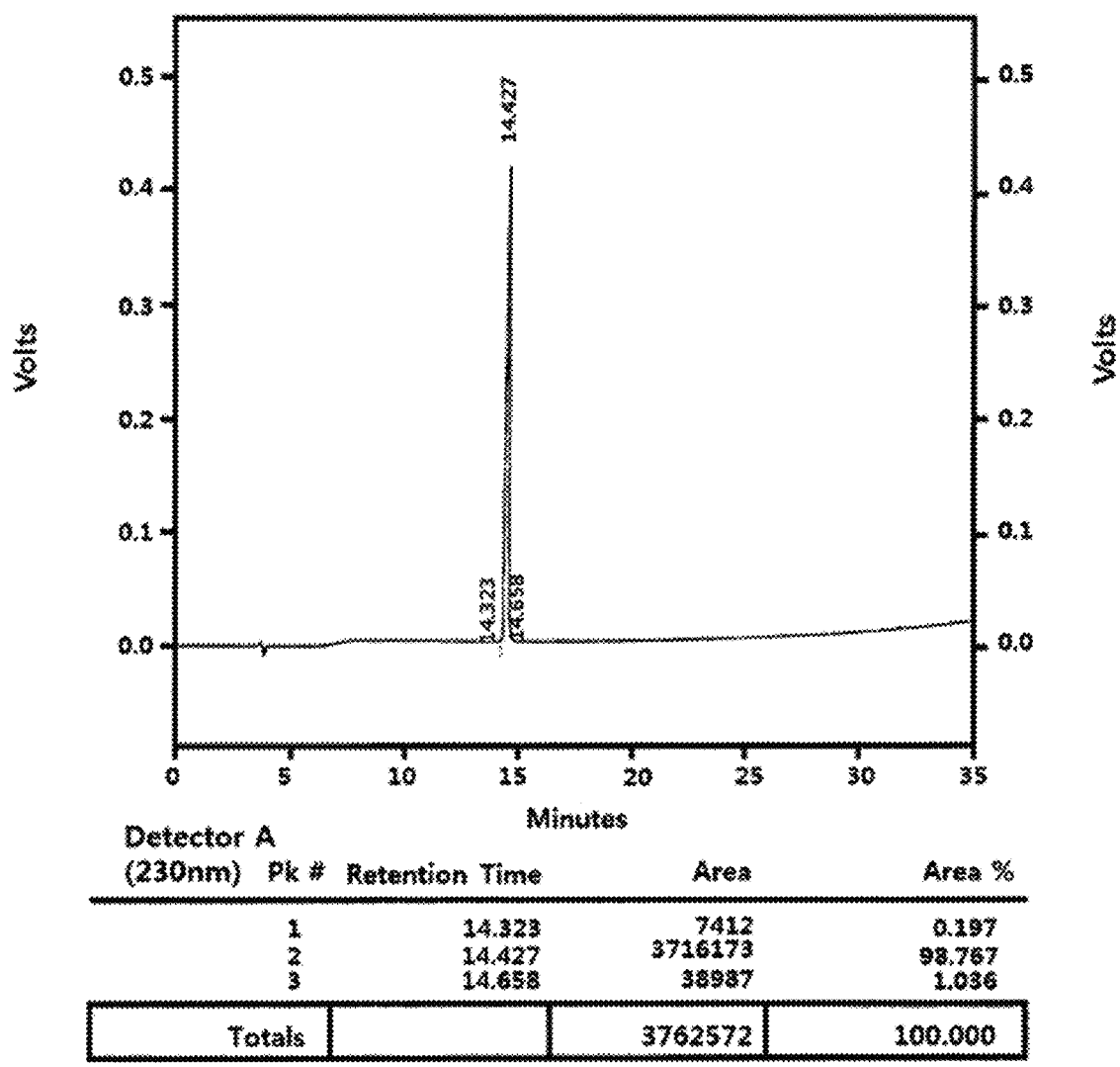
FIG. 41 is a diagram confirming the purity of YDE-038 prepared according to an embodiment of the present invention through HPLC.
Figure 42:
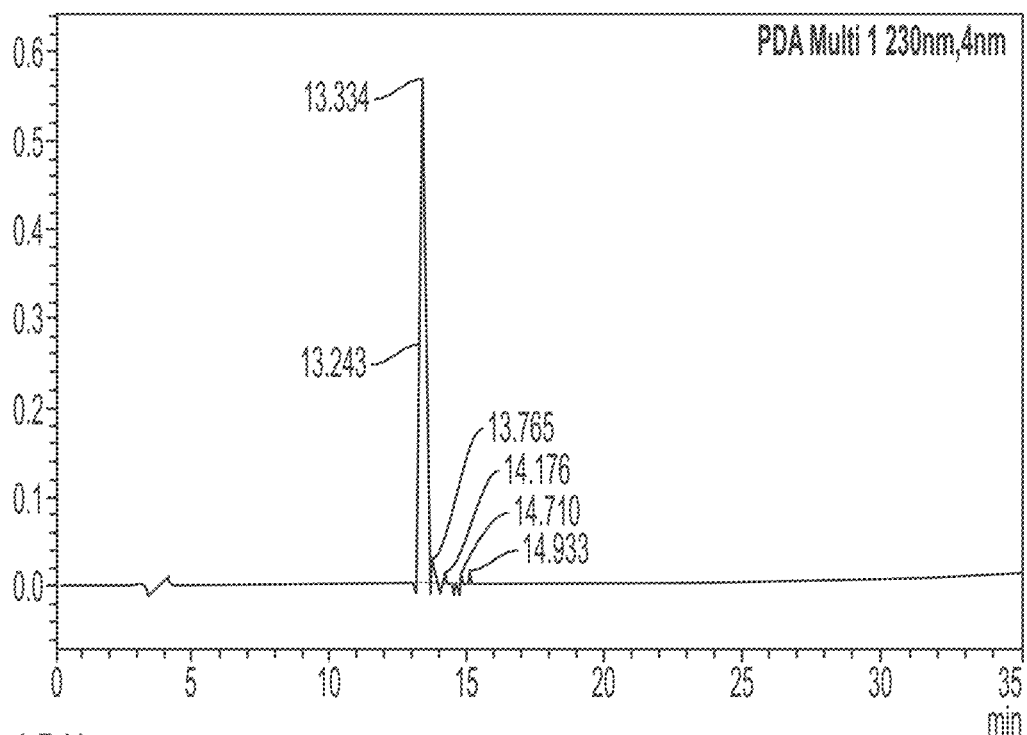
FIG. 42 is a diagram confirming the purity of YDE-039 prepared according to an embodiment of the present invention through HPLC.
Figure 43:
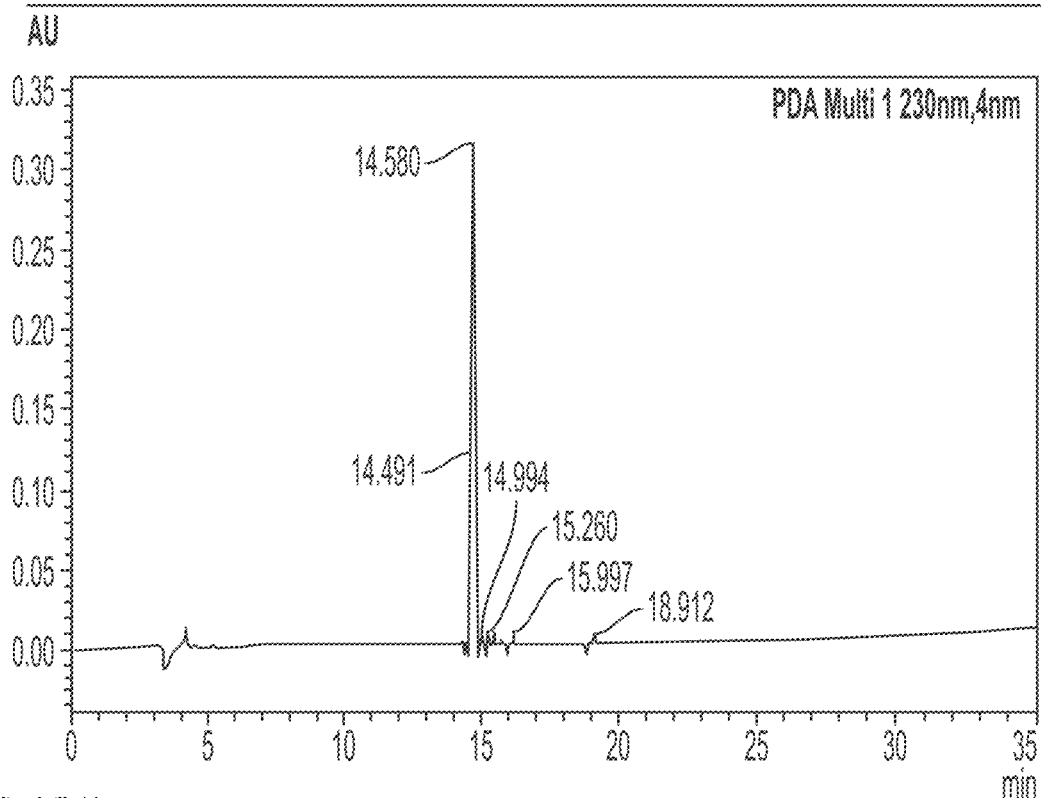
FIG. 43 is a diagram confirming the purity of YDE-040 prepared according to an embodiment of the present invention through HPLC.
Figure 44:
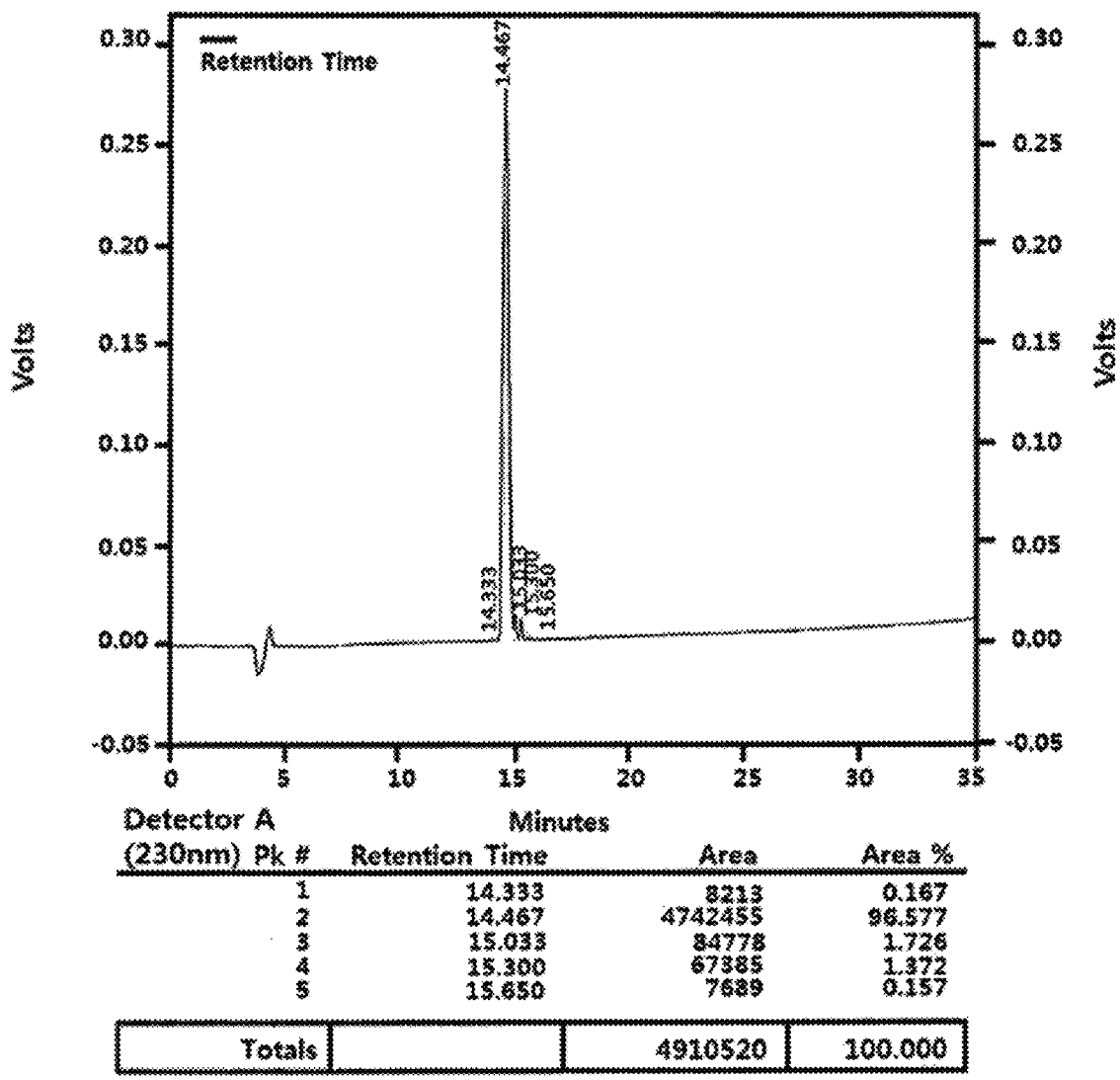
FIG. 44 is a diagram confirming the purity of YDE-041 prepared according to an embodiment of the present invention through HPLC.
Figure 45:
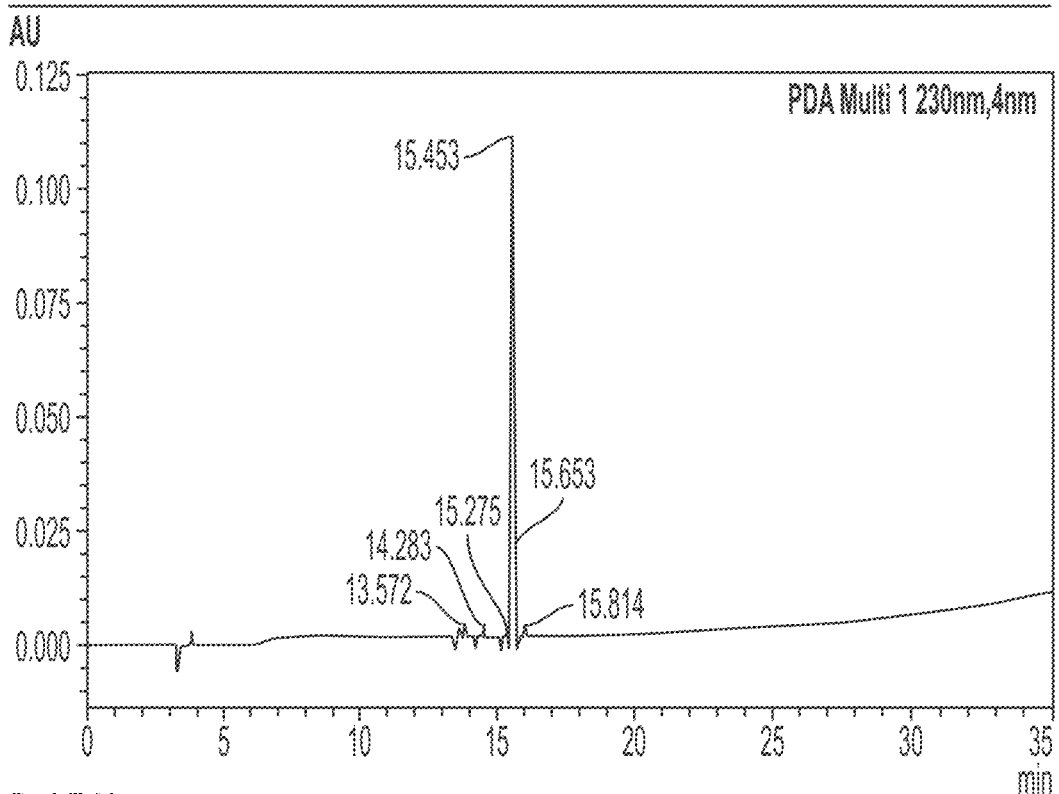
FIG. 45 is a diagram confirming the purity of YDE-042 prepared according to an embodiment of the present invention through HPLC.
Figure 46:
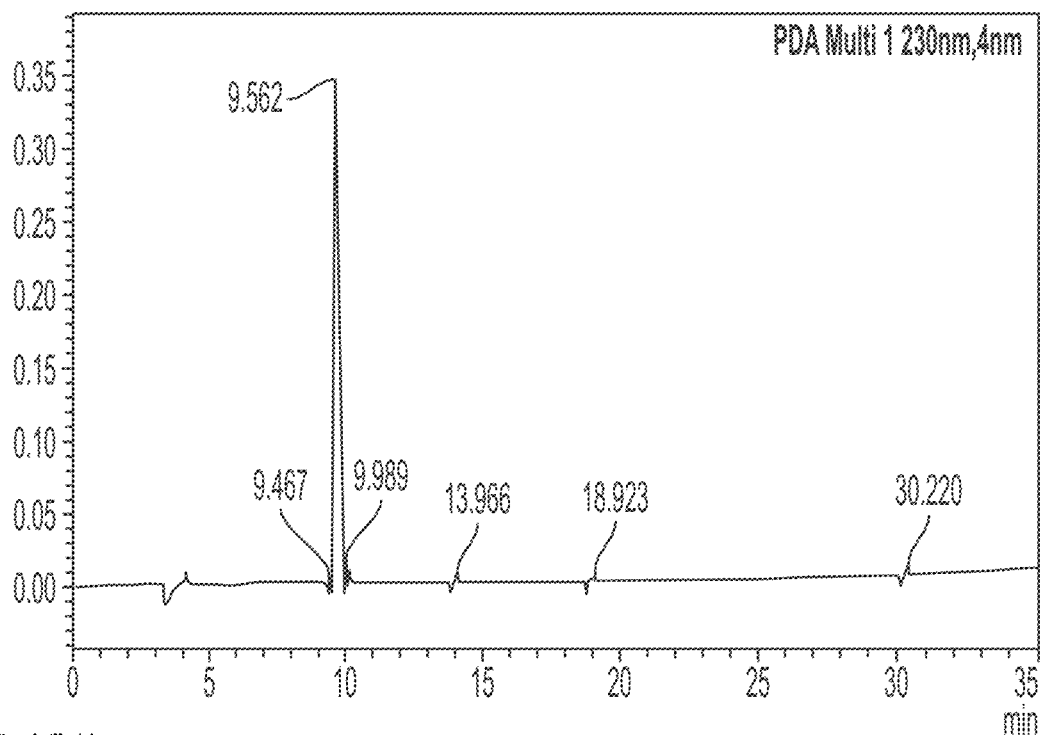
FIG. 46 is a diagram confirming the purity of YDE-043 prepared according to an embodiment of the present invention through HPLC.
Figure 47:
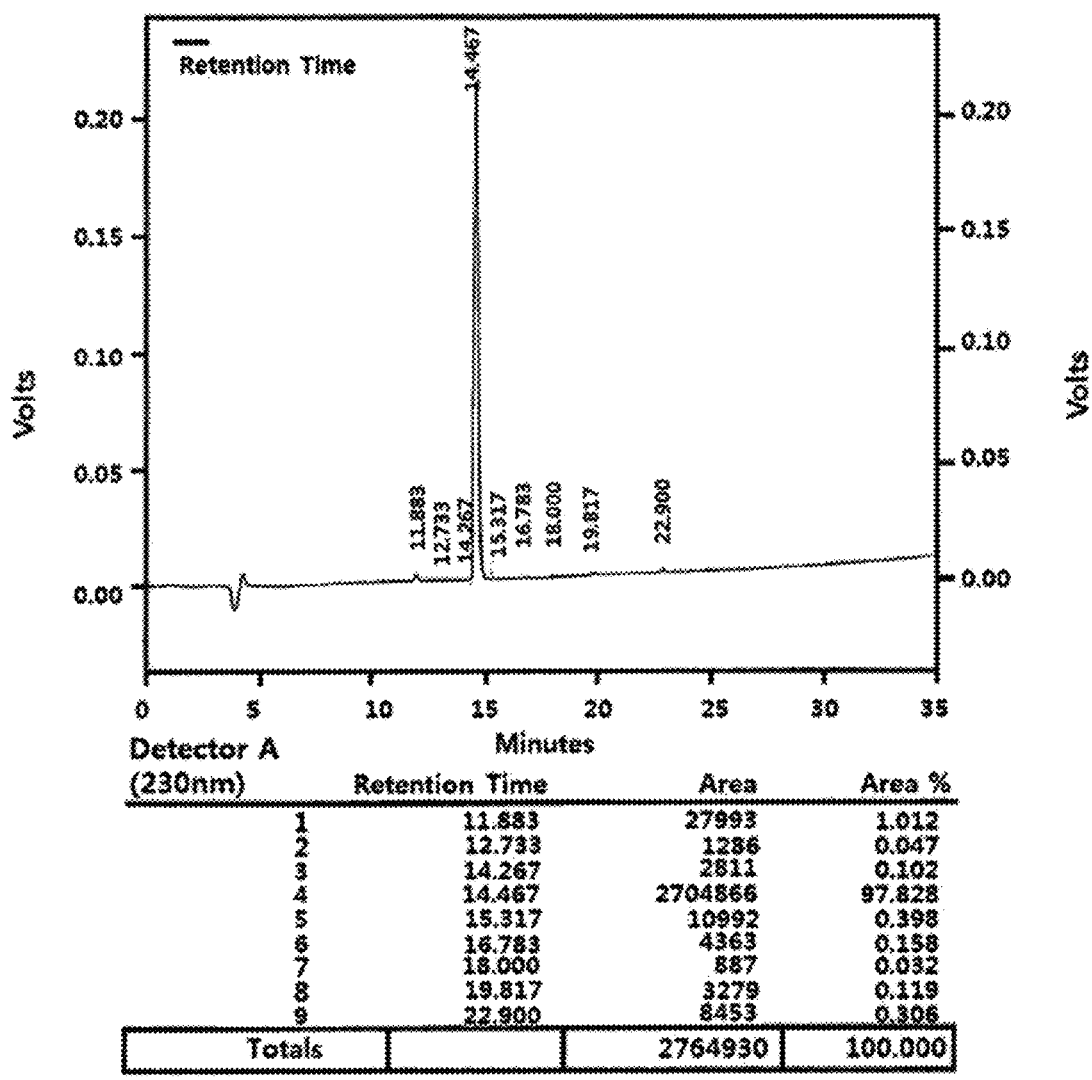
FIG. 47 is a diagram confirming the purity of YDE-044 prepared according to an embodiment of the present invention through HPLC.
Figure 48:
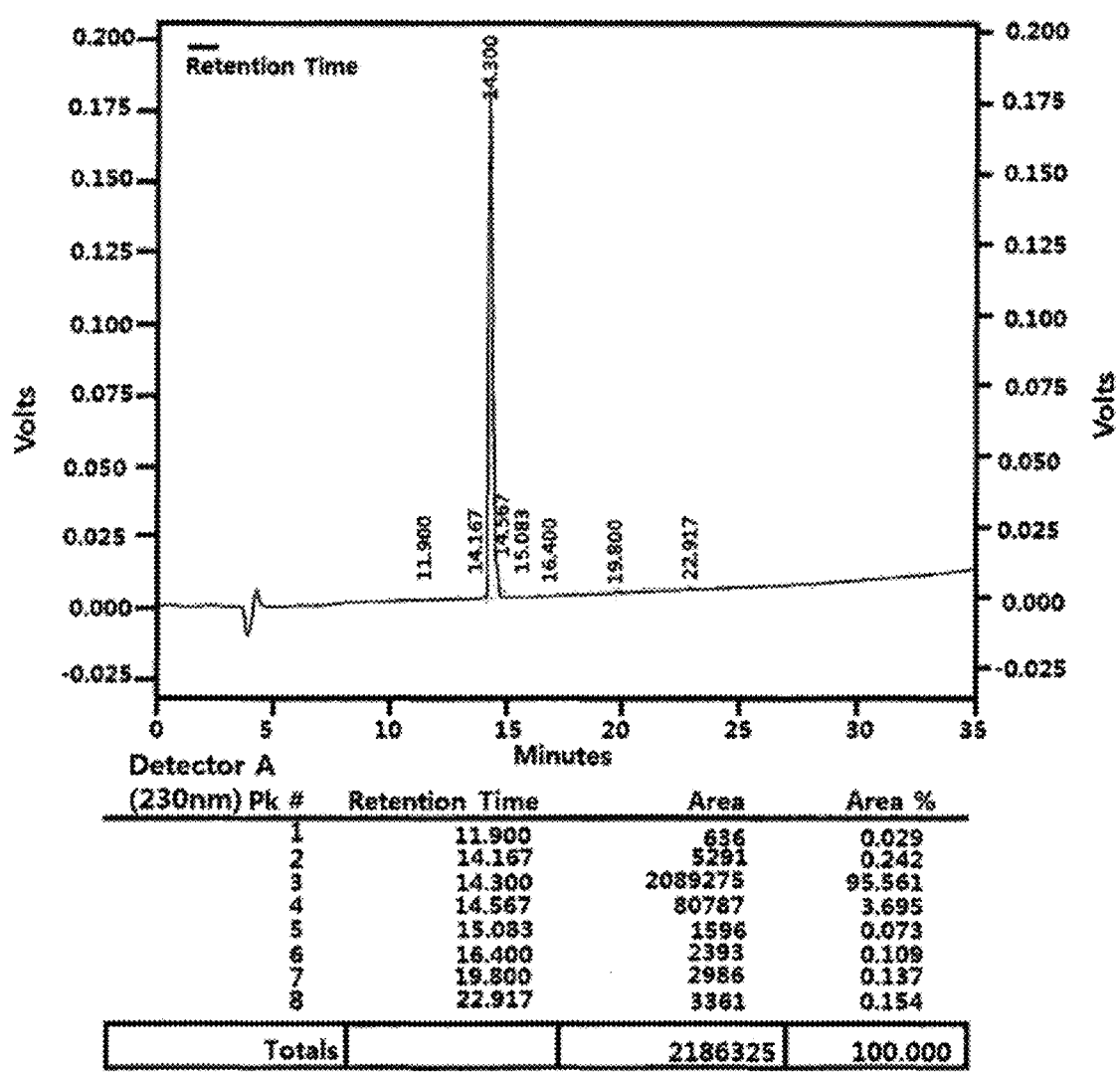
FIG. 48 is a diagram confirming the purity of YDE-045 prepared according to an embodiment of the present invention through HPLC.
Figure 49:
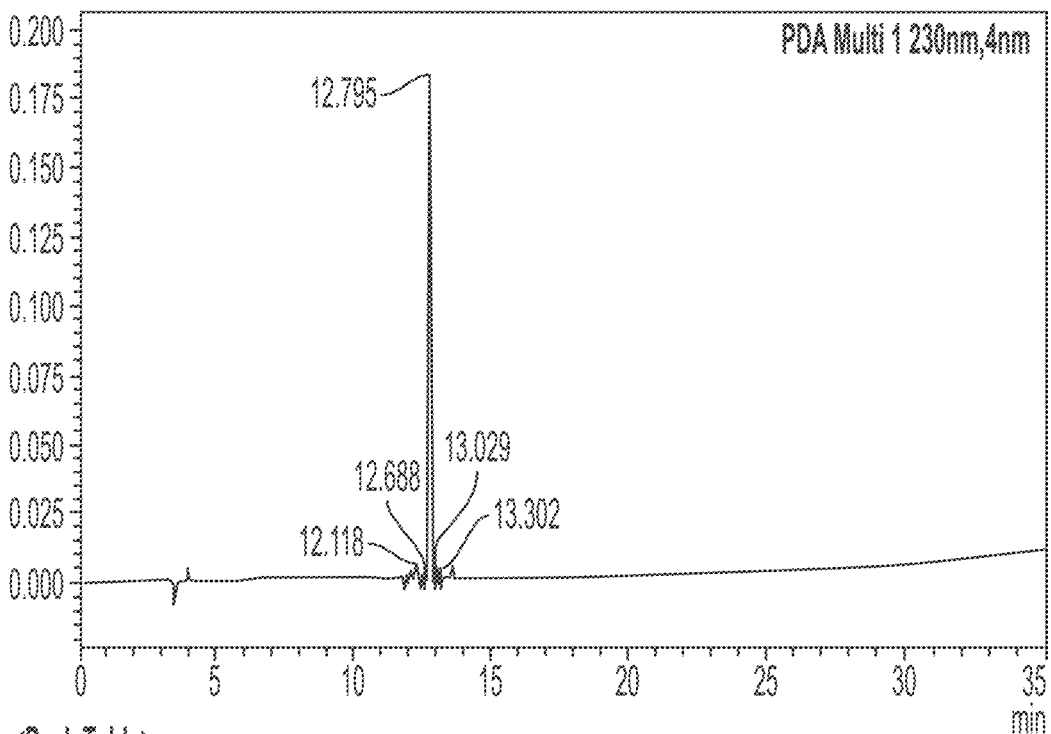
FIG. 49 is a diagram confirming the purity of YDE-047 prepared according to an embodiment of the present invention through HPLC.
Figure 50:
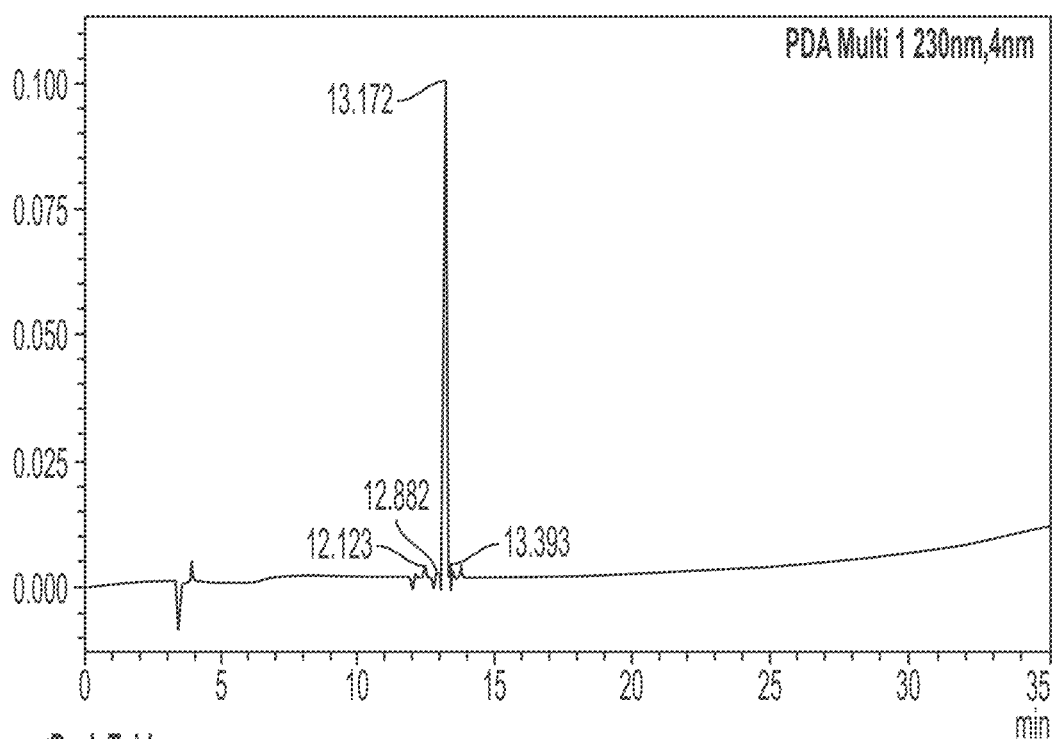
FIG. 50 is a diagram confirming the purity of YDE-048 prepared according to an embodiment of the present invention through HPLC.
Figure 51:
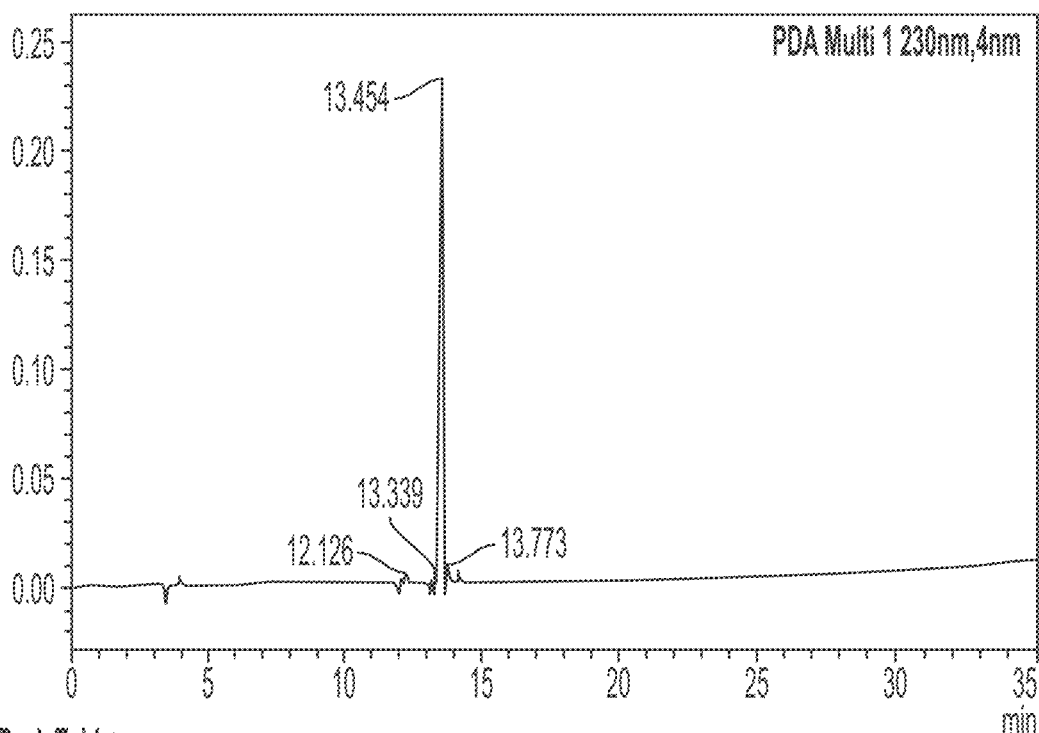
FIG. 51 is a diagram confirming the purity of YDE-049 prepared according to an embodiment of the present invention through HPLC.
Figure 52:
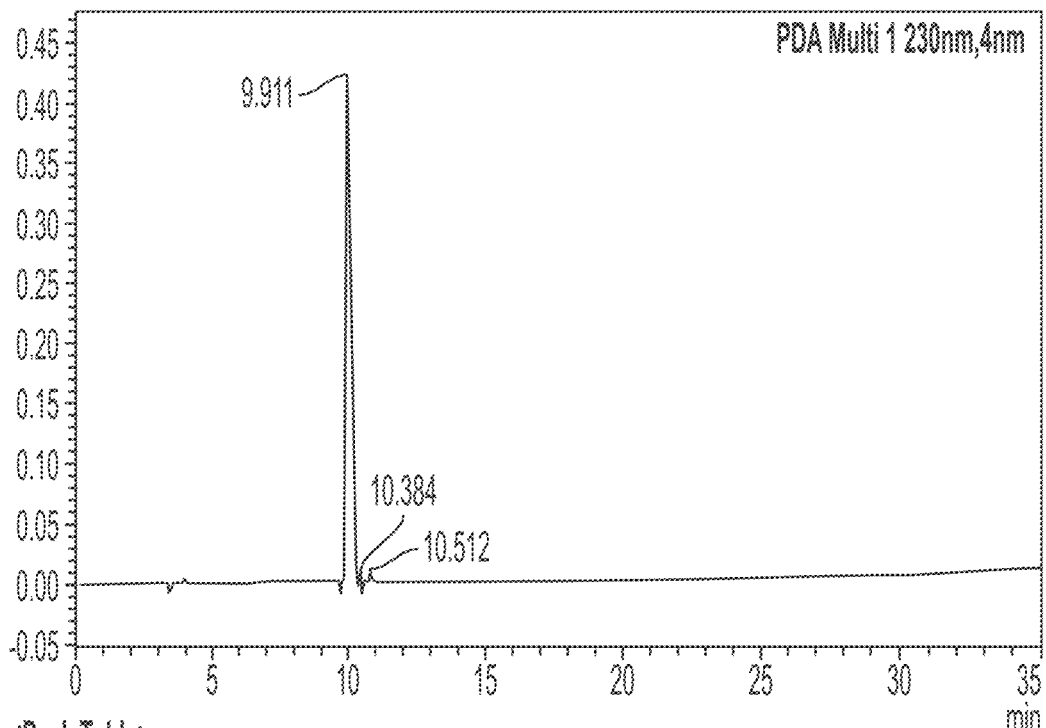
FIG. 52 is a diagram confirming the purity of YDE-050 prepared according to an embodiment of the present invention through HPLC.
Figure 53:
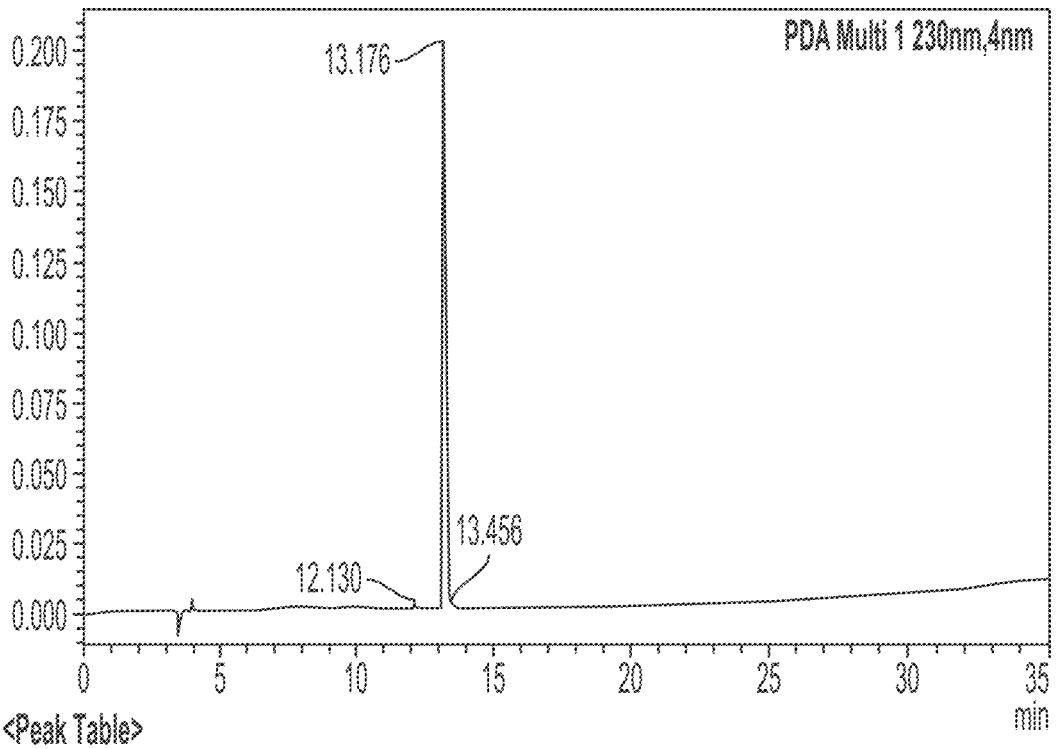
FIG. 53 is a diagram confirming the purity of YDE-051 prepared according to an embodiment of the present invention through HPLC.
Figure 54:
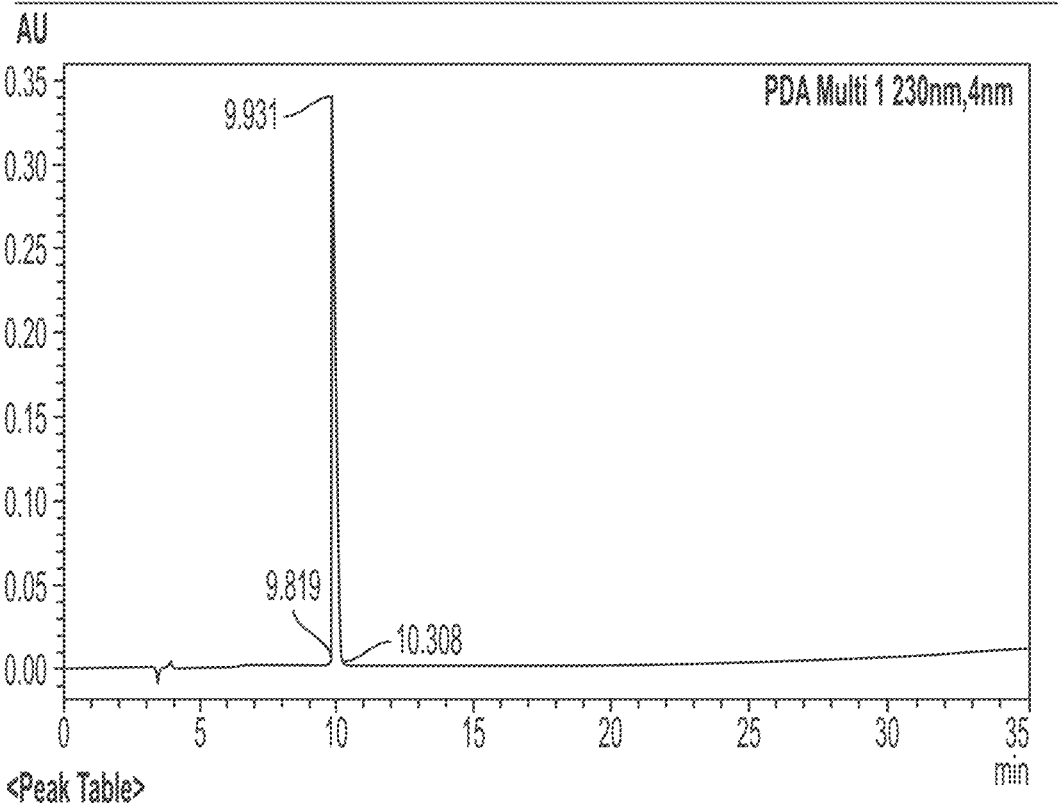
FIG. 54 is a diagram confirming the purity of YDE-052 prepared according to an embodiment of the present invention through HPLC.
Figure 55:
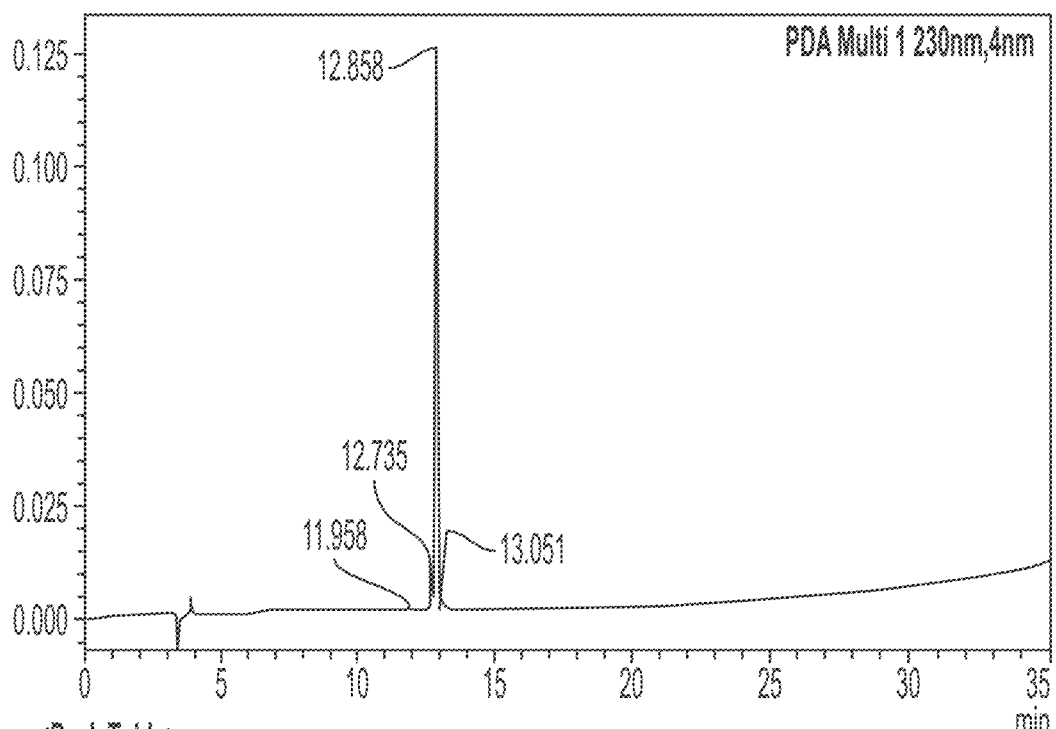
FIG. 55 is a diagram confirming the purity of YDE-053 prepared according to an embodiment of the present invention through HPLC.
Figure 56:
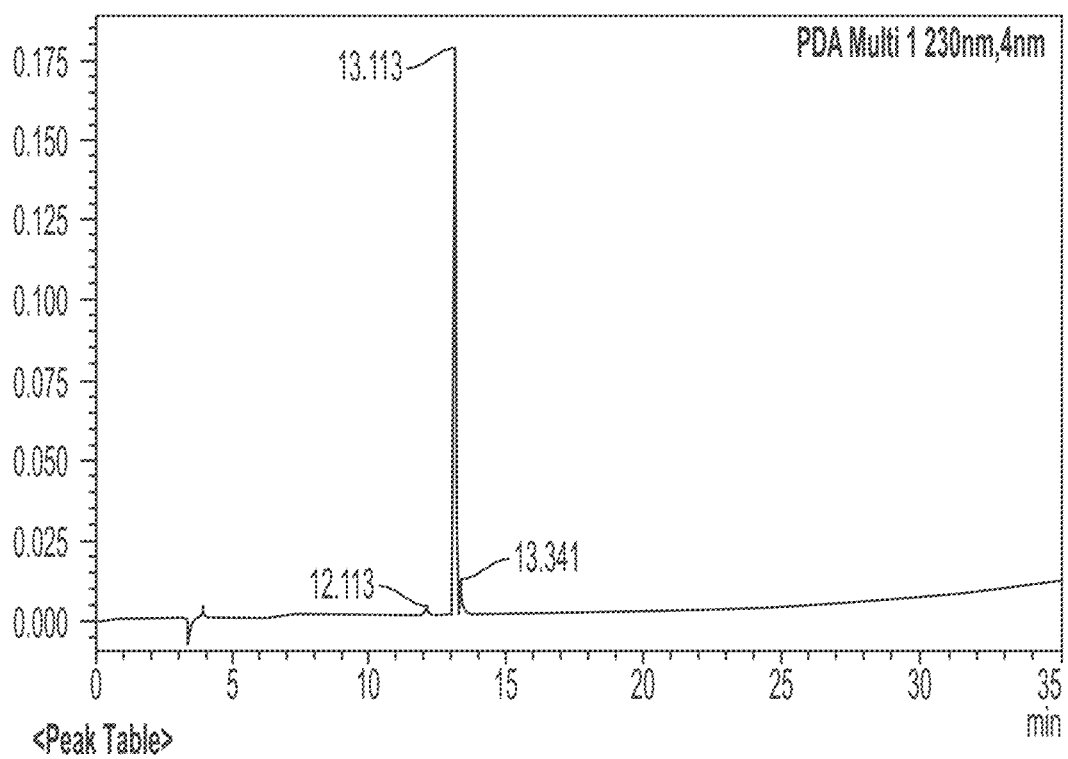
FIG. 56 is a diagram confirming the purity of YDE-054 prepared according to an embodiment of the present invention through HPLC.
Figure 57:
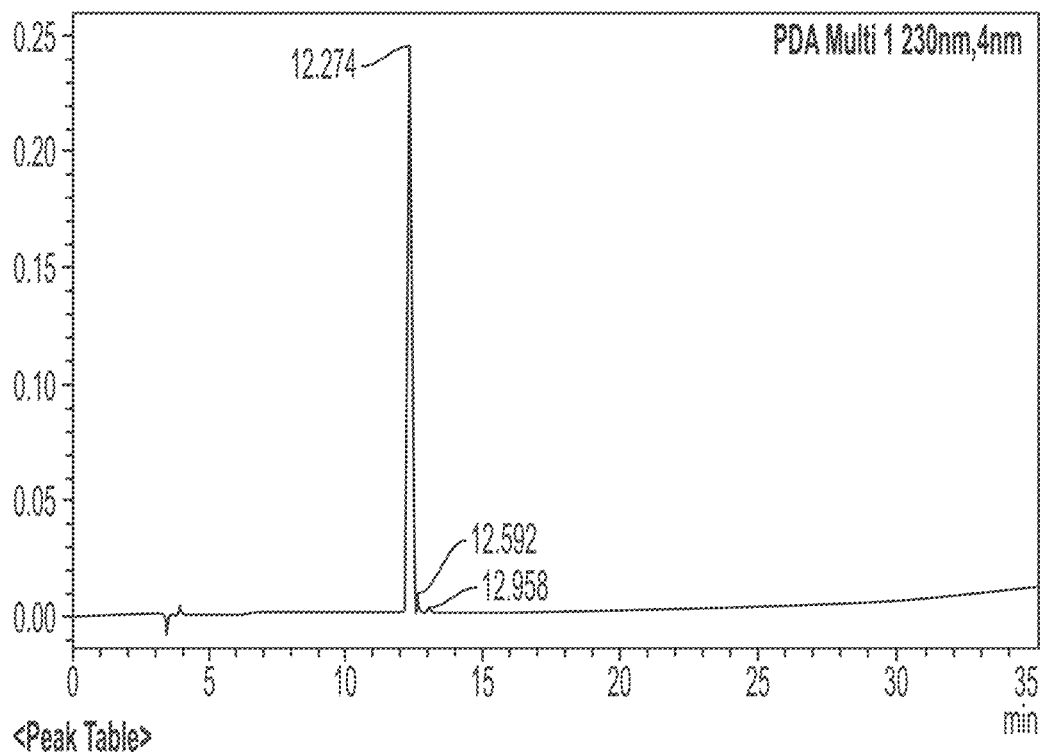
FIG. 57 is a diagram confirming the purity of YDE-055 prepared according to an embodiment of the present invention through HPLC.
Figure 58:
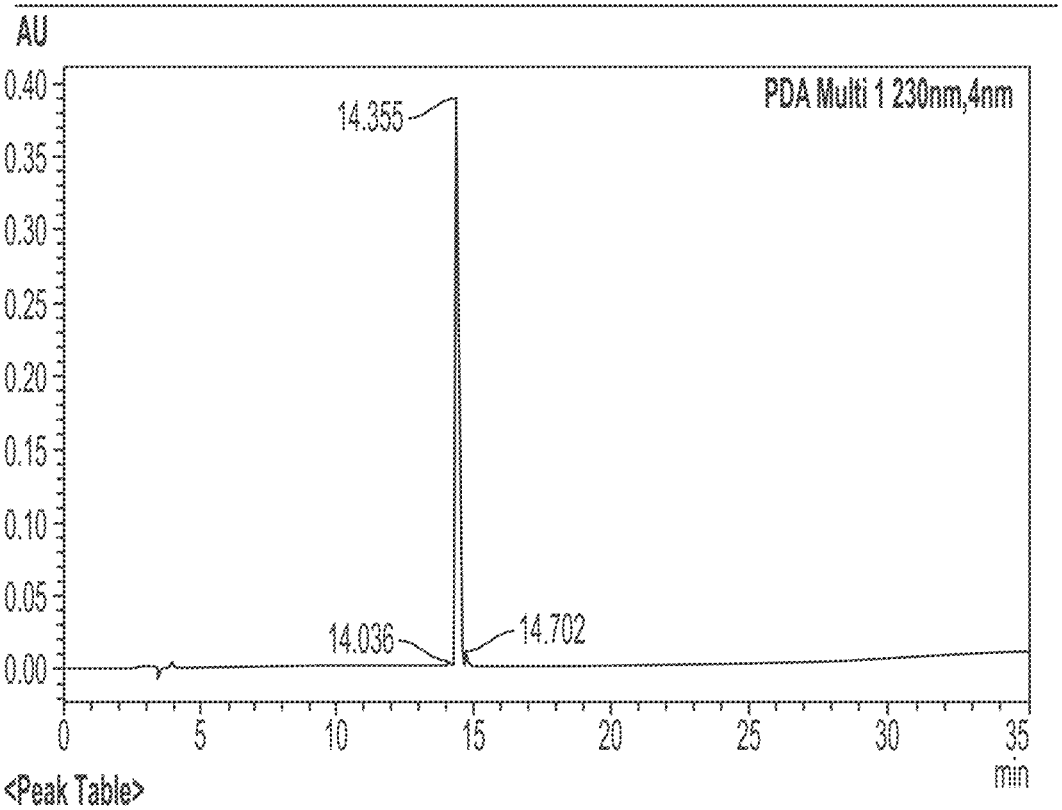
FIG. 58 is a diagram confirming the purity of YDE-056 prepared according to an embodiment of the present invention through HPLC.
Figure 59:
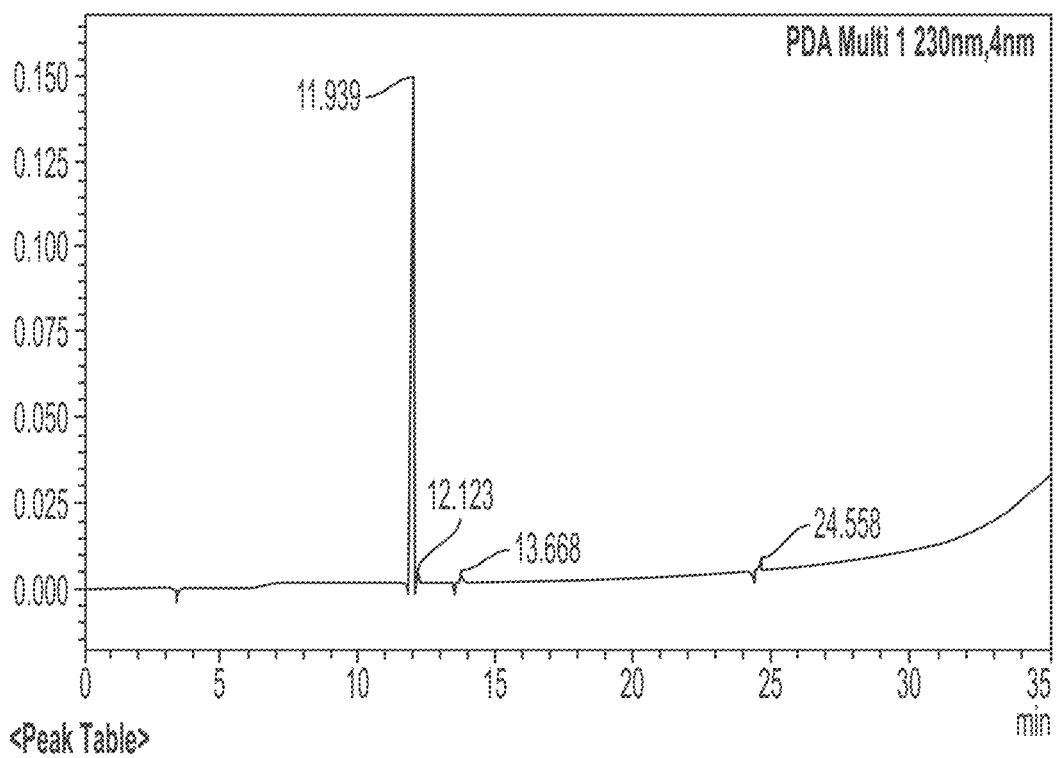
FIG. 59 is a diagram confirming the purity of YDE-057 prepared according to an embodiment of the present invention through HPLC.
Figure 60:
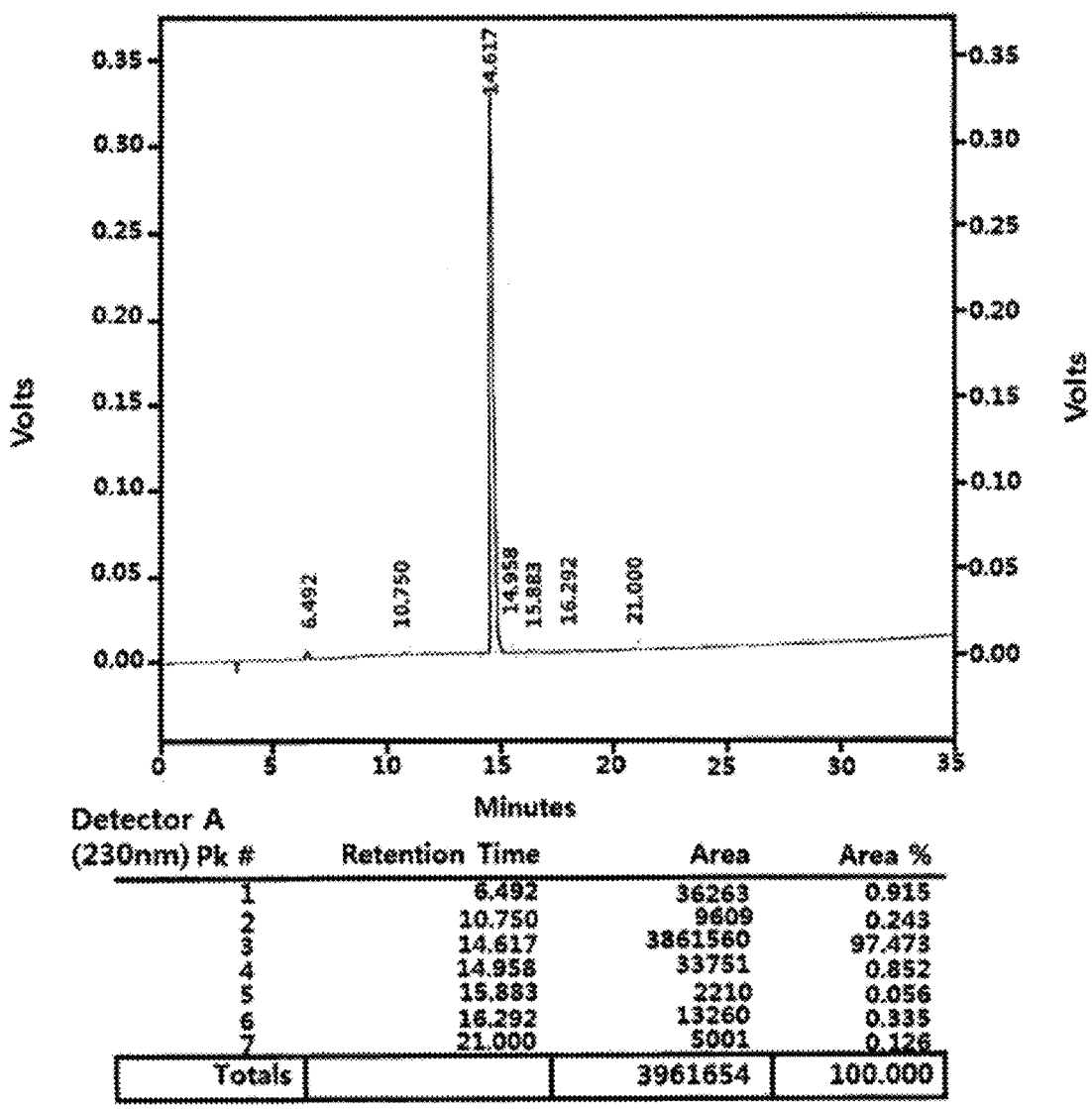
FIG. 60 is a diagram confirming the purity of YDE-058 prepared according to an embodiment of the present invention through HPLC.
Figure 61:
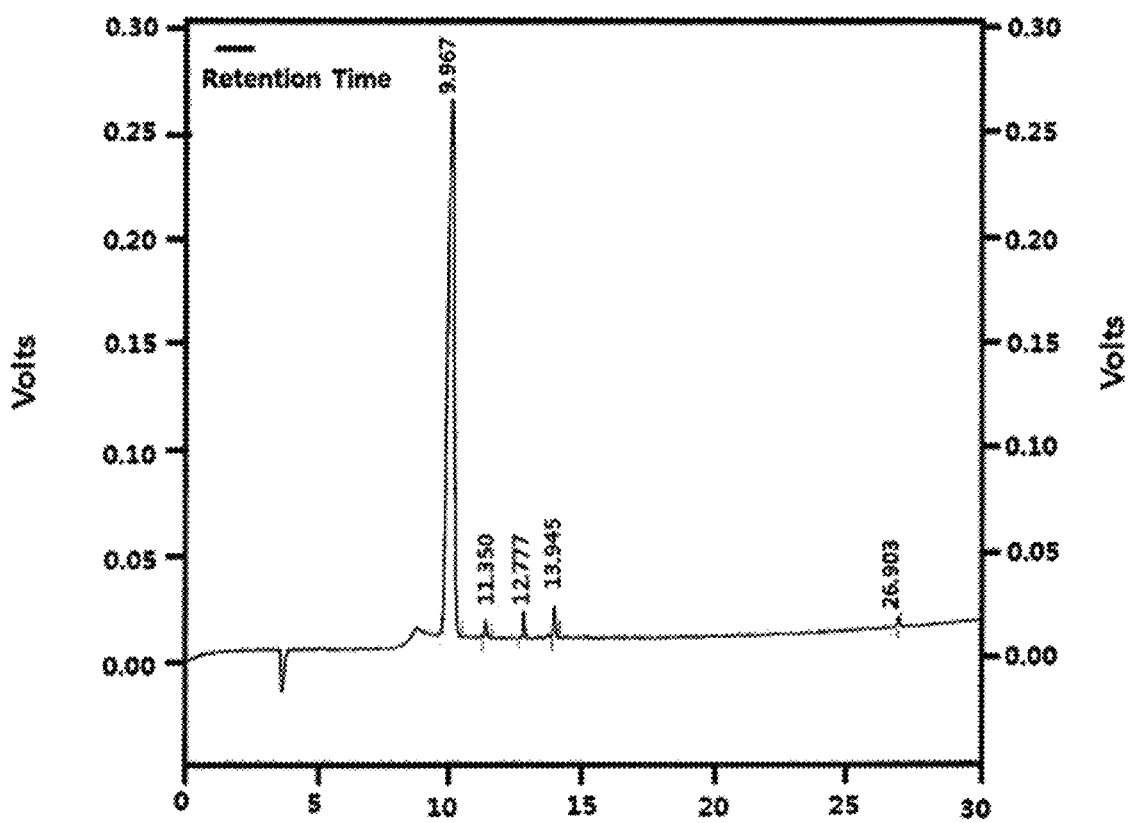
FIG. 61 is a diagram confirming the purity of YDE-059 prepared according to an embodiment of the present invention through HPLC.
Figure 62:
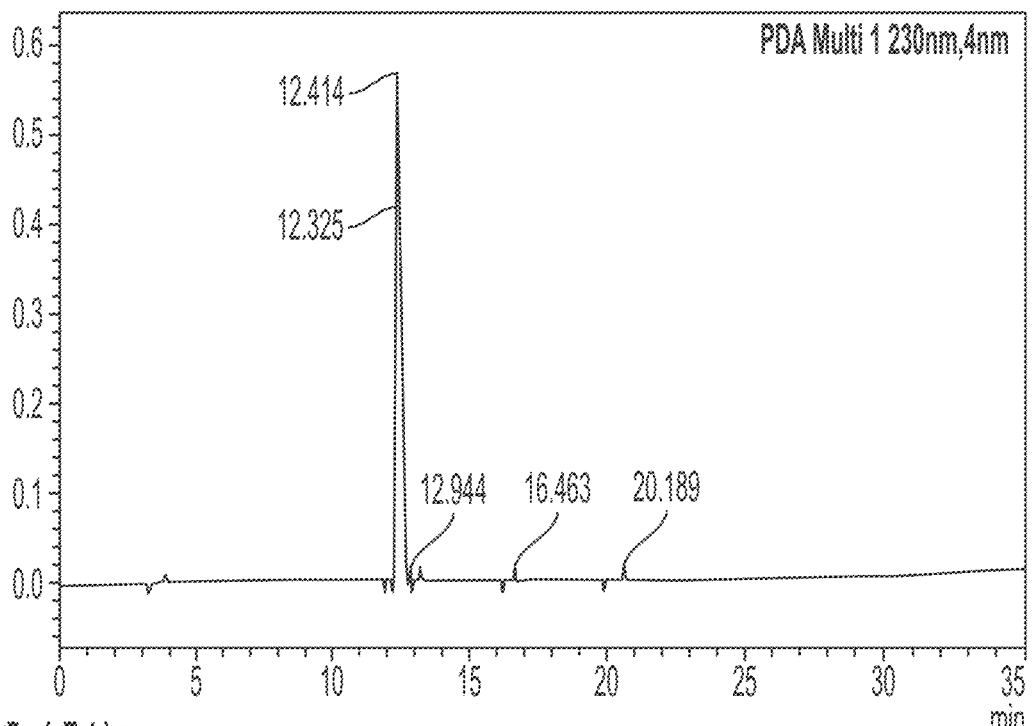
FIG. 62 is a diagram confirming the purity of YDE-060 prepared according to an embodiment of the present invention through HPLC.
Figure 63:
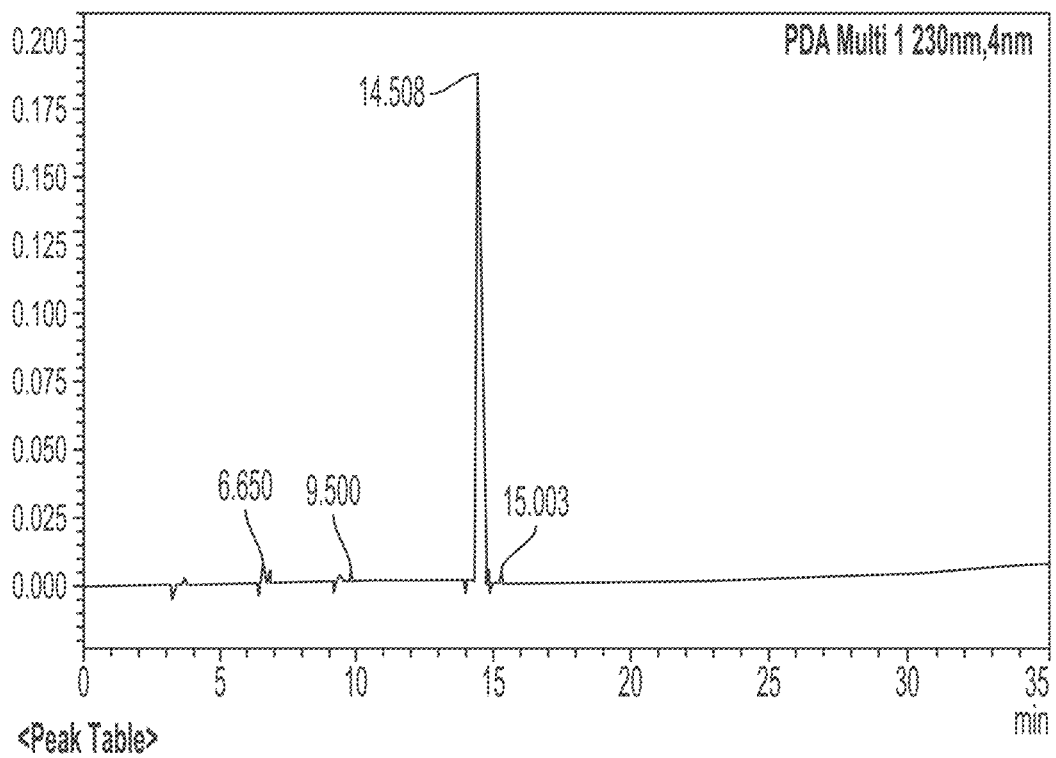
FIG. 63 is a diagram confirming the purity of YDE-064 prepared according to an embodiment of the present invention through HPLC.
Figure 64:
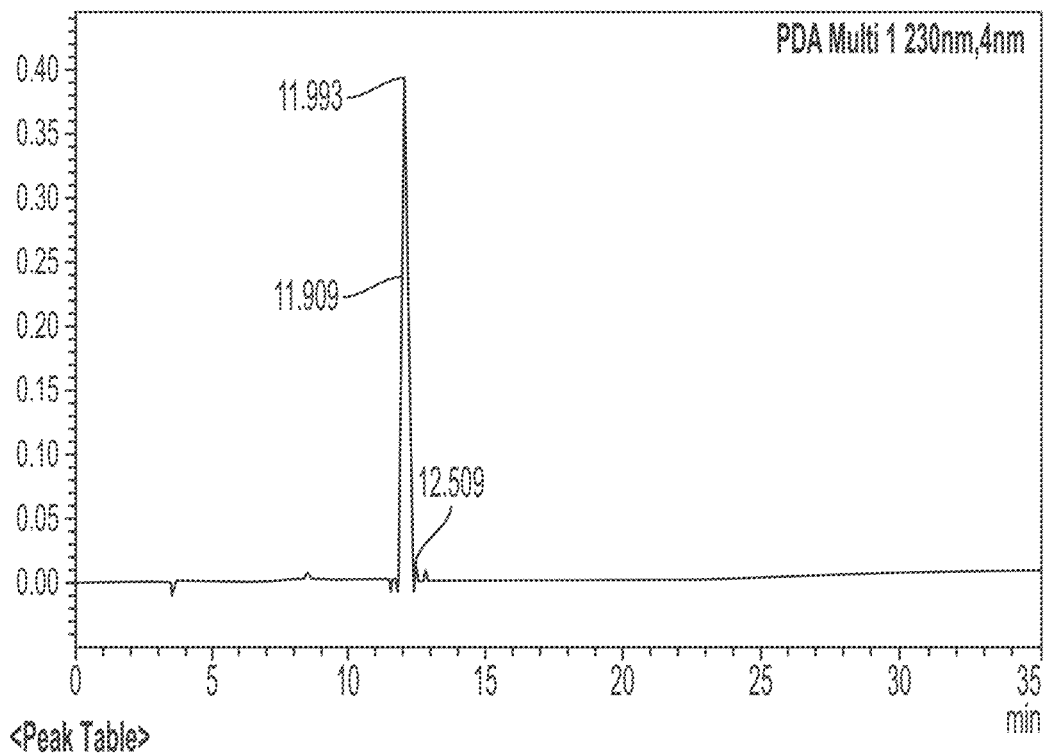
FIG. 64 is a diagram confirming the purity of YDE-066 prepared according to an embodiment of the present invention through HPLC.
Figure 65:
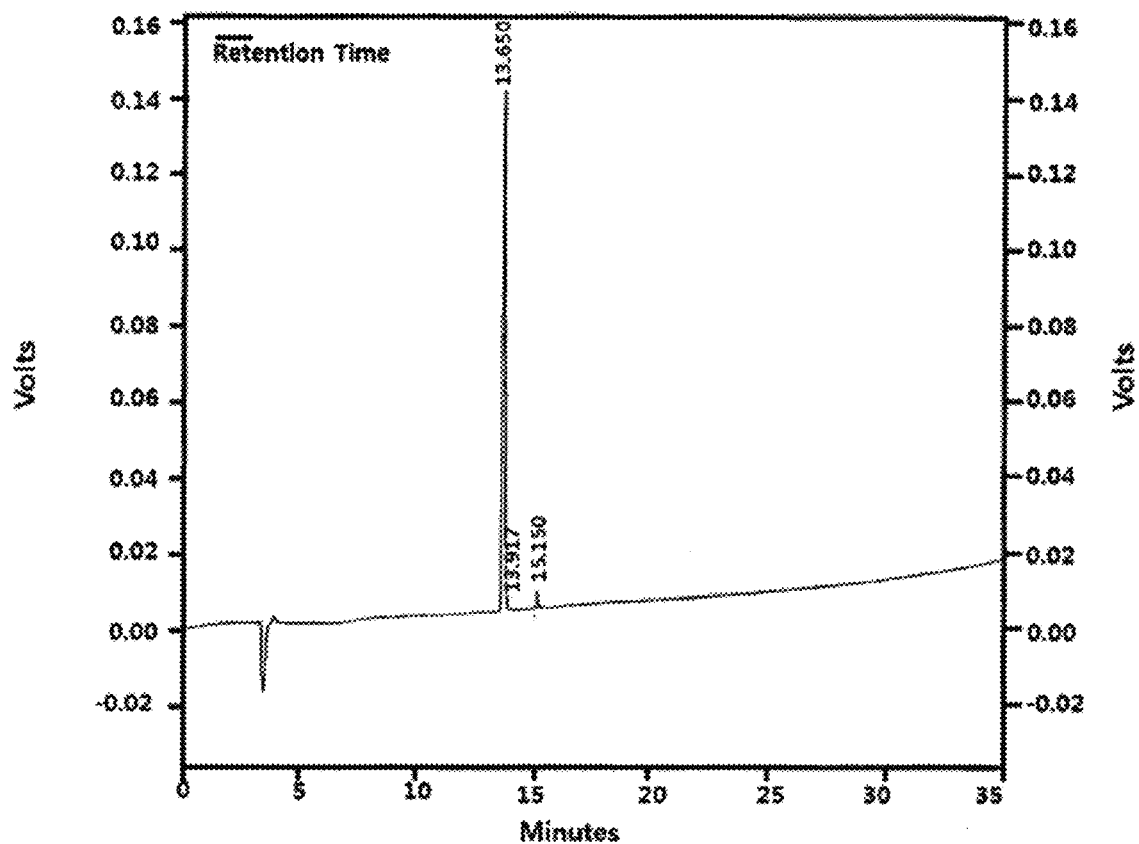
FIG. 65 is a diagram confirming the purity of YDE-072 prepared according to an embodiment of the present invention through HPLC.
Figure 66:
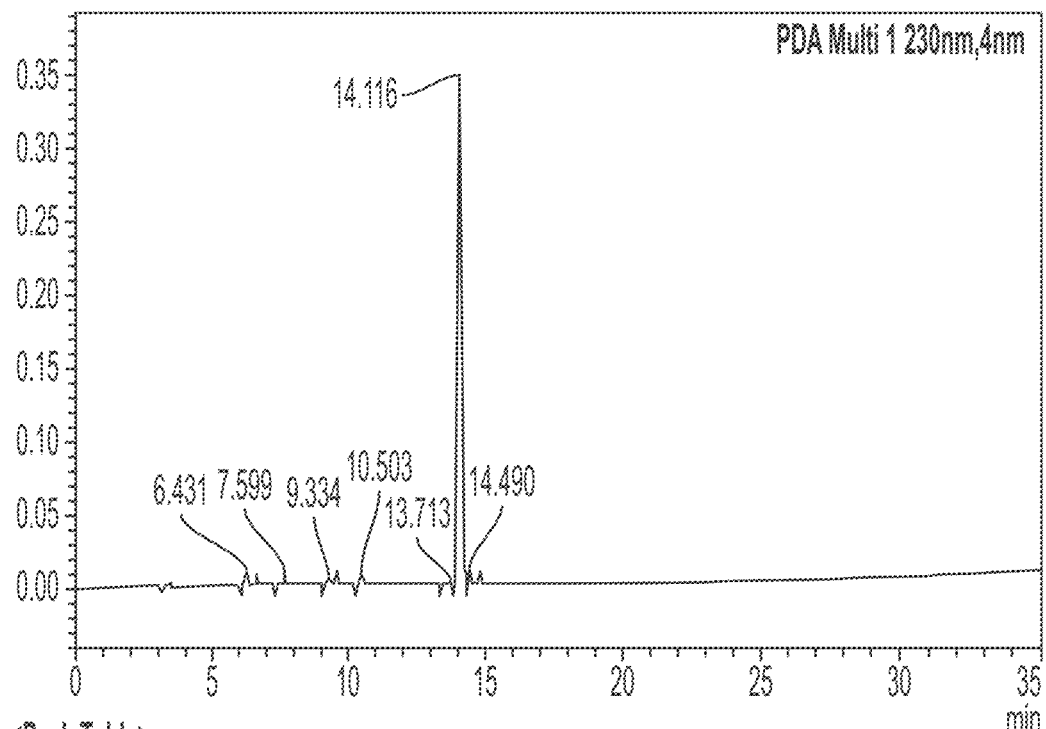
FIG. 66 is a diagram confirming the purity of YDE-073 prepared according to an embodiment of the present invention through HPLC.
Figure 67:
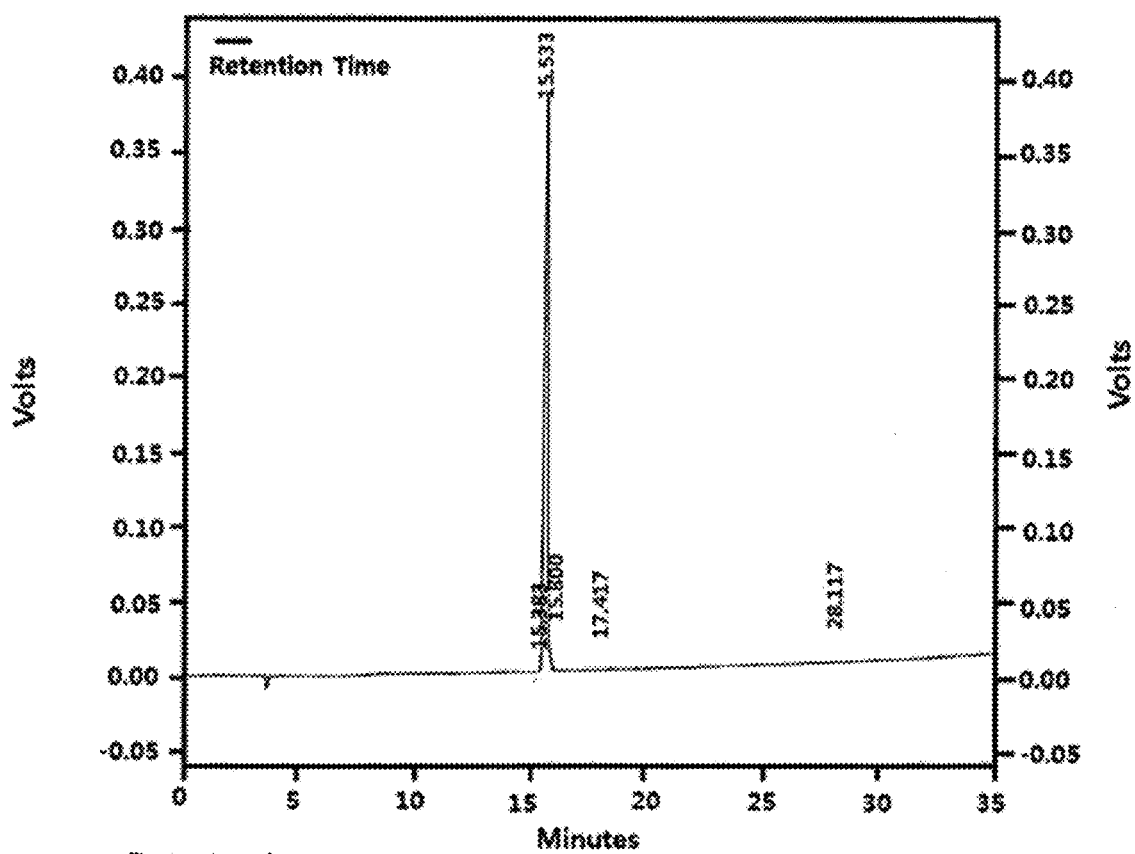
FIG. 67 is a diagram confirming the purity of YDE-074 prepared according to an embodiment of the present invention through HPLC.
Figure 68:
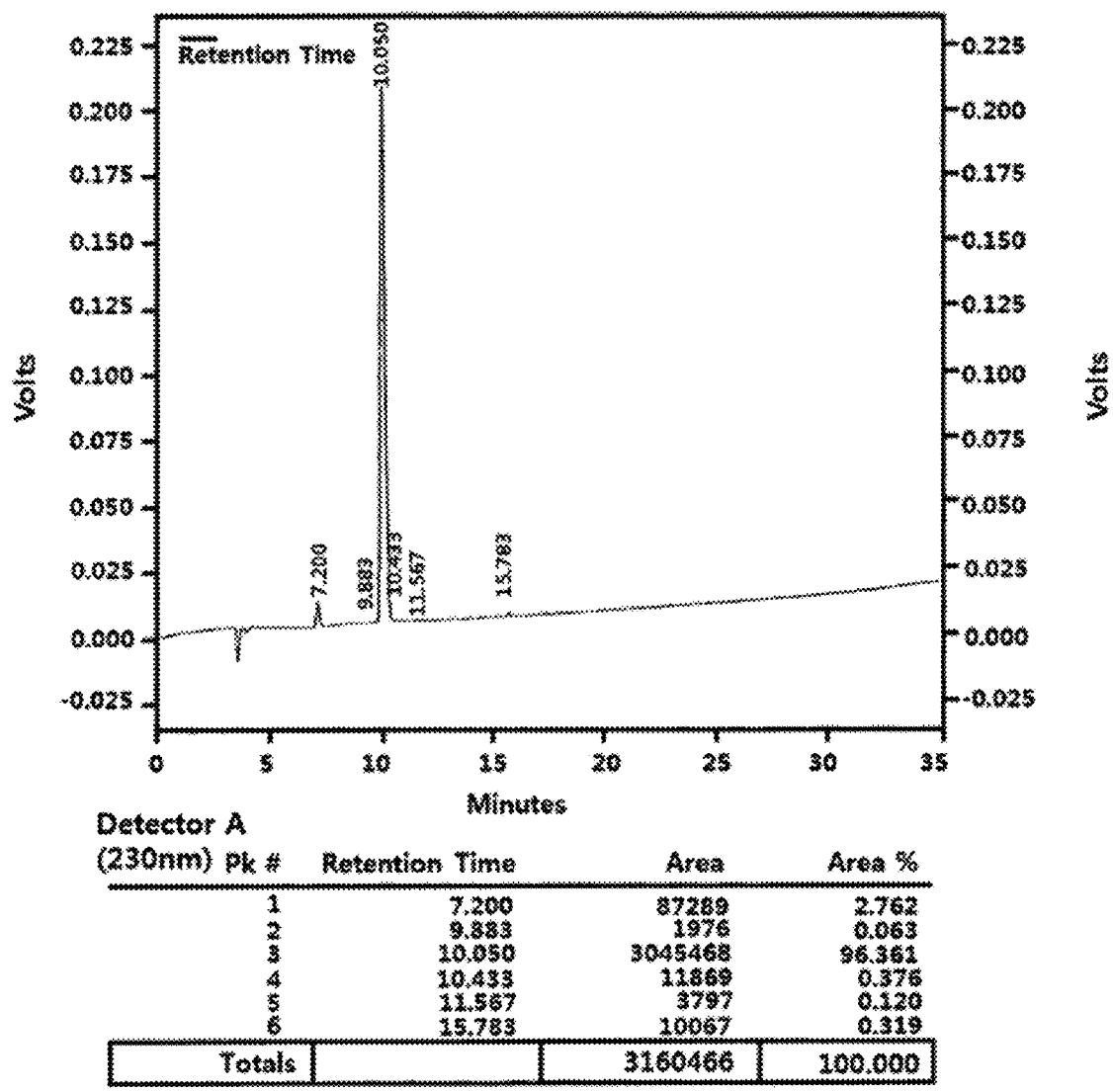
FIG. 68 is a diagram confirming the purity of YDE-075 prepared according to an embodiment of the present invention through HPLC.

The YDE derivatives prepared in Working Example 1 were analyzed by HPLC. As a result, it was confirmed that the purities of synthesized YDE-001, YDE-002, YDE-003, YDE-004, YDE-005, YDE-006, YDE-007, YDE-008, YDE-009, YDE-010, YDE-011, YDE-012, YDE-013, YDE-014, YDE-015, YDE-016, YDE-017, YDE-018, YDE-019, YDE-020, YDE-021, YDE-022, YDE-023, YDE-024, YDE-025, YDE-026, YDE-027, YDE-028, YDE-029, YDE-030, YDE-031, YDE-032, YDE-033, YDE-034, YDE-035, YDE-036, YDE-037, YDE-038, YDE-039, YDE-040, YDE-041, YDE-042, YDE-043, YDE-044, YDE-045, YDE-047, YDE-048, YDE-049, YDE-050, YDE-051, YDE-052, YDE-053, YDE-054, YDE-055, YDE-056, YDE-057, YDE-058, YDE-059, YDE-060, YDE-064, YDE-066, YDE-072, YDE-073, YDE-074, and YDE-075 were 99.7%, 99.7%, 99.7%, 99.7%, 99.5%, 98.9%, 98.0%, 98.8%, 98.1%, 99.0%, 98.3%, 98.9%, 98.7%, 98.5%, 99.1%, 99.4%, 98.0%, 99.6%, 99.6%, 99.2%, 98.1%, 98.3%, 96.1%, 98.9%, 95.1%, 98.6%, 96.9%, 99.5%, 98.0%, 98.1%, 98.8%, 98.2%, 97.2%, 98.6%, 98.8%, 98.7%, 99.2%, 98.7%, 98.1%, 97.5%, 96.5%, 97.4%, 98.7%, 97.8%, 95.5%, 97.5%, 97.2%, 96.9%, 99.3%, 98.0%, 99.4%, 96.4%, 95.1%, 98.6%, 97.4%, 98.8%, 97.4%, 95.8%, 98.9%, 96.9%, 98.8%, 97.7%, 95.0%, 97.9%, and 96.3%, respectively (FIGS. 4 to 68).

Figure 69:
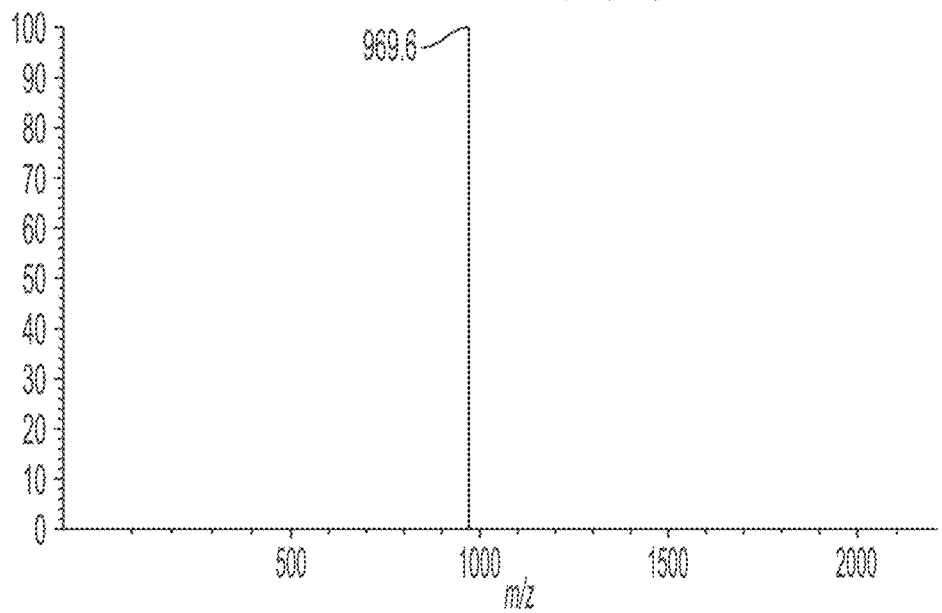
FIG. 69 is a diagram confirming the molecular weight of YDE-001 prepared according to an embodiment of the present invention through Ion-Mass.
Figure 70:
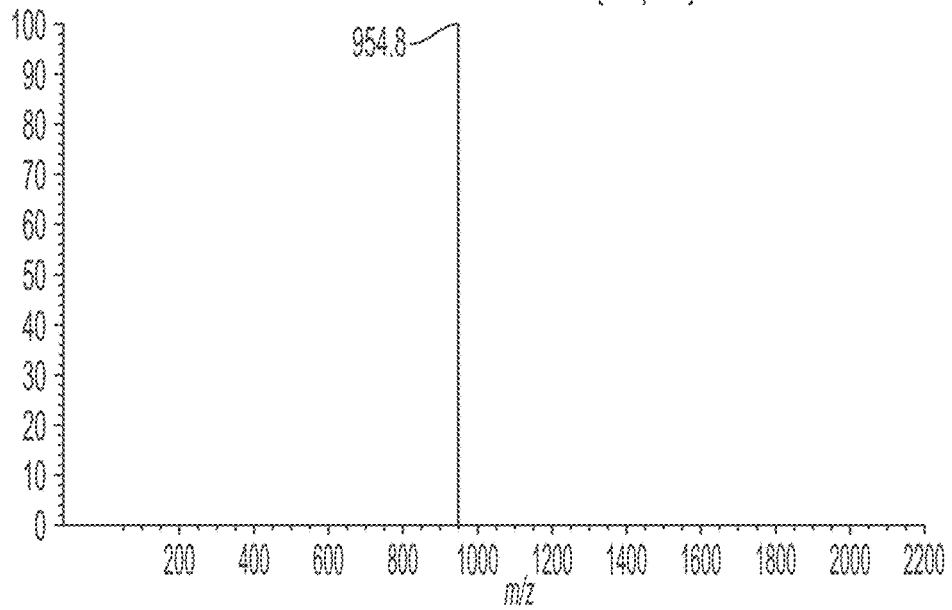
FIG. 70 is a diagram confirming the molecular weight of YDE-002 prepared according to an embodiment of the present invention through Ion-Mass.
Figure 71:
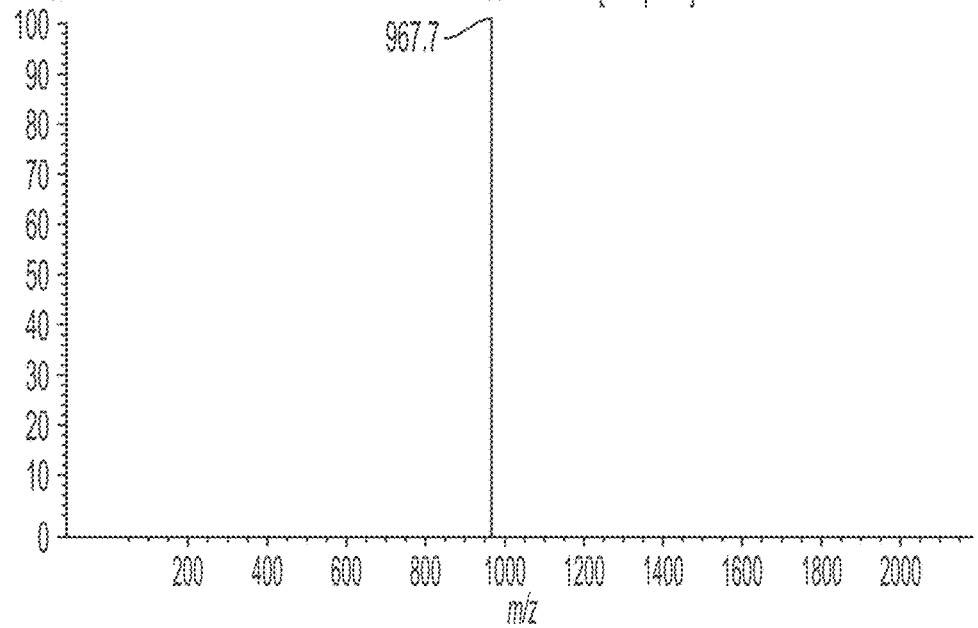
FIG. 71 is a diagram confirming the molecular weight of YDE-003 prepared according to an embodiment of the present invention through Ion-Mass.
Figure 72:
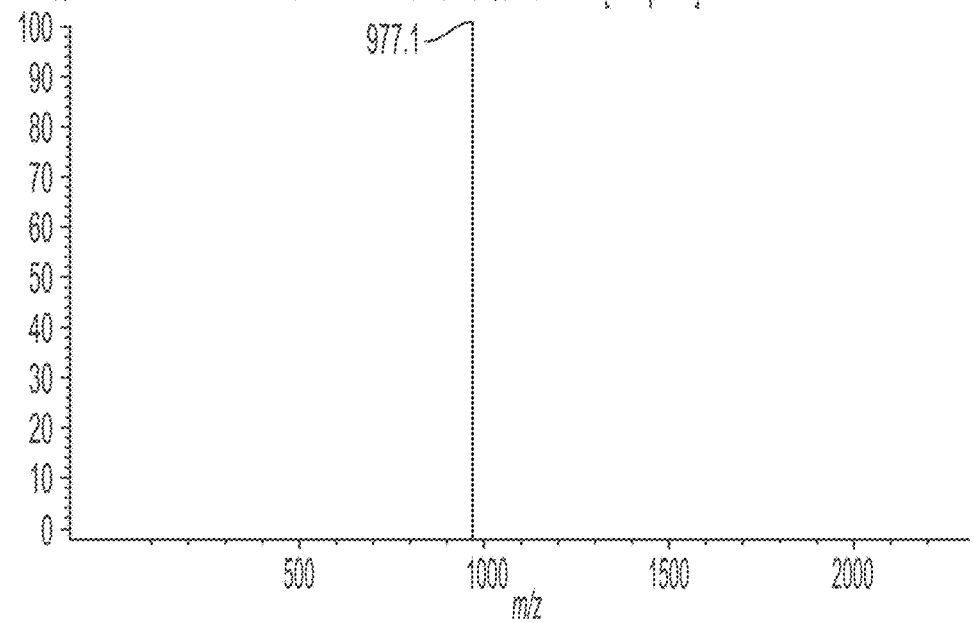
FIG. 72 is a diagram confirming the molecular weight of YDE-004 prepared according to an embodiment of the present invention through Ion-Mass.
Figure 73:
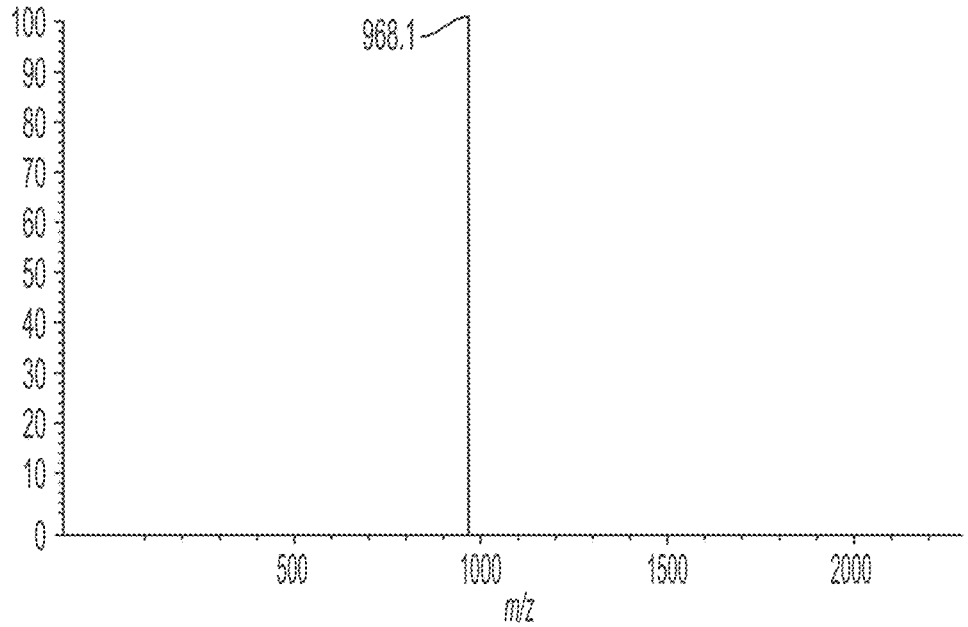
FIG. 73 is a diagram confirming the molecular weight of YDE-005 prepared according to an embodiment of the present invention through Ion-Mass.
Figure 74:
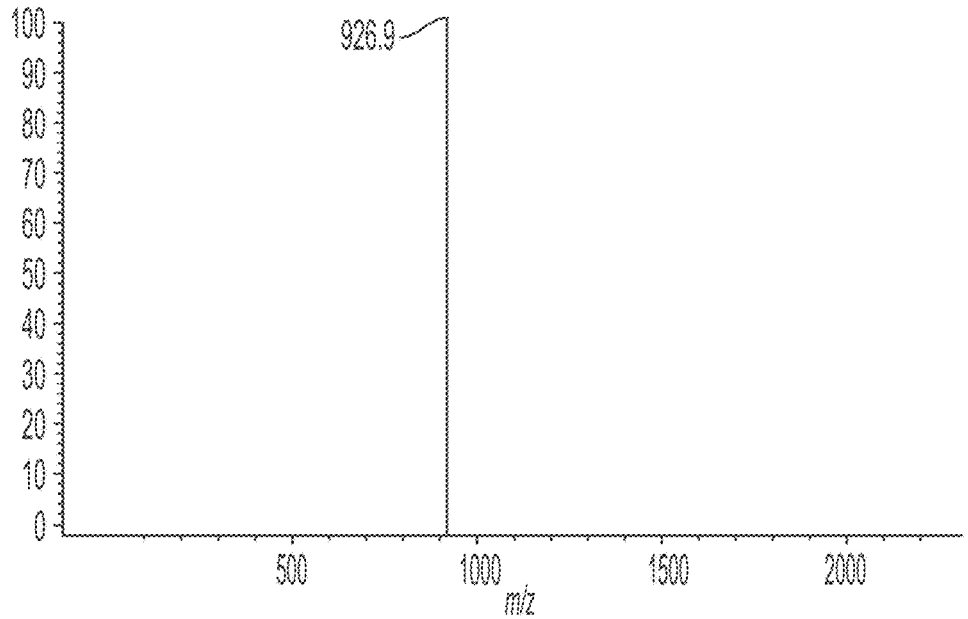
FIG. 74 is a diagram confirming the molecular weight of YDE-006 prepared according to an embodiment of the present invention through Ion-Mass.
Figure 75:
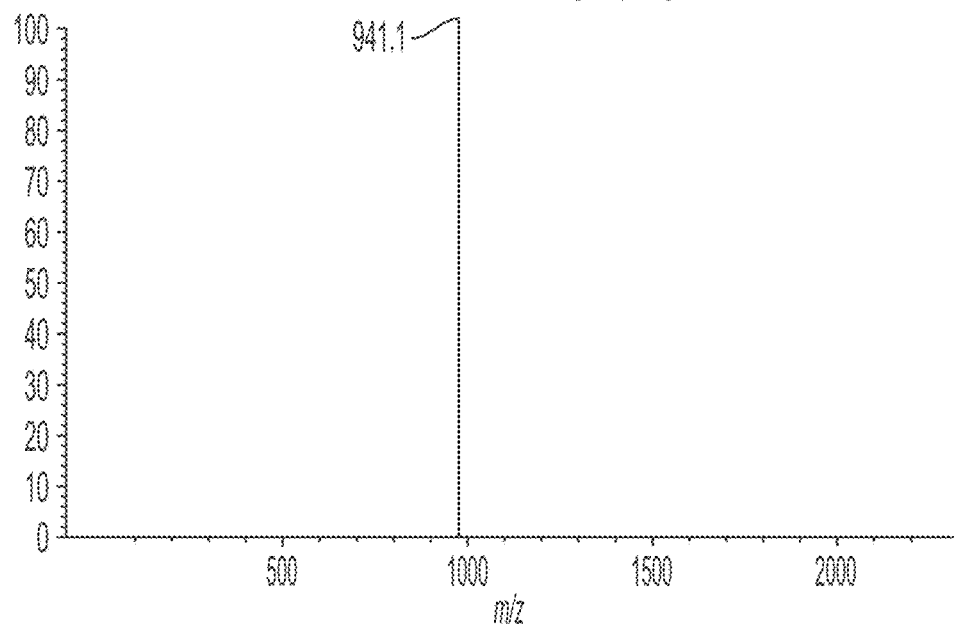
FIG. 75 is a diagram confirming the molecular weight of YDE-007 prepared according to an embodiment of the present invention through Ion-Mass.
Figure 76:
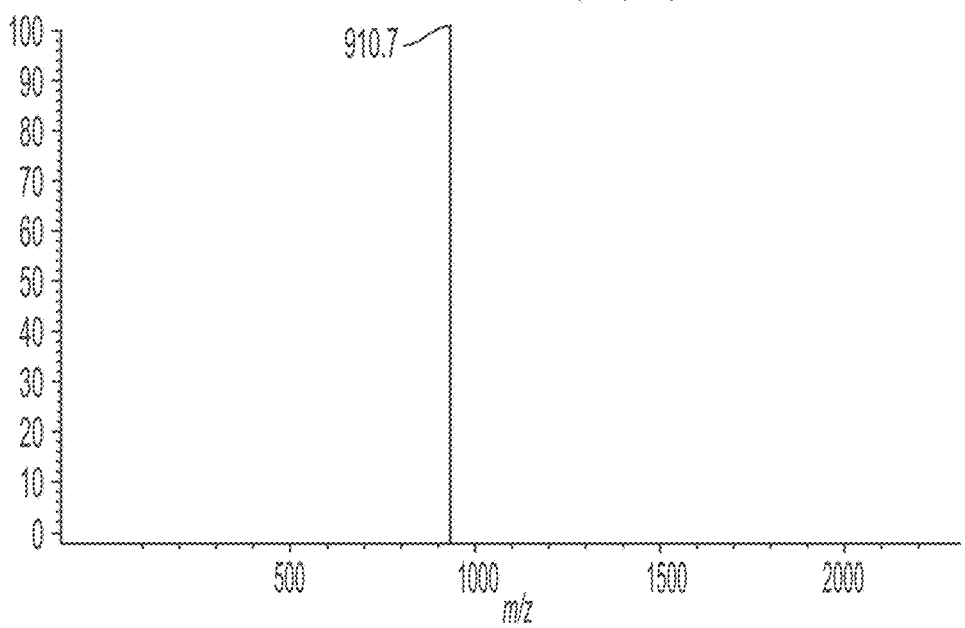
FIG. 76 is a diagram confirming the molecular weight of YDE-008 prepared according to an embodiment of the present invention through Ion-Mass.
Figure 77:
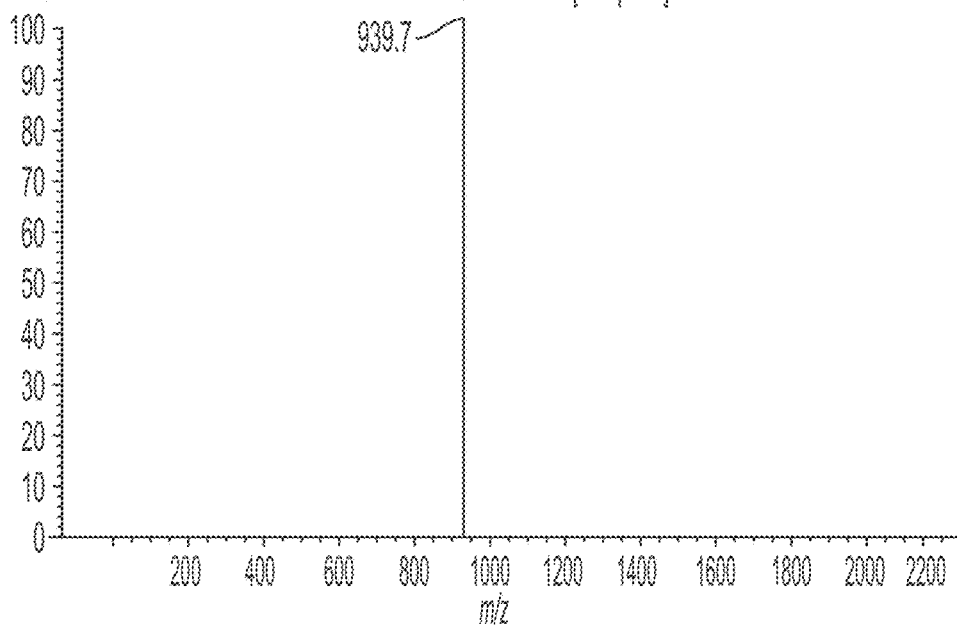
FIG. 77 is a diagram confirming the molecular weight of YDE-009 prepared according to an embodiment of the present invention through Ion-Mass.
Figure 78:
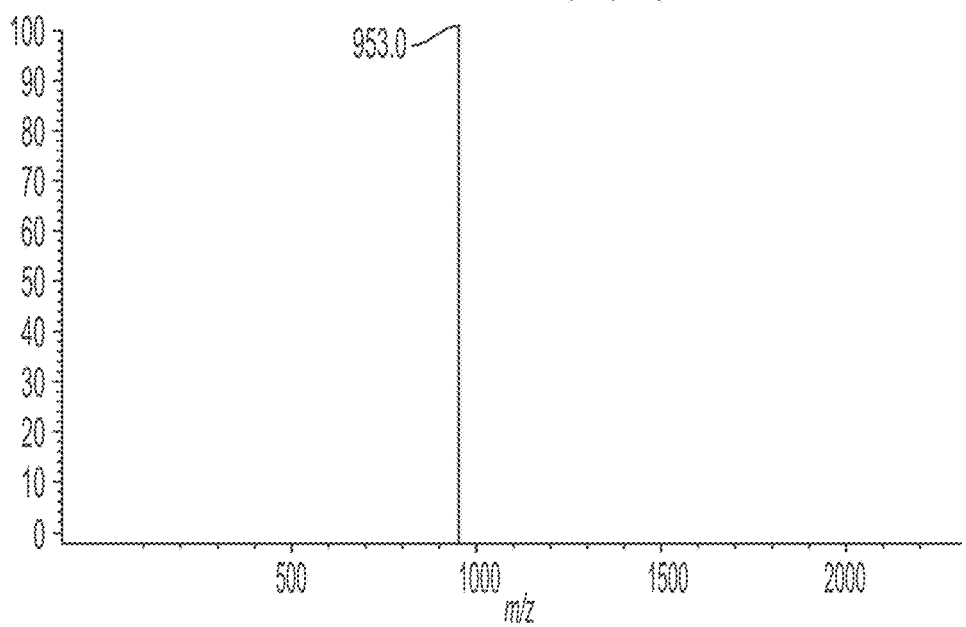
FIG. 78 is a diagram confirming the molecular weight of YDE-010 prepared according to an embodiment of the present invention through Ion-Mass.
Figure 79:
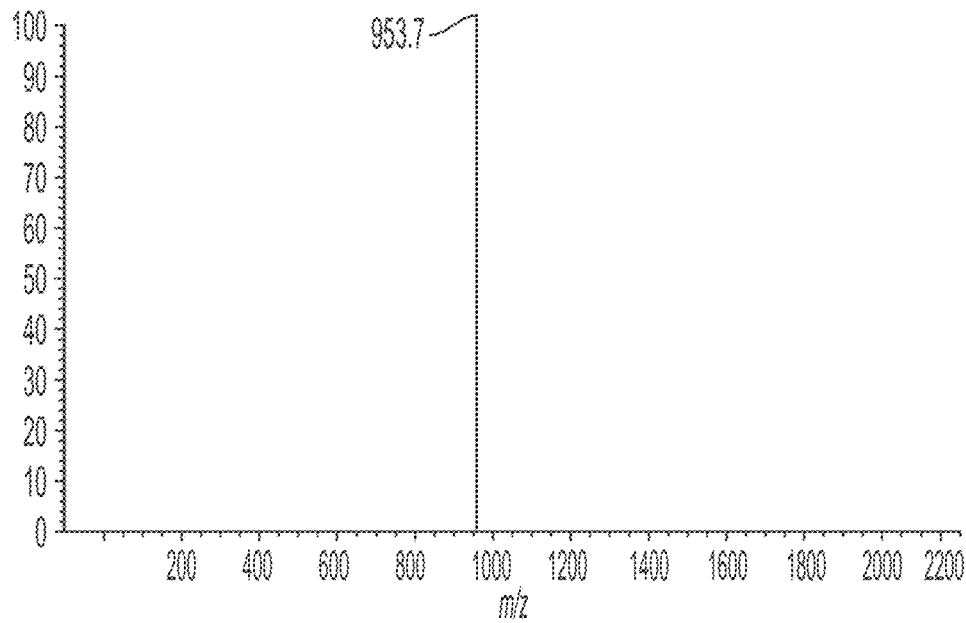
FIG. 79 is a diagram confirming the molecular weight of YDE-011 prepared according to an embodiment of the present invention through Ion-Mass.
Figure 80:
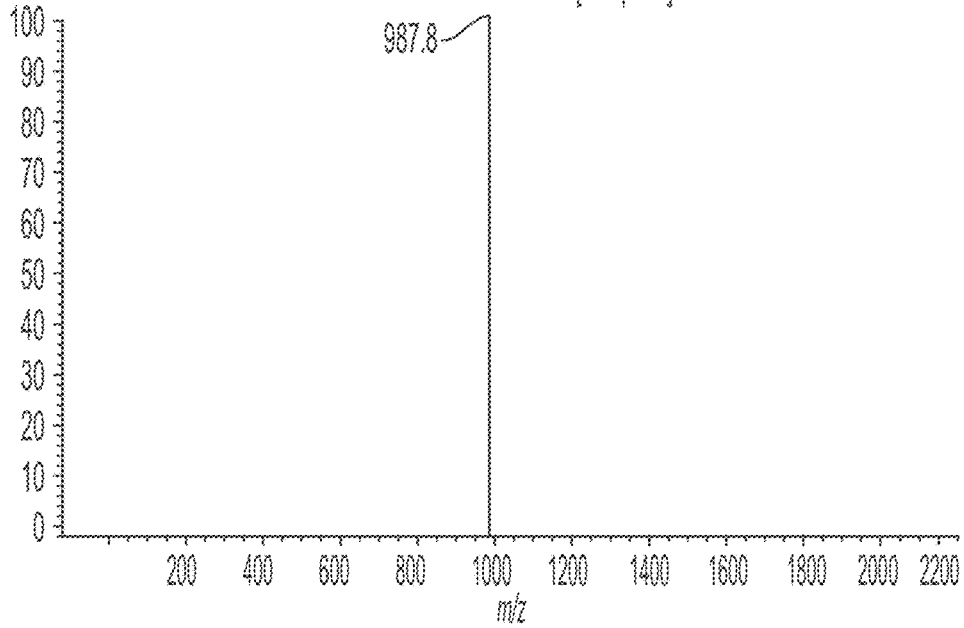
FIG. 80 is a diagram confirming the molecular weight of YDE-012 prepared according to an embodiment of the present invention through Ion-Mass.
Figure 81:
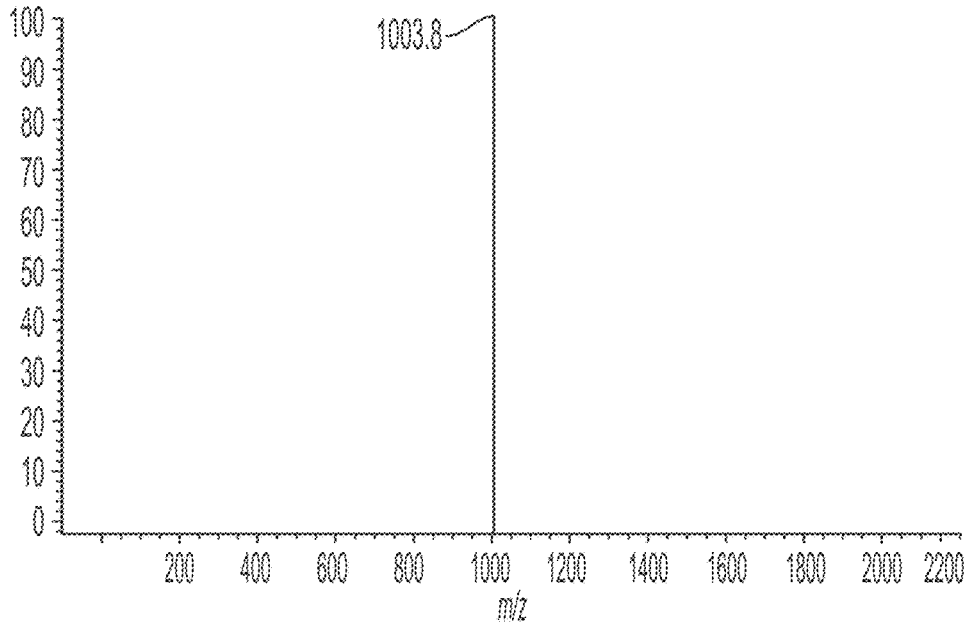
FIG. 81 is a diagram confirming the molecular weight of YDE-013 prepared according to an embodiment of the present invention through Ion-Mass.
Figure 82:
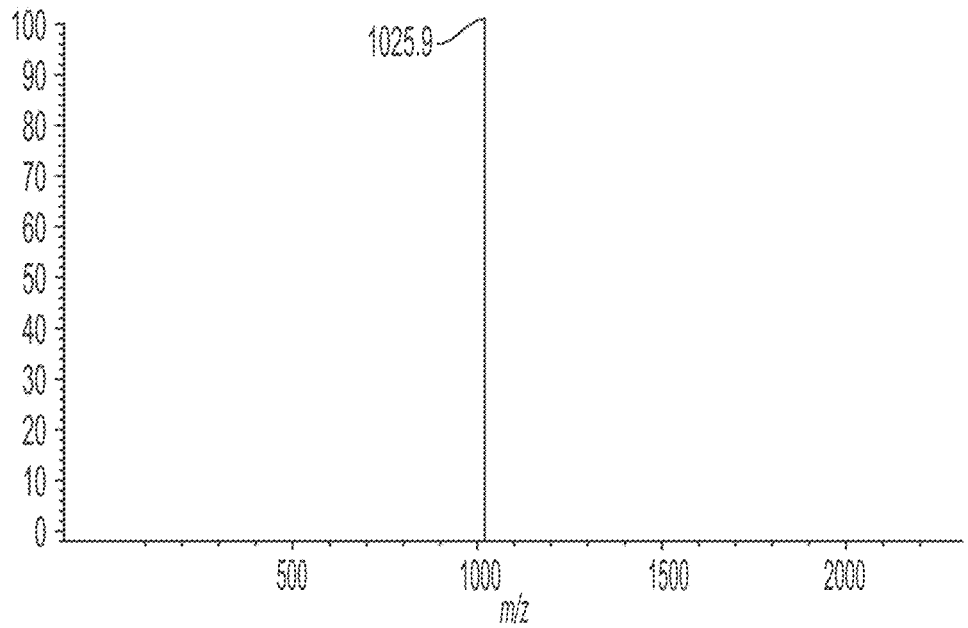
FIG. 82 is a diagram confirming the molecular weight of YDE-014 prepared according to an embodiment of the present invention through Ion-Mass.
Figure 83:
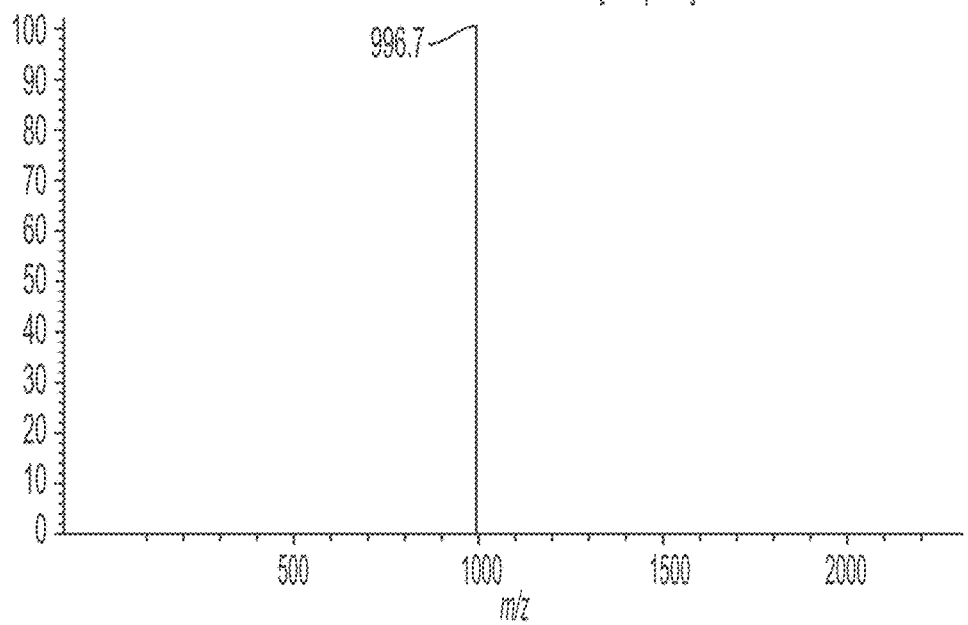
FIG. 83 is a diagram confirming the molecular weight of YDE-015 prepared according to an embodiment of the present invention through Ion-Mass.
Figure 84:
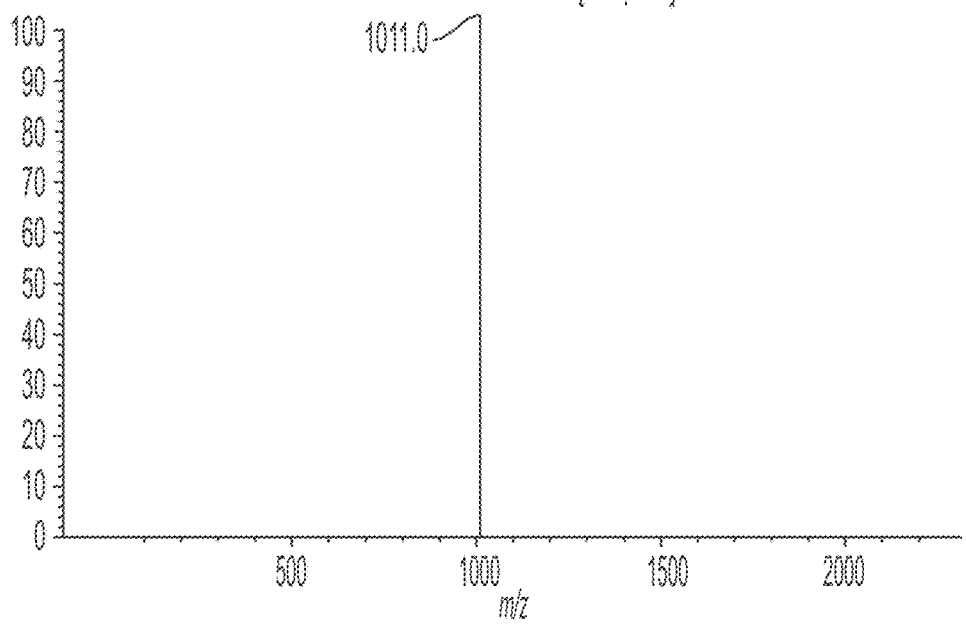
FIG. 84 is a diagram confirming the molecular weight of YDE-016 prepared according to an embodiment of the present invention through Ion-Mass.
Figure 85:
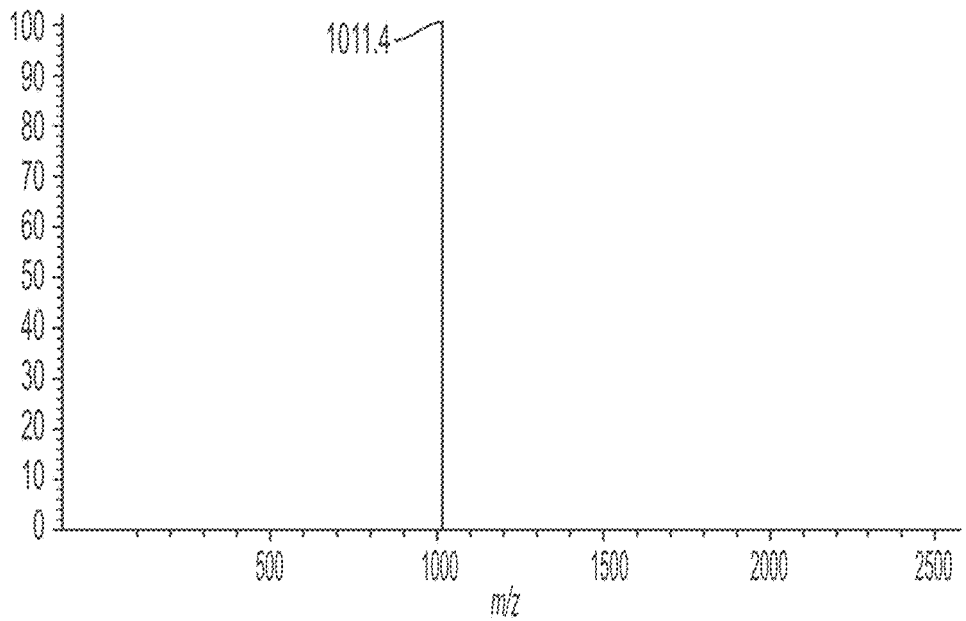
FIG. 85 is a diagram confirming the molecular weight of YDE-017 prepared according to an embodiment of the present invention through Ion-Mass.
Figure 86:
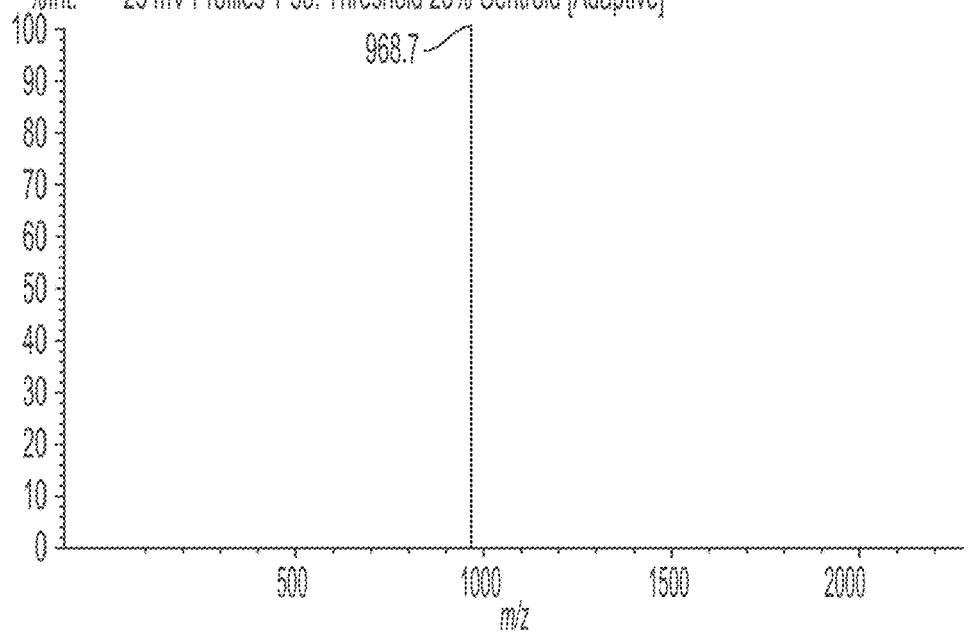
FIG. 86 is a diagram confirming the molecular weight of YDE-018 prepared according to an embodiment of the present invention through Ion-Mass.
Figure 87:
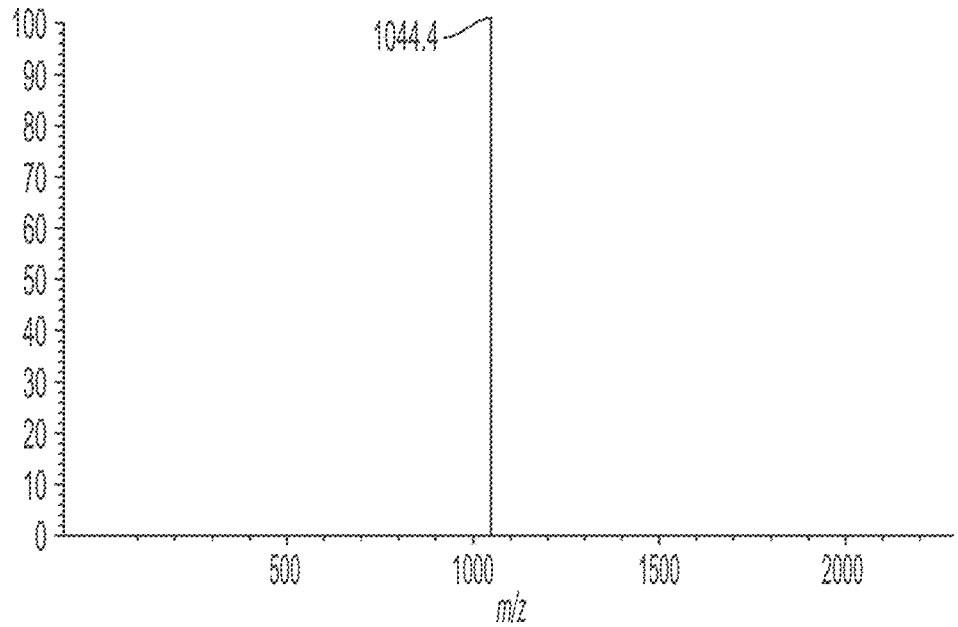
FIG. 87 is a diagram confirming the molecular weight of YDE-019 prepared according to an embodiment of the present invention through Ion-Mass.
Figure 88:
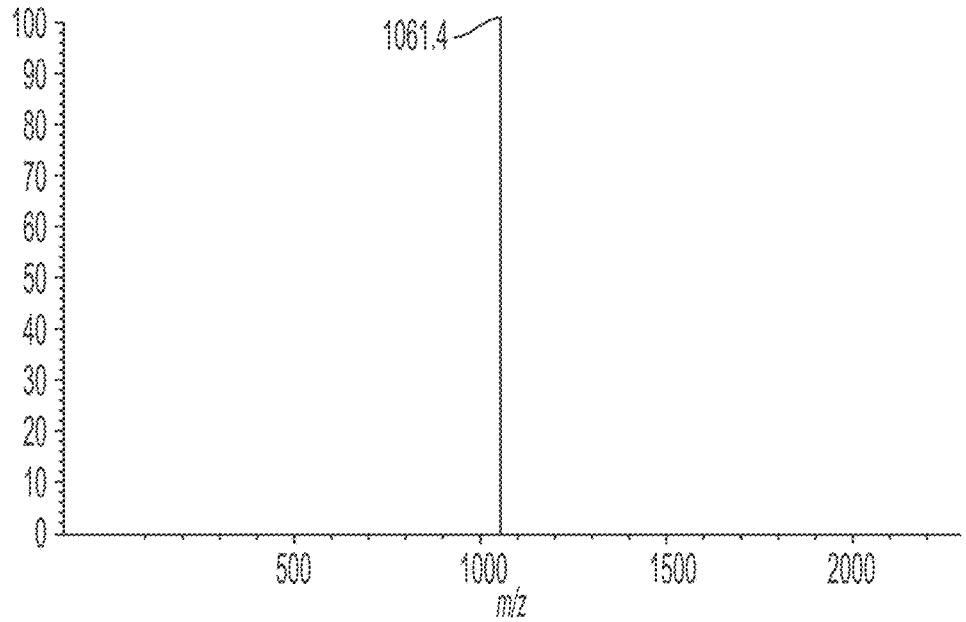
FIG. 88 is a diagram confirming the molecular weight of YDE-020 prepared according to an embodiment of the present invention through Ion-Mass.
Figure 89:
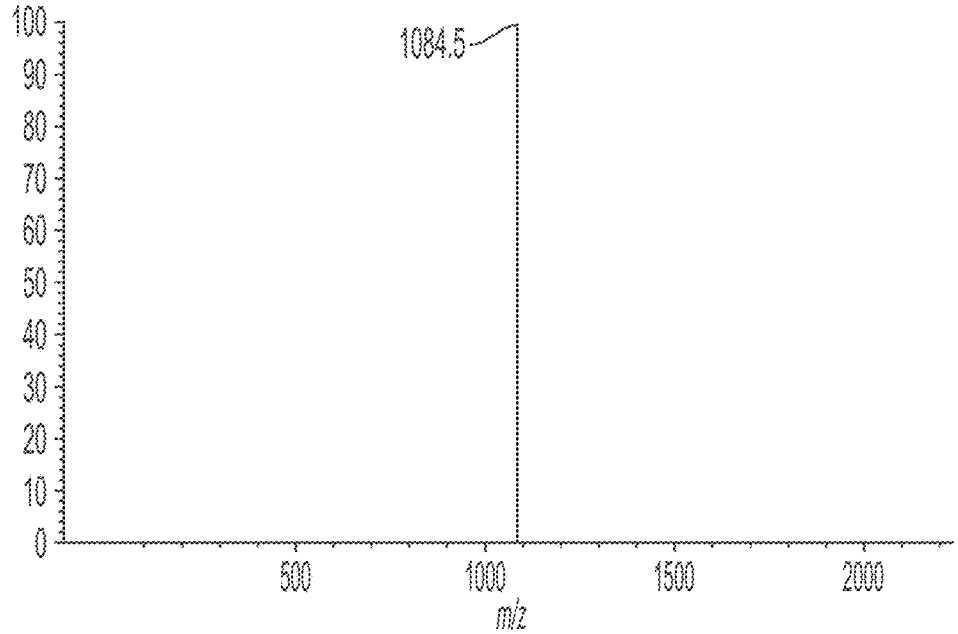
FIG. 89 is a diagram confirming the molecular weight of YDE-021 prepared according to an embodiment of the present invention through Ion-Mass.
Figure 90:
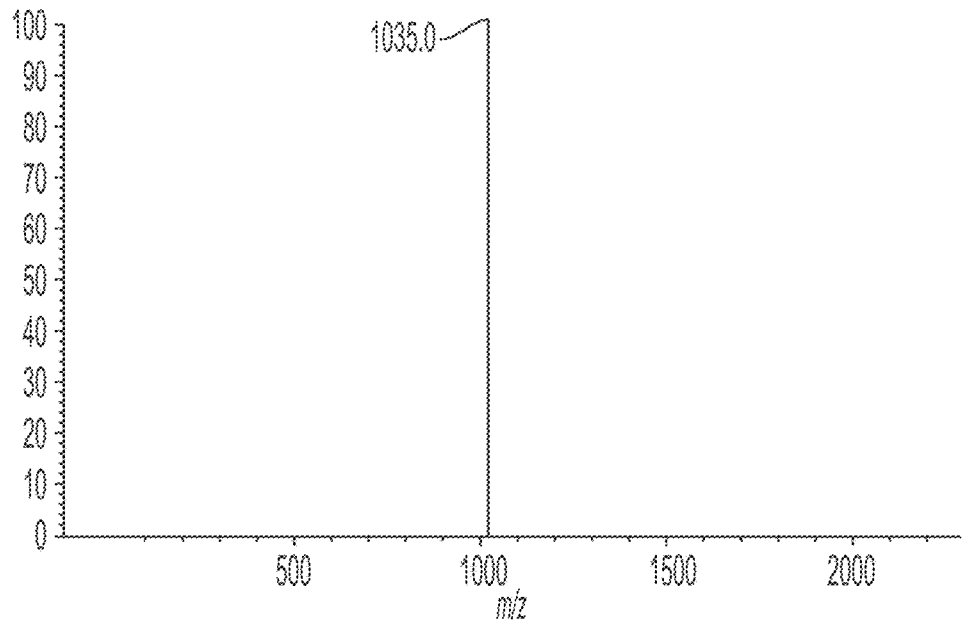
FIG. 90 is a diagram confirming the molecular weight of YDE-022 prepared according to an embodiment of the present invention through Ion-Mass.
Figure 91:
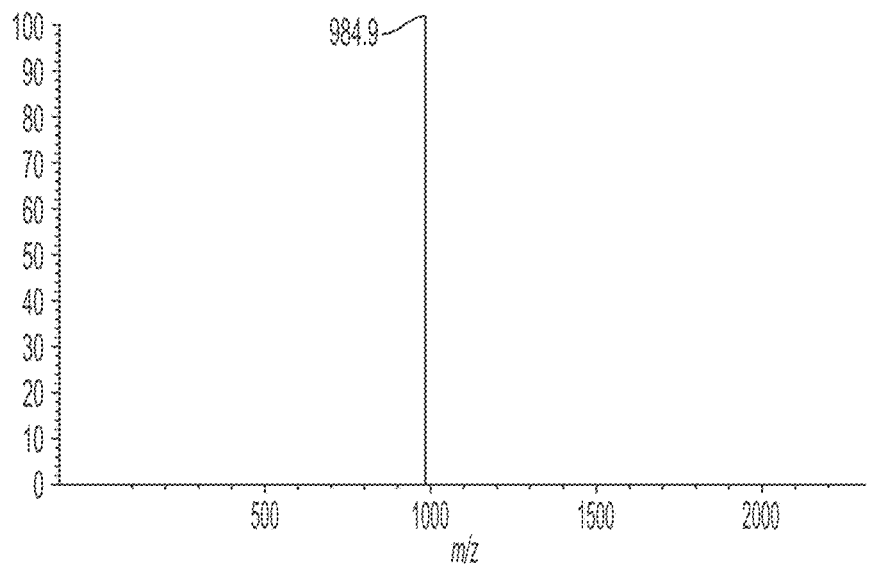
FIG. 91 is a diagram confirming the molecular weight of YDE-023 prepared according to an embodiment of the present invention through Ion-Mass.
Figure 92:
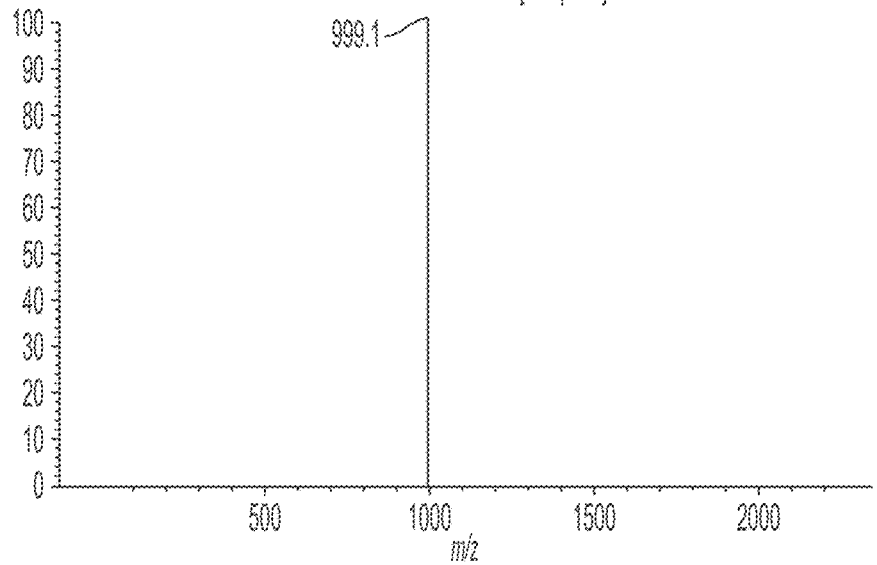
FIG. 92 is a diagram confirming the molecular weight of YDE-024 prepared according to an embodiment of the present invention through Ion-Mass.
Figure 93:
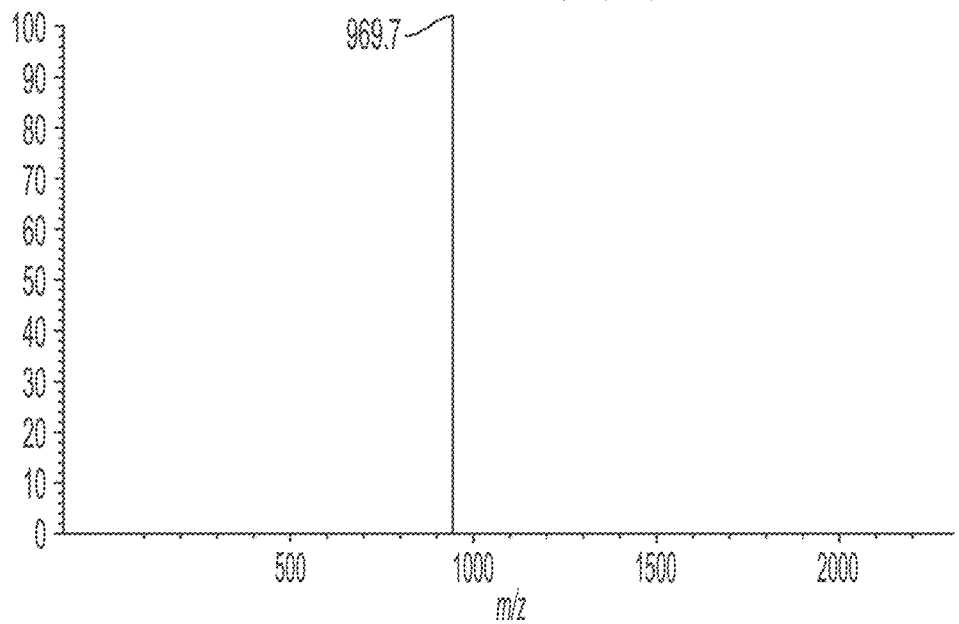
FIG. 93 is a diagram confirming the molecular weight of YDE-025 prepared according to an embodiment of the present invention through Ion-Mass.
Figure 94:
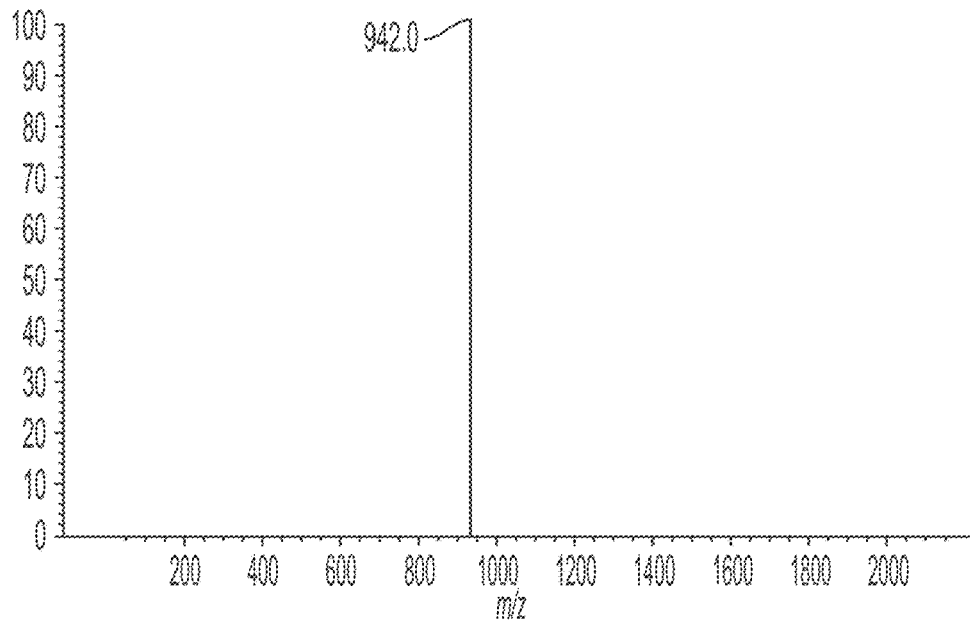
FIG. 94 is a diagram confirming the molecular weight of YDE-026 prepared according to an embodiment of the present invention through Ion-Mass.
Figure 95:
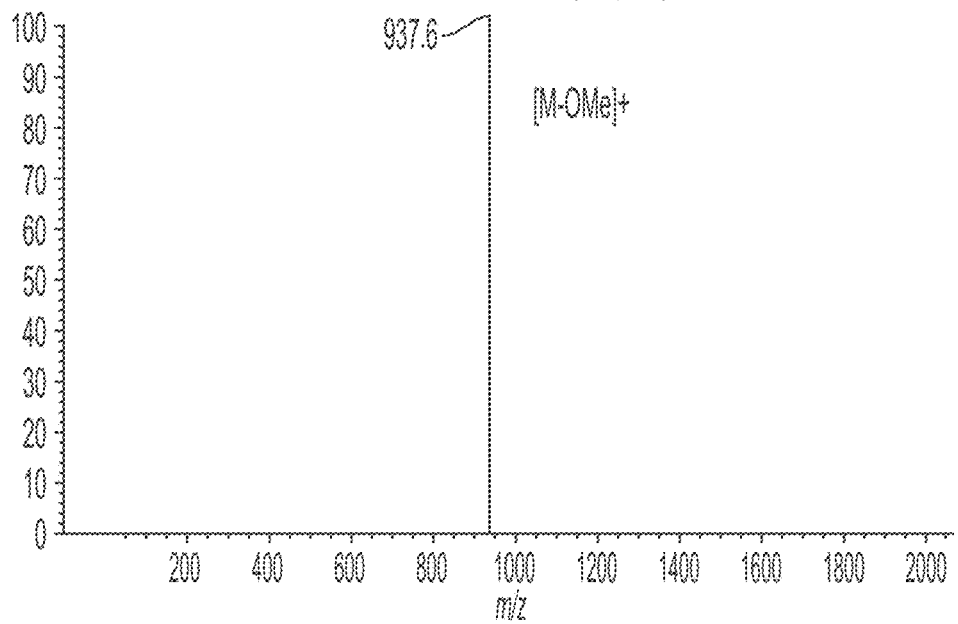
FIG. 95 is a diagram confirming the molecular weight of YDE-027 prepared according to an embodiment of the present invention through Ion-Mass.
Figure 96:
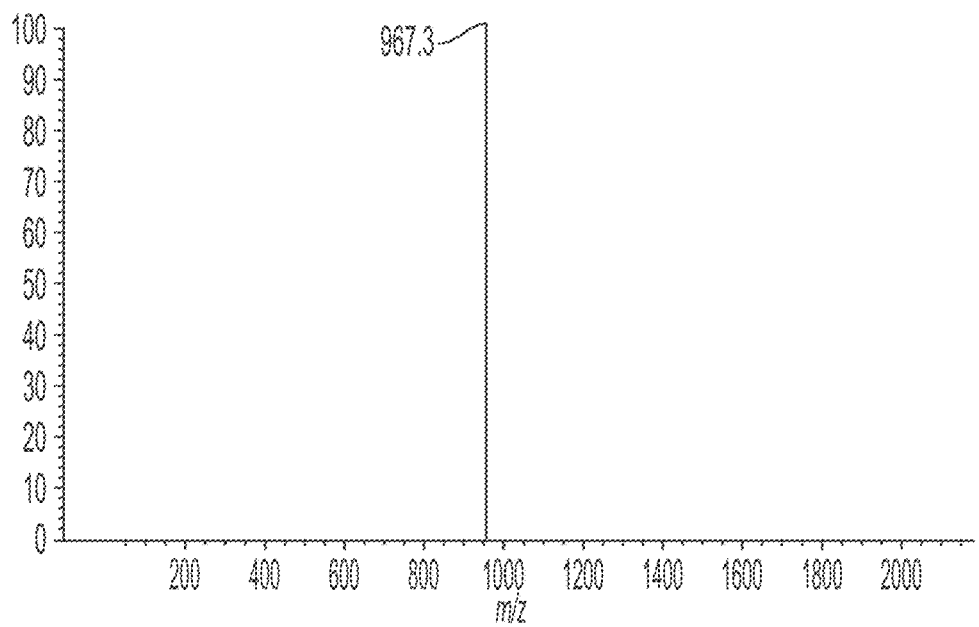
FIG. 96 is a diagram confirming the molecular weight of YDE-028 prepared according to an embodiment of the present invention through Ion-Mass.
Figure 97:
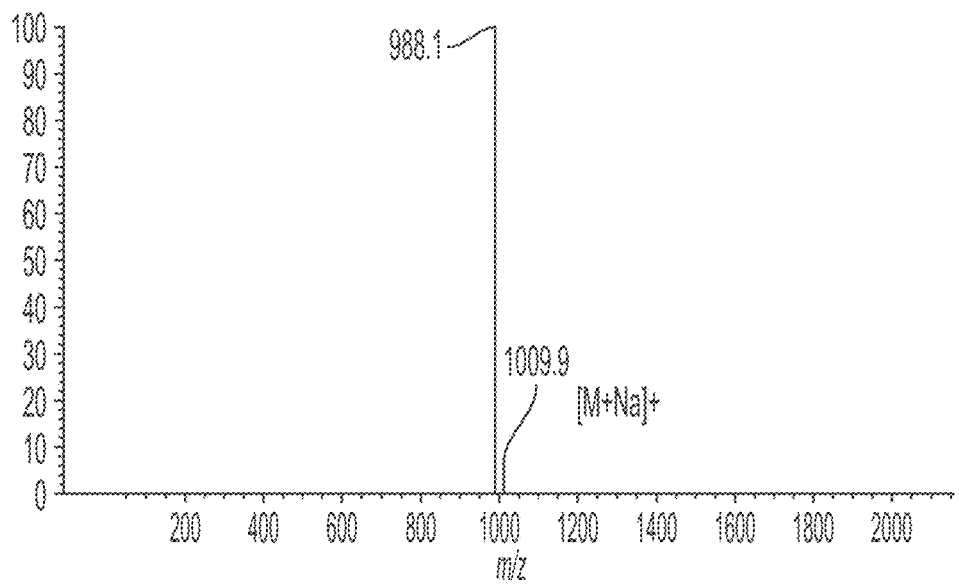
FIG. 97 is a diagram confirming the molecular weight of YDE-029 prepared according to an embodiment of the present invention through Ion-Mass.
Figure 98:
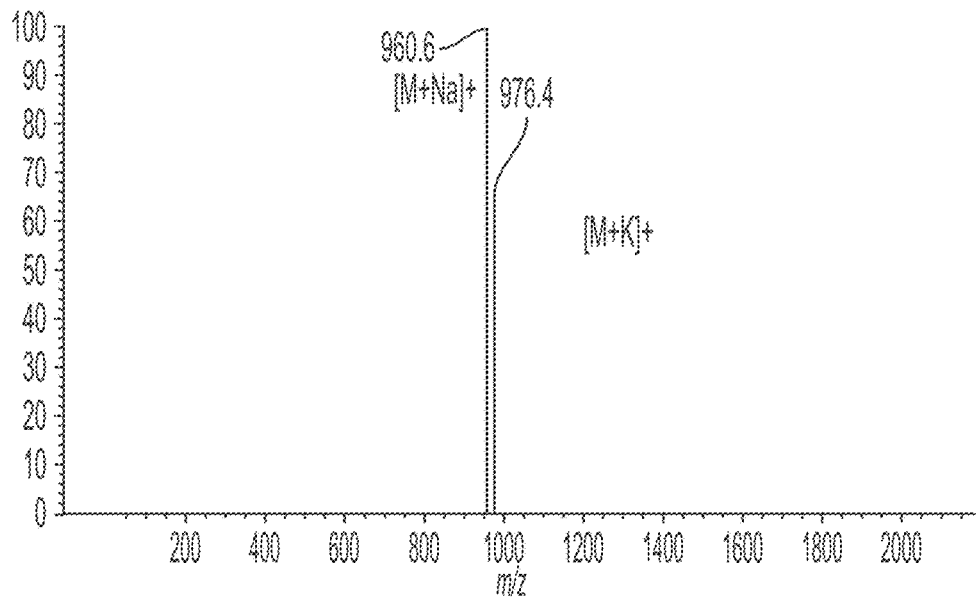
FIG. 98 is a diagram confirming the molecular weight of YDE-030 prepared according to an embodiment of the present invention through Ion-Mass.
Figure 99:
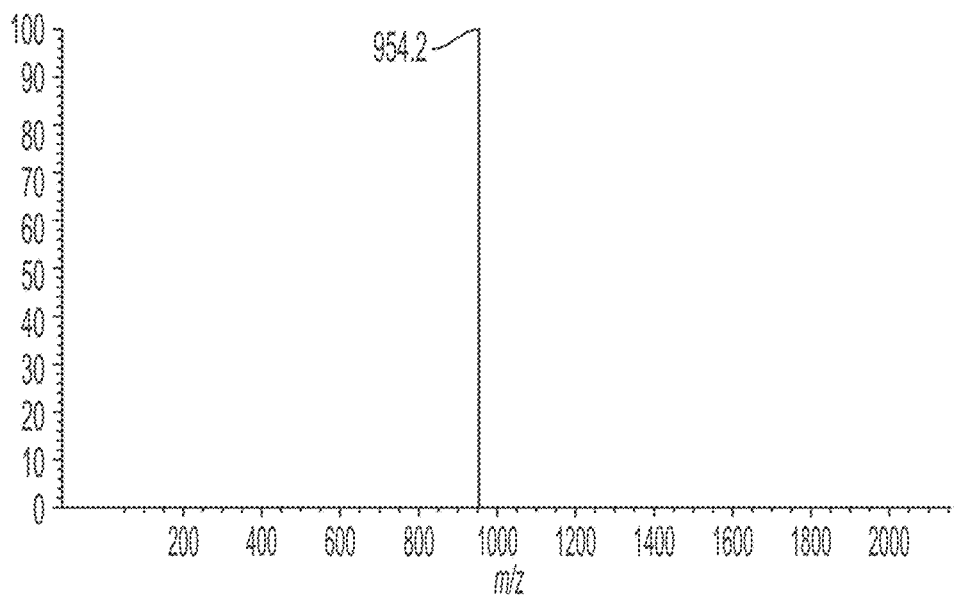
FIG. 99 is a diagram confirming the molecular weight of YDE-031 prepared according to an embodiment of the present invention through Ion-Mass.
Figure 100:
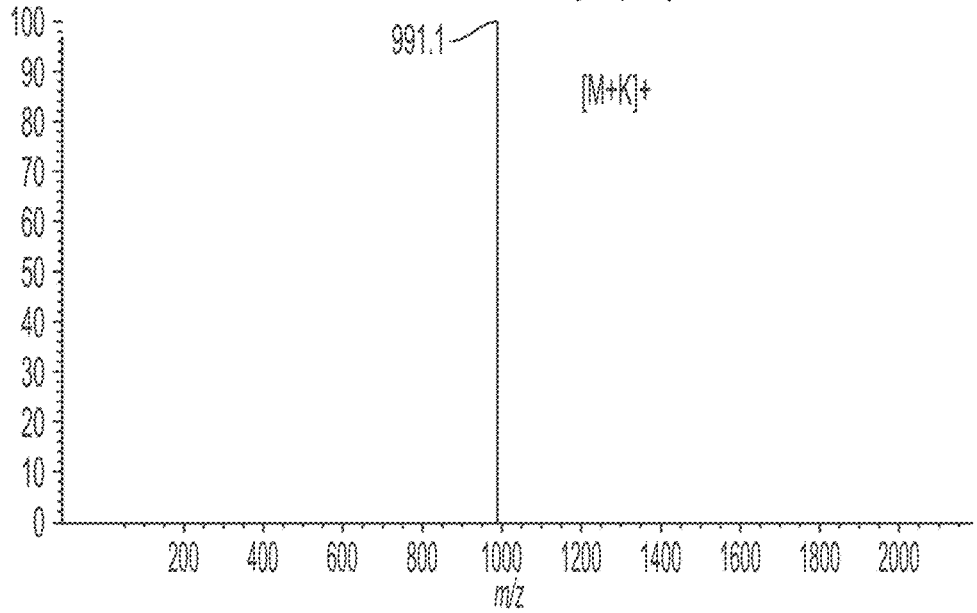
FIG. 100 is a diagram confirming the molecular weight of YDE-032 prepared according to an embodiment of the present invention through Ion-Mass.
Figure 101:
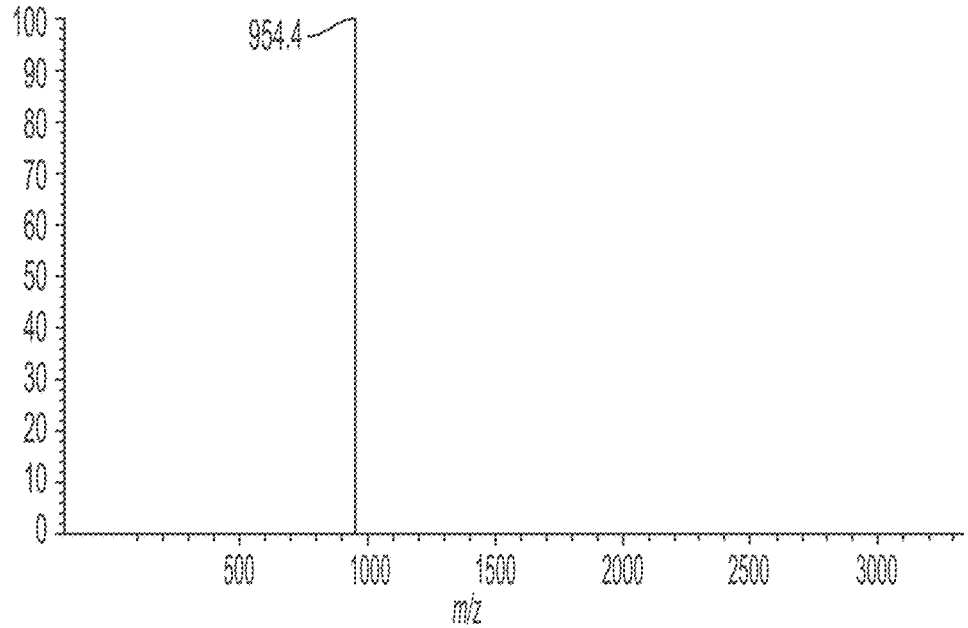
FIG. 101 is a diagram confirming the molecular weight of YDE-033 prepared according to an embodiment of the present invention through Ion-Mass.
Figure 102:
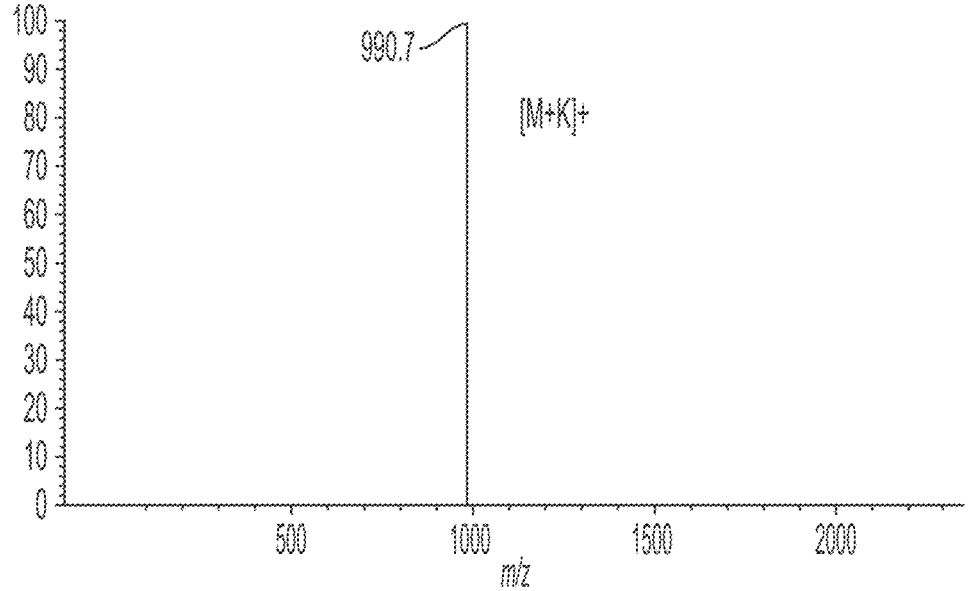
FIG. 102 is a diagram confirming the molecular weight of YDE-034 prepared according to an embodiment of the present invention through Ion-Mass.
Figure 103:
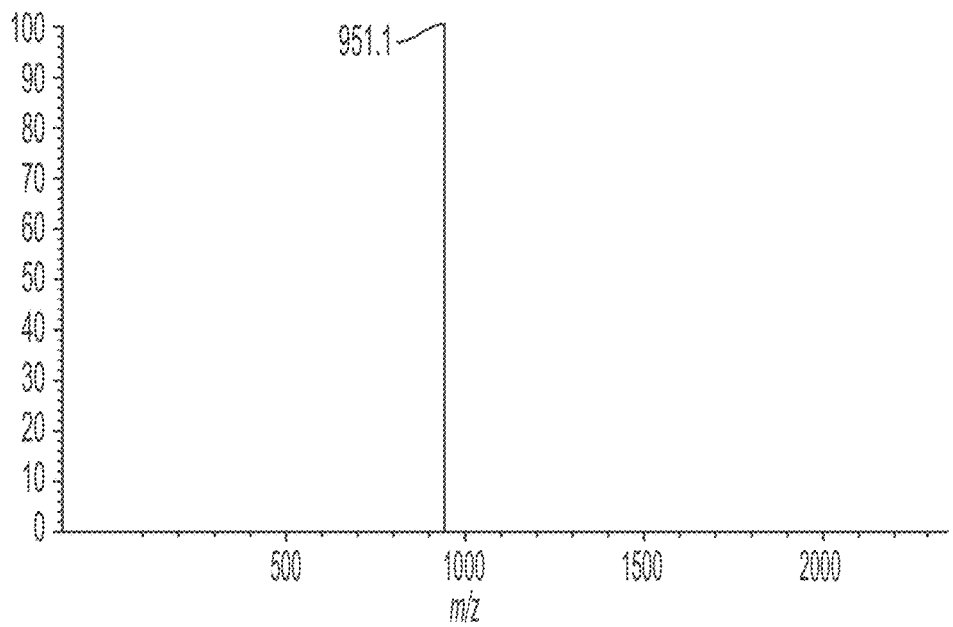
FIG. 103 is a diagram confirming the molecular weight of YDE-035 prepared according to an embodiment of the present invention through Ion-Mass.
Figure 104:
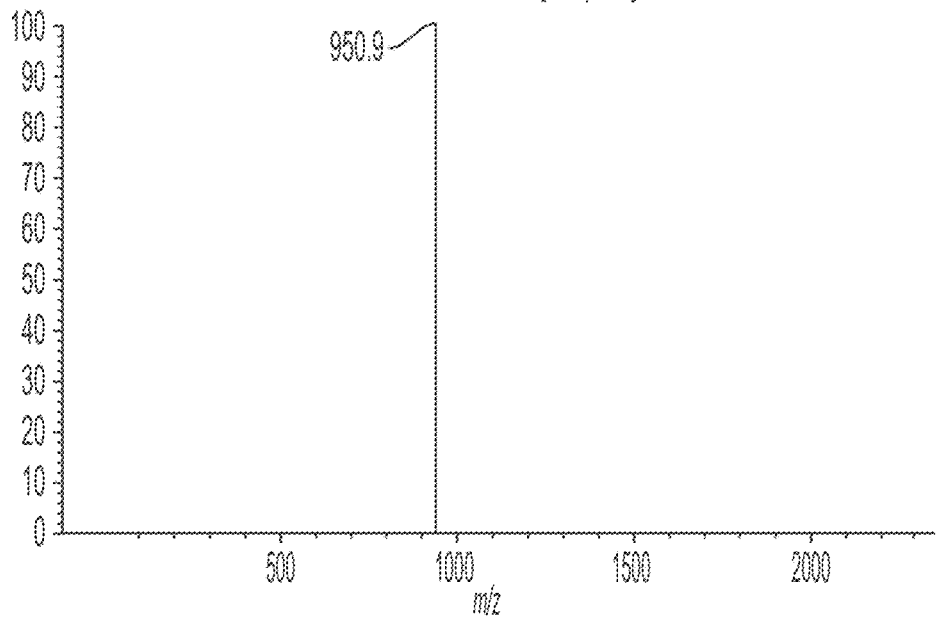
FIG. 104 is a diagram confirming the molecular weight of YDE-036 prepared according to an embodiment of the present invention through Ion-Mass.
Figure 105:
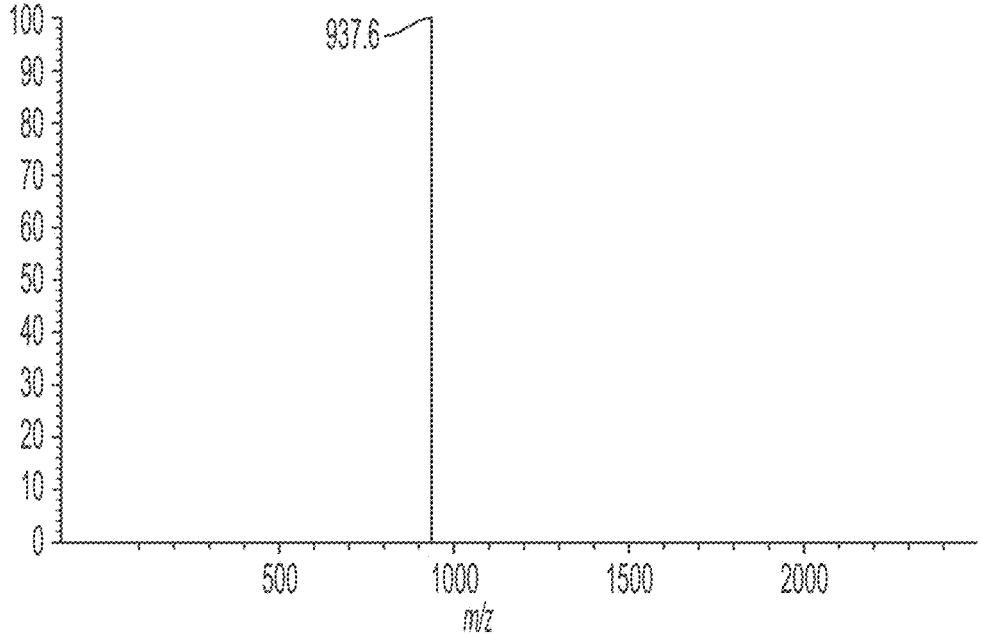
FIG. 105 is a diagram confirming the molecular weight of YDE-037 prepared according to an embodiment of the present invention through Ion-Mass.
Figure 106:
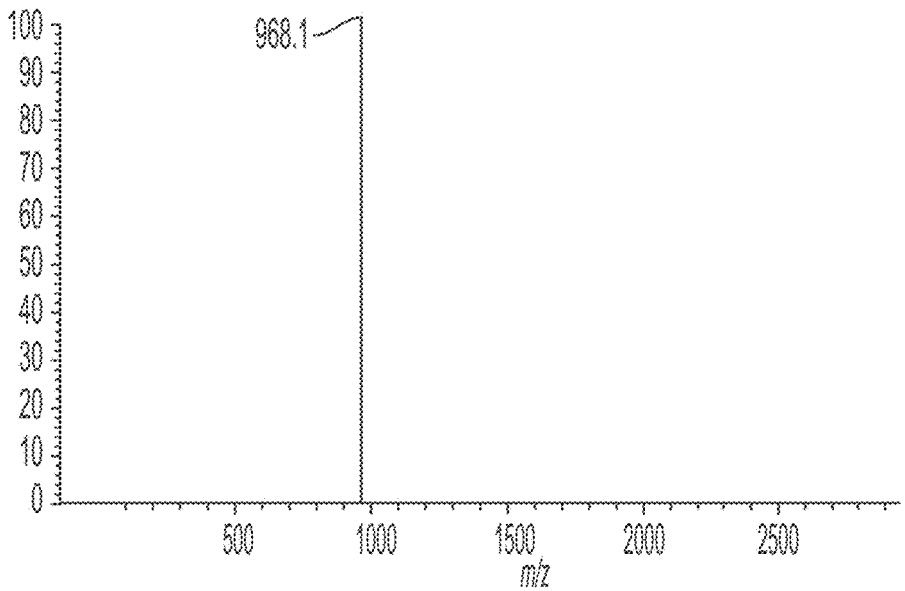
FIG. 106 is a diagram confirming the molecular weight of YDE-038 prepared according to an embodiment of the present invention through Ion-Mass.
Figure 107:
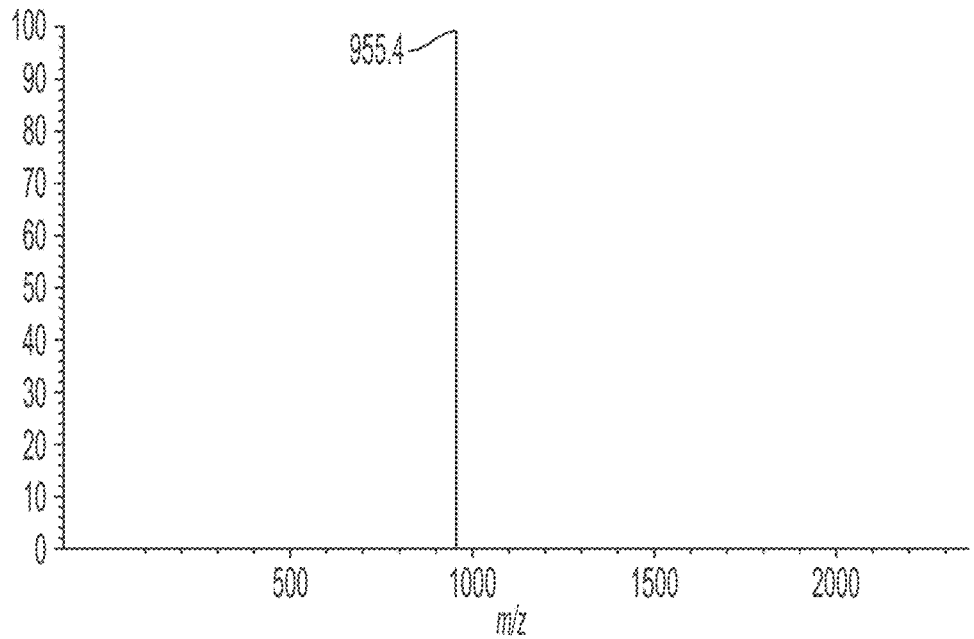
FIG. 107 is a diagram confirming the molecular weight of YDE-039 prepared according to an embodiment of the present invention through Ion-Mass.
Figure 108:
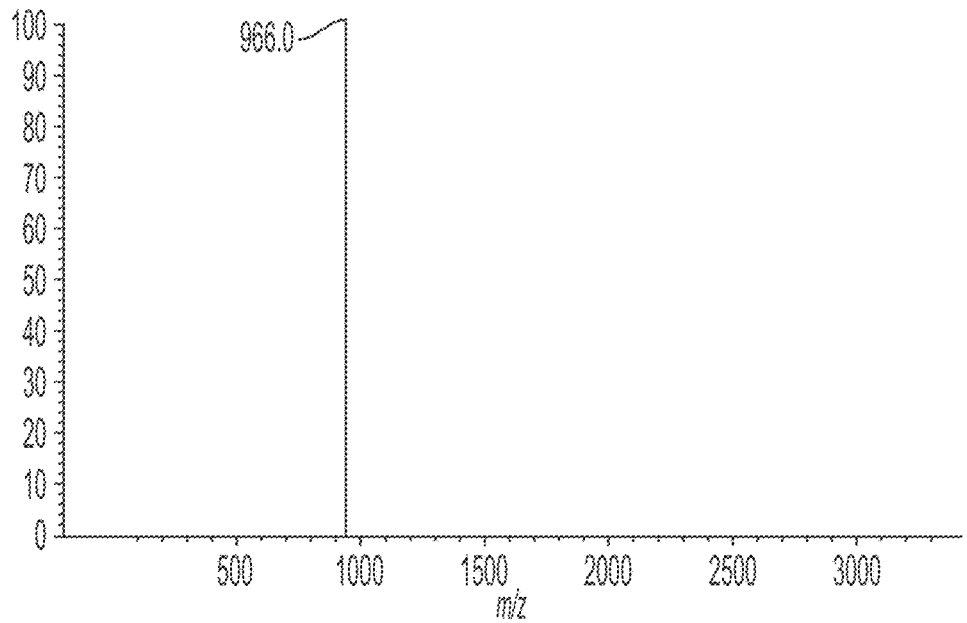
FIG. 108 is a diagram confirming the molecular weight of YDE-040 prepared according to an embodiment of the present invention through Ion-Mass.
Figure 109:
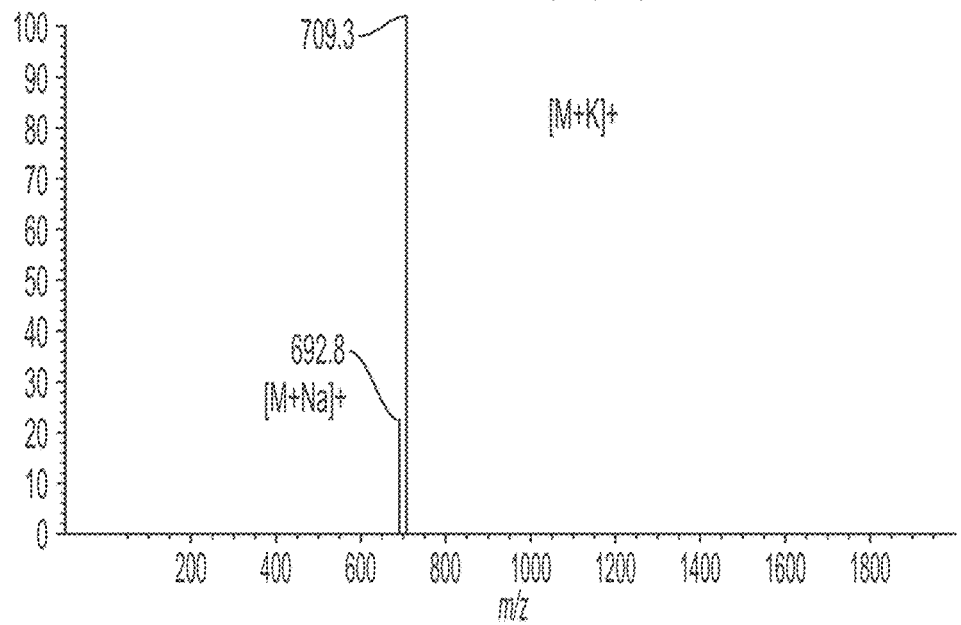
FIG. 109 is a diagram confirming the molecular weight of YDE-041 prepared according to an embodiment of the present invention through Ion-Mass.
Figure 110:
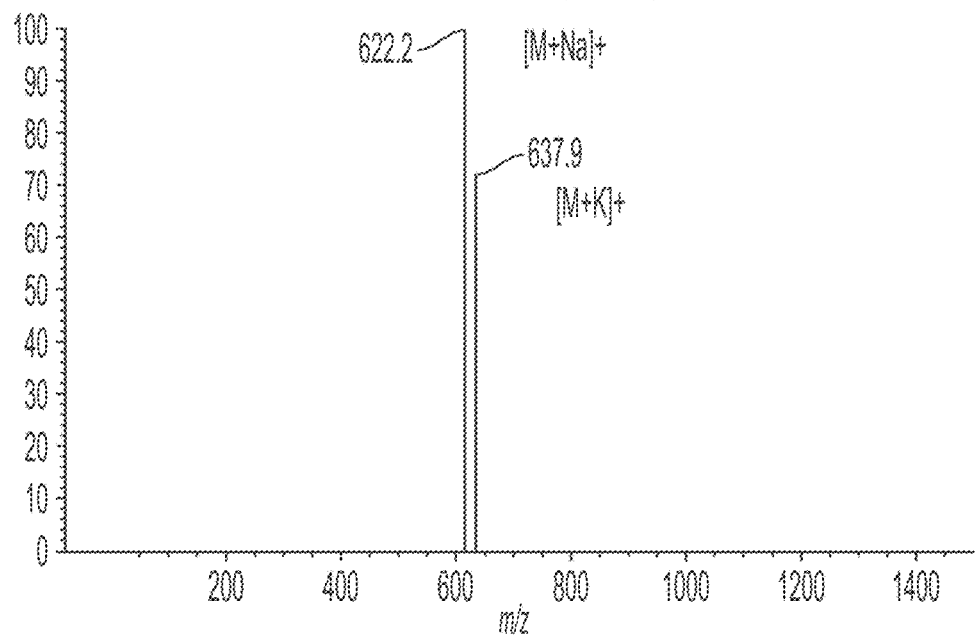
FIG. 110 is a diagram confirming the molecular weight of YDE-042 prepared according to an embodiment of the present invention through Ion-Mass.
Figure 111:
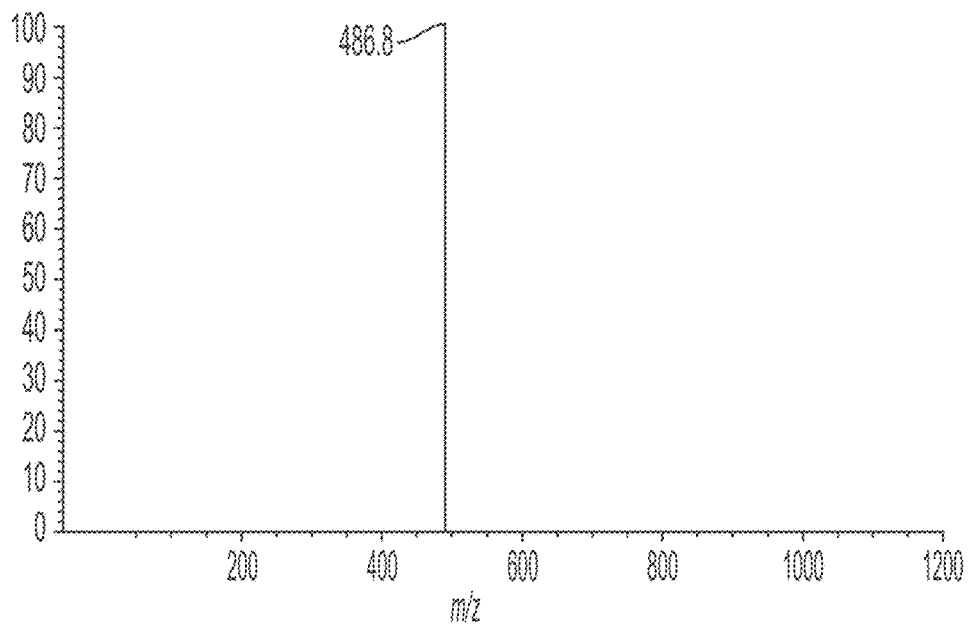
FIG. 111 is a diagram confirming the molecular weight of YDE-043 prepared according to an embodiment of the present invention through Ion-Mass.
Figure 112:
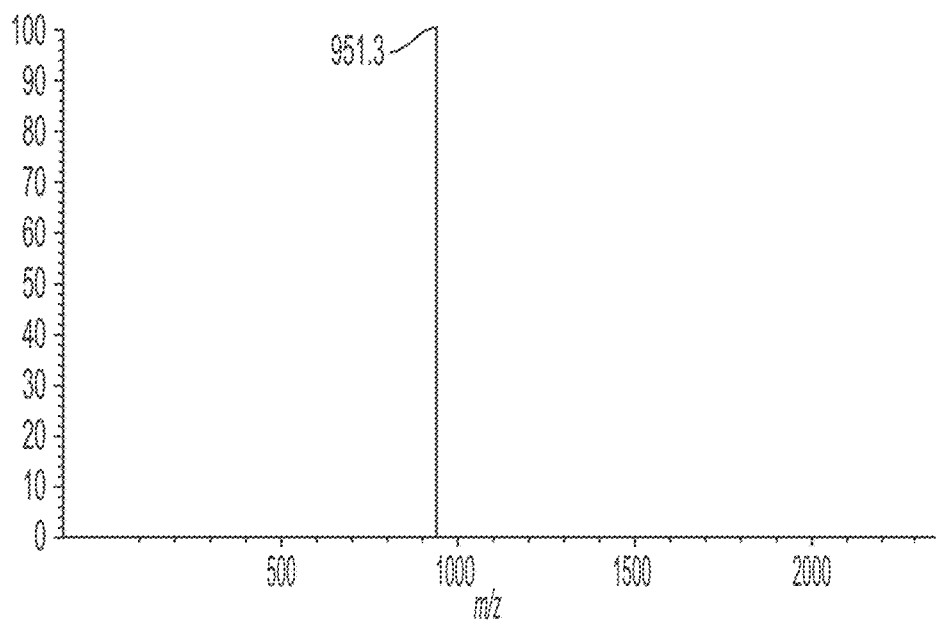
FIG. 112 is a diagram confirming the molecular weight of YDE-044 prepared according to an embodiment of the present invention through Ion-Mass.
Figure 113:
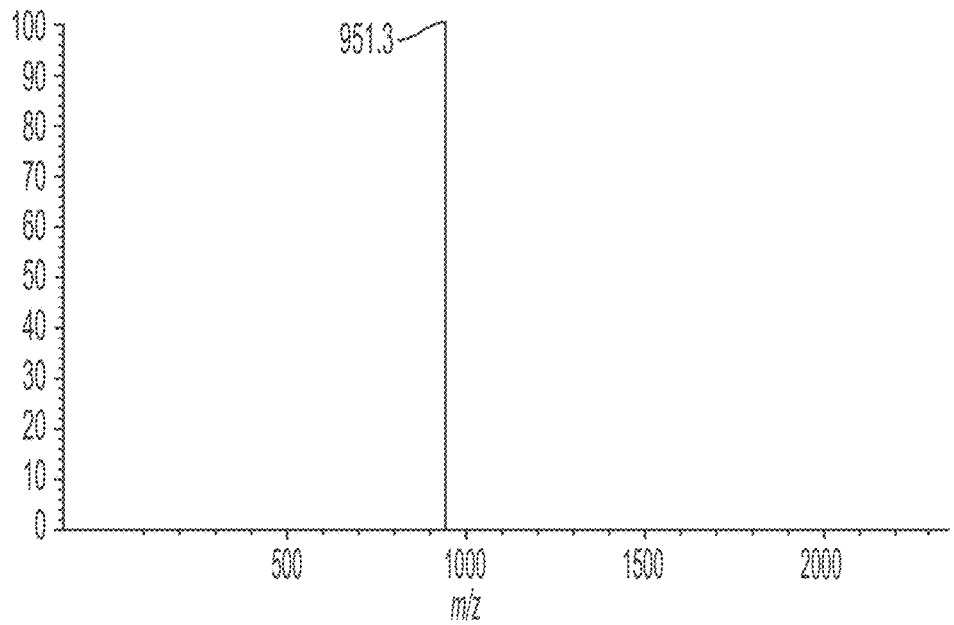
FIG. 113 is a diagram confirming the molecular weight of YDE-045 prepared according to an embodiment of the present invention through Ion-Mass.
Figure 114:
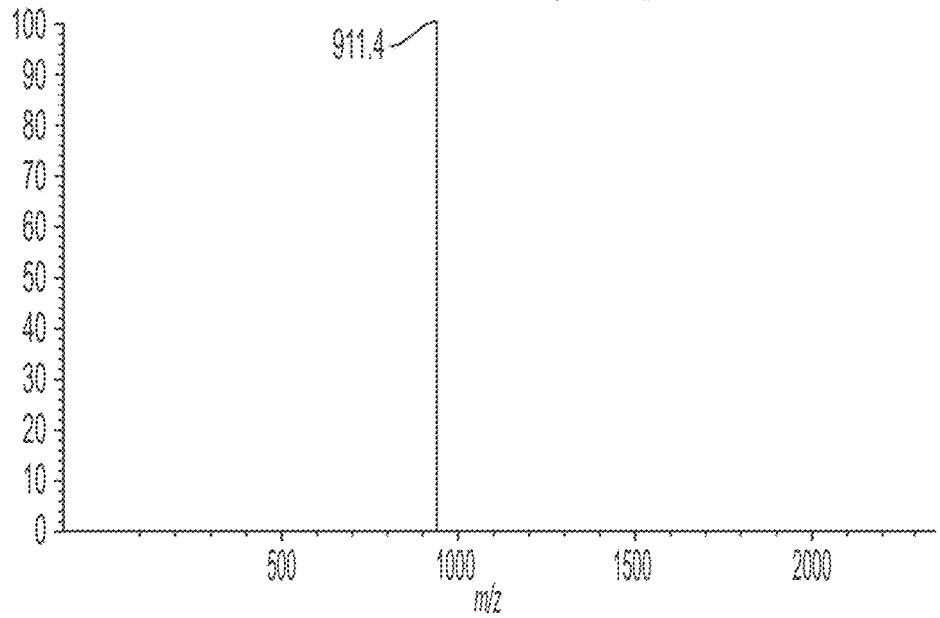
FIG. 114 is a diagram confirming the molecular weight of YDE-047 prepared according to an embodiment of the present invention through Ion-Mass.
Figure 115:
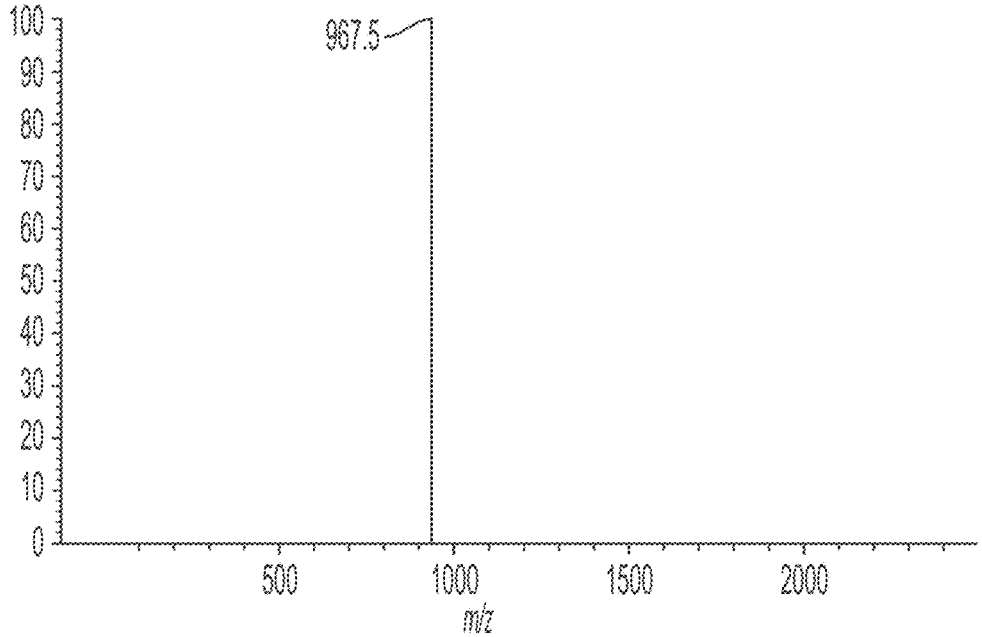
FIG. 115 is a diagram confirming the molecular weight of YDE-048 prepared according to an embodiment of the present invention through Ion-Mass.
Figure 116:
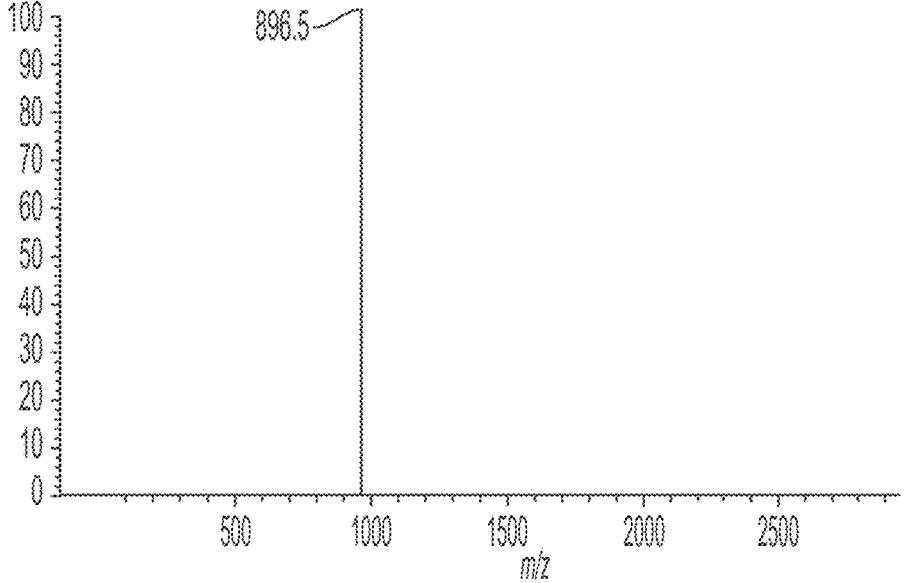
FIG. 116 is a diagram confirming the molecular weight of YDE-049 prepared according to an embodiment of the present invention through Ion-Mass.
Figure 117:
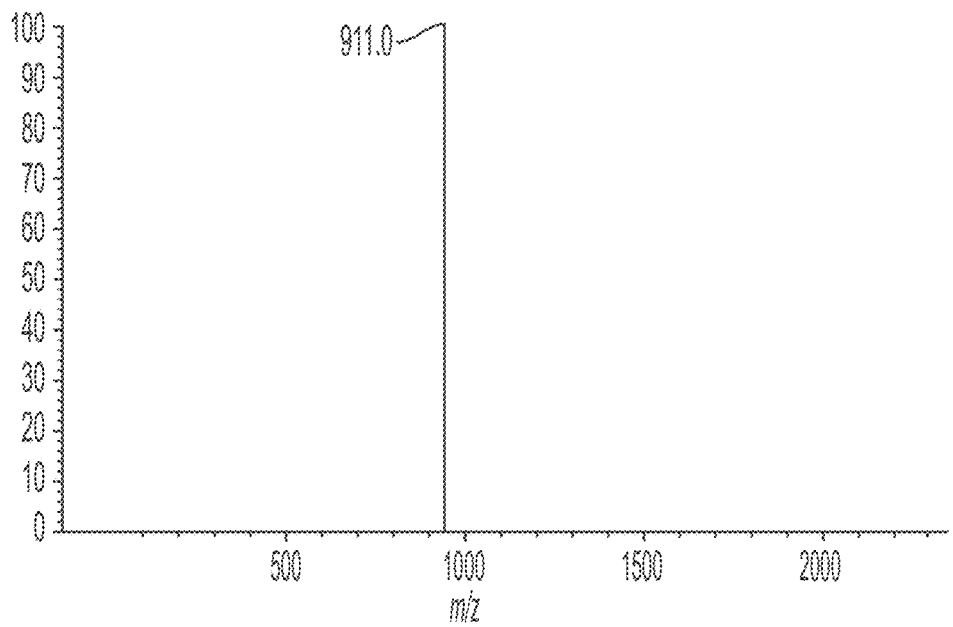
FIG. 117 is a diagram confirming the molecular weight of YDE-050 prepared according to an embodiment of the present invention through Ion-Mass.
Figure 118:
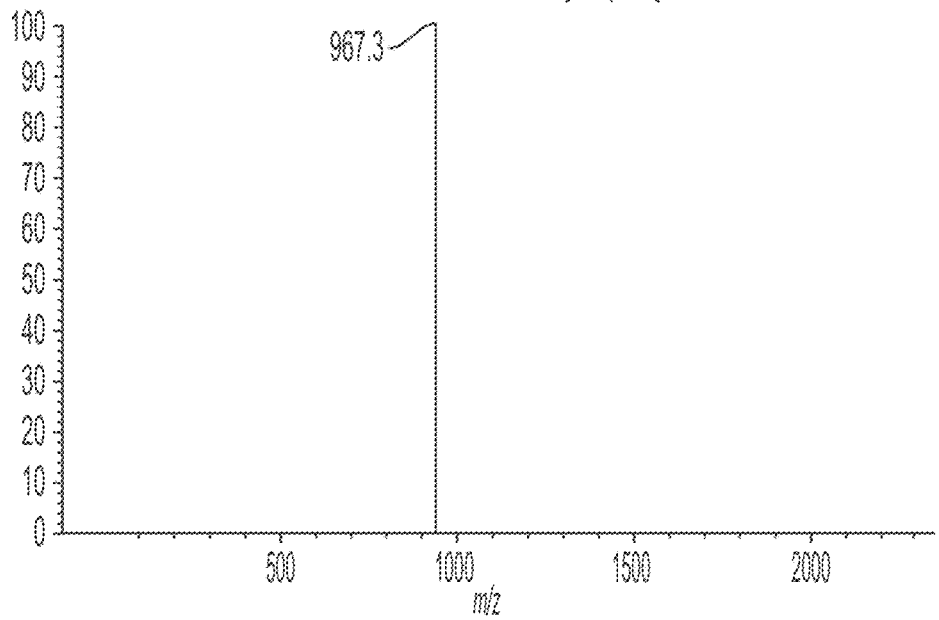
FIG. 118 is a diagram confirming the molecular weight of YDE-051 prepared according to an embodiment of the present invention through Ion-Mass.
Figure 119:
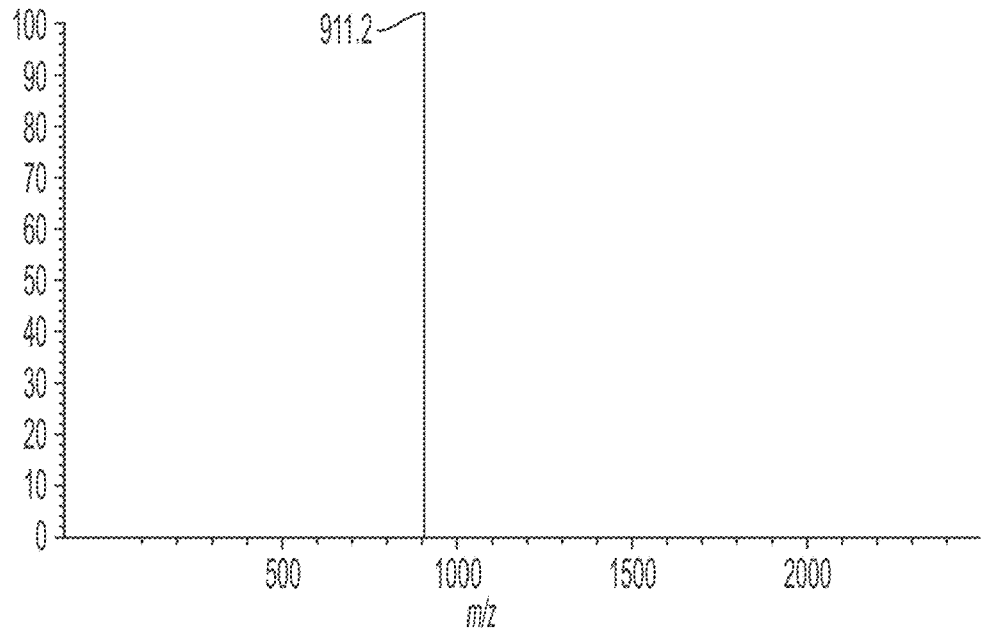
FIG. 119 is a diagram confirming the molecular weight of YDE-052 prepared according to an embodiment of the present invention through Ion-Mass.
Figure 120:
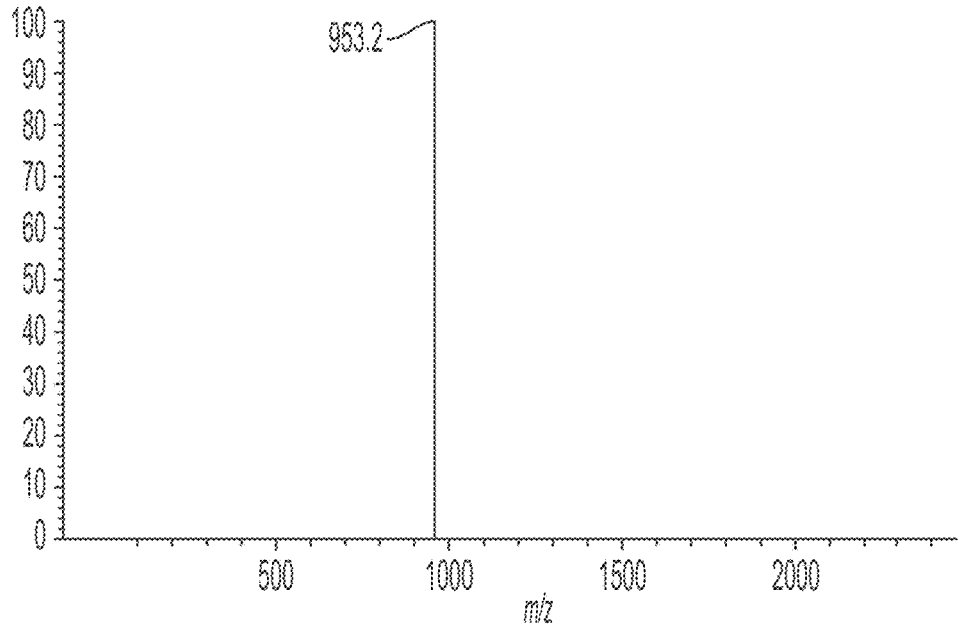
Figure 121:
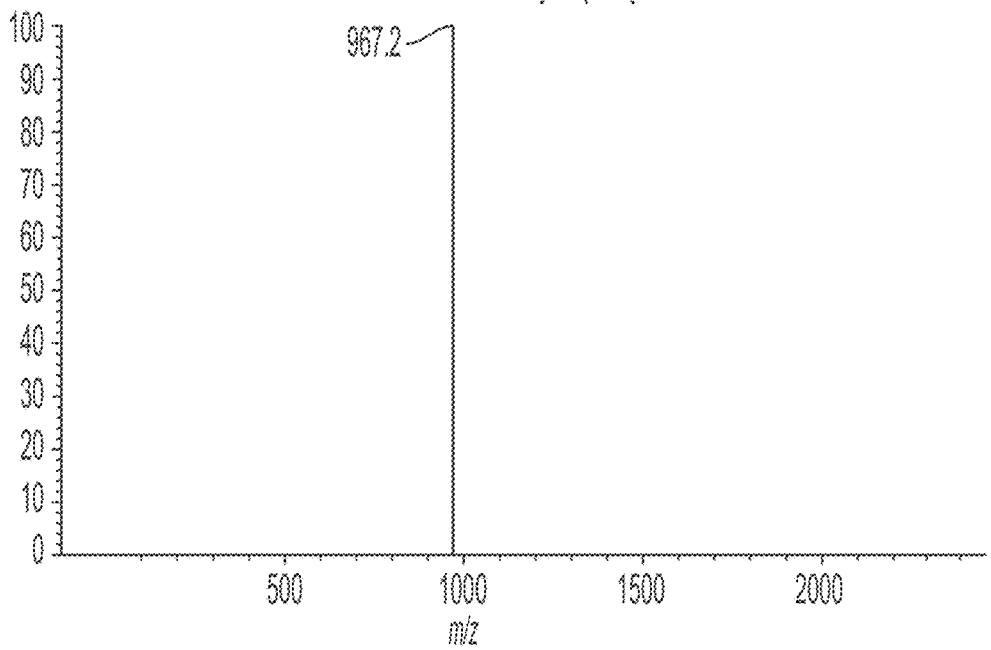
Figure 122:
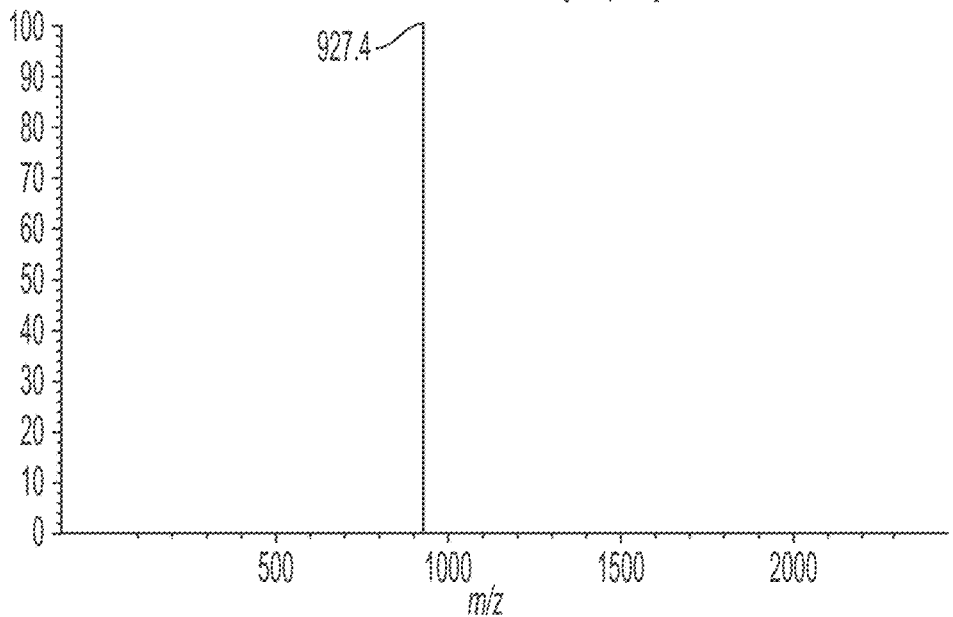
Figure 123:
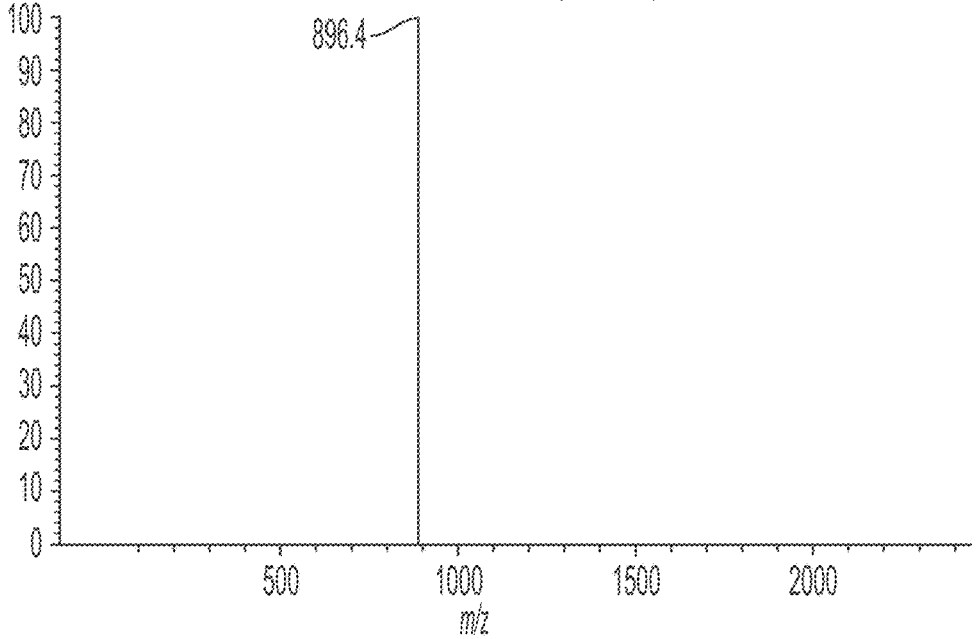
Figure 124:
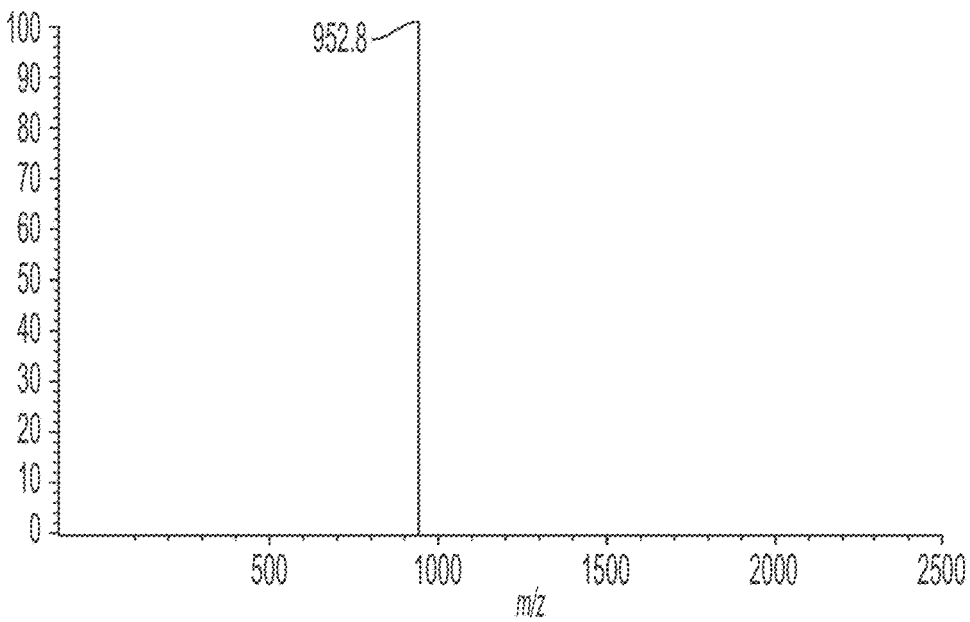
Figure 125:
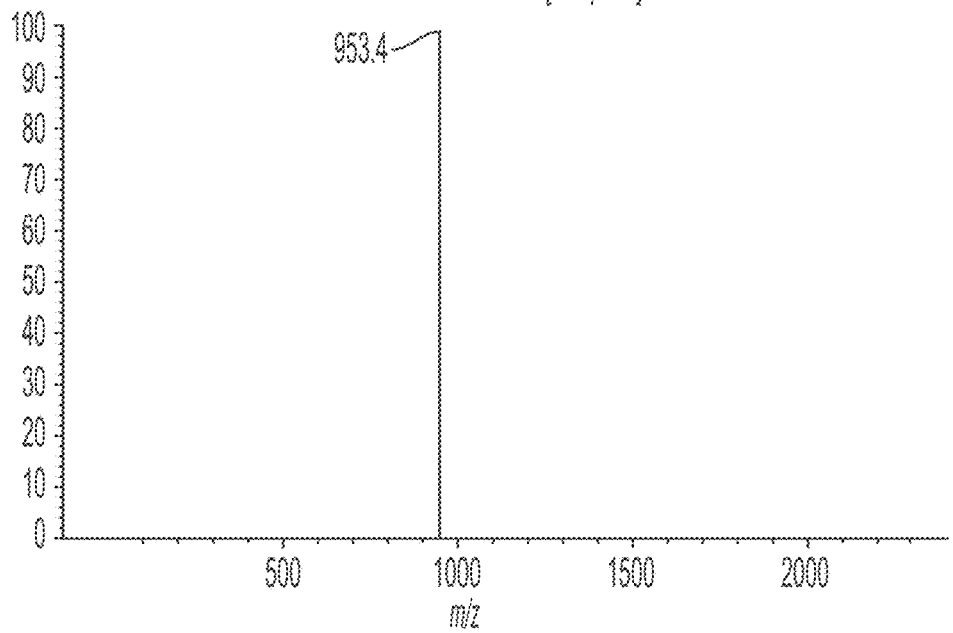
Figure 126:
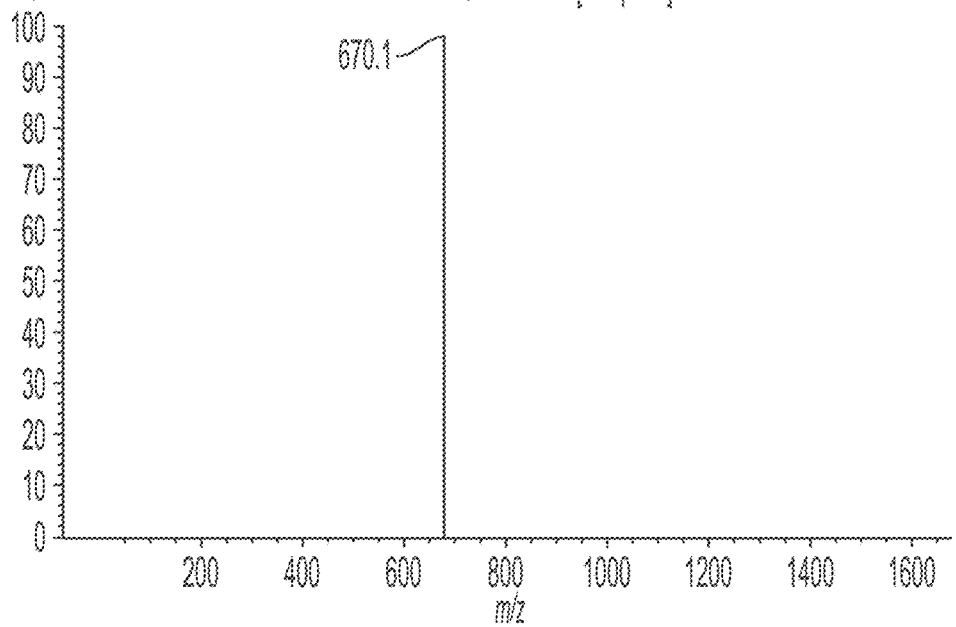
Figure 127:
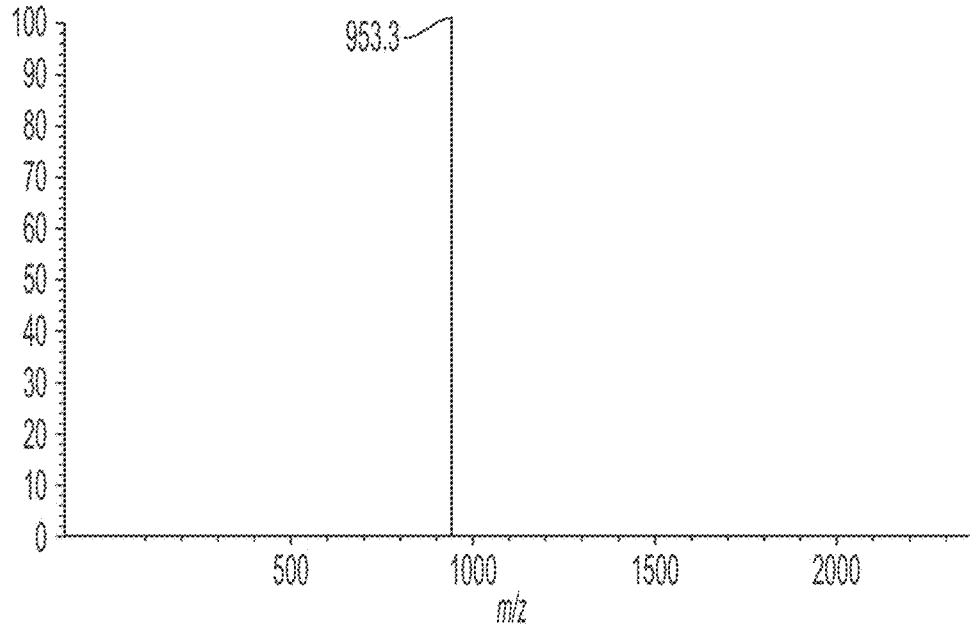
Figure 128:
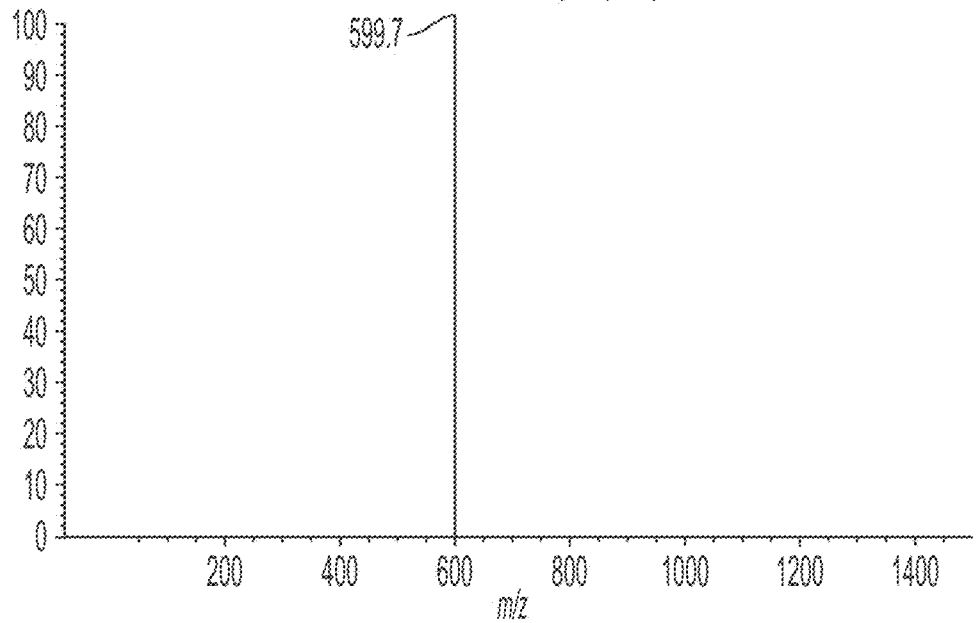
Figure 129:
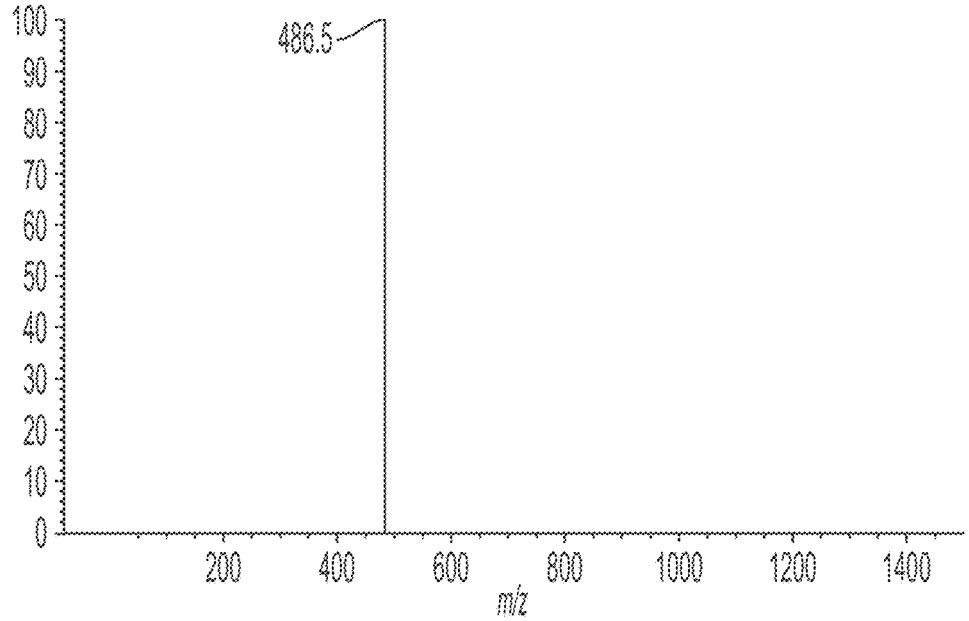
Figure 130:
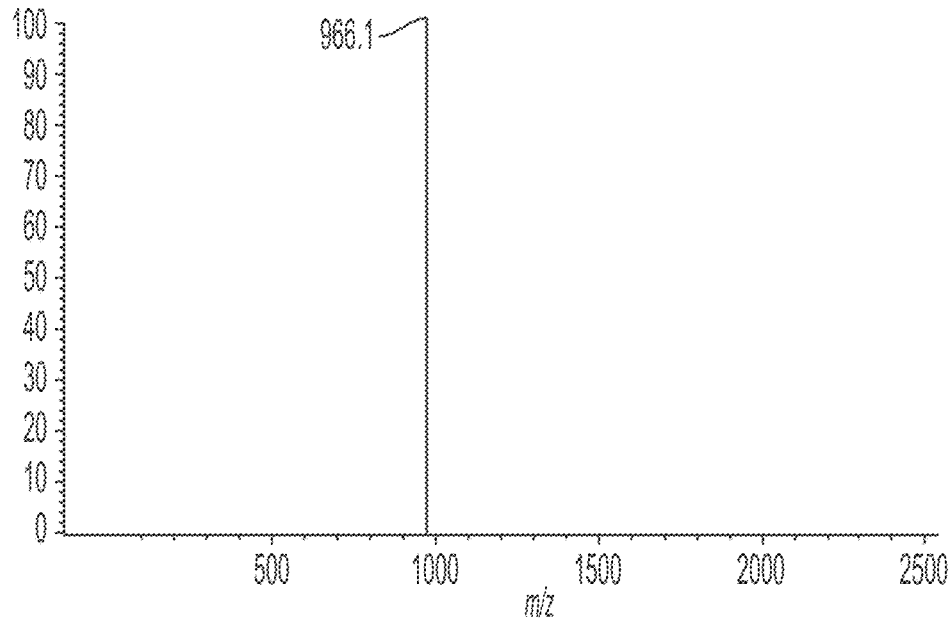
Figure 131:
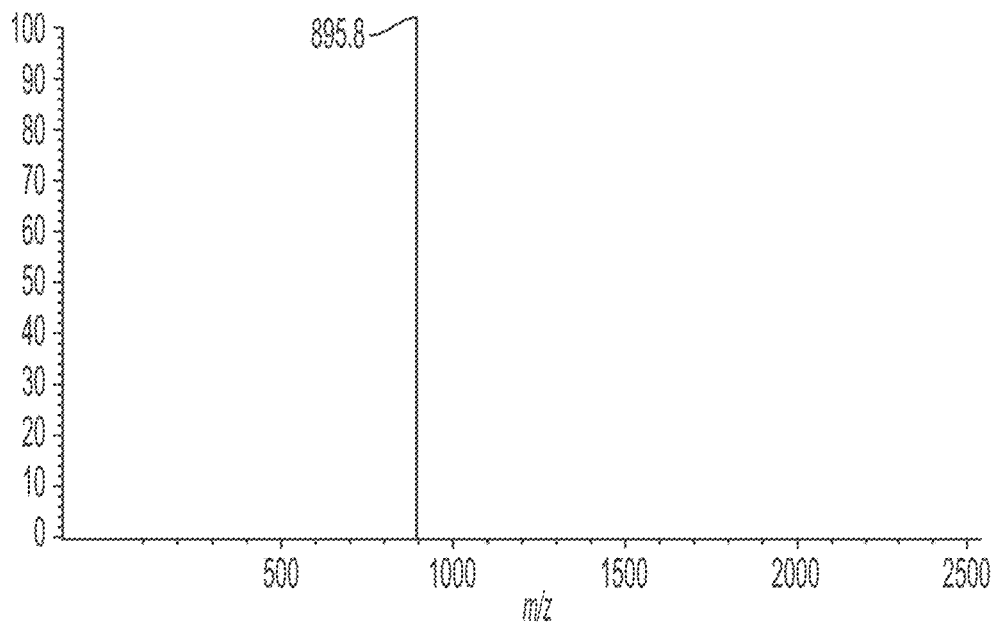

In addition, the YDE derivatives prepared in Working Example 1 were analyzed by Ion-Mass. As a result, it was confirmed that the molecular weights of synthesized YDE-001, YDE-002, YDE-003, YDE-004, YDE-005, YDE-006, YDE-007, YDE-008, YDE-009, YDE-010, YDE-011, YDE-012, YDE-013, YDE-014, YDE-015, YDE-016, YDE-017, YDE-018, YDE-019, YDE-020, YDE-021, YDE-022, YDE-023, YDE-024, YDE-025, YDE-026, YDE-027, YDE-028, YDE-029, YDE-030, YDE-031, YDE-032, YDE-033, YDE-034, YDE-035, YDE-036, YDE-037, YDE-038, YDE-039, YDE-040, YDE-041, YDE-042, YDE-043, YDE-044, YDE-045, YDE-047, YDE-048, YDE-049, YDE-050, YDE-051, YDE-052, YDE-053, YDE-054, YDE-055, YDE-056, YDE-057, YDE-058, YDE-059, YDE-060, YDE-064, YDE-066, YDE-072, YDE-073, YDE-074, and YDE-075 were 969.6, 954.8, 967.7, 977.1, 968.1, 926.9, 941.1, 910.7, 939.7, 953.0, 953.7, 987.8, 1003.8, 1025.9, 996.7, 1011.0, 1011.4, 968.7, 1044.4, 1061.4, 1084.5, 1035.0, 984.9, 999.1, 969.7, 942.0, 937.6, 967.3, 988.1, 960.6, 954.2, 991.1, 954.4, 990.7, 950.9, 937.6, 968.1, 955.4, 966.0, 709.3, 622.2, 486.8, 951.3, 951.3, 911.4, 967.5, 896.5, 911.0, 967.3, 911.2, 953.2, 967.2, 927.4, 896.4, 952.8, 953.4, 670.1, 953.3, 599.7, 486.5, 966.1, 895.8, 909.1, and 486.4, respectively (FIGS. 69 to 133).

Experimental Example 2: Evaluation of the Eye Protection Effect on Dry Eye Syndrome by the YDE Derivatives Experimental Example 2.1: Preparation of Rats with Dry Eye Syndrome In order to evaluate the eye protection effect on dry eye syndrome by YDE-001 to YDE-028 prepared in Working Example 1, a total of 320 Sprague-Dawley-type male rats (OrientBio, Seungnam, Korea) were adapted for 7 days. Thereafter, dry eye syndrome was induced in 264 test rats through extraorbital lacrimal gland excision (hereinafter, ELGE). 8 test rats without the eye abnormality were subjected to a sham operation as a control group.

The rats were systemically anesthetized by inhaling a mixed gas of 2% to 3% of isoflurane (Hana Pharm. Co., Hwasung, Korea), 70% of $N_2O$, and 28.6% of $O_2$ using a rodent anesthesia machine (Surgivet, Waukesha, Wis., USA) and a ventilator (Model 687, Harvard Apparatus, Cambridge, UK). Thereafter, the extraorbital lacrimal gland located in the subdermal area above the masseter muscle and under the optic nerve was excised through a transverse incision in a size of 10 mm on the anterior part of the left ear tragus. The skin was sutured by a general method. The ELGE operation time did not exceed 5 minutes for each rat. After 6 days following the ELGE operation, confirmation was performed through the Schirmer test by measuring the amount of tear secretion whether dry eye syndrome had been induced. Meanwhile, each rat of the control group with the sham operation was checked for the presence and location of the extraorbital lacrimal gland through a skin incision, and the skin was then sutured without the excision thereof (FIG. 134).

The average weight of the ELGE test group measured before the ELGE operation was 241.59±13.56 g, and the average weight measured after 6 days from the ELGE operation was 297.38±34.02 g. The average weight of the control group measured before the sham operation was 240.13±25.63 g, and the average weight measured after 6 days from the sham operation was 297.38±34.02 g (FIG. 135).

The average amount of tear secretion of the control group was 8.34±0.73 $mm^3$, and the average amount of tear secretion of the ELGE test group was 3.55±0.70 $mm^3$. 8 rats per group and a total of 32 groups were selected based on the average amount of tear secretion.

As a reference drug, 3% diquafosol sodium (Santen, Tokyo, Japan; hereinafter, DS), which is currently on the market, was used.

The present animal tests were conducted with a prior approval of the Animal Experimental Ethics Committee of Daegu Haany University (Approval No. DHU2017-003, Jan. 12, 2017). All test animals were caused to fast for 18 hours before the ELGE operation and final sacrifice except for feeding water.

The 32 groups were summarized in Table 12.

TABLE 12

| Group classification | 32 groups in total; 8 rats per group |
|---|---|
| Sham control group | Group administered with physiological saline after the sham operation |
| ELGE control group | Group administered with physiological saline after the ELGE operation |
| Reference | Group administered with DS after the ELGE operation |
| YY-102 | Group administered with a 0.3% YY-102 solution after the ELGE operation |
| YDE series | Group administered with any of 0.3% YDE-01 to YDE-28 solutions (28 groups in total) |

In addition, in order to evaluate the eye protection effect on dry eye syndrome by YDE-029 to YDE-043 prepared in Working Example 1, a total of 200 Sprague-Dawley-type male rats (OrientBio, Seungnam, Korea) were adapted for 7 days. Dry eye syndrome was induced in 165 test rats through the ELGE. 8 test rats without the eye abnormality were subjected to the sham operation as a control group. The ELGE was carried out as described above.

The average weight of the ELGE test group measured before the ELGE operation was 264.09±11.53 g, and the average weight measured after 6 days from the ELGE operation was 316.13±15.77 g. The average weight of the control group measured before the sham operation was 263.50±9.24 g, and the average weight measured after 6 days from the sham operation was 315.25±10.85 g (FIG. 136).

The average amount of tear secretion of the control group was 10.90±1.69 $mm^3$, and the average amount of tear secretion of the ELGE test group was 4.83±0.99 $mm^3$. 8 rats per group and a total of 20 groups were selected based on the average amount of tear secretion.

As a reference drug, 3% DS, which is currently on the market, was used.

The present animal tests were conducted with prior approval of the Animal Experimental Ethics Committee of Daegu Haany University (Approval No. DHU2017-050, Jun. 8, 2017). All test animals were caused to fast for 18 hours before the ELGE operation and final sacrifice except for feeding water.

The 20 groups were summarized in Table 13.

TABLE 13

| Group classification | 20 groups in total; 8 rats per group |
|---|---|
| Sham control group | Group administered with physiological saline after the sham operation |

TABLE 13-continued

| Group classification | 20 groups in total; 8 rats per group |
|---|---|
| ELGE control group | Group administered with physiological saline after the ELGE operation |
| Reference | Group administered with DS after the ELGE operation |
| YY-101 | Group administered with a 0.3% YY-101 solution after the ELGE operation |
| YY-102 | Group administered with a 0.3% YY-102 solution after the ELGE operation |
| YDE series | Group administered with any of 0.3% YDE-01 to YDE-28 solutions (15 groups in total) |

Experimental Example 2.2: Administration of the YDE Derivatives

For YDE-001 to YDE-028, YY-102 and the 28 YDE-series were each dissolved in physiological saline at a concentration of 3 mg/ml and administered at a dose of 5 µl/eye at 9:30 am and 3:30 pm daily for 14 days after 7 days from the ELGE operation for a total of 28 times. The DS solution was dissolved in physiological saline at a concentration of 30 mg/ml and administered at a dose of 5 µl/eye twice a day for 14 days after 7 days from the ELGE operation for a total of 28 times. For the sham control and the ELGE control groups, the same stimulation as the administration was applied. In order to prevent excessive eye dryness, the same volume of physiological saline was applied in the same manner in place of the test substances.

Further, For YDE-029 to YDE-043, YY-102 and the 15 YDE-series were each dissolved in physiological saline at a concentration of 3 mg/ml and administered at a dose of 5 µl/eye at 9:30 am and 3:30 pm daily for 14 days after 7 days from the ELGE operation for a total of 28 times. The DS solution was dissolved in physiological saline at a concentration of 30 mg/ml and administered at a dose of 5 µl/eye twice a day for 14 days after 7 days from the ELGE operation for a total of 28 times. For the sham control and the ELGE control groups, the same stimulation as the administration was applied. In order to prevent excessive eye dryness, the same volume of physiological saline was applied in the same manner in place of the test substances (FIG. 137).

Test Example 2.3: Confirmation of the Changes in the Amount of Tear Secretion by the YDE Derivatives After 6 days from the ELGE surgery, the changes in the amount of tear secretion were measured at day 7 and day 14 after the administration of YDE-001 to YDE-043. The amount of tear secretion was measured by the decrease in the travel distance of tears absorbed by cobalt chloride paper in a size of 1×15 mm (Toyo Roshi Kaisha, Japan).

The cobalt chloride paper was placed in the lateral canthus of a rat for 60 seconds to absorb tears (FIG. 139). The length of the area absorbed from the corner of the cobalt chloride paper was measured with an electronic digital caliper (Mytutoyo, Tokyo, Japan) (FIG. 138).

FIG. 139 shows the results of the test, wherein A is for the sham control group, B is for the ELGE control group, C is for the DS reference group, D is for the YY-102 administered group, and E to AF are for the YDE-001 to YDE-028 administered groups in order.

As a result, it was confirmed that the amount of tear secretion was decreased after 6 days from the ELGE operation at days 7 and 14 after the application of physiological saline in the ELGE control group as compared with the sham control group. In the groups treated with YDE derivatives and the DS reference group, the amount of tear secretion was increased as compared with the ELGE control group, except for the groups treated with a 0.3% solution of YDE-9, YDE-10, YDE-17, YDE-19, YDE-20, YDE-21, YDE-22, YDE-25, YDE-27, and YDE-28, which did not show any significant changes in the amount of tear secretion after the administration thereof for 14 days. Especially, the amount of tear secretion was increased by more than 20% in the groups treated with a 0.3% solution of YDE-15, YDE-11, YDE-08, YDE-26, YDE-16, YDE-01, YDE-23, and YY-102 as compared with the DS reference group.

The specific amounts of tear secretion are shown in FIG. 140 and Table 14.

TABLE 14

| | Tear Volumes (mm$^3$) | |
|---|---|---|
| No. | Day 7 | Day 14 |
| YY-101 | 7.66 ± 0.61 | 6.00 ± 0.69 |
| YY-102 | 4.59 ± 1.43 | 5.77 ± 1.99 |
| YDE-001 | 4.88 ± 1.62 | 5.92 ± 2.19 |
| YDE-002 | 3.84 ± 1.16 | 5.01 ± 1.67 |
| YDE-003 | 4.13 ± 1.76 | 4.88 ± 1.57 |
| YDE-004 | 3.42 ± 1.06 | 5.19 ± 1.84 |
| YDE-005 | 3.85 ± 0.93 | 5.08 ± 1.91 |
| YDE-006 | 3.44 ± 1.69 | 5.35 ± 1.68 |
| YDE-007 | 3.91 ± 1.28 | 5.45 ± 1.26 |
| YDE-008 | 4.57 ± 1.25 | 6.10 ± 2.36 |
| YDE-009 | 3.76 ± 1.21 | 4.54 ± 1.11 |
| YDE-010 | 3.42 ± 1.31 | 4.35 ± 1.36 |
| YDE-011 | 4.22 ± 1.45 | 6.16 ± 2.16 |
| YDE-012 | 3.68 ± 0.99 | 5.67 ± 1.86 |
| YDE-013 | 5.27 ± 1.50 | 5.49 ± 1.92 |
| YDE-014 | 3.81 ± 1.21 | 5.62 ± 1.85 |
| YDE-015 | 4.03 ± 2.19 | 6.65 ± 2.13 |
| YDE-016 | 4.59 ± 1.13 | 5.98 ± 2.27 |
| YDE-017 | 4.00 ± 1.22 | 4.89 ± 1.50 |
| YDE-018 | 3.75 ± 1.54 | 4.99 ± 1.60 |
| YDE-019 | 4.84 ± 1.39 | 4.52 ± 1.07 |
| YDE-020 | 3.41 ± 1.47 | 4.20 ± 1.35 |
| YDE-021 | 4.08 ± 1.33 | 4.90 ± 1.13 |
| YDE-022 | 3.19 ± 0.67 | 4.10 ± 0.95 |
| YDE-023 | 5.32 ± 2.30 | 5.78 ± 2.23 |
| YDE-024 | 3.85 ± 1.30 | 5.72 ± 1.36 |
| YDE-025 | 3.21 ± 0.72 | 4.72 ± 2.19 |
| YDE-026 | 4.32 ± 1.47 | 6.01 ± 1.83 |
| YDE-027 | 2.82 ± 0.86 | 3.95 ± 1.52 |
| YDE-028 | 4.04 ± 0.99 | 4.73 ± 1.18 |

FIG. 141 shows the results of the test, wherein A is for the sham control group, B is for the ELGE control group, C is for the DS reference group, D is for the YY-102 administered group, and E to S are for the YDE-029 to YDE-043 administered groups in order.

As a result, it was confirmed that the amount of tear secretion was decreased after 6 days from the ELGE operation at days 7 and 14 after the application of physiological saline in the ELGE control group as compared with the sham control group. In the groups treated with YDE derivatives and the DS reference group, the amount of tear secretion was increased as compared with the ELGE control group, except for the groups treated with a 0.3% solution of YDE-029, YDE-030, YDE-032, YDE-033, YDE-034, YDE-036, and YDE-41, which did not show any significant changes in the amount of tear secretion after the administration thereof for 14 days. Especially, the amount of tear secretion increased by more than 20% in the groups treated with a 0.3% solution of YDE-040, YDE-043, and YDE-042 in order as compared with the DS reference group.

The specific amounts of tear secretion are shown in FIG. 142 and Table 15.

TABLE 15

| No. | Tear Volumes (mm3) | |
| --- | --- | --- |
| | Day 7 | Day 14 |
| YY-101 | 5.36 ± 0.68 | 6.25 ± 0.68 |
| YY-102 | 5.77 ± 1.01 | 6.60 ± 0.64 |
| YDE-029 | 5.33 ± 1.43 | 6.03 ± 1.71 |
| YDE-030 | 5.69 ± 1.79 | 6.65 ± 2.17 |
| YDE-031 | 5.63 ± 1.97 | 5.91 ± 0.85 |
| YDE-032 | 5.58 ± 0.80 | 5.03 ± 0.93 |
| YDE-033 | 4.99 ± 1.20 | 4.54 ± 1.16 |
| YDE-034 | 6.16 ± 1.01 | 6.43 ± 1.86 |
| YDE-035 | 4.96 ± 0.96 | 6.25 ± 0.79 |
| YDE-036 | 4.95 ± 1.05 | 5.13 ± 1.03 |
| YDE-037 | 4.98 ± 0.66 | 5.80 ± 0.90 |
| YDE-039 | 6.04 ± 1.01 | 6.44 ± 1.96 |
| YDE-040 | 5.77 ± 1.05 | 8.63 ± 1.53 |
| YDE-041 | 5.01 ± 1.26 | 6.25 ± 2.15 |
| YDE-042 | 6.30 ± 1.08 | 7.97 ± 1.48 |
| YDE-043 | 5.90 ± 1.06 | 8.16 ± 1.42 |

Experimental Example 2.4: Confirmation of the Changes in the Corneal Damage by the YDE Derivatives After YDE-001 to YDE-028 were each administered to the eyes 14 times, the changes in the corneal permeability were checked.

In order to measure the corneal permeability, Zolethyl 50™ (Virbac Lab., Carros, France), an animal anesthetic, was intraperitoneally injected at a dose of 25 mg/kg. Thereafter, saline containing a 1% (v/v) fluorescent solution (fluorescein sodium salt, Tokyo Kasei Kogyo Co., Tokyo, Japan) was applied to the eyes at a dose of 5 µl/eye. The eyes thus treated were closed and fixed with a tape. After 1 hour, the remaining fluorescent solution was removed using a cotton swab (FIG. 142). After 12 hours to 24 hours, the corneal permeability was measured using a blue light tungsten lamp and an ophthalmic slit lamp table top model biomicroscope (Model SM-70N; Takaci Seiko Co., Nakano, Japan) (FIG. 143).

FIG. 144 shows the results of the test, wherein A is for the sham control group, B is for the ELGE control group, C is for the DS reference group, D is for the YY-102 administered group, and E to AF are for the YDE-001 to YDE-028 administered groups in order.

As a result, the permeability of the fluorescent dye was increased in the ELGE control group as compared with the sham control group. The permeability of the fluorescent dye was not decreased in the groups treated with a 0.3% solution of YDE-10, YDE-20, YDE-22, YDE-25, YDE-27, and YDE-28 as compared with the ELGE control group at day 14 after the administration. In the groups treated with YDE derivatives and the DS reference group, the corneal permeability of the fluorescent dye was decreased as compared with the ELGE control group, except for the groups treated with a 0.3% solution of YDE-10, YDE-20, YDE-22, YDE-25, YDE-27, and YDE-28. Especially, the permeability of the fluorescent dye was decreased by more than 20% in the groups treated with a 0.3% solution of YDE-15, YDE-11, YDE-08, YDE-26, YDE-16, YDE-01, YDE-23, and YY-102, as compared with the DS reference group.

The specific permeabilities of the fluorescent dye are shown in FIG. 145 and Table 16.

TABLE 16

| No. | Permeability of fluorescent dye (%) |
| --- | --- |
| YY-101 | 27.53 ± 5.62 |
| YY-102 | 27.48 ± 14.37 |
| YDE-001 | 25.49 ± 11.62 |
| YDE-002 | 38.26 ± 11.25 |
| YDE-003 | 40.45 ± 6.46 |
| YDE-004 | 35.05 ± 11.74 |
| YDE-005 | 37.98 ± 11.53 |
| YDE-006 | 33.23 ± 13.26 |
| YDE-007 | 32.79 ± 10.77 |
| YDE-008 | 20.32 ± 11.87 |
| YDE-009 | 41.50 ± 7.86 |
| YDE-010 | 49.29 ± 12.06 |
| YDE-011 | 18.11 ± 11.61 |
| YDE-012 | 31.01 ± 11.38 |
| YDE-013 | 32.24 ± 7.84 |
| YDE-014 | 31.15 ± 10.87 |
| YDE-015 | 15.95 ± 6.48 |
| YDE-016 | 24.57 ± 10.34 |
| YDE-017 | 39.76 ± 7.42 |
| YDE-018 | 38.19 ± 10.96 |
| YDE-019 | 40.39 ± 12.57 |
| YDE-020 | 47.84 ± 13.47 |
| YDE-021 | 37.00 ± 10.49 |
| YDE-022 | 47.82 ± 10.01 |
| YDE-023 | 26.51 ± 8.18 |
| YDE-024 | 30.63 ± 10.41 |
| YDE-025 | 47.10 ± 11.45 |
| YDE-026 | 22.63 ± 11.23 |
| YDE-027 | 50.24 ± 11.94 |
| YDE-028 | 41.17 ± 10.25 |

In addition, YDE-029 to YDE-043 were each administered to the eyes 14 times, and the changes in the corneal permeability were then checked. The measurement of the corneal permeability was carried out in the same manner as described above (FIG. 146).

As a result, the permeability of the fluorescent dye was increased in the ELGE control group as compared with the sham control group. The permeability of the fluorescent dye was not decreased in the groups treated with a 0.3% solution of YDE-29, YDE-32, YDE-33, YDE-36, and YDE-41 as compared with the ELGE control group at day 14 after the administration. In the groups treated with YDE derivatives and the DS reference group, the corneal permeability of the fluorescent dye was decreased as compared with the ELGE control group, except for the groups treated with a 0.3% solution of YDE-29, YDE-32, YDE-33, YDE-36, and YDE-41. Especially, the permeability of the fluorescent dye was decreased by more than 20% in the groups treated with a 0.3% solution of YDE-40, YDE-43, and YDE-42, as compared with the DS reference group.

The specific permeabilities of the fluorescent dye are shown in FIG. 147 and Table 17.

TABLE 17

| No. | Permeability of fluorescent dye (%) |
| --- | --- |
| YY-101 | 33.80 ± 11.11 |
| YY-102 | 27.89 ± 7.10 |
| YDE-029 | 63.45 ± 11.57 |
| YDE-030 | 30.60 ± 13.61 |
| YDE-031 | 33.35 ± 11.01 |
| YDE-032 | 58.90 ± 19.81 |
| YDE-033 | 60.55 ± 21.22 |
| YDE-034 | 32.17 ± 12.94 |
| YDE-035 | 27.62 ± 6.51 |
| YDE-036 | 57.87 ± 22.91 |
| YDE-037 | 36.30 ± 9.75 |
| YDE-039 | 29.94 ± 11.40 |
| YDE-040 | 18.33 ± 9.41 |

TABLE 17-continued

| No. | Permeability of fluorescent dye (%) |
|---|---|
| YDE-041 | 46.38 ± 26.65 |
| YDE-042 | 20.72 ± 11.37 |
| YDE-043 | 19.04 ± 7.36 |

Experimental Example 3: Evaluation of the Stability of the YDE Derivatives

In order to confirm the stability of each test substance in an aqueous solution, 10 mg of each sample was dissolved in 1 ml of water to a concentration of 1 mg/ml, which was then charged to a glass vial, plugged with a rubber cap, sealed with an aluminum cap, and stored under long-term storage conditions (25° C., 75% RH). The stability of the test substance was evaluated by measuring the amount of related substances at the time of one week, two weeks, four weeks, eight weeks, and twelve weeks under the long-term storage conditions.

As a result, 66.5% of related substances was generated in YY-101 after two weeks. In contrast, 1.1% to 30.6% of related substances was generated in YDE-001 to YDE-028 after 12 weeks. The specific amounts are shown in Table 18.

TABLE 18

| No. | Amount of related substances (%; after 12 weeks) |
|---|---|
| YY-101 | 66.51 (after 2 weeks) |
| YDE-001 | 3.92 |
| YDE-002 | 4.93 |
| YDE-003 | 6.86 |
| YDE-004 | 2.11 |
| YDE-005 | 2.97 |
| YDE-006 | 3.67 |
| YDE-007 | 3.76 |
| YDE-008 | 4.42 |
| YDE-009 | 4.71 |
| YDE-010 | 4.39 |
| YDE-011 | 3.83 |
| YDE-012 | 3.57 |
| YDE-013 | 5.92 |
| YDE-014 | 6.72 |
| YDE-015 | 13.05 |
| YDE-016 | 11.33 |
| YDE-017 | 11.88 |
| YDE-018 | 25.39 |
| YDE-019 | 13.43 |
| YDE-020 | 21.54 |
| YDE-021 | 21.33 |
| YDE-022 | 19.23 |
| YDE-023 | 30.66 |
| YDE-024 | 20.59 |
| YDE-025 | 5.17 |
| YDE-026 | 10.15 |
| YDE-027 | 12.74 |
| YDE-028 | 1.15 |

Test Example 4: Evaluation of Recovery of Corneal Damage by the YDE Derivatives

In order to confirm whether the YDE derivatives could recover corneal damage, the cellular growth rate of human primary corneal epithelial cells was checked.

Specifically, primary corneal epithelial cells (ATCC, ATCC PCS-700-010) were seeded on a 96-well culture plate (Perkin Elmer, 6005680) containing the Corneal Epithelial Cell Basal Medium (ATCC, ATCC PCS-700-030) in the Corneal Epithelial Cell Growth Kit (ATCC, ATCC PCS-700-040) in an amount of $5 \times 10^3$ cells per well, which was then cultured for 24 hours under the conditions of 37° C. and 5% $CO_2$.

YDE-001 to YDE-075 were each dissolved in 100% DMSO (Sigma, D2660) to a concentration of 10 mM, which was then diluted with 100% DMSO to a concentration of the compound of 6, 1.9, 0.6, 0.2, 0.06, 0.02, 0.006, and 0.002 mM. 20 µl of the diluted YDE derivative was added to a 96-well microplate (Greiner Bio-One, 651201) containing 380 µl of the Corneal Epithelial Cell Basal Medium such that the concentration of DMSO was diluted to 5%.

After 24 hours, 20 µl of each of the YDE derivatives diluted in the 96-well microplate was added to the 96-well culture plate containing the cells. As a control group, hEGF (Sigma, E9644) was treated at the same concentration as the YDE derivatives. The cells treated with the YDE-derivatives or hEGF were cultured for 48 hours and 72 hours under the conditions of 37° C. and 5% $CO_2$ (FIGS. 148 to 155).

The cultured cells were treated with the CellTiter-Glo luminescent reagent (Promega, G7573) according to the manufacturer's instructions and reacted for 30 minutes at room temperature. Thereafter, the fluorescent signal (or luminescence signal) was checked using an Envision 2014 Multi-label plate reader. The measured values were normalized using a vehicle control (100% proliferation cell).

As a result, the cell proliferation was observed at concentrations of 0.3 µM or less in YY-101, YY-102, YDE-011, YDE-038, YDE-042, YDE-043, YDE-044, YDE-045, YDE-049, YDE-054, YDE-057, YDE-058, YDE-059, and YDE-060. Especially, a high cell proliferation rate was shown in YY-102, YDE-011, YDE-045, YDE-057, and YDE-060 (FIGS. 156 to 173).

What is claimed is:

1. A compound represented by Formula 1:

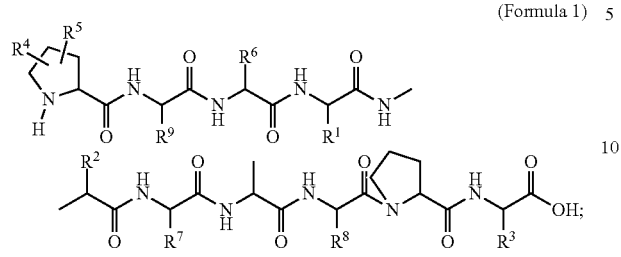

(Formula 1)

wherein $R^1$, $R^2$, and $R^3$ are each independently hydrogen, substituted or unsubstituted $C_{1-6}$ alkyl, substituted or unsubstituted $C_{1-10}$ alkoxy, substituted or unsubstituted $C_{1-10}$ haloalkyl, substituted or unsubstituted $C_{2-10}$ alkenyl, substituted or unsubstituted $C_{2-10}$ alkynyl, substituted or unsubstituted $C_{1-10}$ alkylene, substituted or unsubstituted $C_{1-10}$ alkenylene, substituted or unsubstituted $C_{1-10}$ alkynylene, substituted or unsubstituted $C_{5-12}$ aryl, substituted or unsubstituted $C_{7-12}$ arylalkyl, substituted or unsubstituted $C_{5-14}$ arylalkynyl, substituted or unsubstituted $C_{8-16}$ arylalkenyl, substituted or unsubstituted $C_{3-10}$ heteroalkyl, substituted or unsubstituted $C_{3-10}$ cycloalkyl, substituted or unsubstituted $C_{3-10}$ heterocycloalkyl, or substituted or unsubstituted $C_{5-12}$ heteroaryl; and the $C_{3-10}$ heteroalkyl, the $C_{3-10}$ heterocycloalkyl, or the $C_{5-12}$ heteroaryl contain at least one of N, O, and S;

the substitution refers to a substitution with a non-hydrogen substituent, the non-hydrogen substituent may be at least one selected from $-X_1$, $-R_a$, $-O-$, $=O$, $-OR_a$, $-SR_a$, $-S-$, $-N(R_a)_2$, $-N^+(R_a)_3$, $=NR_a$, $-C(X_1)_3$, $-CN$, $-OCN$, $-SCN$, $-N=C=O$, $-NCS$, $-NO$, $-NO_2$, $=N-OH$, $=N_2$, $-N_3$, $-NHC(=O)R_a$, $-C(=O)R_a$, $-C(=O)NR_aR_a$, $-S(=O)_2O-$, $-S(=O)_2OH$, $-S(=O)_2R_a$, $-OS(=O)_2OR_a$, $-S(=O)_2NR_a$, $-S(=O)R_a$, $-OP(=O)(OR_a)_2$, $-C(=O)R_a$, alkylene-$C(=O)R_a$, $-C(=S)R_a$, $-C(=O)OR_a$, alkylene-$C(=O)OR_a$, $-C(=O)O-$, alkylene-$C(=O)O-$, $-C(=S)OR_a$, $-C(=O)SR_a$, $-C(=S)SR_a$, $-C(=O)NR_aR_a$, alkylene-$C(=O)NR_aR_a$, $-C(=S)NR_aR_a$, and $-C(-NR_a)NR_aR_a$;

$X_1$ is F, Cl, Br, or I;

$R_a$ is hydrogen, $C_{1-6}$ alkyl, $C_{5-12}$ aryl, $C_{7-12}$ arylalkyl, or heterocycle;

$R^4$ and $R^5$ are each independently hydrogen, substituted or unsubstituted $C_{1-6}$ alkyl, $-X_2$, $-R_b$, $-O-$, $=O$, $-CH_2OR_b$, or $-OR_b$;

provided that at least one of $R^4$ or $R^5$ is not hydrogen;

$X_2$ is F, Cl, Br, or I;

$R_b$ is hydrogen, substituted or unsubstituted $C_{1-6}$ alkyl, substituted or unsubstituted $C_{5-12}$ aryl, substituted or unsubstituted $C_{7-12}$ arylalkyl, or substituted or unsubstituted heterocycle, $R^6$ is hydrogen or substituted or unsubstituted $C_{1-6}$ alkyl, and the substituent of $R^6$ is $C(=O)NH_2$;

$R^7$ is hydrogen or $C_{1-6}$ alkyl; and $R^8$ and $R^9$ are hydrogen or unsubstituted $C_{1-6}$ alkyl;

further wherein the compound is not:

(SEQ ID NO: 105)

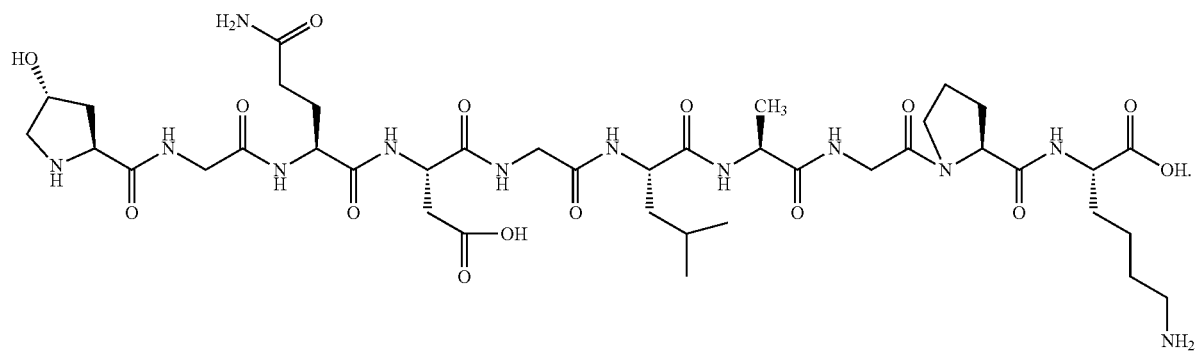

2. The compound of claim 1, wherein:
$R^1$ is selected from substituted or unsubstituted $C_{1-6}$ alkyl,

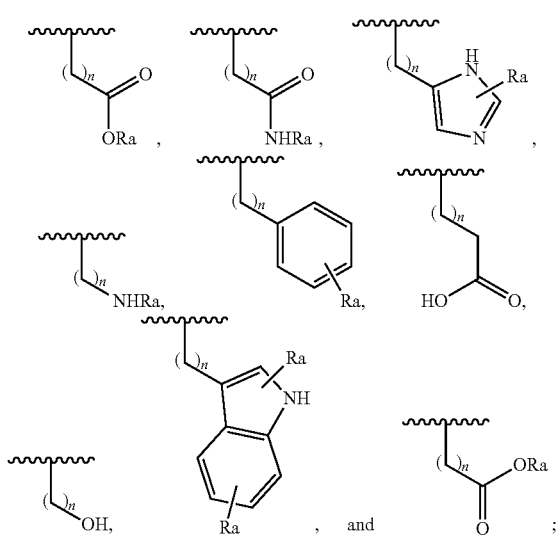

$R_a$ is hydrogen or $C_{1-6}$ alkyl; and
n is an integer of 1 to 10.

3. The compound of claim 1, wherein:
$R^2$ is selected from hydrogen, substituted or unsubstituted $C_{1-6}$ alkyl,

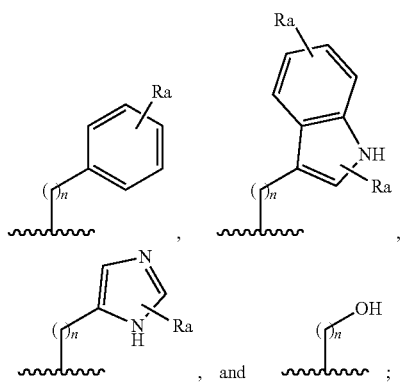

$R_a$ is hydrogen or $C_{1-6}$ alkyl; and
n is an integer of 1 to 10.

4. The compound of claim 1, wherein:
$R^3$ is selected from substituted or unsubstituted $C_{1-6}$ alkyl,

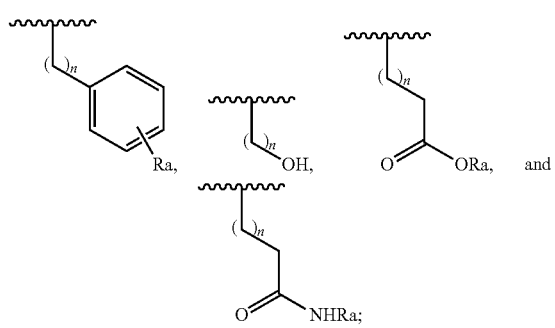

$R_a$ is hydrogen or $C_{1-6}$ alkyl; and
n is an integer of 1 to 10.

5. The compound of claim 1, wherein $R^4$ and $R^5$ are each independently selected from hydrogen, substituted or unsubstituted $C_{1-6}$ alkyl, —$OR_b$, =O, —$CH_2OR_b$, and —$X_2$, provided that at least one of $R^4$ or $R^5$ is not hydrogen; and $R_b$ is hydrogen or $C_{1-6}$ alkyl.

6. The compound of claim 5, wherein at least one of $R^4$ and $R^5$ is $X_2$.

7. The compound of claim 1, wherein $R^6$, $R^7$, $R^8$, and $R^9$ are each independently hydrogen or substituted or unsubstituted $C_{1-6}$ alkyl, and wherein the substituent of $R^6$, $R^7$, $R^8$, and $R^9$ is —C(=O)$NH_2$.

8. The compound of claim 2, wherein $R^1$ is selected from

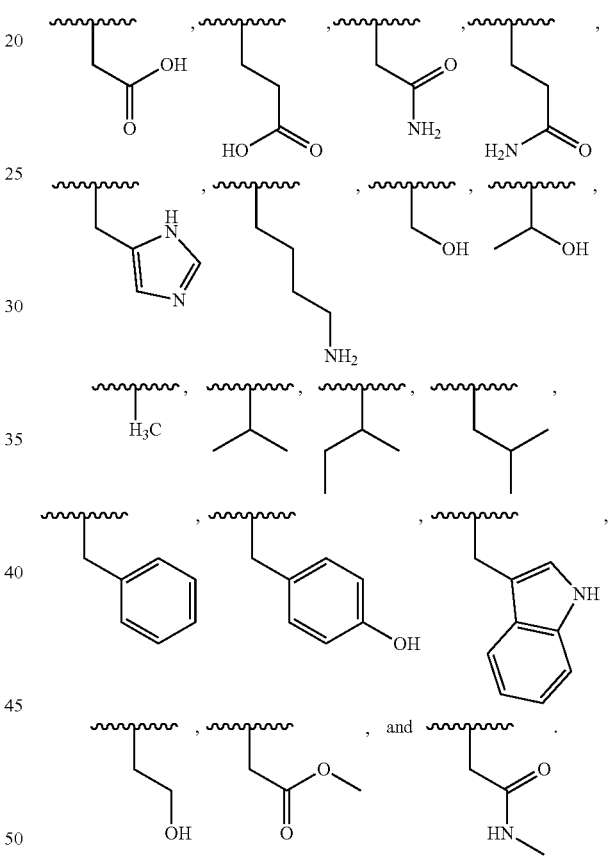

9. The compound of claim 3, wherein $R^2$ is selected from

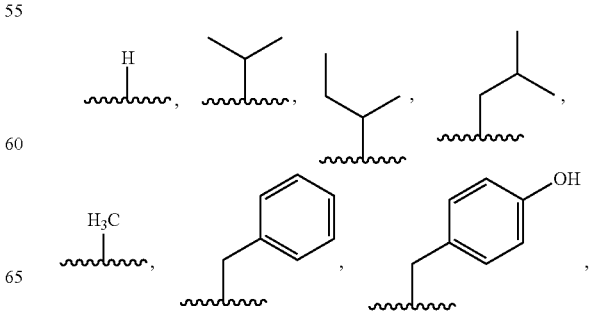

-continued

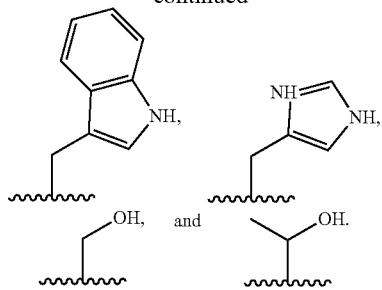

10. The compound of claim 4, wherein $R^3$ is selected from

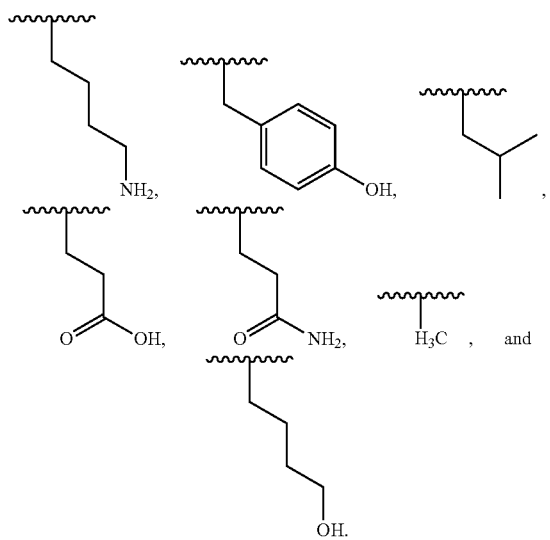

11. The compound of claim 6, wherein $R^4$ is selected from hydrogen, —OH, =O, and —CH$_3$.

12. The compound of claim 1, which is selected from HyP-Gly-Gln-Glu-Gly-Leu-Ala-Gly-Pro-Lys (SEQ ID NO: 1), HyP-Gly-Gln-Asn-Gly-Leu-Ala-Gly-Pro-Lys (SEQ ID NO: 2), HyP-Gly-Gln-Gln-Gly-Leu-Ala-Gly-Pro-Lys (SEQ ID NO: 3), HyP-Gly-Gln-His-Gly-Leu-Ala-Gly-Pro-Lys (SEQ ID NO: 4), HyP-Gly-Gln-Lys-Gly-Leu-Ala-Gly-Pro-Lys (SEQ ID NO: 5), HyP-Gly-Gln-Ser-Gly-Leu-Ala-Gly-Pro-Lys (SEQ ID NO: 6), HyP-Gly-Gln-Thr-Gly-Leu-Ala-Gly-Pro-Lys (SEQ ID NO: 7), HyP-Gly-Gln-Ala-Gly-Leu-Ala-Gly-Pro-Lys (SEQ ID NO: 8), HyP-Gly-Gln-Val-Gly-Leu-Ala-Gly-Pro-Lys (SEQ ID NO: 9), HyP-Gly-Gln-Ile-Gly-Leu-Ala-Gly-Pro-Lys (SEQ ID NO: 10), HyP-Gly-Gln-Leu-Gly-Leu-Ala-Gly-Pro-Lys (SEQ ID NO: 11), HyP-Gly-Gln-Phe-Gly-Leu-Ala-Gly-Pro-Lys (SEQ ID NO: 12), HyP-Gly-Gln-Tyr-Gly-Leu-Ala-Gly-Pro-Lys (SEQ ID NO: 13), HyP-Gly-Gln-Trp-Gly-Leu-Ala-Gly-Pro-Lys (SEQ ID NO: 14), HyP-Gly-Gln-Ser(Homo)-Gly-Leu-Ala-Gly-Pro-Lys (SEQ ID NO: 15), HyP-Gly-Gln-Asp(Me)-Gly-Leu-Ala-Gly-Pro-Lys (SEQ ID NO: 16), HyP-Gly-Gln-Asn(Me)-Gly-Leu-Ala-Gly-Pro-Lys (SEQ ID NO: 17), $_D$-HyP(2R, 4S)-Gly-Gln-Leu-Gly-Leu-Ala-Gly-Pro-Lys (SEQ ID NO: 18), $_D$-Hyp(2R,4S)-Gly-$_D$-Gln-$_D$-Leu-Gly-$_D$-Leu-$_D$-Ala-Gly-$_D$-Pro-$_D$-Lys (SEQ ID NO: 19), $_D$-Hyp(2R, 4R)-Gly-$_D$-Gln-$_D$-Leu-$_D$-Gly-$_D$-Ala-Gly-$_D$-Pro-$_D$-Lys (SEQ ID NO: 20), HyP-Gly-Gln-Asp-Val-Leu-Ala-Gly-Pro-Lys (SEQ ID NO: 21), HyP-Gly-Gln-Asp-Ile-Leu-Ala-Gly-Pro-Lys (SEQ ID NO: 22), HyP-Gly-Gln-Asp-Leu-Leu-Ala-Gly-Pro-Lys (SEQ ID NO: 23), HyP-Gly-Gln-Asp-Ala-Leu-Ala-Gly-Pro-Lys (SEQ ID NO: 24), HyP-Gly-Gln-Asp-Phe-Leu-Ala-Gly-Pro-Lys (SEQ ID NO: 25), HyP-Gly-Gln-Asp-Tyr-Leu-Ala-Gly-Pro-Lys (SEQ ID NO: 26), HyP-Gly-Gln-Asp-Trp-Leu-Ala-Gly-Pro-Lys (SEQ ID NO: 27), HyP-Gly-Gln-Asp-His-Leu-Ala-Gly-Pro-Lys (SEQ ID NO: 28), HyP-Gly-Gln-Asp-Ser-Leu-Ala-Gly-Pro-Lys (SEQ ID NO: 29), HyP-Gly-Gln-Asp-Thr-Leu-Ala-Gly-Pro-Lys (SEQ ID NO: 30), HyP-Gly-Gln-Leu-Ala-Leu-Ala-Gly-Pro-Lys (SEQ ID NO: 32) HyP-Gly-Gln-Leu-Gly-Leu-Ala-Gly-Pro-Tyr (SEQ ID NO: 33), HyP-Gly-Gln-Leu-Gly-Leu-Ala-Gly-Pro-Leu (SEQ ID NO: 34), HyP-Gly-Gln-Leu-Gly-Leu-Ala-Gly-Pro-Glu (SEQ ID NO: 35), HyP-Gly-Gln-Leu-Gly-Leu-Ala-Gly-Pro-Gln (SEQ ID NO: 36), HyP-Gly-Gln-Leu-Gly-Leu-Ala-Gly-Pro-Nle(6-OH) (SEQ ID NO: 37), HyP-Gly-Gln-Leu-Gly-Leu-Ala-Gly-Pro-Ala (SEQ ID NO: 38), $_D$-HyP(2R, 4S)-Gly-Gln-Leu-Gly-Leu-Ala-Gly-Pro-Ala (SEQ ID NO: 39), Hyp(2S, 4S)-Gly-Gln-Leu-Gly-Leu-Ala-Gly-Pro-Lys (SEQ ID NO: 63), (4-oxo)Pro-Gly-Gln-Leu-Gly-Leu-Ala-Gly-Pro-Lys (SEQ ID NO: 40), (5-oxo)Pro-Gly-Gln-Leu-Gly-Leu-Ala-Gly-Pro-Lys (SEQ ID NO: 41), (4-hydroxyMe)Pro-Gly-Gln-Leu-Gly-Leu-Ala-Gly-Pro-Lys (SEQ ID NO: 43), (4-Fluoro)Pro-Gly-Gln-Leu-Gly-Leu-Ala-Gly-Pro-Lys (SEQ ID NO: 44), (4-Dimethyl)Pro-Gly-Gln-Leu-Gly-Leu-Ala-Gly-Pro-Lys (SEQ ID NO: 45), (4-Me)Pro-Gly-Gln-Leu-Gly-Leu-Ala-Gly-Pro-Lys (SEQ ID NO: 46), (5-Me)Pro-Gly-Gln-Leu-Gly-Leu-Ala-Gly-Pro-Lys (SEQ ID NO: 47), Hyp-Gly-Ala-Leu-Gly-Leu-Ala-Gly-Pro-Lys (SEQ ID NO: 48), Hyp-Gly-Gln-Leu-Gly-Ala-Ala-Gly-Pro-Lys (SEQ ID NO: 49), Hyp-Gly-Gln-Leu-Gly-Leu-Ala-Ala-Pro-Lys (SEQ ID NO: 50), Hyp-Ala-Gln-Leu-Gly-Leu-Ala-Gly-Pro-Lys (SEQ ID NO: 51), $_D$-Hyp(2R, 4S)-Ala-Gln-Leu-Gly-Leu-Ala-Gly-Pro-Lys (SEQ ID NO: 53), and $_D$-Hyp(2R, 4S)-Ala-Gln-Leu-Gly-Leu-Ala-Gly-Pro-Ala (SEQ ID NO: 52).

13. A pharmaceutical composition for treating an eye disease selected from retinopathy, keratitis, dry-macular degeneration, wet-macular degeneration, dry eye syndrome, keratoconjunctivitis sicca, and keratoconjunctival epithelium disorder, which comprises the compound according to claim 1 as an active pharmaceutical ingredient.

14. A peptide having the amino acid sequence represented by:
(a) HyP-Gly-Gln-Xaa$^1$-Gly-Leu-Ala-Gly-Pro-Lys (SEQ ID NO: 120), wherein Xaa$^1$ is selected from Glu, Asn, Gln, His, Lys, Ser, Thr, Ala, Val, Ile, Leu, Phe, Tyr, Trp, homo-Ser, Asp(Me), and Asn(Me);
(b) HyP-Gly-Gln-Asp-Xaa$^2$-Leu-Ala-Gly-Pro-Lys (SEQ ID NO: 121), wherein Xaa$^2$ is selected from Val, Ile, Leu, Ala, Phe, Tyr, Trp, Ser, Thr, and (N-Me)Gly;
(c) HyP-Gly-Gln-Leu-Gly-Leu-Ala-Gly-Pro-Xaa$^3$ (SEQ ID NO: 122), wherein Xaa$^3$ is selected from Tyr, Leu, Glu, Gln, Ala, and Nle(6-OH);
(d) PD-Gly-Gln-Leu-Gly-Leu-Ala-Gly-Pro-Lys (SEQ ID NO: 123), wherein PD is selected from:

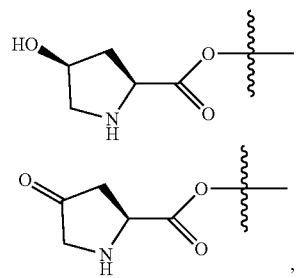

-continued

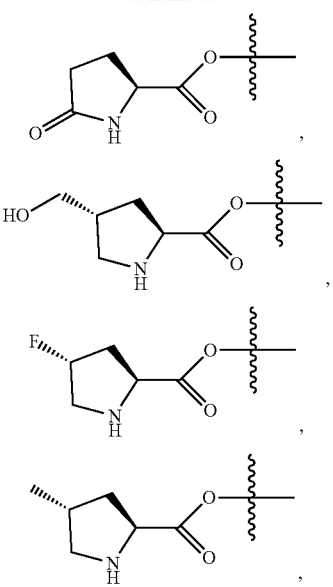

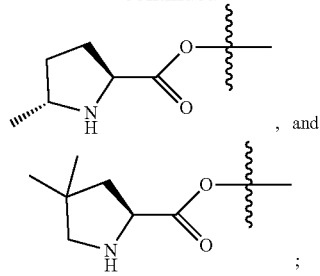

or
(e) Ala-Gly-Gln-Leu-Gly-Leu-Ala-Gly-Pro-Lys (SEQ ID NO: 54), Hyp-Gly-Gln-Leu-Gly-Leu-Ala-Gly-Ala-Lys (SEQ ID NO: 55), HyP-Gly-Gln-Leu-Gly-Leu-Ala (SEQ ID NO: 56), HyP-Gly-Gln-Glu-Gly-Lys-Gly (SEQ ID NO: 125), HyP-Gly-Gln-Leu-Gly-Leu (SEQ ID NO: 58), D-HyP(2R, 4S)-Gly-D-Gln-D-Leu-Gly-D-Leu (SEQ ID NO: 59), HyP-Gly-Gln-Leu-Gly (SEQ ID NO: 60), HyP-Gly-Gln-$_D$-Leu-Gly (SEQ ID NO: 61), and $_D$-HyP(2R, 4S)-Gly-Gln-Leu-Gly (SEQ ID NO: 126).

15. A compound represented by Formula 8 or Formula 10:

(Formula 8; SEQ ID NO: 100)

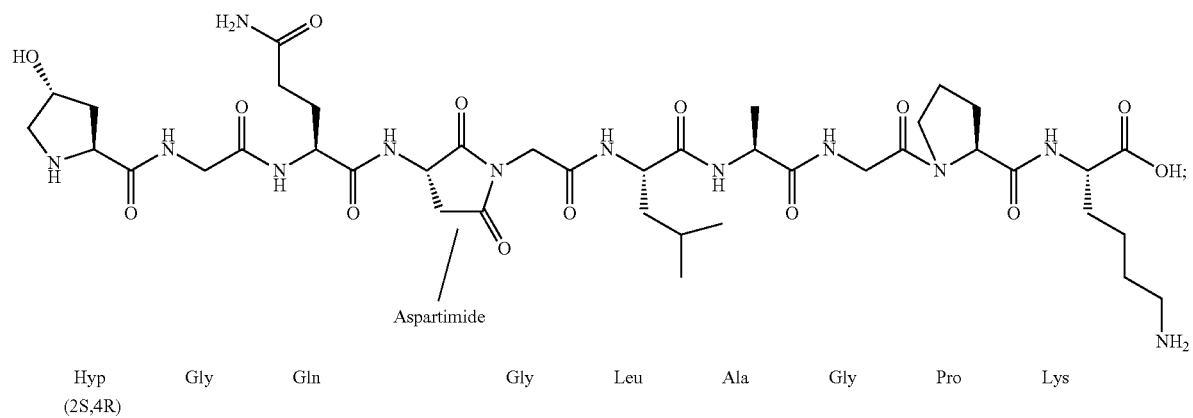

| Hyp (2S,4R) | Gly | Gln | | Gly | Leu | Ala | Gly | Pro | Lys | or (Formula 10; SEQ ID NO: 102)

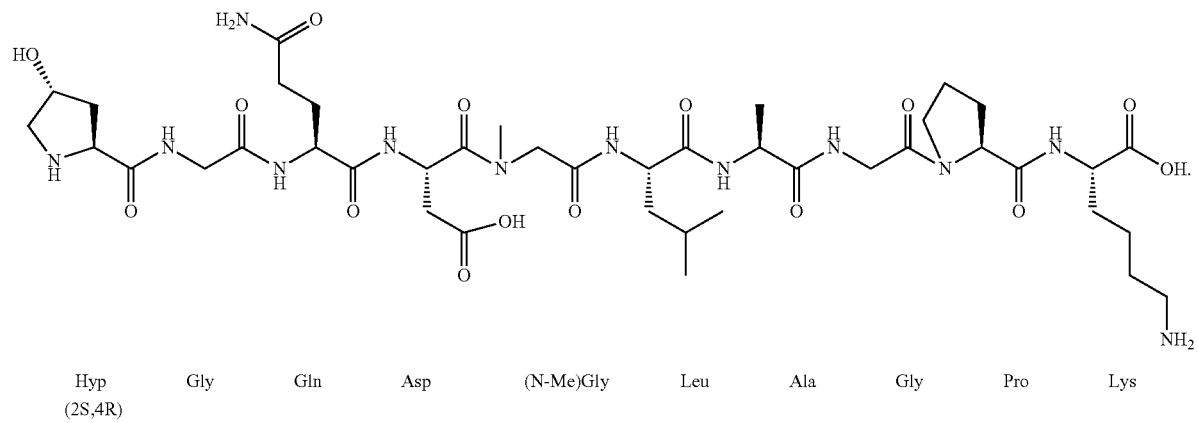

| Hyp (2S,4R) | Gly | Gln | Asp | (N-Me)Gly | Leu | Ala | Gly | Pro | Lys |

16. A method for treating an eye disease selected from retinopathy, keratitis, dry-macular degeneration, wet-macular degeneration, dry eye syndrome, keratoconjunctivitis sicca, and keratoconjunctival epithelium disorder, which comprises administering the compound according to claim 1 to a subject in need thereof.

\* \* \* \* \*